(12) United States Patent
Almeida De Pinho Ribeiro et al.

(10) Patent No.: US 11,400,136 B2
(45) Date of Patent: Aug. 2, 2022

(54) METHODS AND COMPOSITIONS FOR TREATING A MICROBIAL INFECTION

(71) Applicants: PRESIDENT AND FELLOWS OF HARVARD COLLEGE, Cambridge, MA (US); THE CHILDREN'S MEDICAL CENTER CORPORATION, Boston, MA (US)

(72) Inventors: Felipe Almeida De Pinho Ribeiro, Cambridge, MA (US); Pankaj Baral, Arlington, MA (US); Isaac M. Chiu, Cambridge, MA (US); Nicole J. Yang, Cambridge, MA (US); Michael Wessels, Brookline, MA (US); Buket Baddal, Boston, MA (US)

(73) Assignees: PRESIDENT AND FELLOWS OF HARVARD COLLEGE, Cambridge, MA (US); THE CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 16/624,036

(22) PCT Filed: Jun. 19, 2018

(86) PCT No.: PCT/US2018/038293
§ 371 (c)(1),
(2) Date: Dec. 18, 2019

(87) PCT Pub. No.: WO2018/236873
PCT Pub. Date: Dec. 27, 2018

(65) Prior Publication Data
US 2021/0145937 A1    May 20, 2021

Related U.S. Application Data

(60) Provisional application No. 62/662,457, filed on Apr. 25, 2018, provisional application No. 62/541,129, filed on Aug. 4, 2017, provisional application No. 62/521,776, filed on Jun. 19, 2017, provisional application No. 62/521,785, filed on Jun. 19, 2017.

(51) Int. Cl.
*A61K 38/00* (2006.01)
*A61K 38/22* (2006.01)
*A61P 31/04* (2006.01)

(52) U.S. Cl.
CPC ............ *A61K 38/225* (2013.01); *A61P 31/04* (2018.01)

(58) Field of Classification Search
CPC .............................. A61K 38/225; A61P 31/04
See application file for complete search history.

(56) References Cited

U.S. PATENT DOCUMENTS

| 10,201,594 B2 | 2/2019 | Ruegg et al. |
| 2005/0058729 A1 | 3/2005 | Staggs |
| 2011/0189205 A1 | 8/2011 | Dickerson et al. |
| 2014/0005597 A1 | 1/2014 | Jankowski |
| 2014/0315820 A1 | 10/2014 | Borodic |
| 2015/0291690 A1 | 10/2015 | Zeller et al. |
| 2017/0037117 A1 | 2/2017 | Dillin et al. |
| 2017/0065681 A1 | 3/2017 | Sveinsson |

FOREIGN PATENT DOCUMENTS

| EP | 2336363 A1 | 6/2011 |
| WO | 2012041761 A2 | 4/2012 |
| WO | 2017001434 A1 | 1/2017 |

OTHER PUBLICATIONS

Durham et al. Insights Into the Mechanism of OnabotulinumtoxinA in Chronic Migraine (Headache. Nov.-Dec. 2011; 51(10): 1573-1577). (Year: 2011).*
Kim et al. The effect of resiniferatoxin on the sensory nerve of the rat prostate. ICS Abstract (Year: 2006).*
Baral et al. "Nociceptor sensory neurons suppress neutrophil and γσ T cell responses in bacterial lung infections and lethal pneumonia." Nature medicine 24(4): 417-426 (2018).
Chiu et al. "Nociceptor neurons regulate lung infections and bacterial host defense." J. Immunol. 198(1): 131-134 (2017).
Pinho-Ribeiro et al. "Blocking Neuronal Signaling to Immune Cells Treats Streptococcal Invasive Infection." Cell 173(5): 1-15 (2018).
Pinho-Ribeiro et al. "Nociceptor Sensory Neuron-Immune Interactions in Pain and Inflammation." Trends Immunol. 38(1): 5-19 (2017).

* cited by examiner

*Primary Examiner* — Christina Bradley
*Assistant Examiner* — Mercy H Sabila
(74) *Attorney, Agent, or Firm* — Nixon Peabody LLP; David S. Resnick; Nicole D. Kling

(57) ABSTRACT

Described herein are methods and compositions for treating and/or preventing a microbial infection. Aspects of the invention relate to administering to a subject an agent that inhibits CGRP release and CGRP receptors. In some embodiments of any of the aspects, a subject has been diagnosed with having, or is at risk of having, a microbial infection.

12 Claims, 83 Drawing Sheets
Specification includes a Sequence Listing.

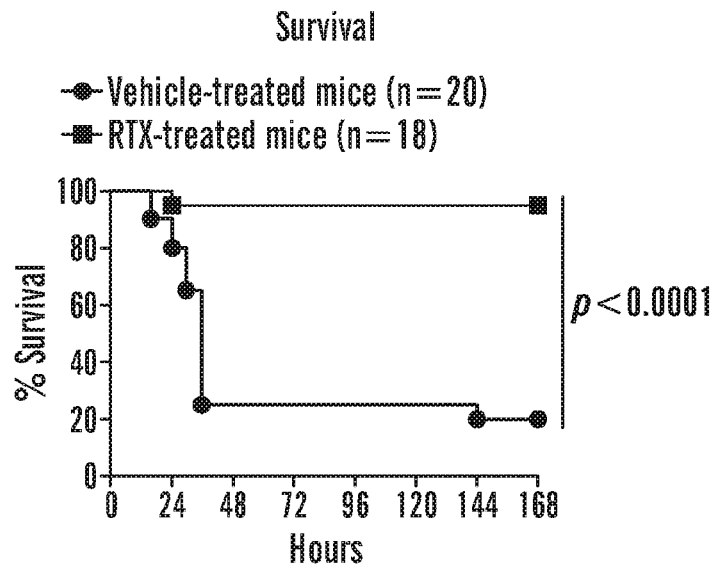
FIG. 2A
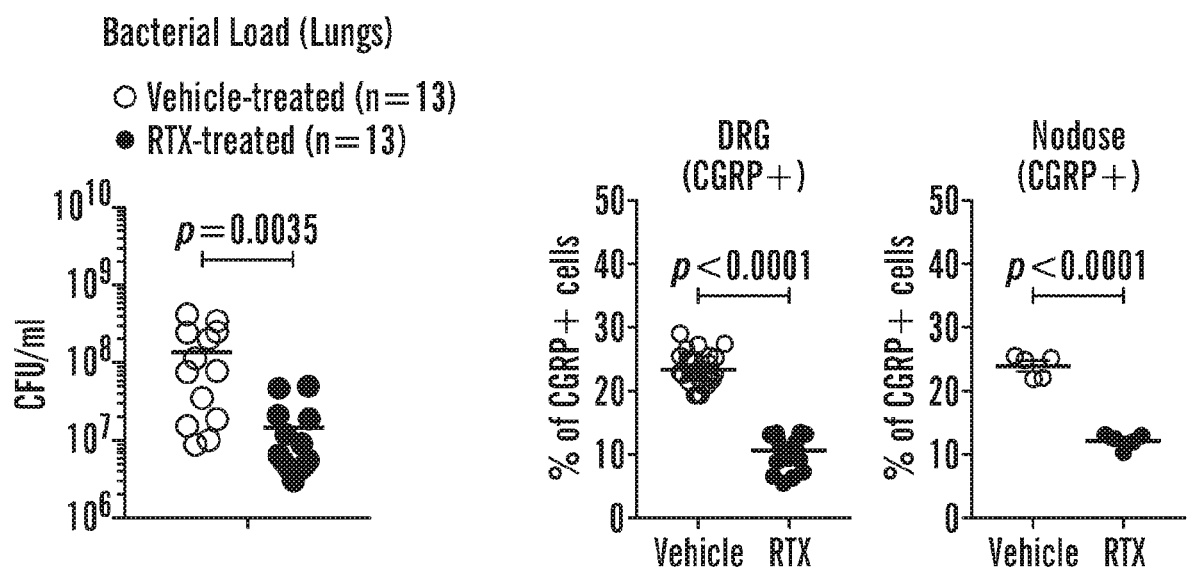
FIG. 2B
FIG. 2C

FIG. 17E Intrathecal BoNT/A

FIG. 17F Vehicle / BoNT/A Day 8

FIG. 17G Dermonecrosis
—▽— intrathecal vehicle
—△— intrathecal BoNT/A

FIG. 17H Weight loss
—▽— intrathecal vehicle
—△— intrathecal BoNT/A

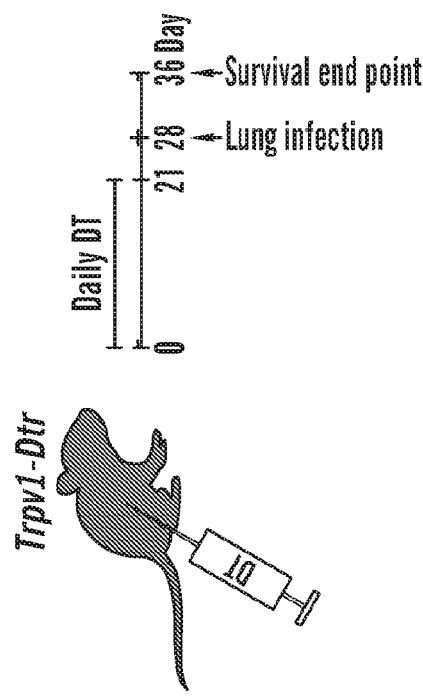
FIG. 26A
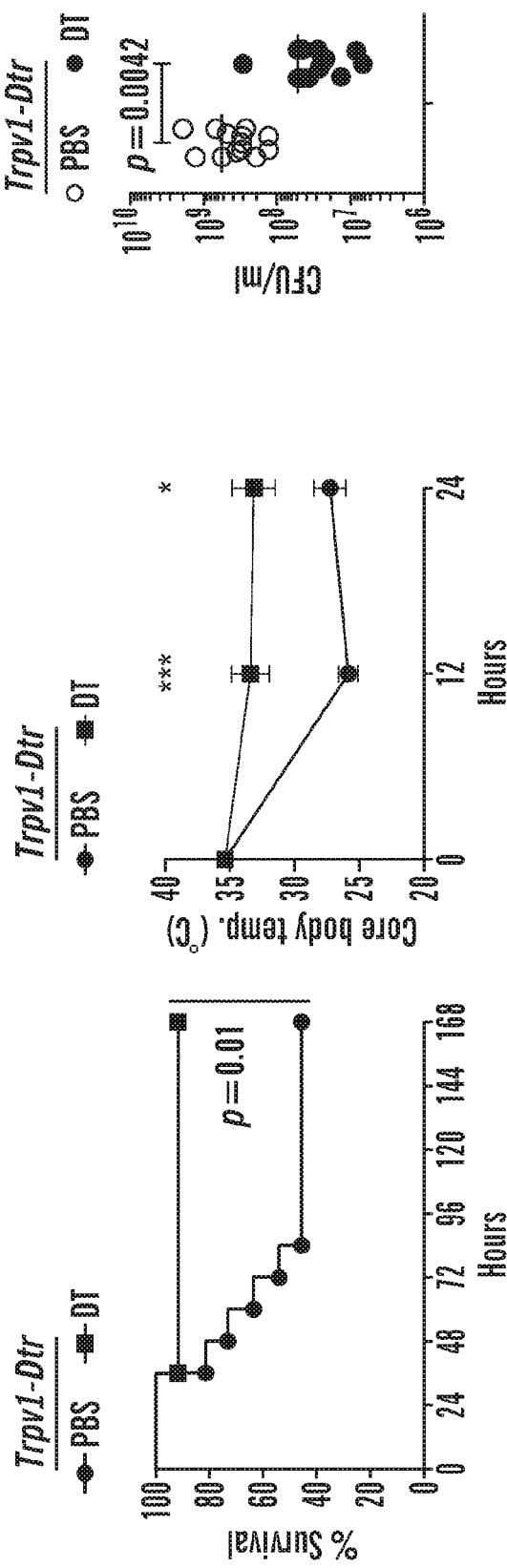
FIG. 26C
FIG. 26B

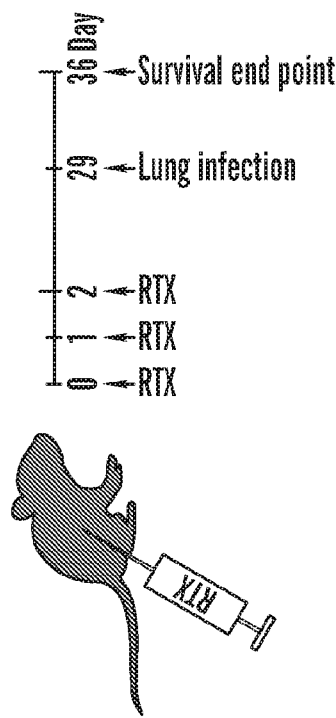
FIG. 26D
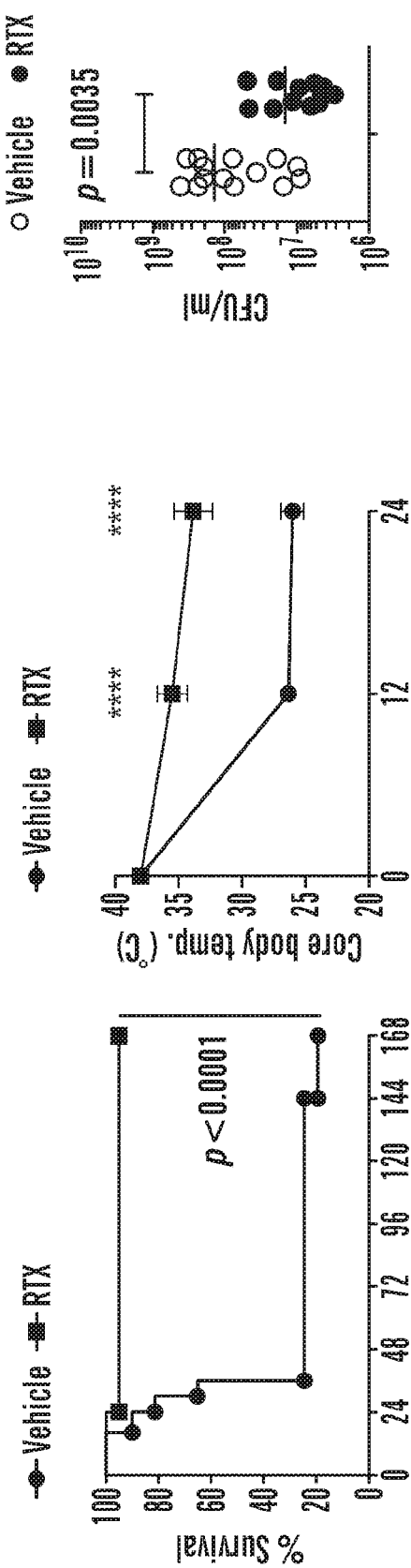
FIG. 26F
FIG. 26E

METHODS AND COMPOSITIONS FOR TREATING A MICROBIAL INFECTION

CROSS-REFERENCE TO RELATED APPLICATIONS

This Application is a 35 U.S.C. § 371 National Phase Entry Application of International Application No. PCT/US2018/038293 filed Jun. 19, 2018, which designates the U.S. and claims benefit under 35 U.S.C. § 119(e) of the U.S. Provisional Application No. 62/521,776 filed Jun. 19, 2017; U.S. Provisional Application No. 62/521,785 filed Jun. 19, 2017; U.S. Provisional Application No. 62/541,129 filed Aug. 4, 2017; and U.S. Provisional Application No. 62/662,457 filed Apr. 25, 2018, the contents of each of which are incorporated herein by reference in their entireties.

GOVERNMENT SUPPORT

This invention was made with Government support under Grant numbers K22AI114810, DP2AT009499, and R01AI130019 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jul. 24, 2018, is named 002806-089891WOPT_SL.txt and is 6,499 bytes in size.

FIELD OF THE INVENTION

The field of the invention relates to methods for treating and/or preventing microbial infections.

BACKGROUND

Severe microbial infections, particularly by antibiotic resistant bacterial pathogens, can pose potentially lethal health complications as well as inflict significant morbidity and suffering on a patient. Acute bacterial pneumonia, meningitis, and sepsis, for example, are leading causes of death in hospital acquired infections. Current treatment methods to combat microbial infections include treatment with antibiotics and antimicrobial agents. However, the bacterial pathogens often develop resistance to common drugs and in some instances, the antibiotics do not effectively reach infected tissue areas, thus allowing rapid spread of the infection. In other instances, highly invasive skin and soft tissue infections such as necrotizing fasciitis are difficult to treat, with high incidences of mortality, and surgical exploration and removal of dead tissue is often critical to stopping the spread of severe infections, sometimes culminating in amputation. Chronic infections, such as diabetic foot ulcers, are also difficult to treat. As microbes evolve new ways to evade our treatment methods, we must counter this by developing new treatment modalities for the most serious cases of infection.

SUMMARY

It is increasingly clear that the nervous system plays an important role in regulating bacterial host defenses. Work described herein shows that neurons release neuropeptides that act on immune cells to suppress cytokine production and bacterial killing. As described herein, one of the ways by which this occurs is that neurons release neuropeptides that silence the recruitment of immune cells, e.g., neutrophils, and their bactericidal activity during infection. Exemplary neurons that perform such function include TRPV1 expressing nociceptor neurons. An exemplary mechanism by which these neurons silence immune cells is through their release of the neuropeptide Calcitonin gene-related peptide (CGRP). CGRP binds to its receptor complex, RAMP1/CALCRL, which is expressed by immune cells. As demonstrated herein CGRP and its receptor signaling modifies the ability of immune cells to effectively combat bacterial pathogens, including antibiotic-resistant bacterial pathogens. Therefore, targeting neuronal CGRP activity, release, and subsequent signaling to immune cells could be utilized to treat infections.

The methods and compositions described herein are based, in part, on the discovery that 1) Blockade of neuronal release of CGRP using Botulinum neurotoxin A (BoNT/A), 2) Denervation of these neurons using resiniferatoxin (RTX), or 3) Pharmacological blockade of CGRP receptor signaling are effective in treating and/or preventing microbial infections. Accordingly, one aspect of the invention described herein provides a method for treating a microbial infection in a subject, the method comprising; administering to a subject in need thereof an agent that inhibits Calcitonin gene-related peptide (CGRP) activity, CGRP release, and/or CGRP receptor signaling in an amount and for a duration sufficient to treat a microbial infection.

Another aspect of the invention described herein provides a method for preventing a microbial infection in a subject, the method comprising; administering to a subject at risk of a microbial infection an agent that inhibits CGRP activity, CGRP release, and/or CGRP receptor signaling in an amount and for a duration sufficient to prevent a microbial infection.

In one embodiment of any aspect, the agent is a botulinum neurotoxin. A botulinum neurotoxin can include, but is not limited to, botulinum neurotoxin serotype A, botulinum neurotoxin serotype B, botulinum neurotoxin serotype C, botulinum neurotoxin serotype D, botulinum neurotoxin serotype E, botulinum neurotoxin serotype F, and botulinum neurotoxin serotype G.

In one embodiment of any aspect, the agent is an inhibitor of Transient Receptor Potential Vanilloid 1 (TRPV1) expressing neurons.

In one embodiment of any aspect, the agent that inhibits the TRPV1 expressing neurons is Resiniferatoxin (RTX).

In one embodiment of any aspect, the agent comprises a competitive inhibitor of CGRP.

In one embodiment of any aspect, the agent comprises an antagonist of CGRP receptors and their signaling.

In one embodiment of any aspect, the agent comprises an anti-CGRP antibody or antibody reagent. Exemplary anti-CGRP antibodies include, but are not limited to, ALD403, LY2951742, AMG 334, and TEV-48125.

In one embodiment of any aspect, the agent is a compound that inhibits CGRP activity, release, or receptor signaling.

In one embodiment of any aspect, the agent inhibits the expression of CGRP. In one embodiment of any aspect, the agent inhibits the expression of CGRP at least 10%, at least 20%, at least 30%, at least 40%, at least 50%, at least 60%, at least 70%, at least 80%, at least 90%, or more as compared to an appropriate control.

In one embodiment of any aspect, the agent inhibits with the function of CGRP. In one embodiment of any aspect, the agent inhibits the function of CGRP at least 10%, at least 20%, at least 30%, at least 40%, at least 50%, at least 60%, at least 70%, at least 80%, at least 90%, or more as compared to an appropriate control.

In one embodiment of any aspect, the agent comprises a small molecule that inhibits CGRP. Exemplary small molecules that inhibit CGRP include olcegepant, obrogepant, tacagepant, Avitriptan, eletriptan, naratriptan, rizatriptan, sumatriptan, zolmitriptan, galcanezumab, eptinezumab, erenumab, fremanezumab, (piperidin-1-yl)piperidin-1-yl)propan-2-yl)piperidine-1-carboxamide (BMS 694153), atogepant, and MK-3207.

In one embodiment of any aspect, the agent inhibits a CGRP receptor. In one embodiment of any aspect, the CGRP receptor is RAMP1/CALCRL.

In one embodiment of any aspect, the agent comprises a nucleic acid that encodes an inhibitor of CGRP.

In one embodiment of any aspect, the agent comprises a polypeptide that inhibits CGRP. In one embodiment, the polypeptide comprises $CGRP_{8-37}$ peptide.

In one embodiment of any aspect, the agent comprises siRNA that inhibits CGRP activity, release, or receptor signaling.

In one embodiment of any aspect, the agent comprises shRNA that inhibits CGRP activity, release, or receptor signaling.

In one embodiment of any aspect, the agent comprises miRNA that inhibits CGRP activity, release, or receptor signaling.

In one embodiment of any aspect, the microbial infection comprises a bacterium which is resistant to at least one antibiotic.

In one embodiment of any aspect, the microbial infection comprises a bacterium which is resistant to at least two antibiotics.

In one embodiment of any aspect, the microbial infection comprises a gram-positive bacterial infection.

In one embodiment of any aspect, the microbial infection comprises a *Streptococcus* infection.

In one embodiment of any aspect, the *Streptococcus* infection comprises Group A *Streptococcus*.

In one embodiment of any aspect, the *Streptococcus* infection comprises Group B *Streptococcus*.

In one embodiment of any aspect, the *Streptococcus* infection comprises *Streptococcus pneumoniae*.

In one embodiment of any aspect, the *Streptococcus* infection comprises *Streptococcus pyogenes*.

In one embodiment of any aspect, the microbial infection comprises a *Staphylococcus* infection.

In one embodiment of any aspect, the *Staphylococcus* infection comprises *Staphylococcus aureus*. In one embodiment of any aspect, *Staphylococcus aureus* is methicillin resistant *Staphylococcus aureus*.

In one embodiment of any aspect, the microbial infection is selected from the group consisting of: a *Corynebacterium* infection, a *Listeria* infection, a *Clostridium* infection, a *Pseudomonas aeruginosa* infection, an *Escherichia coli* infection, a *Klebsiella* infection, an *Aeromonas* infection, and a *Neisseria* infection.

In one embodiment of any aspect, the microbial infection is a skin, soft tissue, or subcutaneous infection. Exemplary skin, soft tissue, or subcutaneous infections include impetigo, bullous impetigo, scalded skin syndrome, folliculitis, furuncles, carbuncles, cellulitis, myositis, necrotizing fasciitis, streptococcal toxic shock, toxic shock syndrome, acne, and gangrene.

In one embodiment of any aspect, the microbial infection is a respiratory tract or lung infection.

Exemplary respiratory tract or lung infections include scarlet fever, bacterial respiratory tract infection, pneumonia, lethal pneumonia, acute lung injury, acute respiratory distress syndrome, bacterial sepsis, endotoxin shock, and bacterial meningitis, acute rhinosinusitis, acute bacterial rhinosinusitis, pharyngitis, bacterial tracheitis, and bronchitis.

In one embodiment of any aspect, the microbial infection is a systemic infection. In one embodiment, the systemic infection is bacterial sepsis or endotoxin shock.

In one embodiment of any aspect, the microbial infection is meningitis.

In one embodiment of any aspect, the microbial infection is encephalitis.

In one embodiment of any aspect, the microbial infection is scarlet fever.

In one embodiment of any aspect, the microbial infection is a urinary tract infection.

In one embodiment of any aspect, the microbial infection is a sexually transmitted disease.

In one embodiment of any aspect, the microbial infection comprises a fungal infection.

In one embodiment of any aspect, the subject further has a burn. In one embodiment, the burn comprises a microbial infection.

In one embodiment of any aspect, the microbial infection is acute or chronic.

In one embodiment of any aspect, the method further comprises administering to a subject a second therapeutic agent. Exemplary second therapeutic agent include an antibiotic, antifungal, or antimicrobial agent.

In one embodiment of any aspect, the subject has previously been diagnosed with having an infection.

In one embodiment of any aspect, the method further comprises, prior to administering, diagnosing a subject with a microbial infection.

One aspect of the invention described herein provides a method for treating a microbial infection in a subject, the method comprising; administering to a subject at risk of a microbial infection a botulinum neurotoxin in an amount and for a duration sufficient to treat a microbial infection.

Another aspect of the invention described herein provides a method for preventing a microbial infection in a subject, the method comprising; administering to a subject at risk of a microbial infection a botulinum neurotoxin in an amount and for a duration sufficient to prevent a microbial infection.

Another aspect of the invention described herein provides a method for treating a *Staphylococcus aureus* infection in a subject, the method comprising; administering to a subject in need thereof an agent that inhibits nociception in an amount and for a duration sufficient to treat a microbial infection.

In one embodiment of any aspect, the agent inhibits Transient receptor potential vanilloid 1 (TRPV1).

In one embodiment of any aspect, the agent that inhibits or denervates TRPV1-expressing neurons is Resiniferatoxin (RTX).

In one embodiment of any aspect, the *Staphylococcus aureus* is methicillin resistant *Staphylococcus aureus*.

In one embodiment of any aspect, the *Staphylococcus aureus* is resistant to at least 2 antibiotics.

In one embodiment of any aspect, the *Staphylococcus aureus* infection is a skin, soft tissue, subcutaneous respiratory tract, and/or lung infection.

In one embodiment of any aspect, the *Staphylococcus aureus* infection is a systemic infection.

In one embodiment of any aspect, the method further comprises administering to a subject a second therapeutic agent.

In one embodiment of any aspect, the subject has previously been diagnosed with having a *Staphylococcus aureus* infection.

In one embodiment of any aspect, the method further comprises, prior to administering, diagnosing a subject with a *Staphylococcus aureus* infection.

Another aspect of the invention described herein provides a composition for treating a microbial infection in a subject, the composition comprising; an amount of a CGRP inhibitory agent sufficient to treat a microbial infection.

Yet another aspect of the invention described herein provides a composition for preventing a microbial infection in a subject, the composition comprising; an amount of a CGRP inhibitory agent sufficient to prevent a microbial infection.

In one embodiment of any aspect, the composition further comprises a pharmaceutically acceptable carrier.

In one embodiment of any aspect, the composition further comprises a second therapeutic agent.

Another aspect of the invention described herein provides a kit for treating a microbial infection in a subject, the kit comprising; an amount of an agent that inhibits CGRP activity, CGRP release, and/or CGRP receptor signaling sufficient to treat a microbial infection.

Yet another aspect of the invention described herein provides a kit for preventing a microbial infection in a subject, the kit comprising; an amount of an agent that inhibits CGRP activity, CGRP release, and/or CGRP receptor signaling sufficient to prevent a microbial infection.

In one embodiment of any aspect, the kit further comprises a second therapeutic agent.

Another aspect of the invention described herein provides a use for any of the compositions or kits described herein for the treatment of a microbial infection.

Yet another aspect of the invention described herein provides a use for any of the compositions or kits described herein for the prevention of a microbial infection.

Definitions

As used herein, an "infection" refers to an abnormal and/or undesired presence of bacteria and/or fungus in or on a subject. "Microbial infection" refers to an infection comprising bacteria and/or fungus. The presence can be abnormal in that the microbe is a noncommensal species, e.g. one not typically found in or on a healthy subject, it can be abnormal as in in a localization that the bacteria does not normally colonize (e.g., in the bladder, which has no known bacterial colonization), or it can be abnormal in that the microbe is present at abnormally high levels, e.g. at least twice the level found in or on a healthy subject (e.g. twice the level, three times the level, four times the level, five times the level, or greater), or it can be abnormal in that the presence of the microbe is causing or contributing to disease or symptoms thereof, e.g. necrosis, disfigurement, delayed wound healing, etc.

As used herein, a "subject" means a human or animal. Usually the animal is a vertebrate such as a primate, rodent, domestic animal or game animal. Primates include, for example, chimpanzees, cynomologous monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of infection e.g., *Staphylococcus aureus* infection. A subject can be male or female.

A subject can be one who has been previously diagnosed with or identified as suffering from or having a microbial infection in need of treatment (e.g., *S. aureus* infection) or one or more complications related to such an infection, and optionally, have already undergone treatment for the infection or the one or more complications related to the infection. Alternatively, a subject can also be one who has not been previously diagnosed as having such infection or related complications. For example, a subject can be one who exhibits one or more risk factors for the infection or one or more complications related to the infection or a subject who does not exhibit risk factors.

As used herein, an "agent" refers to e.g., a molecule, protein, peptide, antibody, or nucleic acid, that inhibits expression of a polypeptide or polynucleotide, or binds to, partially or totally blocks stimulation, decreases, prevents, delays activation, inactivates, desensitizes, or down regulates the activity of the polypeptide or the polynucleotide. Agents that inhibit CGRP, e.g., inhibit expression, e.g., translation, post-translational processing, stability, degradation, or nuclear or cytoplasmic localization of a polypeptide, or transcription, post transcriptional processing, stability or degradation of a polynucleotide or bind to, partially or totally block stimulation, DNA binding, transcription factor activity or enzymatic activity, decrease, prevent, delay activation, inactivate, desensitize, or down regulate the activity of a polypeptide or polynucleotide. An agent can act directly or indirectly.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property or can be selected from a library of diverse compounds.

The agent can be a molecule from one or more chemical classes, e.g., organic molecules, which may include organometallic molecules, inorganic molecules, genetic sequences, etc. Agents may also be fusion proteins from one or more proteins, chimeric proteins (for example domain switching or homologous recombination of functionally significant regions of related or different molecules), synthetic proteins or other protein variations including substitutions, deletions, insertion and other variants.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "RNAi" as used herein refers to interfering RNA or RNA interference. RNAi refers to a means of selective post-transcriptional gene silencing by destruction of specific mRNA by molecules that bind and inhibit the processing of mRNA, for example inhibit mRNA translation or result in mRNA degradation. As used herein, the term "RNAi" refers to any type of interfering RNA, including but are not limited to, siRNA, shRNA, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein).

Methods and compositions described herein require that the CGRP activity, release, or receptor signaling is inhibited. As used herein, calcitonin gene-related peptide "CGRP" refers to 37 amino acid peptide is produced in neurons that functions in pain neurotransmission and neurogenic inflammation. CGRP sequences are known for a number of species, e.g., human CGRP (NCBI Gene ID: 796) and mRNA (NCBI Ref Seq NM_001033952.2, and NCBI Ref Seq NP_001029124.1). CGRP can refer to human CGRP, including naturally occurring variants and alleles thereof. In some embodiments of any of the aspects, e.g., in veterinary applications, CGRP can refer to the CGRP of, e.g., dog, cat, cow, horse, pig, and the like. Homologs and/or orthologs of human CGRP are readily identified for such species by one of skill in the art, e.g., using the NCBI ortholog search function or searching available sequence data for a given species for sequence similar to a reference CGRP sequence. In one embodiment, CGRP is any known CGRP isoform, for example, Alpha-CGRP or Beta-CGRP.

As used herein, "inhibition of CGRP" refers to the inhibition of CGRP activity, CGRP release, or CGRP receptor signaling".

As used herein, "CGRP activity" refers to the function of CGRP, e.g., to suppresses the recruitment and bactericidal activity of neutrophils required to mount a host defense following the development of an infection, e.g., a microbial infection described herein. "CGRP activity" can be altered (e.g., decreased) by a decrease in CGRP mRNA or protein expression, and/or levels. CGRP is produced on both peripheral neurons, e.g., nociceptive neurons, and central neurons. Functional CGRP must be released from the nocireceptive neuron, e.g., from the nerve terminal. As used herein, "CGRP release" refers to the process of CGRP from nociceptive neurons upon identification of a harmful stimuli, e.g., a microbial infection, e.g., via calcium influx. "CGRP release" can be inhibited by directly or indirectly inhibiting the release process, e.g., inhibition of the nociceptor neuron (e.g., TRPV1), or upstream factors that regulate such nociceptor.

CGRP mediates its effects through a heteromeric receptor composed of a G protein-coupled receptor called calcitonin receptor-like receptor (CALCRL) and a receptor activity-modifying protein (RAMP1). As used herein, "CGRP receptor signaling" refers to the receptor/ligand binding and activation of downstream targets. Inhibition of "CGRP receptor signaling" can be achieved by inhibition, e.g., of CGRP binding to CALCRL, of CALCRL, or of RAMP1. Alternatively, inhibition of "CGRP receptor signaling" can be achieved direct inhibition of downstream factors which are activated by CGRP receptor signaling, or direct activation of downstream targets which are inhibited by CGRP receptor signaling.

The term "gene" used herein can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto. The term "gene product(s)" as used herein refers to include RNA transcribed from a gene, or a polypeptide encoded by a gene or translated from RNA.

The term "decrease", "reduced", "reduction", or "inhibit" are all used herein to mean a decrease by a statistically significant amount. In some embodiments, "decrease", "reduced", "reduction", or "inhibit" typically means a decrease by at least 10% as compared to an appropriate control (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to an appropriate control.

The terms "increase", "enhance", or "activate" are all used herein to mean an increase by a reproducible statistically significant amount. In some embodiments, the terms "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, a 20 fold increase, a 30 fold increase, a 40 fold increase, a 50 fold increase, a 6 fold increase, a 75 fold increase, a 100 fold increase, etc. or any increase between 2-fold and 10-fold or greater as compared to an appropriate control. In the context of a marker, an "increase" is a reproducible statistically significant increase in such level.

As used herein, an "appropriate control" refers to an untreated, otherwise identical cell or population (e.g., a patient who was not administered an agent described herein or was administered by only a subset of agents described herein, as compared to a non-control cell).

As used herein, "denervate" or "denervation" refers to a loss (e.g., complete) of nerve supply and a loss of physiological function of the nerve, for example, the release of CGRP. RTX-mediated denervation of TRVP1-expressing neurons results in the loss of, or inhibits, CGRP release from the TRVP1-expressing neurons.

The terms "inhibitor" and "antagonist" refers to an agent that inhibits expression of a polypeptide or polynucleotide, or binds to, partially or totally blocks stimulation, decreases, prevents, delays activation, inactivates, desensitizes, or down regulates the activity of the polypeptide or the polynucleotide. Inhibitors are agents that, e.g., inhibit expression, e.g., translation, post-translational processing, stability, degradation, or nuclear or cytoplasmic localization of a polypeptide, or transcription, post transcriptional processing, stability or degradation of a polynucleotide or bind to, partially or totally block stimulation, DNA binding, transcription factor activity or enzymatic activity, decrease, prevent, delay activation, inactivate, desensitize, or down regulate the activity of a polypeptide or polynucleotide. An inhibitor can act directly or indirectly. An inhibitor or antagonist of CGRP and/or CGRP receptors can target CGRP activity, CGRP binding to its receptor, the receptor activity, or downstream targets of CGRP signaling, for its inhibition. An inhibitor or antagonist of CGRP and/or CGRP receptors can target any combination of the said targets. An inhibitor or antagonist of CGRP and/or CGRP receptors can bind to and neutralize CGRP activity. An inhibitor or antagonist of CGRP and/or CGRP receptors can specifically target RAMP1/CALCRL for its inhibition. Inhibition is achieved when the activity value of a polypeptide or polynucleotide is about at least 10% less, at least 20% less, at least 30% less, at least 40% less, at least 50% less, at least 60% less, at least 70% less, at least 80% less, at least 90% less, or absent or undetectable in comparison to a reference or control level in the absence of the inhibitor.

The terms "significantly different than", "statistically significant," and similar phrases refer to comparisons between data or other measurements, wherein the differences between two compared individuals or groups are evidently or reasonably different to the trained observer, or statistically significant (if the phrase includes the term "statistically" or if there is some indication of statistical test, such as a p-value, or if the data, when analyzed, produce a statistical difference by standard statistical tests known in the art).

The term "effective amount" is used interchangeably with the terms "sufficient amount" and "therapeutically effective amount" and refers to the amount of at least one agent, e.g., an inhibitor of CGRP, at dosages and for periods of time necessary to achieve the desired therapeutic result, for example, to reduce or stop at least one symptom of a bacterial infection, for example a symptom of fever, in the subject. For example, an effective amount using the methods as disclosed herein would be considered as the amount sufficient to reduce a symptom of microbial infection by at least 10%, at least 20%, at least 30%, at least 40%, at least 50%, at least 60%, at least 70%, at least 90%, at least 99%, as measured by any standard technique. An effective amount as used herein would also include an amount sufficient to prevent or delay the development of a symptom of the disease, alter the course of a symptom disease (for example but not limited to, slow the progression of a symptom of the infection), or reverse a symptom of the infection. Accordingly, the term "effective amount" or "therapeutically effective amount" as used herein refers to the amount of therapeutic agent (e.g. at least one CGRP inhibitory agent as disclosed herein) of pharmaceutical composition to alleviate at least one symptom of a microbial infection. Stated another way, "therapeutically effective amount" of a CGRP inhibitory agent as disclosed herein is the amount of CGRP inhibitory agent which exerts a beneficial effect on, for example, the symptoms of microbial infection. The dosage administered, as single or multiple doses, to an individual will vary depending upon a variety of factors, including pharmacokinetic properties of the CGRP inhibitory agent, the route of administration, conditions and characteristics (sex, age, body weight, health, size) of subjects, extent of symptoms, concurrent treatments, frequency of treatment and the effect desired. A therapeutically effective amount is also one in which any toxic or detrimental effects of the CGRP inhibitory agent are outweighed by the therapeutically beneficial effects. The effective amount in each individual case can be determined empirically by a skilled artisan according to established methods in the art and without undue experimentation. In general, the phrases "therapeutically-effective" and "effective for the treatment, prevention, or inhibition", are intended to qualify the CGRP inhibitory agent as disclosed herein which will achieve the goal of reduction in the severity of at least one symptom of a microbial infection.

As used herein, the terms "treat," "treatment," "treating," or "amelioration" refer to therapeutic treatments, wherein the object is to reverse, alleviate, ameliorate, inhibit, slow down or stop the progression or severity of a condition associated with microbial infection. The term "treating" includes reducing or alleviating at least one adverse effect or symptom of a microbial infection. Treatment is generally "effective" if one or more symptoms or clinical markers are reduced. Alternatively, treatment is "effective" if the progression of a microbial infection is reduced or halted. That is, "treatment" includes not just the improvement of symptoms or markers, but can also include a cessation or at least slowing of progress or worsening of symptoms that would be expected in absence of treatment. Beneficial or desired clinical results include, but are not limited to, alleviation of one or more symptom(s) of an infection, diminishment of extent of an infection, stabilized (i.e., not worsening) state of an infection, delay or slowing of progression of an infection, amelioration or palliation of the infection, and remission (whether partial or total), whether detectable or undetectable. The term "treatment" of an infection also includes providing relief from the symptoms or side-effects of the infection (including palliative treatment).

As used herein, the terms "preventing" and "prevention" have their ordinary and customary meanings, and include one or more of: preventing an increase in the growth of a population of a microbe in a subject, or on a surface or on a porous material; preventing development of a disease caused by a microbe in a subject; and preventing symptoms of an infection or disease caused by a microbial infection in a subject. As used herein, the prevention lasts at least about 0.5 days, 1 day, 2 days, 3 days, 4 days, 5 days, 6 days, 7 days, 10 days, 12 days, 15 days, 20 days, 25 days, 30 days, 35 days, 40 days or more days after administration or application of the effective amount of the agent that inhibits CGRP, as described herein. In one embodiment, the prevention results in an at least 10%, at least 20%, at least 30%, at least 40%, at least 50%, at least 60%, at least 70%, at least 80%, at least 90%, at least 99%, or more, reduction in the presence, the severity of, and/or the risk of having an infection as compared to an appropriate control. Used herein, an appropriate control refers to a subject not administered any of the agents described herein.

The "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably.

The term "administered" is used interchangeably in the context of treatment of a disease or disorder. Both terms refer to a subject being treated with an effective dose of pharmaceutical composition comprising, e.g., at least an CGRP inhibitory agent of the invention, by methods of administration, for example subcutaneous or systemic administration.

The phrases "systemic administration," "administered systemically", "peripheral administration" and "administered peripherally" as used herein mean the administration of a pharmaceutical composition comprising at least an CGRP inhibitory agent as disclosed herein such that it enters the subject's system and, thus, is subject to metabolism and other like processes, for example, subcutaneous administration.

The term "optional" or "optionally" means that the subsequent described event, circumstance or substituent may or may not occur, and that the description includes instances where the event or circumstance occurs and instances where it does not.

As used herein, the term "comprising" means that other elements can also be present in addition to the defined elements presented. The use of "comprising" indicates inclusion rather than limitation. The term "consisting of" refers to compositions, methods, and respective components thereof as described herein, which are exclusive of any element not recited in that description of the embodiment. The term permits the presence of elements that do not materially affect the basic and novel or functional characteristic(s) of that embodiment of the invention.

The term "statistically significant" or "significantly" refers to statistical significance and generally means a two standard deviation (2SD) or greater difference.

As used herein the term "comprising" or "comprises" is used in reference to compositions, methods, and respective component(s) thereof, that are essential to the method or composition, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

BRIEF DESCRIPTION OF THE DRAWINGS

(FIGS. 1A and 2B) Mice ablated of nociceptive neurons show significantly improved survival (FIG. 1A) and clearance of bacteria following infection (FIG. 1B) compared to unablated mice. (FIGS. 1C and 1D) Staining for CGRP in nodose ganglion and dorsal root ganglia (DRG) shows significant loss of CGRP in mice treated with Diptheria toxin (DT).

FIGS. 2A-2C demonstrate that Resiniferatoxin (RTX) treatment to ablate TRPV1+CGRP+ neurons improves outcome of MRSA lung infections and lethal pneumonia. RTX is a high-affinity TRPV1 agonist, and its injections leads to denervation and loss of nociceptor neurons expression CGRP. (FIGS. 2A and 2B) RTX treated mice show significantly improved survival and clearance of bacteria than vehicle treated mice. (FIG. 2C) RTX treated mice show significant loss of CGRP+ nociceptive neurons in the dorsal root ganglia (DRG) and nodose ganglia.

FIGS. 6A and 6B 6 show that lung CGRP levels increase upon bacterial infection. Mice were intratracheally infected with $S.\ aureus$ in the lung to produce pneumonia. Bronchiolar lavage fluid (BAL) was collected at 12 hr timepoint and analyzed for CGRP levels. There is significant induction of CGRP release by infection (FIG. 6A), and this was significantly reduced by RTX mediated ablation of sensory neurons (FIG. 6B).

Figure 7B:
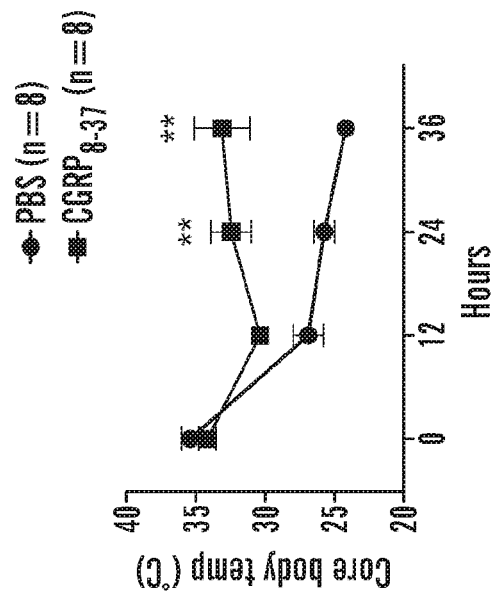
FIGS. 7A and 7B show that CGRP receptor antagonist treatment improves outcome of bacterial lung infection and lethal pneumonia. The CGRP receptor antagonist CGRP8-
Figure 7A:
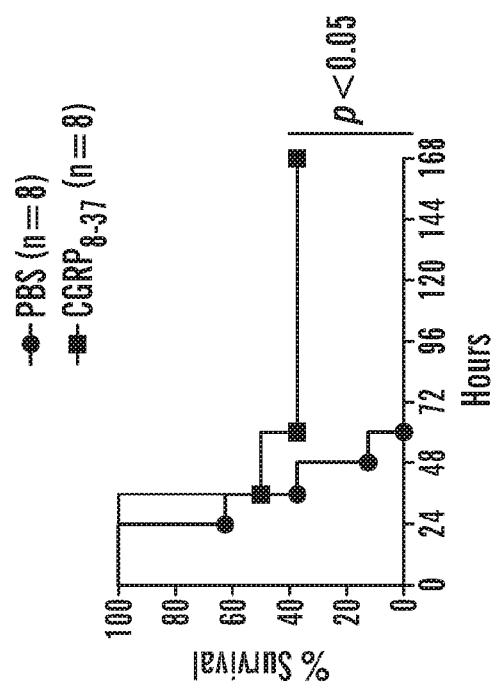

37 was injected into mice intraperitoneally 12 hours prior to infection and 12 hours after intratracheal infection with methicillin-resistant *S. aureus* (107 CFU). There was significantly improved survival (FIG. 7A) and maintenance of core-body temperature (FIG. 7B) in CGRP receptor antagonist CGRP8-37 treated compared to vehicle treated mice.

Figures 8, 9:
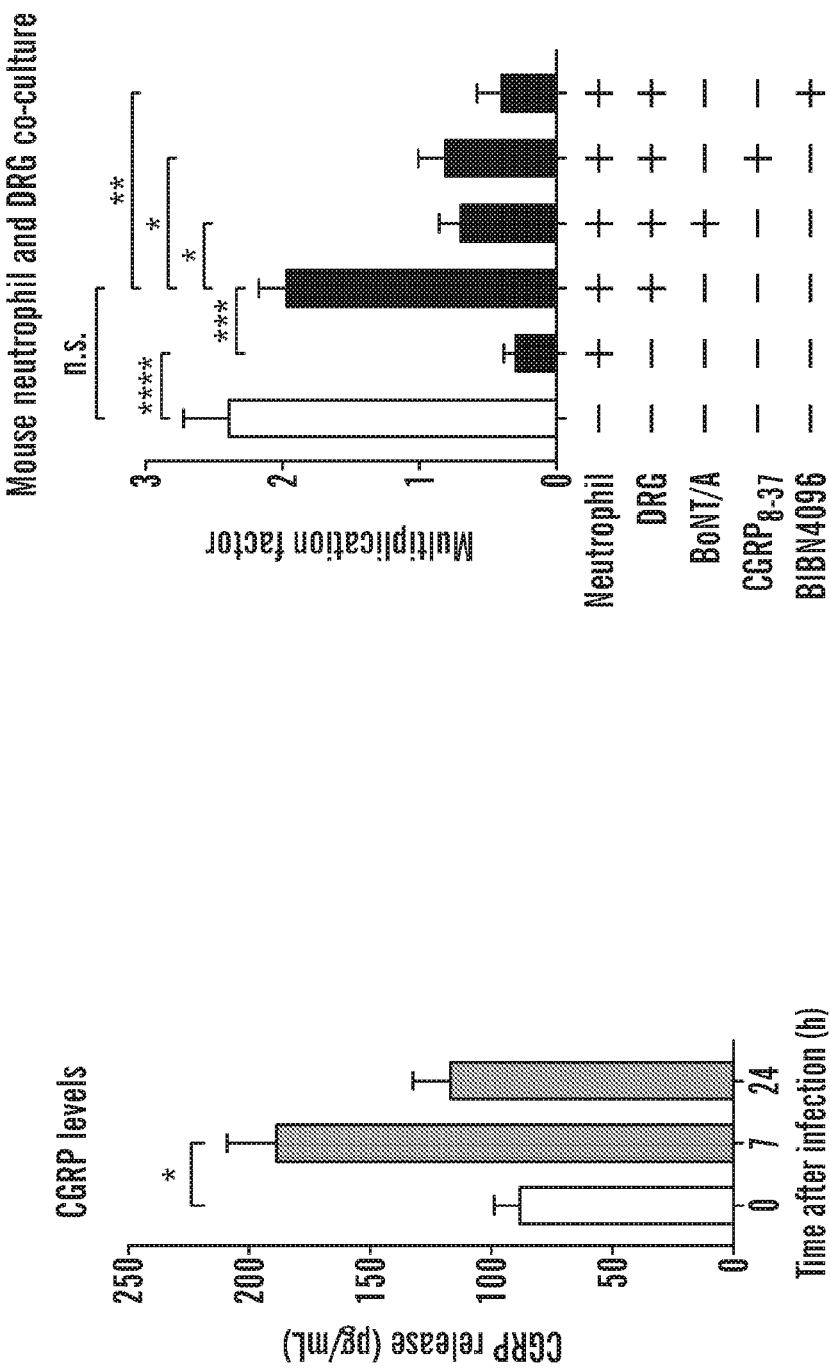

FIG. 8 demonstrates that CGRP increases in *S. pyogenes* skin infection. CGRP levels were measured in flank skin at different timepoints following infection by *S. pyogenes* M1T1 strain (107 CFU).

FIG. 9 shows that blockade of CGRP and its receptor signaling through CGRP8-37 or BIBN4096 enhances *S. pyogenes* killing that was inhibited by nociceptive neurons. Mouse nociceptive neurons were co-cultured with *S. pyogenes*, and in combination with mouse neutrophils, BoNT/A to inhibit CGRP release, CGRP8-37 to antagonize CGRP signaling, or BIBN4096 to antagonize CGRP signaling. Both CGRP8-37 and BIBN4096 enhances neutrophil killing of bacteria which were suppressed by neurons. **P<0.0001; *, P<0.001; **P<0.01; *P<0.05 by t-test.

Figure 10:
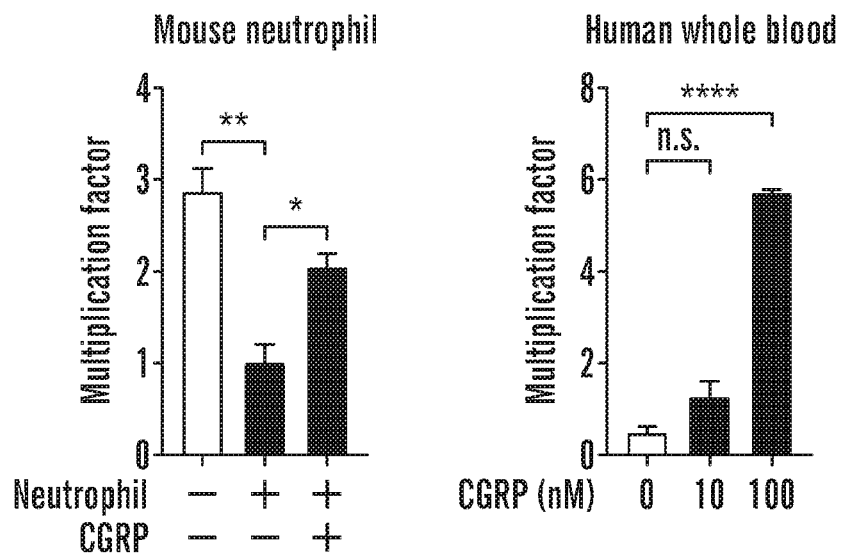

FIG. 10 shows that CGRP inhibits human whole blood and mouse neutrophil killing of *S. pyogenes*. In the left panel, *S. pyogenes* was co-cultured in the presence of complement and neutrophils, or complement and neutrophils and 100 nM CGRP. The presence of CGRP inhibits killing of bacteria, measured by multiplication factor 2 hours post-infection. In the right panel, the Lancefield assay was used, where human whole blood was co-cultured with *S. pyogenes* in the presence of different concentrations of CGRP. Increasing CGRP inhibits killing of the bacteria, as indicated by multiplication factor.

Figure 11:
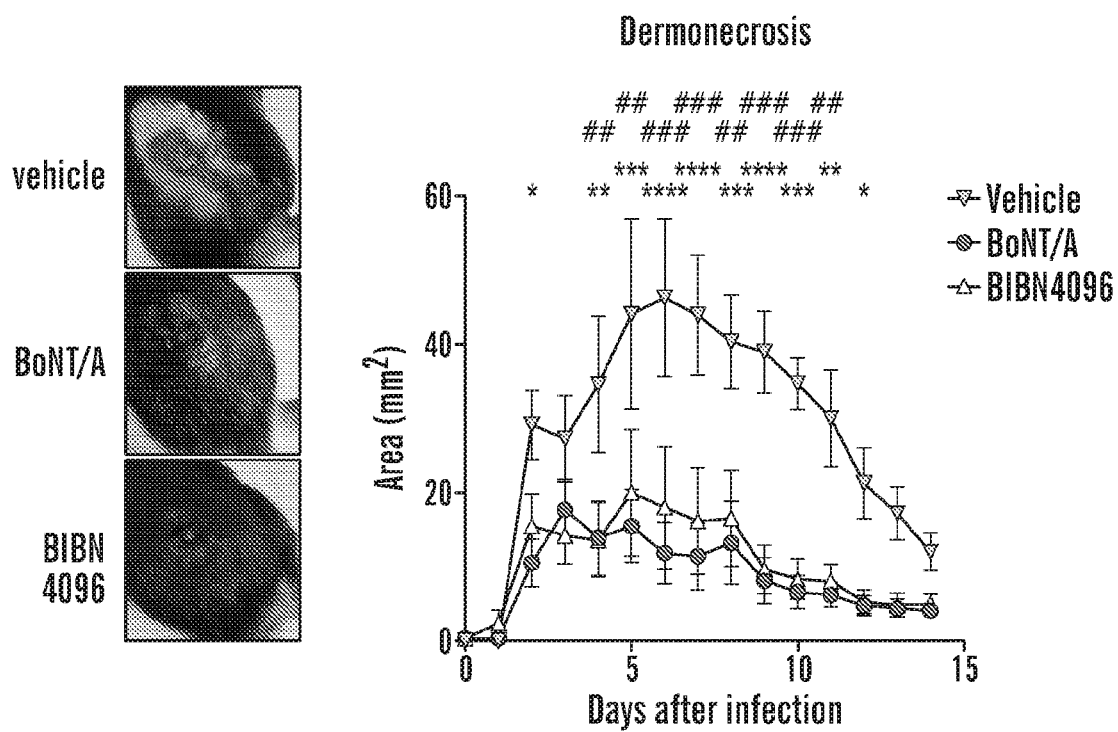

FIG. 11 demonstrates that BoNT/A, which inhibits CGRP release, and BIBN4096, which antagonizes CGRP and its receptor signaling can treat *S. pyogenes* necrotizing infections. *S. pyogenes* was infected into the flank skin of mice, and BoNT/A injected intradermally or BIBN4096 injected intraperitoneally at 2 hours post-infection. The progression of dermonecrotic lesion was quantified by micrometer. There is significantly smaller lesion formation in mice treated with BoNT/A or BIBN4096. BoNT/A vs. untreated (*P<0.5; P<0.01; *P<0.001; ****P<0.0001), BIBN4096 vs. untreated (#P<0.05; ##P<0.01; ###P<0.001; ####P<0.0001), Two-way ANOVA with Bonferroni Post-tests.

FIGS. 12A-12E show *S. pyogenes* induces pain associated behaviors and directly activates sensory neurons. (FIG. 12A) Representative images of mouse hind paws at different time points after subcutaneous injection of *S. pyogenes* M1 or M3 strains ($5 \times 10^7$ cfu). (FIG. 12B) Histopathology of skin and soft tissue biopsies 72 h after injection of vehicle, M1 or M3 ($5 \times 10^7$ cfu). Scale bars, 100 μm. (FIG. 12C) Spontaneous pain reflexes (lifting/licking of hind paw) over 1 h after injection of different inoculums of M1 (n=4/group) or M3 (n=9-11/group). (FIG. 12D) Mechanical sensitivity after injection of vehicle, *S. pyogenes* M1 (n=8-9/group) or M3 (n=7-10/group). (FIG. 12E) Representative Fura-2 ratiometric fields (Left) and calcium traces (Center) of DRG neurons at baseline and after stimulation in vitro with live *S. pyogenes* M3 ($5 \times 10^9$ cfu/mL), capsaicin (1 μm), and KCl (40 mM). Scale bars, 50 μm. Proportions (Right) of capsaicin non-responsive (Cap−) and capsaicin responsive (Cap+) neurons that responded to M3 (n=3-4 fields/condition). Statistical analysis: (FIG. 12C) One-way ANOVA, Tukey post-tests. (FIG. 12D) Two-way ANOVA, Bonferroni post-tests. (FIG. 12E) Two-way ANOVA, Bonferroni post-tests. (FIGS. 12C and 12E) *p<0.05 p<0.01 *p<0.001 **p<0.0001. (FIG. 12D) veh vs $5 \times 10^7$ cfu: *p<0.001 ****p<0.0001, veh vs $5 \times 10^6$ cfu: †p<0.05 ††p<0.01 †††p<0.001 ††††p<0.0001, veh vs $5 \times 10^5$ cfu: §§ p<0.01 §§§§ p<0.0001. ns=not significant. Mean±SEM.

FIGS. 13A-13E show *S. pyogenes* induces neuronal activation and CGRP release through SLS. (FIG. 13A) Representative Fura-2 ratiometric fields (left) and calcium traces (center) of DRG neurons responding to filtered supernatant from *S. pyogenes* M1 ($5 \times 10^9$ cfu/mL), capsaicin (1 μm), and KCl (40 mM). Proportions (Right) of capsaicin non-responsive (Cap−) and capsaicin responsive (Cap+) neurons that responded to M1 supernatant (n=3-4 fields/condition). (FIG. 13B-13D) Representative Fura-2 ratiometric fields (FIG. 13B) and calcium traces (FIG. 13C) of DRG neurons stimulated with filtered supernatant from *S. pyogenes* M1 (wt) or isogenic mutants lacking SLS (ΔsagA), both SLO and SLS (ΔsloΔsagA), or double mutant bacteria in which sagA expression was restored (ΔsloΔsagA+pDL:sagA). (FIG. 13D) Proportions of responding DRG neurons to bacterial supernatant from *S. pyogenes* M1 (wt) or isogenic mutant strains (n=3 fields/condition). (FIG. 13E) DRG neurons stimulated for 30 min with supernatant from *S. pyogenes* M1 (wt), isogenic mutants, or medium, analyzed for in vitro release of CGRP (n=5 samples/group). Statistical analysis: (FIG. 13A) Two-way ANOVA, Bonferroni post-tests. (FIGS. 13D and 13E) One-way ANOVA, Tukey post-tests. *p<0.05 *p<0.001 **p<0.0001. ns=not significant. Scale bars, 50 μm. Mean±SEM.

FIGS. 14A-14F show SLS is necessary for pain during *S. pyogenes* infection. (FIGS. 14A and 14B) Spontaneous lifting/licking pain over 1 h after injection of vehicle, *S. pyogenes* M1 or M3 ($5 \times 10^8$ cfu) wt, ΔsagA, Δslo, or ΔsloΔsagA strains (M1, n=8/group; M3, n=12/group). (FIGS. 14C and 14D) Mechanical (n=10/group) and heat (n=9-10/group) sensitivity after injection of *S. pyogenes* M3 wt or isogenic mutants ($5 \times 10^7$ cfu). (FIG. 14E) Spontaneous pain over 1 h in mice injected with *S. pyogenes* M1 ($5 \times 10^8$ cfu) and treated with anti-SLS or control IgG (n=4-5/group). (FIG. 14F) Spontaneous pain over 1 h after injection of *S. pyogenes* M1 ($5 \times 10^8$ cfu) wt or isogenic mutants complemented with plasmid encoding sagA (pDL:sagA) or empty plasmid (pDL278) (n=8/group). Statistical analysis: (FIGS. 14A, 14B, 14E, and 14F) One-way ANOVA, Tukey post-tests, p<0.01 *p<0.001 ****p<0.0001; (FIGS. 14C and 14D) Two-way ANOVA, Bonferroni post-tests, ΔsagA vs wt *p<0.05 *p<0.001 **p<0.0001, ΔsloΔsagA vs wt ††††p<0.0001. ns=not significant. nd=not detected. Mean±SEM.

FIGS. 15A-15H show TRPV1 neurons that mediate pain inhibit host defenses against *S. pyogenes* infection. (FIG. 15A) Heat sensitivity measured in Trpv1-Cre/Dta mice and control littermates after *S. pyogenes* M1 injection ($5 \times 10^7$ cfu, n=7-8/group). (FIG. 15B) Mechanical sensitivity of ipsilateral (ipsi) and contralateral (contra) hind paws after *S. pyogenes* M1 injection ($5 \times 10^7$ cfu) in Trpv1-Cre/Dta and control littermates (n=5/group). (FIG. 15C) Heat sensitivity in RTX and vehicle-treated mice after *S. pyogenes* M1 injection ($5 \times 10^7$ cfu, n=5/group). (FIG. 15D) Mechanical sensitivity of ipsilateral and contralateral hind paws of RTX and vehicle-treated mice after *S. pyogenes* M1 injection ($5 \times 10^7$ cfu, n=5/group). (FIG. 15E-15H) *S. pyogenes* M1 ($5 \times 10^6$ cfu) was injected subcutaneously into the flank of mice: (FIG. 15E) Representative pictures of flank lesions, and (FIG. 15F) Quantification of dermonecrosis and weight loss at different time points after *S. pyogenes* M1 injection in Trpv1-Cre/Dta or control littermates (n=14-16/group). (FIG. 15G) Representative pictures of flank lesions, and (FIG. 15H) Quantification of dermonecrosis and weight loss after *S. pyogenes* M1 injection in RTX or vehicle-treated mice (n=15/group). Statistical analysis: (FIG. 15A-15H) two-way ANOVA, Bonferroni post-tests. *p<0.05 p<0.01 *p<0.001 **p<0.0001. (FIG. 15B) Trpv1-Cre/Dta (ipsi) vs Control (ipsi). (FIG. 15D**) RTX (ipsi) vs Veh (ipsi). Mean±SEM. See Figure S4 for related data.

FIGS. 16A-16H show nociceptors suppress recruitment of neutrophils that mediate host protection against *S. pyogenes* infection. (FIG. 16A) Histopathology of flank biopsies from vehicle or RTX-treated mice 3 days after injection of *S. pyogenes* M1 ($5 \times 10^6$ cfu). Scale bars, 50 µm. (FIG. 16B) Bacterial load recovery ($\log_{10}$ cfu) from flank lesions and spleens in RTX or vehicle-treated mice after *S. pyogenes* M1 injection ($5 \times 10^6$ cfu, n=4/group). (FIG. 16C-16E) Flow cytometry of leukocyte recruitment in necrotizing lesions 1 day after *S. pyogenes* M1 injection ($5 \times 10^6$ cfu): (FIG. 16C) Representative FACS plots showing neutrophils (CD11b$^+$ Ly6G$^+$ gates) in lesion samples. (FIG. 16D-16E) Quantification of immune cell populations by flow cytometry in flank biopsies from infected Trpv1-Cre/Dta mice or control littermates (n=4/group), or from uninfected mice, infected vehicle-treated mice, or infected RTX-treated mice (n=4-5/group). (FIG. 16F-16H) Measurement of CGRP release ex vivo from flank skin punch biopsies. (FIG. 16G) CGRP release from uninfected skin (0 h), 7 h, or 24 h after *S. pyogenes* M1 injection ($5 \times 10^6$ cfu) (n=3/group). (FIG. 16H) CGRP release from uninfected skin or 7 h after *S. pyogenes* M1 ($5 \times 10^6$ cfu) injection of Trpv1-Cre/Dta mice or control littermates, or Vehicle or RTX-treated mice (n=3/group). Statistical analysis: (FIGS. 16B, 16D, 16E, and 16H) Two-way ANOVA, Bonferroni post-tests. (FIG. 16G) One-way ANOVA, Tukey post-tests. *p<0.05 p<0.01 *p<0.001 **p<0.0001. ns=not significant. nd=none detected. Mean±SEM. See FIG. S5** for related data.

FIGS. 17A-17J show local vs. intrathecal BoNT/A injection dissociates pain perception from peripheral neuro-immune suppression. (FIG. 17A-17D) Subcutaneous administration of BoNT/A (25 pg/100 µL) or vehicle 6 days prior to *S. pyogenes* M1 injection in flank skin ($5 \times 10^6$ cfu). (FIG. 17B) Representative images of lesions (day 8), (FIG. 17C) Dermonecrosis size measurements, and (FIG. 17D) Weight loss over time after injection of *S. pyogenes* (n=5-10/group). (FIG. 17E-17H) Intrathecal administration of BoNT/A or vehicle 1 day prior to *S. pyogenes* M1 injection in flank skin ($5 \times 10^6$ cfu). (FIG. 17F) Representative images of lesions (day 8), (FIG. 17G) Dermonecrosis size measurements, and (FIG. 17H) Weight loss over time after injection of *S. pyogenes* (n=6/group). (FIG. 17I) DRG neurons exposed to BoNT/A (25 pg/200 µL) or medium for 24 h were stimulated with *S. pyogenes* supernatant ($5 \times 10^9$ cfu/mL) for 30 min, and CGRP was measured in neuronal supernatant (n=5/group). (FIG. 17J) CGRP release from skin punch biopsies of mice treated intrathecally or locally with BoNT/A, 7 h after *S. pyogenes* M1 ($5 \times 10^6$ cfu) injection (n=3/group). Statistical analysis: (FIGS. 17C, 17D, 17G, and 17H) Two-way ANOVA, Bonferroni post-tests. (FIGS. 17I and 17J) One-way ANOVA, Tukey post-tests. *p<0.05 p<0.01 *p<0.001 ****p<0.0001. ns=not significant. Mean±SEM. See Figure S6 for related data.

Figure 18A:
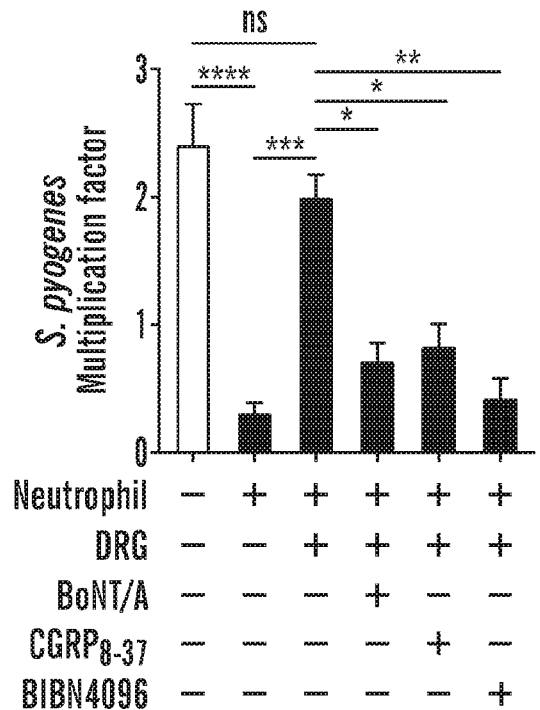
Figure 18B:
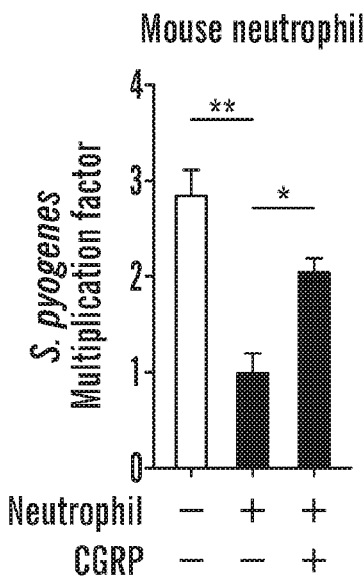
Figure 18C:
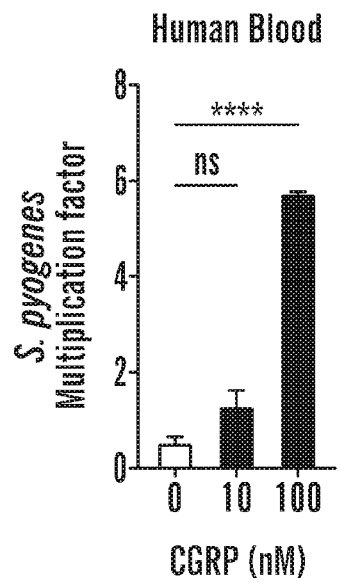
Figure 18D:
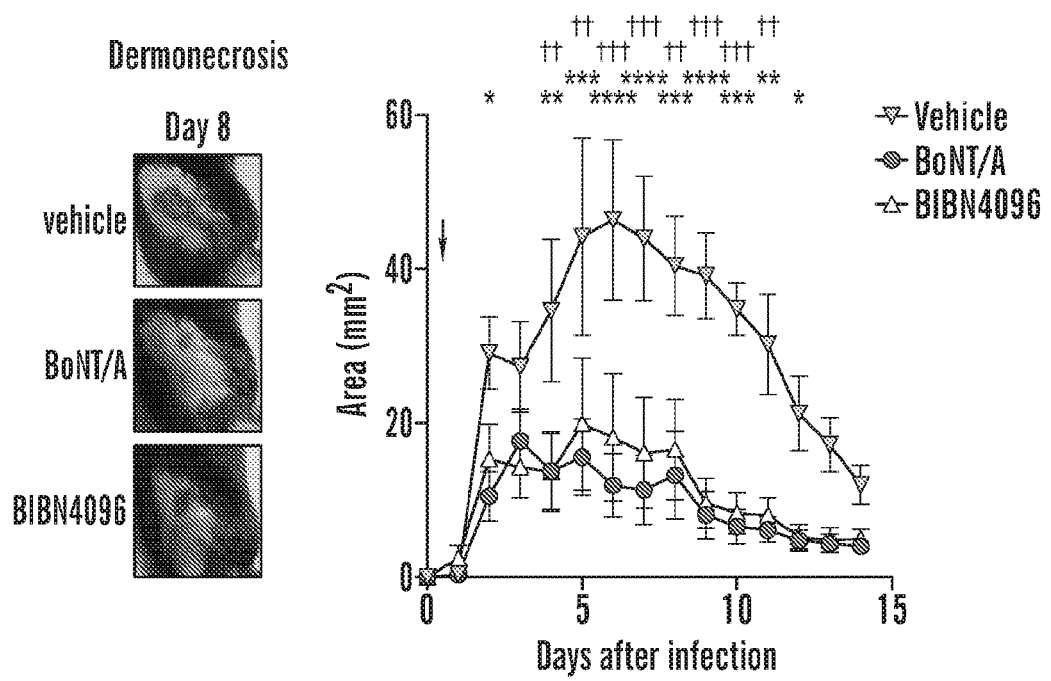
Figure 18E:
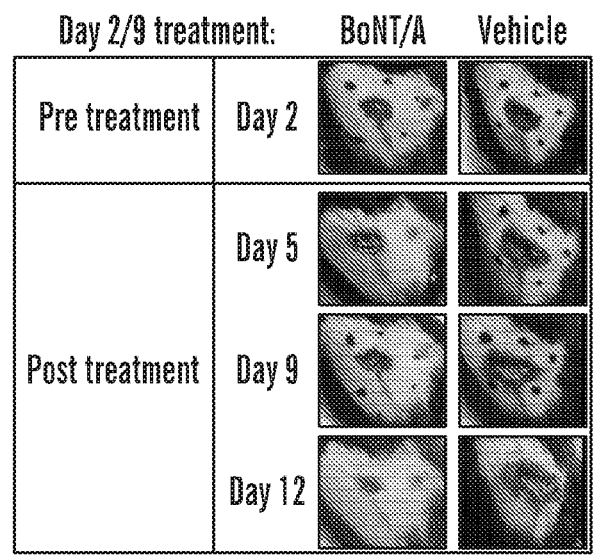

FIGS. 18A-18G show BoNT/A and CGRP antagonism block neural modulation of immunity to treat bacterial invasion. (FIG. 18A) DRG neurons were pretreated with BoNT/A for 24 h, or with CGRP antagonists (CGRP$_{8-37}$ or BIBN4096) immediately before co-incubation with mouse neutrophils and *S. pyogenes* M1 for 1 h. Bacterial survival was measured as the multiplication factor of surviving colonies/starting inoculum (n=3-4 replicates/group). (FIG. 18B) Mouse neutrophils were incubated with *S. pyogenes* M1 in presence of CGRP or vehicle for 1 h, and bacterial survival measured (n=4/group). (FIG. 18C) Human whole blood was incubated with *S. pyogenes* M1 in presence of CGRP or vehicle for 3 h, and bacterial survival measured (n=3/group). (FIG. 18D) Representative images of lesions at day 8 (left) and dermonecrosis size (right) of mice treated 2 h after *S. pyogenes* M1 injection ($5 \times 10^6$ cfu) with vehicle, BoNT/A, or BIBN4096 (n=6-7/group). (FIG. 18E-18G) Mice were treated subcutaneously with BoNT/A or vehicle at day 2 and day 9 following flank injection of *S. pyogenes* M1 ($5 \times 10^6$ cfu). Representative images show lesions before and after treatment (FIG. 18E). Dermonecrotic lesions (FIG. 18F) and abscess sizes (FIG. 18G) were measured over time (n=10/group). Dots show injection sites at day 2 and day 9. Arrows show BoNT/A treatments. Statistical analysis: (FIG. 18A-18C) One-way ANOVA, Tukey post-tests. (FIG. 18D-18G) Two-way ANOVA, Bonferroni post-tests. (FIGS. 18A-18C, and 18F-18G) *p<0.05 p<0.01 *p<0.01 **p<0.0001. (FIG. 18D**) BIBN4096 vs veh: *p<0.05 p<0.01 *p<0.001 ****p<0.0001, BoNT/A vs veh: †p<0.05 ††p<0.01 †††p<0.001 ††††p<0.0001. ns=not significant. Mean±SEM. See Figure S7 for related data.

FIGS. 19A-19G show *S. pyogenes* M1 and M3 infection induces pain and cutaneous nerve loss. (FIG. 19A) Weight changes over time in mice injected with $5 \times 10^7$ cfu of vehicle or M1 *S. pyogenes* (n=10 mice/group), and vehicle or M3 *S. pyogenes* (n=8-10 mice/group). (FIG. 19B) Kaplan-Meier survival curves for mice infected with $5 \times 10^5$-$5 \times 10^7$ cfu of M1 *S. pyogenes* (n=9-10 mice/group) or M3 *S. pyogenes* (n=14-16 mice/group). (FIG. 19C) Bacterial load recovery from cutaneous/subcutaneous tissue of paw samples collected at different time points after infection with *S. pyogenes* M1 ($5 \times 10^7$ cfu) determined by quantitative culture (Log cfu plotted, n=4 samples/time point). (FIG. 19D) Time course of lifting/licking behavior in mice following injection of *S. pyogenes* M3 ($5 \times 10^8$ cfu, n=8 mice) or vehicle (n=12 mice). (FIG. 19E) Spontaneous flinches quantified over 1 h time period after injection of vehicle or different doses ($5 \times 10^6$-$5 \times 10^7$ cfu) *S. pyogenes* M1 (n=4 mice/group) or *S. pyogenes* M3 (n=9-11 mice/group). (FIG. 19F) DRG neuron analysis following *S. pyogenes* infection. Mice were injected in the footpad with M1 *S. pyogenes* ($5 \times 10^7$ cfu). L4-L6 DRG were isolated at 48 h or 72 h post-injection to the infection site, or from naïve, uninfected mice and analyzed for proportions of TRPV1+ (green, top), CGRP+ (green, center), or NF200+ (green, bottom) cells out of total βIII-tubulin+ neurons (blue), with each data point used representing a single mouse, obtained as an average of at least three imaging fields per mouse. (Naïve: n=3 mice, 48 h: n=3 mice, 72 h: n=3). Scale bars, 100 µm. (FIG. 19G) Mice were injected with vehicle or with M1 *S. pyogenes*; skin tissues were isolated 72 h post-injection and stained for PGP9.5 (green), CGRP (red) or DAPI (blue). White dotted lines delineate skin border. Representative low and high magnification images of skin lesion center, bordering region, and a skin sample remote from the injection site are shown for *S. pyogenes* infected mice. High magnification images on right are of yellow inset areas in left images. Scale bars, 100 µm. Statistical analysis: (FIGS. 19A and 19D) Two-way ANOVA with Bonferroni post-tests (FIGS. 19C, 19E, and 19F) One-way ANOVA with Tukey post-tests. (FIGS. 19A, 19C, 19D, 19E, and 19F) *p<0.05, p<0.01, *p<0.001, ****p<0.0001. ns=not significant. Error bars, mean±SEM.

Figure 20A:
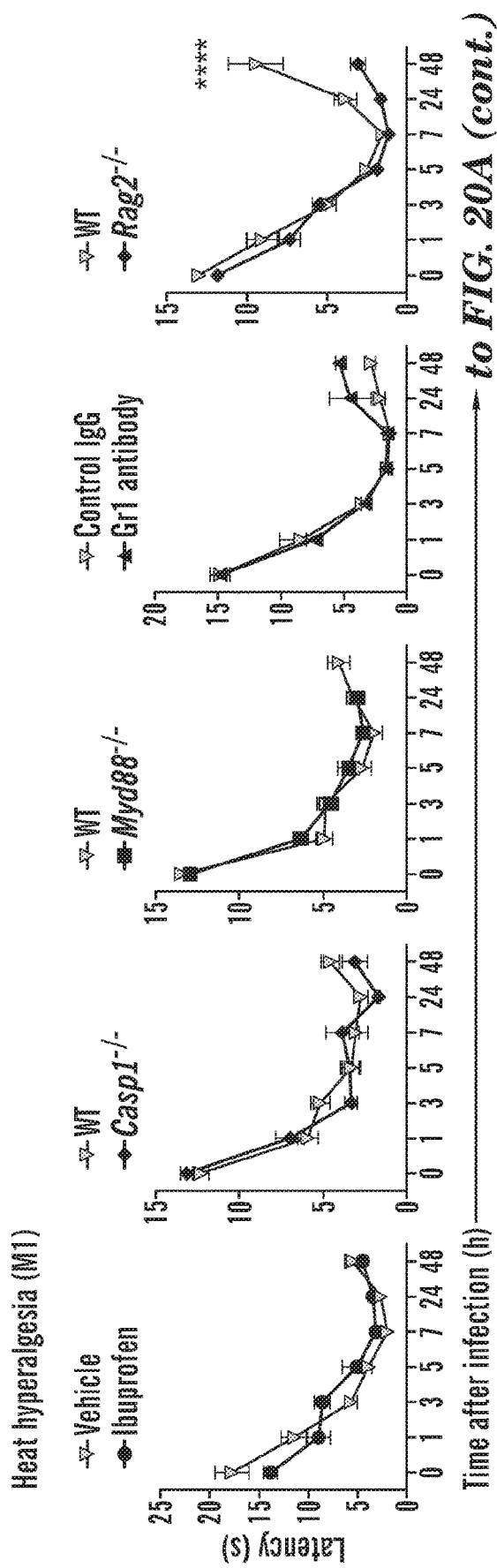
Figure 20A:
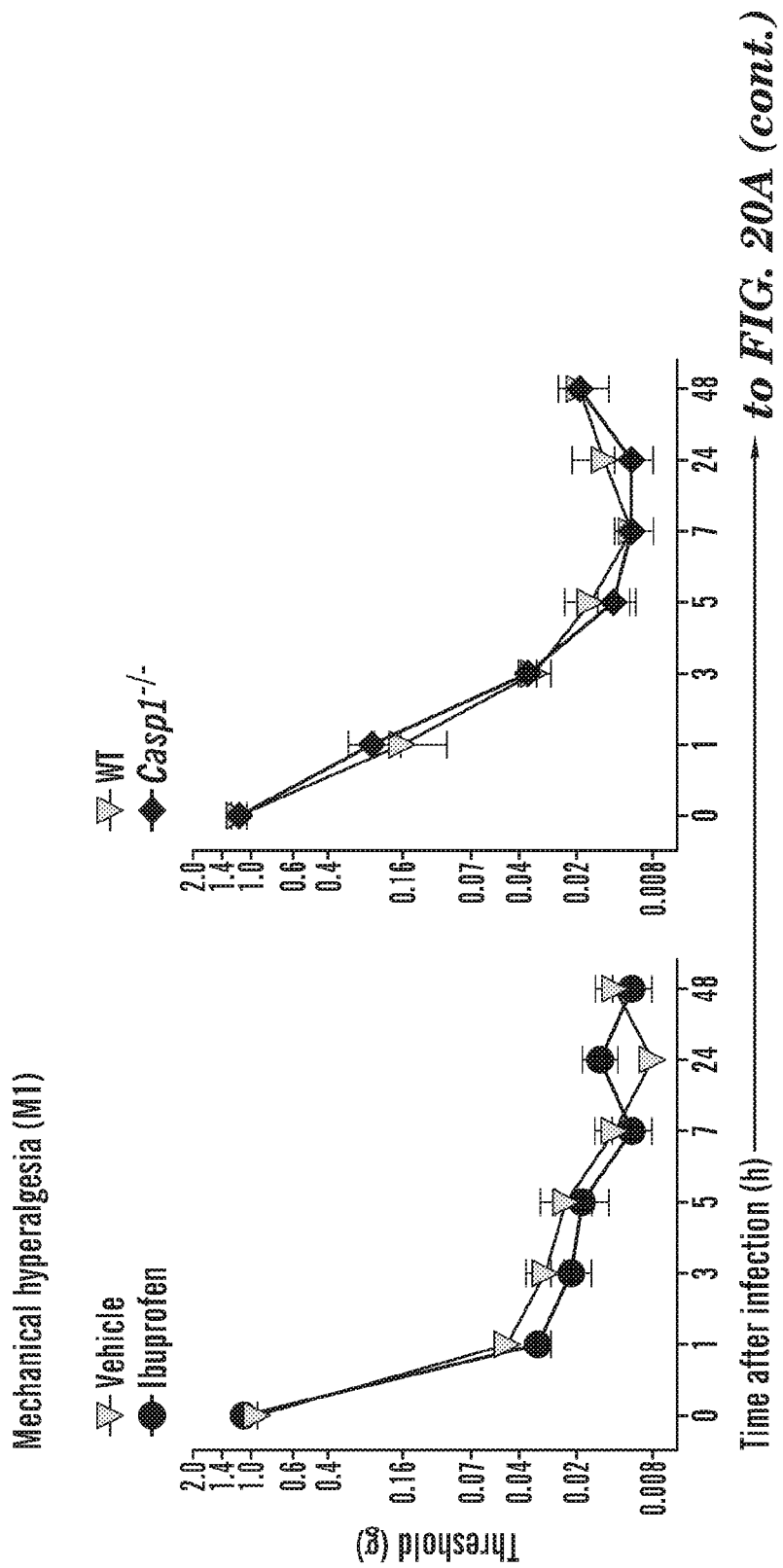
Figure 20A:
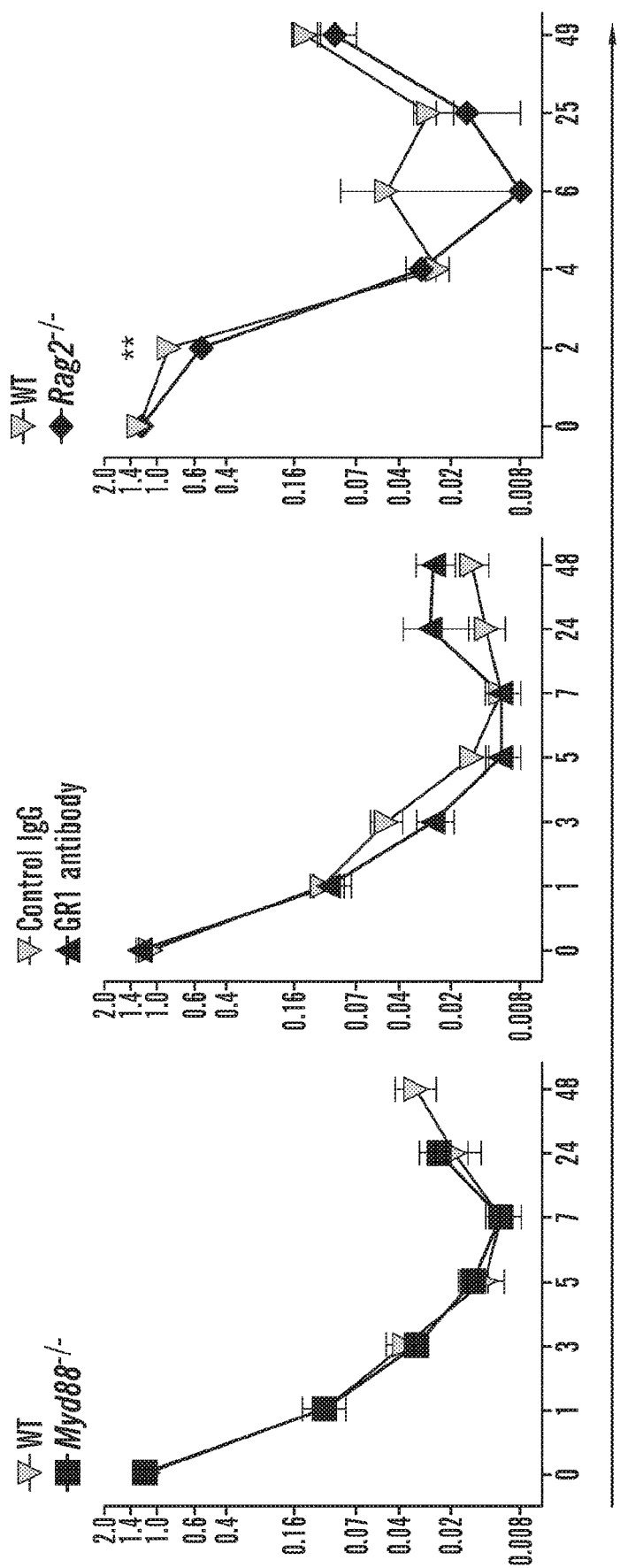
Figure 20B:
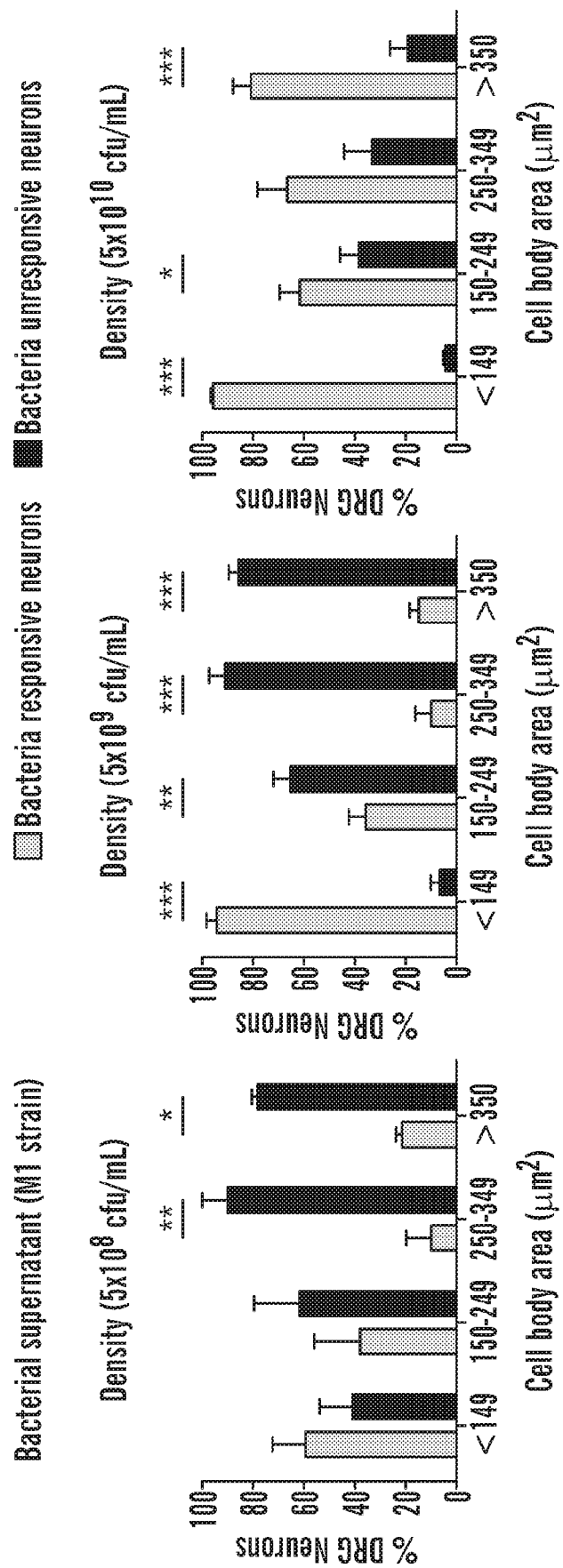
Figure 20D:
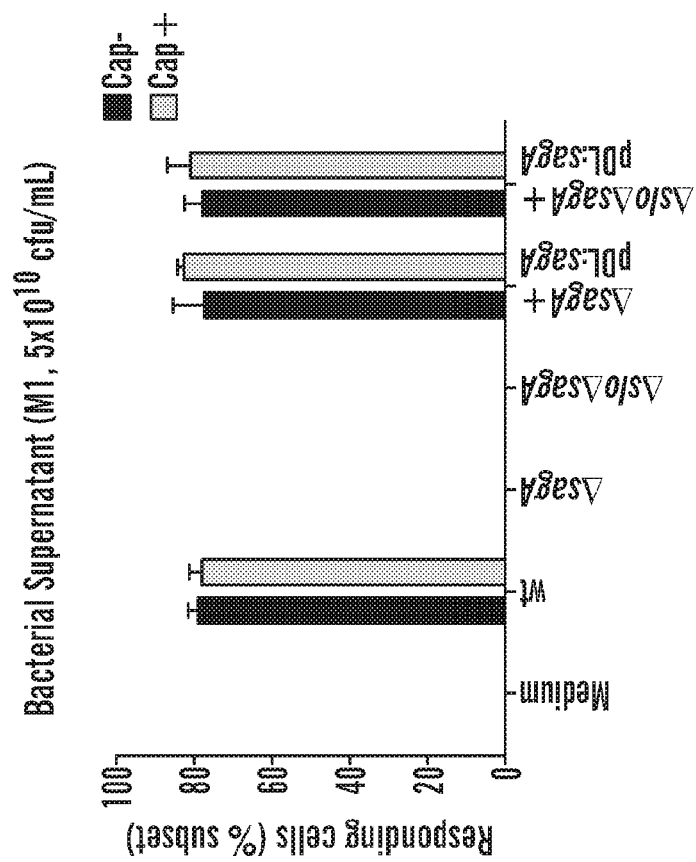

FIGS. 20A-20D show *S. pyogenes* directly activates neurons and induces hyperalgesia independently of inflammatory pathways. (FIG. 20A) Mice lacking inflammatory mediators or immune cells were compared to wild-type controls for induction of heat hyperalgesia (top row) and mechanical hyperalgesia (bottom row), as measured by the latency to response in the Hargreaves radiant heat test, at different time points after infection with *S. pyogenes* M1 ($5 \times 10^7$ cfu). Comparisons are, from left to right: 1) ibuprofen-treated mice (50 mg/kg) vs. vehicle-treated mice, 2) Casp1$^{-/-}$ mice (Caspase-1 deficient mice) vs. wt mice; 3) Myd88$^{-/-}$ mice (Myeloid differentiation factor 88-deficient mice) vs. wt mice, 4) Gr1 antibody-treated mice vs. Rat IgG-treated mice, and 5) Rag2$^{-/-}$ mice (Recombination activating gene 2-deficient mice) vs. wt mice (n=5-6 mice/genotype or treatment group). (FIG. 20B) *S. pyogenes* supernatant preferentially activates smaller size DRG neurons. DRG neurons were stimulated with supernatant from M1 *S. pyogenes* at three concentrations and imaged by Fura-2 calcium imaging. Cell size was determined by marking individual bacteria-responsive cells or bacteria-unresponsive cells from 3 separate neuronal fields/condition, and binning by cell body area. (FIG. 20C-20D) DRG neurons were stimulated with medium or filtered bacterial supernatant from M1 *S. pyogenes* strains grown in neurobasal medium (with BSA) at two different concentrations (FIG. 20C, $5 \times 10^9$ cfu/mL) or (FIG. 20D, $5 \times 10^{10}$ cfu/mL). Strains used included wt, isogenic mutants lacking SLS (ΔsagA), SLS and SLO (ΔsloΔsagA), or complemented with sagA (ΔsagA+pDL:sagA, ΔsloΔsagA+pDL:sagA). Data analyzed out of total DRG neurons responding to bacterial supernatant (left), or Cap+ or Cap− subsets responding to bacterial supernatant (right). Statistical analysis: (FIG. 20A) Two-way ANOVA with Bonferroni post-tests. (FIGS. 20B, 20C, and 20D) One-way ANOVA with Tukey post-tests, *p<0.05, p<0.01, *p<0.001, ****p<0.0001. ns=not significant. Mean±SEM.

FIGS. 21A-21E show anti-SLS blocks flinching pain and effects of SLS on other infection parameters. (FIG. 21A) Lactate dehydrogenase (LDH) release from DRG neurons after 20 minutes of stimulation with *S. pyogenes* M1 supernatant (n=3-6 samples/group). (FIG. 21B) SLO hemolytic activity of filtered bacterial supernatants of *S. pyogenes* measured on sheep erythrocytes in PBS after 30 minute incubation at 37° C. Hemolytic units correspond to the reciprocal of the dilution of supernatant that yielded 50% lysis, where 100% lysis corresponds to that caused by 1% Triton X-100. Hemolytic activities were also determined after pre-treatment of samples with SLO inhibitor, cholesterol at 250 μg/mL (n=3 samples/group). (FIG. 21C) Tissue swelling of mouse hind paws was measured using a digital caliper 1 h after injection with *S. pyogenes* ($5 \times 10^8$ cfu) M1 (left panel), or M3 (right panel) wt bacteria or isogenic mutants deficient in production of SLS (ΔsagA), SLO (Δslo), or both SLO and SLS (ΔsloΔsagA). Swelling was determined as change in thickness from baseline to 1 h after bacterial injection (n=8-12 mice/group). (FIG. 21D) Bacterial load recovery (plotted as log cfu) was determined in hind paw tissue samples 1 h after injection with *S. pyogenes* ($5 \times 10^8$ cfu) M1 (left panel), or M3 (right panel) (n=8-12 mice/group). (FIG. 21E) Acute flinching behaviors are inhibited by anti-SLS but not control rabbit IgG. Mice were injected with anti-SagA (anti-SLS) peptide antibody or control rabbit IgG at the time of injection with *S. pyogenes* M1 ($5 \times 10^8$ cfu). Spontaneous flinches were quantified for 1 h post-injection. Statistical analysis: (FIG. 21A-21E) One-way ANOVA with Tukey post-tests. *p<0.05, p<0.01, *p<0.001, ****p<0.0001. ns=not significant. Mean±SEM.

Figures 22A, 22B:
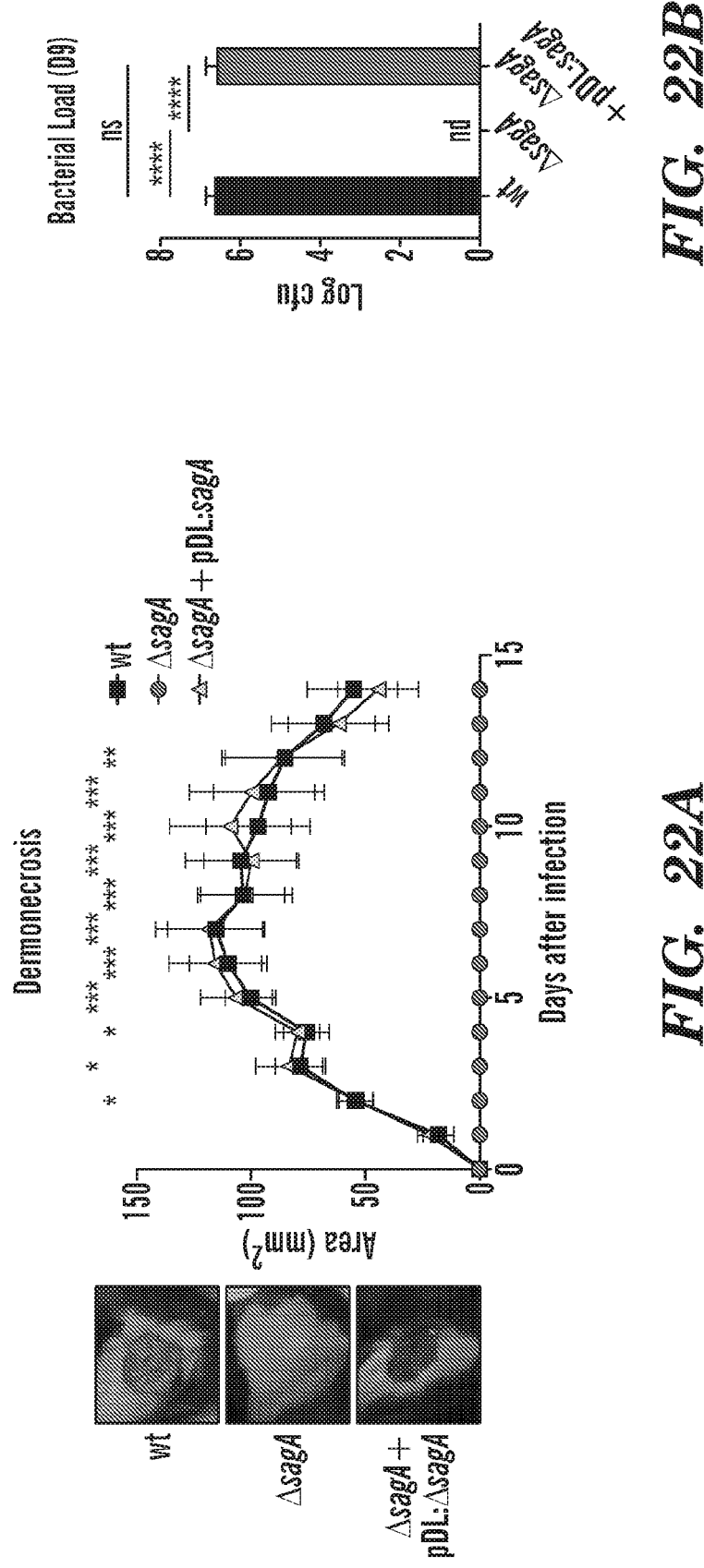

FIGS. 22A-22H show SLS (sagA) is required for bacterial pathogenesis, and TRPV1 neurons mediate pain during *S. pyogenes* infection. (FIG. 22A-22D) Mice were infected in the flank skin with wt, ΔsagA, and ΔsagA+pDL:sagA bacterial strains ($5 \times 10^6$ cfu M1 *S. pyogenes*). (FIG. 22A) Dermonecrotic lesion size over time (n=7 mice/group), (FIG. 22B) bacterial load recovery at day 9 (n=4 mice/group), (FIG. 22C) abscess size over time (n=7 mice/group), and (FIG. 22D) weight loss over time were measured after infection (n=7 mice/group). In FIG. 22A, left pictures show representative images of the injection site in mice infected with wt, ΔsagA, and ΔsagA+pDL:sagA at day 8 post-injection. (FIG. 22E) Spontaneous pain behaviors (licking/lifting or flinches over 1 h post-injection) were compared between Trpv1-Cre$^{+/-}$/Dta$^{+/-}$ mice or control littermates (Trpv1-Cre$^{-/-}$/Dta$^{+/-}$) following injection with M1 *S. pyogenes* ($5 \times 10^8$ cfu, n=4-5 mice per group). (FIG. 22F) Representative pictures of lumbar DRG sections from Trpv1-Cre/Dta or control littermates stained for TRPV1 (green), CGRP (green) and βIII tubulin (blue). Percentage of TRPV1$^+$ or CGRP$^+$ neurons out of total βIII-tubulin$^+$ neurons was quantified (n=3-5 mice/group). (FIG. 22G) Spontaneous pain behaviors (licking/lifting or flinches over 1 h) were compared between RTX and vehicle-treated mice following injection with M1 *S. pyogenes* ($5 \times 10^8$ cfu, n=5 mice/group). (FIG. 22H) Mice were treated with RTX or vehicle over three days (see Methods for details). Representative images of lumbar DRG sections from RTX-treated or vehicle-treated mice stained for TRPV1 (green), CGRP (green), and βIII tubulin (blue). Percentage of TRPV1$^+$ or CGRP$^+$ neurons out of total βIII-tubulin$^+$ neurons was quantified (n=3-4 mice/group). Statistical analysis: (FIGS. 22A, 22C, and 22D) Two-way ANOVA with Bonferroni post-tests. (FIG. 22B) One-way ANOVA with Tukey post-tests. (FIGS. 22E, 22F, 22G, and 22H) Unpaired t-tests. p<0.01, *p<0.001, ****p<0.0001. nd=not detected. ns=not significant. Mean±SEM.

FIGS. 23A-23F show CD11b$^+$Ly6G$^+$ neutrophils are required for protective effects of TRPV1 nociceptor ablation host defense against *S. pyogenes* infection. (FIG. 23A) Abscess area measurements after subcutaneous injection with *S. pyogenes* M1 ($5 \times 10^6$ cfu) in the flank of RTX-treated nociceptor deficient mice or vehicle-treated control mice (n=14-16 mice/group). (FIG. 23B) Gram staining of flank tissue samples collected at day 3 after injection with *S. pyogenes* M1 ($5 \times 10^6$ cfu) from vehicle-treated mice (upper panel) or RTX-treated mice (lower panel). In samples from vehicle-treated animals, more bacteria accumulation was observed compared to RTX-treated animals (arrows). Scale bars, 50 μm. (FIG. 23C) Spleen weights were increased in *S. pyogenes* M1 ($5 \times 10^6$ cfu) infected vehicle-treated mice compared to RTX-treated mice at day 14 after infection (n=4 spleens/group). (FIG. 23D) Representative FACS plots showing depletion of neutrophils (CD11b$^+$Ly6G$^+$) in skin lesions isolated from Gr1-treated, RTX-treated mice but not control rat IgG-treated, RTX-treated mice. (FIG. 23E-23F) Neutrophil depletion with Gr1 antibody abolishes the protective effects of RTX-mediated nociceptor ablation in *S. pyogenes* infection. (FIG. 23E) Dermonecrotic lesion size and weight loss were measured over 14 days after injection of *S. pyogenes* M1 ($5 \times 10^6$ cfu) in RTX-treated or vehicle-treated control mice receiving Gr1 antibody (125 μg i.p.) or rat IgG control (125 μg i.p.) (n=7-11 mice/group). (FIG. 23F) Abscess area measurements (n=7-11 mice/group) and Kaplan-Meier survival curves (n=10-11 mice/group) in RTX-treated or vehicle-treated control mice receiving Gr1 antibody (125 μg i.p.) or rat IgG control (125 μg i.p.).

Statistical analysis: (FIGS. 23A, 23E, and 23F) two-way ANOVA with Bonferroni post-tests, (FIG. 23C) one-way ANOVA with Tukey post-tests. (FIGS. 23A, and 23C) vehicle vs RTX=*p<0.05, p<0.01, *p<0.001, ****p<0.0001. (FIGS. 23E and 23F) RTX+IgG vs RTX+Gr1=*p<0.05, p<0.01, *p<0.001, ****p<0.0001. Mean±SEM.

FIG. 24A-24F show BoNT/A intrathecal vs. local injections dissociate central pain perception from peripheral neural modulation of immunity. (FIG. 24A) BoNT/A local injection at the site of infection blocks *S. pyogenes* infection. BoNT/A (25 pg in 100 μL) was injected 6 days prior to injection of *S. pyogenes* M1 ($5\times10^6$ cfu). Abscess size was measured daily in the flank skin for 14 days (n=5-10 mice/group). (FIG. 24B-24C) Local injection of BoNT/A at the site of infection does not block central pain perception. (FIG. 24B) Spontaneous pain behaviors (paw licking/lifting and flinches) quantified over 1 h after injection with *S. pyogenes* M1 ($5\times10^8$ cfu) in mice injected subcutaneously 6 days prior to infection with BoNT/A (25 pg in 5 μL) or vehicle alone at the site of bacterial injection (n=6 mice/group). (FIG. 24C) Heat hyperalgesia and mechanical hyperalgesia after infection with *S. pyogenes* M1 ($5\times10^7$ cfu) in mice injected subcutaneously 6 days prior to infection with BoNT/A (25 pg in 5 μL) or vehicle alone at the site of bacterial injection (n=5 mice/group). (FIG. 24D-24E) Intrathecal injection of BoNT/A blocks pain transmission. (FIG. 24D) Acute spontaneous pain behaviors (paw licking/lifting and flinches) quantified over 1 h after injection with *S. pyogenes* M1 ($5\times10^8$ cfu) were quantified in mice treated intrathecally 24 h prior to infection with BoNT/A (25 pg in 5 μL) or vehicle alone (n=6 mice/group). (FIG. 24E) Heat hyperalgesia, the sensitivity to pain evoked by radiant heat (Hargreaves test) and mechanical hyperalgesia, sensitivity to pain evoked by mechanical pressure (von Frey test), were analyzed in mice treated intrathecally with BoNT/A (25 pg in 5 μL) or vehicle 24 h prior to infection with *S. pyogenes* M1 ($5\times10^7$ cfu). An additional baseline measurement was performed immediately before infection to ensure the injections did not produce changes in basal threshold (n=4-6 mice/group). (FIG. 24F) Intrathecal administration of BoNT/A does not affect the outcome of *S. pyogenes* infection. BoNT/A was injected intrathecally (25 pg in 5 μL) 24 h prior to infection with *S. pyogenes* M1 ($5\times10^6$ cfu); abscess area was measured daily in mice infected for 14 days (n=5-10 mice/group). Statistical analysis: (FIGS. 24A, 24C, 24E, and 24F) two-way ANOVA with Bonferroni post-tests, (FIGS. 24B and 24D) unpaired t-test. *p<0.05, p<0.01, *p<0.001, ****p<0.0001. Mean±SEM.

Figure 25A:
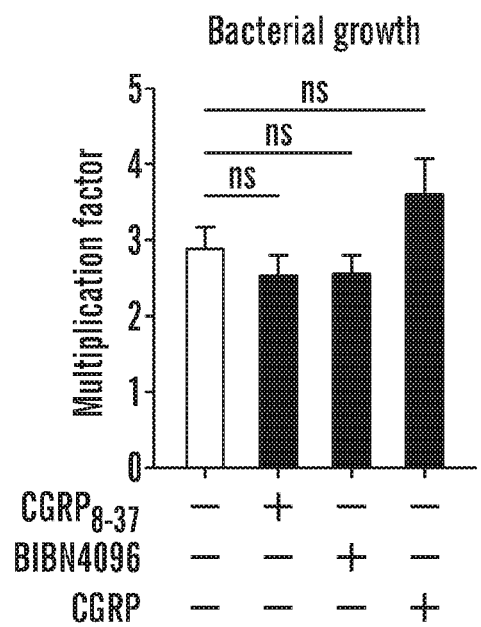

FIGS. 25A-25 show blockade of CGRP release and signaling treats *S. pyogenes* necrotizing fasciitis. (FIGS. 25A and 25B) *S. pyogenes* M1 bacteria were incubated with $CGRP_{8-37}$ (1 BIBN4096 (1 μM) or CGRP (1 μM) for 1 h in neurobasal medium. Viable bacteria were enumerated by quantitative cultures and quantified as a multiplication factor of surviving colonies relative to starting inoculum (n=4 biological replicates/condition). Similar experiments were conducted for bacteria in neurobasal medium with or without BoNT/A (25 pg in 200 μL) (n=4 biological replicates/condition). (FIG. 25C) Myeloperoxidase (MPO) activity of neutrophils is decreased by CGRP treatment. Mouse neutrophils were incubated in the presence of M1 *S. pyogenes* and different concentrations of CGRP for 30 minutes at 37° C. Neutrophil supernatant was collected and MPO activity measured (n=3-4 biological replicates/condition). (FIG. 25D) BoNT/A injection or BIBN4096 treatment during infection decreases flank skin and spleen bacterial burdens. Mice infected with *S. pyogenes* ($5\times10^6$ cfu M1) were treated with single BoNT/A local injection (25 pg in 50 μL) or BIBN4096 systemic injection (30 mg/kg) 2 h after subcutaneous injection of bacteria. At 9 days after injection of bacteria, flank skin and spleens were isolated, and bacterial load recovery determined (n=6 mice/group). (FIG. 25E) BoNT/A injection or BIBN4096 treatment after infection significantly decreases abscess formation but not weight loss following *S. pyogenes* infection. Mice were injected with *S. pyogenes* M1 ($5\times10^6$ cfu) in the flank followed by post-treatment with either BoNT/A (25 pg in 50 μL) or BIBN4096 (30 mg/kg) 2 h after infection. Abscess area and body weight were measured daily for 14 days (n=6-7 mice/group). (FIG. 25F) Flow cytometry of neutrophil ($CD11b^+Ly6G^+$ gates) recruitment in necrotizing lesions 1 day after *S. pyogenes* M1 injection ($5\times10^6$ cfu) in mice treated with vehicle, BoNT/A local injection (25 pg in 50 μL), or BIBN4096 systemic injection (30 mg/kg) 2 h after subcutaneous injection of bacteria (n=4-5 mice/group). (FIG. 25G) Mice were treated subcutaneously with BoNT/A or vehicle at day 2 and day 9 following flank injection of *S. pyogenes* M1 ($5\times10^6$ cfu), and weight loss was measured over time (n=10 mice/group). Arrows show BoNT/A treatments. Statistical analysis: (FIGS. 25A, 25C, 25D, and 25F) One-way ANOVA with Tukey post-tests, (FIG. 25B) Unpaired t-test, (FIGS. 25E and 25G) Two-way ANOVA with Bonferroni post-tests. *p<0.05, p<0.01, p<0.0001. (FIG. 25E) BIBN4096 vs vehicle=p<0.01, ****p<0.0001; BoNT/A vs vehicle (†p<0.05, ††p<0.01, †††p<0.0001). ns=not significant. Mean±SEM.

FIGS. 26A-26F present data that show TRPV1 neurons regulate survival and the outcome of lethal *S. aureus* pneumonia. (FIG. 26A) To genetically ablate $TRPV1^+$ neurons, Trpv1-Dtr mice 5-7 weeks of age were treated with diphtheria toxin (DT) (200 ng/mouse i.p.) daily for 21 days. Mice were rested 7 days prior to intra-tracheal inoculation with *S. aureus* USA300 ($1.3-1.4\times10^8$ CFU/mouse). (FIG. 26B) Left, Kaplan-Meier survival curves of PBS-treated Trpv1-Dtr mice (n=11) and DT-treated Trpv1-Dtr mice (n=13); Log-rank (Mantel-Cox) test (p=0.01). Right, Core body temperature measurements over time in PBS-treated (n=7) and DT-treated Trpv1-Dtr mice (n=8); Two-way repeated (RM) ANOVA with Bonferroni post-tests (***p=0.001, *p=0.014). (FIG. 26C) Lung bacterial burdens 12 h after infection in PBS-treated (n=13) and DT-treated Trpv1-Dtr mice (n=12); Two-tailed unpaired t-test (p=0.0042). (FIG. 26D) Resiniferatoxin (RTX)-mediated chemical ablation of $TRPV1^+$ neurons. WT mice 4 weeks of age were injected subcutaneously daily with three escalating doses of RTX or vehicle. Mice were rested for 4 weeks prior to intra-tracheal inoculation with *S. aureus* USA300 ($0.8-1\times10^8$ CFU/mouse). (FIG. 26E) Left, Kaplan-Meier survival curves of vehicle-treated (n=20) and RTX-treated mice (n=18); Log-rank test (p<0.0001). Right, Core body temperature measurements in vehicle-treated (n=5) and RTX-treated mice (n=5); Two-way repeated (RM) ANOVA with Bonferroni post-tests (****p<0.001). (FIG. 1F) Lung bacterial load recovery 12 h after *S. aureus* infection in vehicle-treated (n=13) and RTX-treated mice (n=13); two-tailed unpaired t-tests (p=0.0035). Data were pooled from 2 independent experiments for FIG. 26B and from 3 independent experiments for FIGS. 26C, 26E, and 26F. Data shown in FIGS. 26B AND 26C (core body temperature) are mean±s.e.m; and mean for FIGS. 26C and 26F.

Figure 27A:
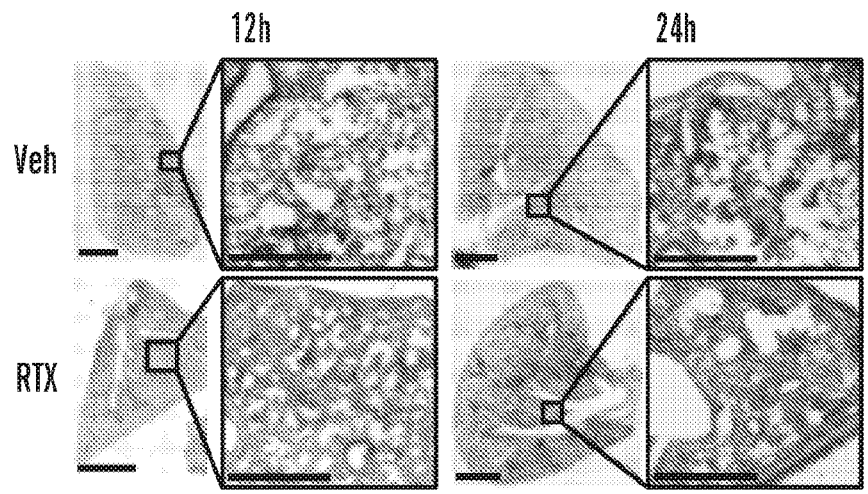
Figure 27B:
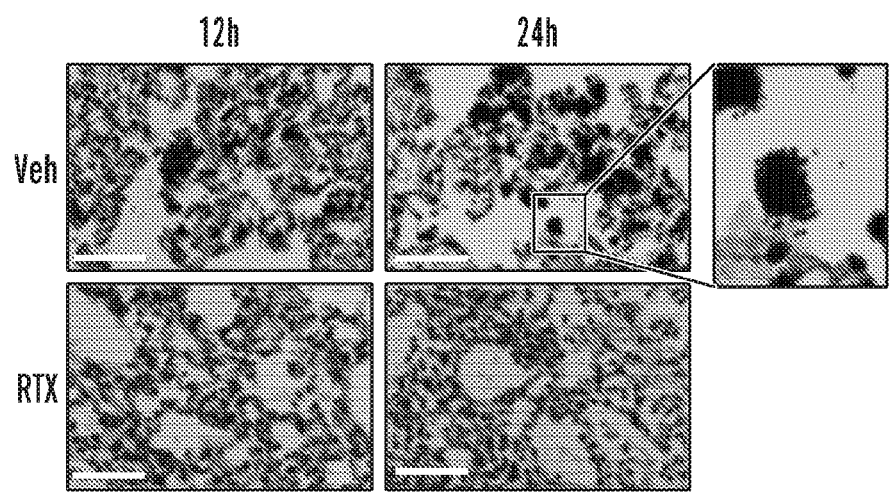
Figure 27C:
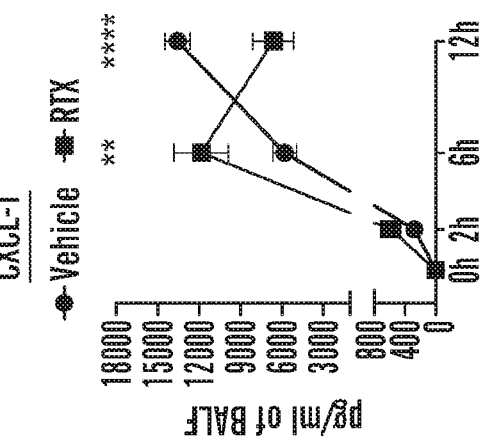
Figure 27C:
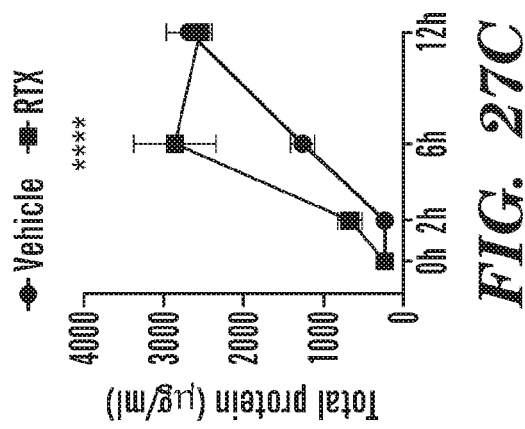
Figure 27D:
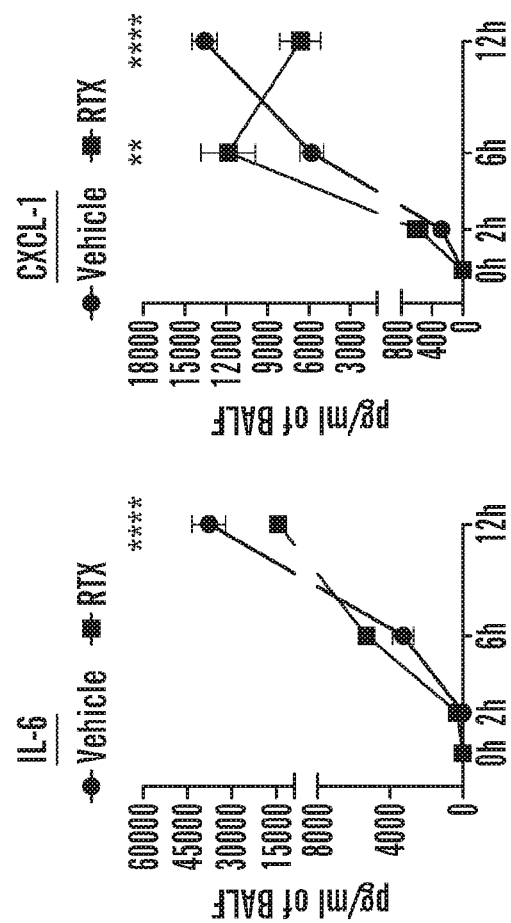

FIGS. 27A-27D present data that show TRPV1 neurons suppress lung inflammation and cytokine induction during *S. aureus* infection. (FIG. 27A) Haematoxylin and Eosin stained lung sections from vehicle-treated and RTX-treated mice at 12 h or 24 h after *S. aureus* infection. Representative images were chosen from 15 lung lobes imaged from 3 mice in each group (Vehicle and RTX). Scale bars, black (500 µm) and (100 µm). (FIG. 27B) Brown and Brenn gram stained images of bacterial colonies in lung sections from vehicle-treated and RTX-treated mice, 12 h and 24 h after infection. Representative images were chosen from 15 lung lobes imaged from 3 mice in each group (Vehicle and RTX). Inset, purple-colored bacterial cocci are *S. aureus* colonies. Scale bars, 50 µm. (FIG. 27C) Quantification of total protein levels in broncho-alveolar lavage fluid (BALF) at different time points following *S. aureus* infection ($1 \times 10^8$ CFU/mouse); vehicle-treated group, 0 h (n=6), 2 h (n=8), 6 h (n=8), 12 h (n=9); RTX-treated group, 0 h (n=6), 2 h (n=7), 6 h (n=6), 12 h (n=10); Two-way RM ANOVA with Bonferroni post-tests (****p<0.001). (FIG. 2D) Levels of IL-6, TNF-α, and CXCL-1 in BALF of mice at different time points following *S. aureus* infection ($1 \times 10^8$ CFU/mouse). TNF-α: vehicle-treated group, 0 h (n=6), 2 h (n=10), 6 h (n=10), 12 h (n=10); RTX-treated group, 0 h (n=6), 2 h (n=7), 6 h (n=6), 12 h (n=10); IL-6: vehicle-treated group, 0 h (n=6), 2 h (n=10), 6 h (n=10), 12 h (n=10); RTX-treated group, 0 h (n=6), 2 h (n=7), 6 h (n=6), 12 h (n=10); CXCL-1: vehicle-treated group, 0 h (n=6), 2 h (n=8), 6 h (n=8), 12 h (n=10); RTX-treated group, 0 h (n=6), 2 h (n=7), 6 h (n=6), 12 h (n=10); Statistical analysis for all cytokines by two-way RM ANOVA with Bonferroni post-tests (p=0.0013 and **p<0.0001). Data from one experiment with multiple biological replicates are shown in FIGS. 27A and 27B; Data pooled from 2 independent experiments are shown in FIGS. 27C-27D. Data shown in FIGS. 27C-27D are the mean±s.e.m.

Figures 28A, 28B:
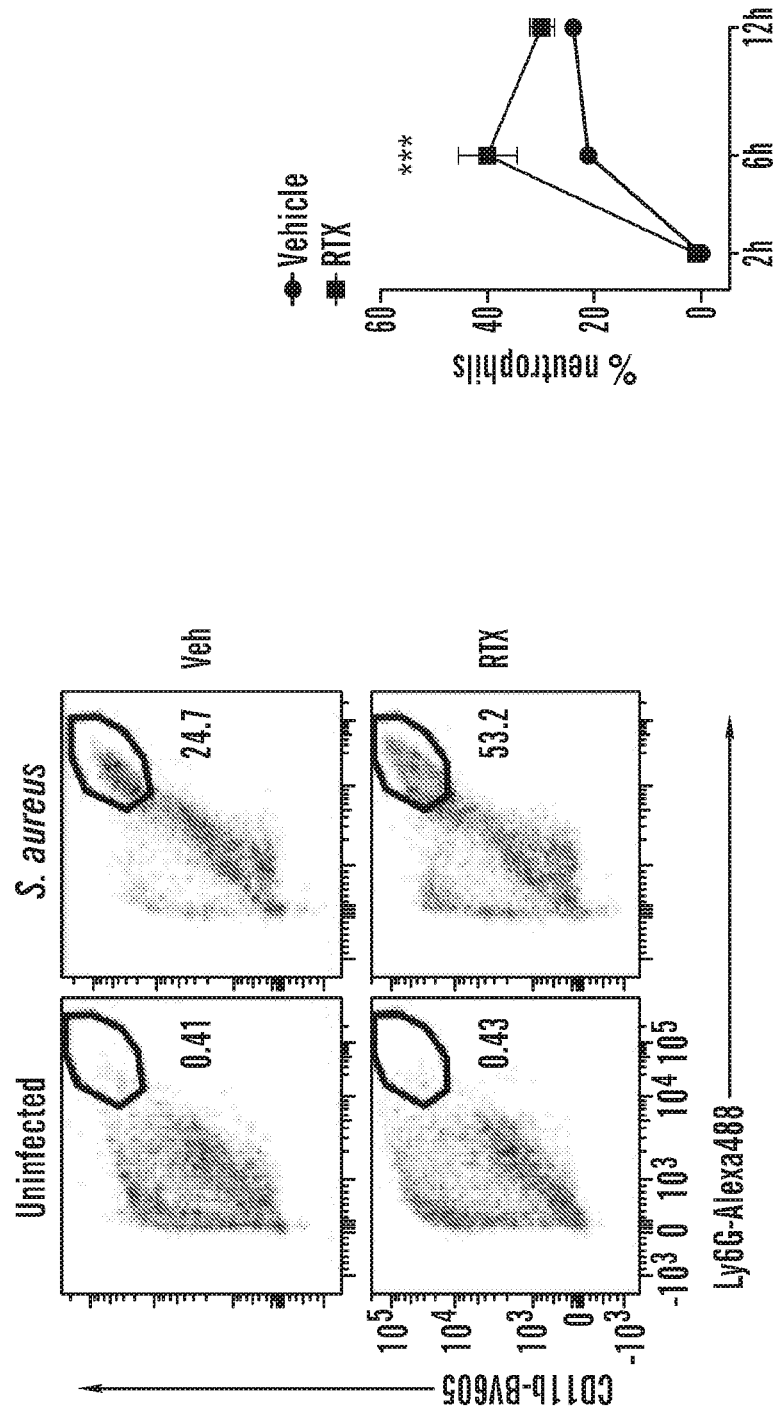
Figure 28C:
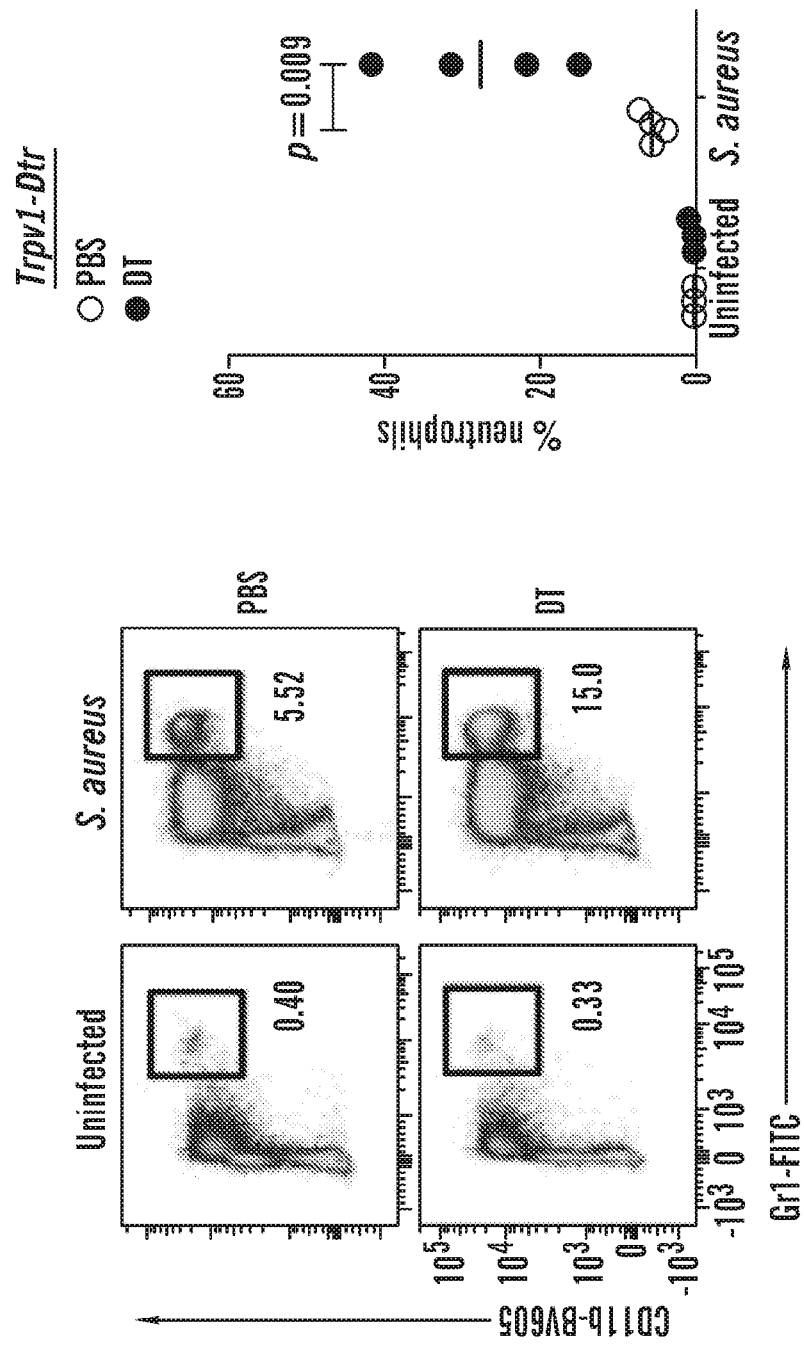
Figure 28D:
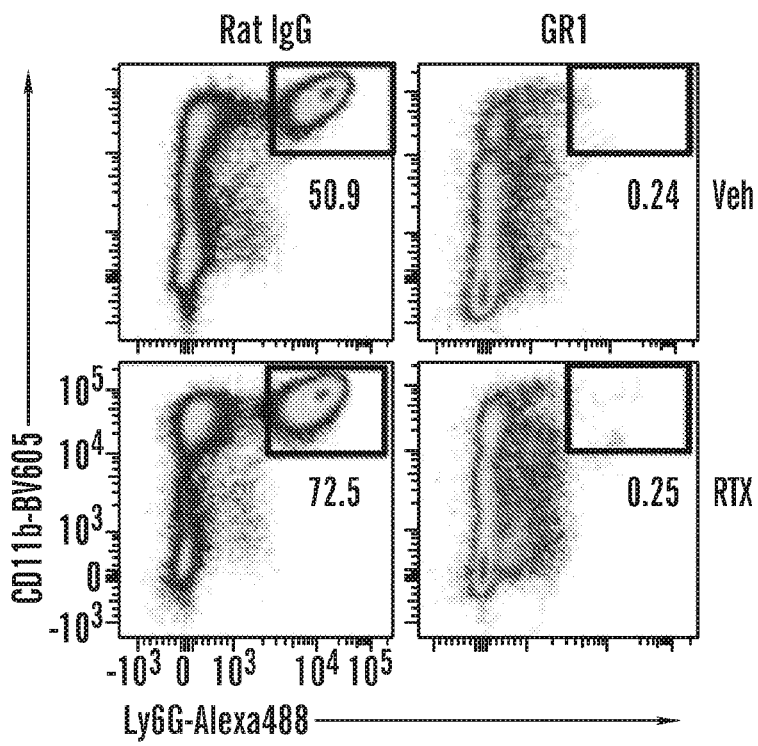
Figure 28E:
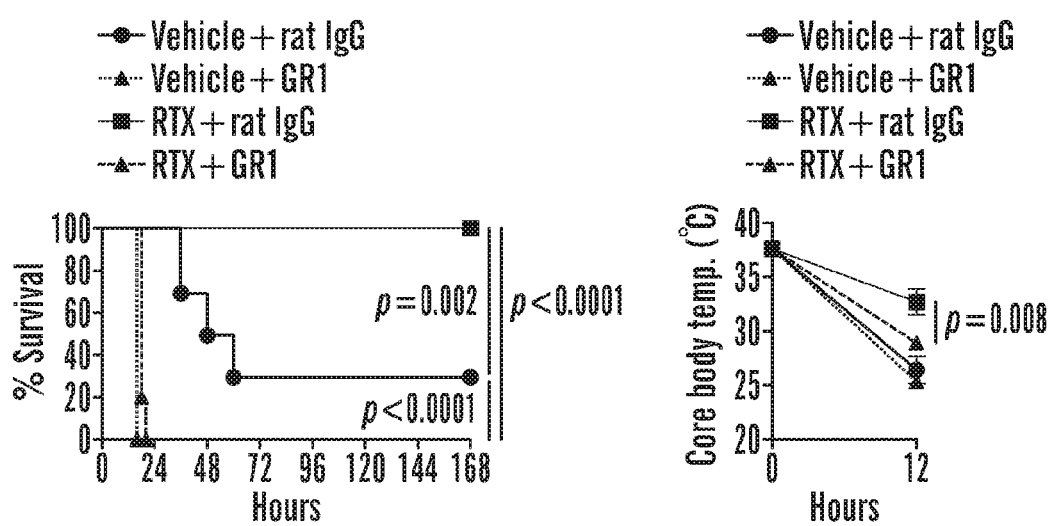

FIGS. 28A-28E present data that show TRPV1 neurons suppress recruitment of Ly6G$^+$ neutrophils essential for host defense against lethal pneumonia. (FIG. 28A) Representative fluorescence activated cell sorting (FACS) plots of neutrophils (CD11b$^+$Ly6G$^+$, out of CD45$^+$ cells) in vehicle-treated and RTX-treated mice in BALF collected at 6 h post-infection with *S. aureus* ($0.8 \times 10^8$ CFU/mouse). Representative FACS plots were chosen from 4 mice in each group (Vehicle and RTX). (FIG. 28B) Time-course of CD11b$^+$Ly6G$^+$ neutrophil recruitment in the BALF of RTX-treated mice compared to vehicle-treated mice following lethal *S. aureus* infection. n=4 mice in each group (Vehicle and RTX) for 2 h, 6 h and 12 h data sets; Two-way ANOVA with Bonferroni post-tests (***p=0.001). (FIG. 28C) Representative FACS plots (left) and quantification data (right), showing neutrophils (Gr1$^{hi}$CD11b$^+$ cells) in the lung homogenates of DT-treated (n=4) and PBS-treated Trpv1-Dtr mice (n=4) 12 h after *S. aureus* infection ($1.3 \times 10^8$ CFU/mouse). (FIG. 28D) FACS plots showing GR1 antibody mediated ablation of lung neutrophils in vehicle (n=3) and RTX-treated (n=3) mice 12 h after *S. aureus* infection ($0.8 \times 10^8$ CFU/mouse). (FIG. 28E) Left, Kaplan-Meier survival curves after *S. aureus* lung infection ($1.2-1.35 \times 10^8$ CFU/mouse) of vehicle+rat IgG mice (n=10), vehicle+GR1 mice (n=10), RTX+rat IgG mice (n=9), and RTX+GR1 mice (n=10); statistical analysis by log-rank test, p<0.0001 (RTX+rat IgG vs. RTX+GR1), p<0.0001 (Vehicle+rat IgG vs. Vehicle+GR1), and p=0.002 (Vehicle+rat IgG vs. RTX+rat IgG). Right, Core body temperature was measured after *S. aureus* infection with or without neutrophil depletion: vehicle+rat IgG, (n=5); vehicle+GR1 (n=5); RTX+rat IgG (n=4); RTX+GR1 (n=5); statistical analysis by two-way RM ANOVA with Bonferroni post-tests (p=0.008, RTX+rat IgG vs. RTX+GR1). Data from two independent experiments are shown in FIGS. 28B and 28E and one experiment with multiple biological replicates in FIG. 28C. Data shown in FIGS. 28B and 28C (neutrophil proportions) and FIG. 283E (core body temp.) are the mean±s.e.m.

Figure 29A:
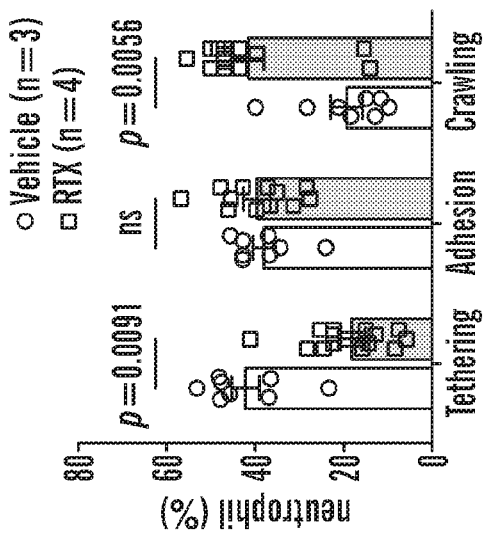
Figure 29B:
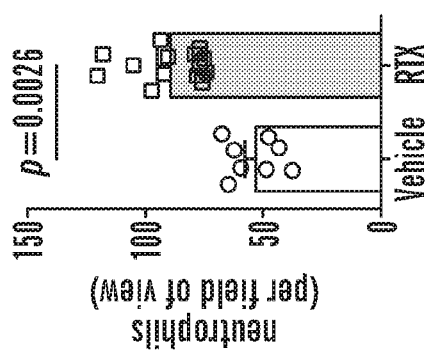
Figure 29C:
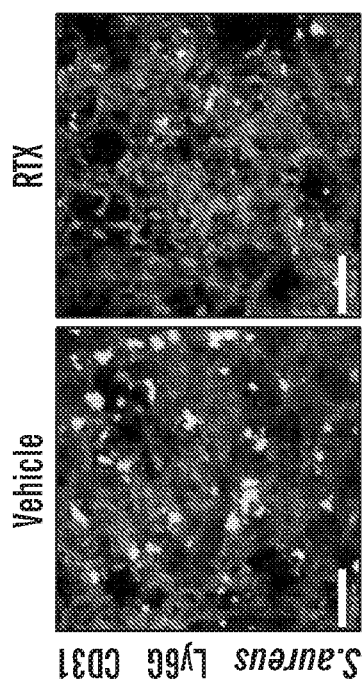
Figure 29D:
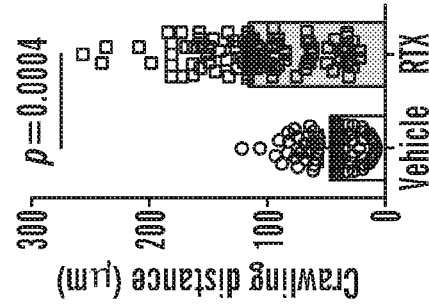
Figure 29E:
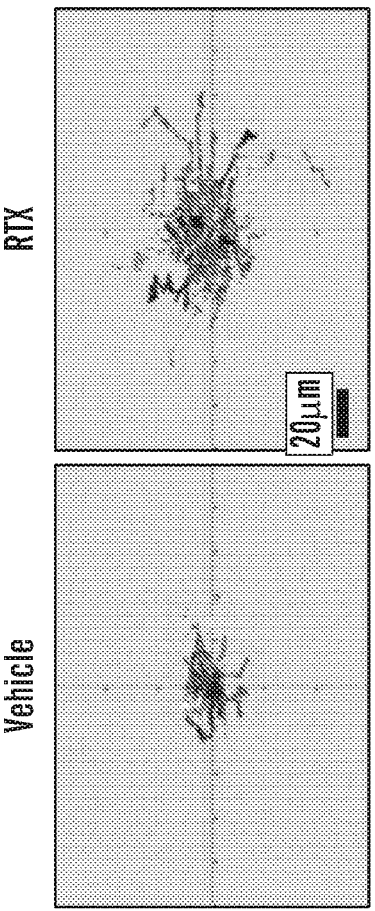

FIGS. 29A-29E present data that show Neutrophil dynamics are altered in TRPV1 neuron ablated mice. (FIG. 29A) In vivo imaging of neutrophils in the lungs following lethal GFP-*S. aureus* USA300 lung infection in live vehicle-treated and RTX-treated mice at 4 h post-infection. (FIG. 29B) Total neutrophils were determined per field of view. (FIG. 294C) Neutrophil behavior was phenotyped and quantified as tethering, adhesion or crawling. (FIG. 29D) Crawling tracks are displayed for individual neutrophils, and (FIG. 29E) Distances for individual neutrophils was determined. 3 individual experiments were performed for vehicle-treated mice and 4 for RTX-treated mice. For statistical analyses, values for each parameter (FIGS. 29B, 29C, and 29E) were averaged for each animal, and two-tailed unpaired t-tests performed comparing vehicle-treated and RTX-treated mouse groups. Data shown in FIGS. 29B, 29C, and 29E are the mean±s.e.m.

FIGS. 30A-30G present data that show TRPV1 neurons regulate lung γδ T cells that mediate host protection against *S. aureus* pneumonia. (FIGS. 30A-30C) To detect differences at steady state, lung tissues from nociceptor-depleted (RTX-treated, n=8) an non-depleted mice (vehicle-treated, n=8) were analyzed by flow cytometry for myeloid immune cells (FIG. 30A), lymphoid immune cells (FIG. 30B), and γδ T cell populations (FIG. 30C) Statistical analysis in FIGS. 30A-30C by two-tailed unpaired t-tests. (FIG. 30D) Representative FACS plots showing γδ T cells in WT or Tcrd$^{-/-}$ mice (RTX or vehicle treated) that are uninfected, or 12 h post-infection with *S. aureus* ($1 \times 10^8$ CFU/mouse); vehicle-treated groups: WT uninfected (n=8), WT infected (n=4), Tcrd$^{-/-}$ infected (n=3); RTX-treated groups: WT uninfected (n=8), WT infected (n=4), Tcrd$^{-/-}$ infected (n=3). (FIG. 5E) Left, Kaplan-Meier survival curves for vehicle-treated WT mice (n=7), vehicle-treated Tcrd$^{-/-}$ mice (n=6), RTX-treated WT mice (n=5), and RTX-treated Tcrd$^{-/-}$ mice (n=6) after lethal *S. aureus* infection ($1 \times 10^8$ CFU/mouse); Statistical analysis by log-rank test (p=0.01, RTX-treated WT vs. RTX-treated Tcrd$^{-/-}$; p=0.08, Vehicle-treated \VT vs. Vehicle-treated Tcrd$^{-/-}$). Right, Core body temperature measurements in vehicle-treated WT mice (n=5), vehicle-treated Tcrd$^{-/-}$ mice (n=5), RTX-treated WT mice (n=5), and RTX-treated mice (n=4); Two-way RM ANOVA with Bonferroni post-tests (p<0.0001, RTX-treated WT vs. RTX-treated Tcrd$^{-/-}$). (FIG. 5F) Representative FACS plots of CD11b$^-$Siglecr alveolar macrophages following intra-tracheal administration of clodronate-laden liposomes (CLL) or PBS-liposomes (PBS-L) in vehicle-treated and RTX-treated mice 12 h post-infection; vehicle-treated groups, uninfected (n=8), PBS-L infected (n=3), CLL infected (n=3); RTX-treated groups, uninfected (n=8), PBS-L infected (n=4), CLL infected (n=3). (FIG. 5G) Left, Kaplan-Meier survival curves after *S. aureus* lung infection ($1 \times 10^8$ CFU/mouse) with or without alveolar macrophage depletion: vehicle+PBS-L (n=10), vehicle+CLL (n=10), RTX+CLL (n=10), RTX+PBS-L (n=8); Log-rank test (p=0.37, RTX+PBS-L vs. RTX+CLL and p=0.22, Vehicle+PBS-L vs. Vehicle+CLL). Right, Core body temperature measurements: vehicle+PBS-L (n=4), vehicle+CLL, (n=4), RTX+CLL (n=4), RTX+PBS-L (n=4); Two-way RM ANOVA with Bonferroni post-tests. One experiment with multiple biological replicates for FIG. 30E and two independent experiments were performed for FIGS. 30A-30D, and 30F-30G. Data shown in FIGS.

Figure 30A:
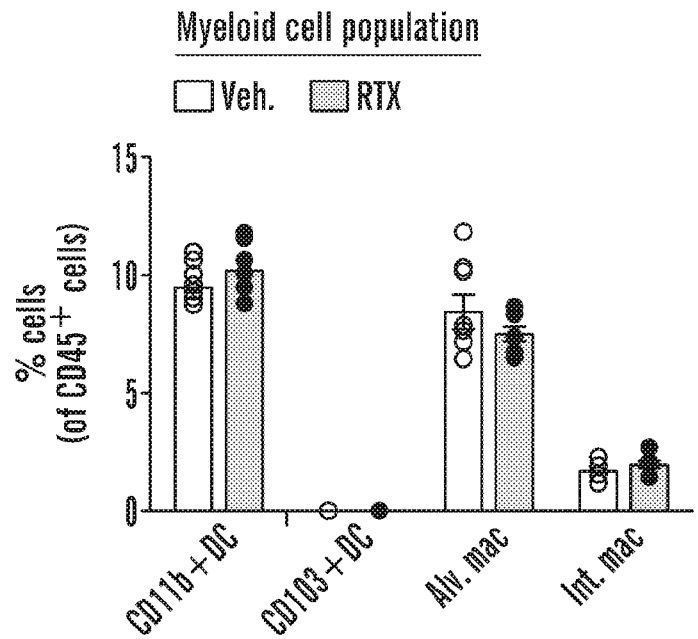
Figure 30B:
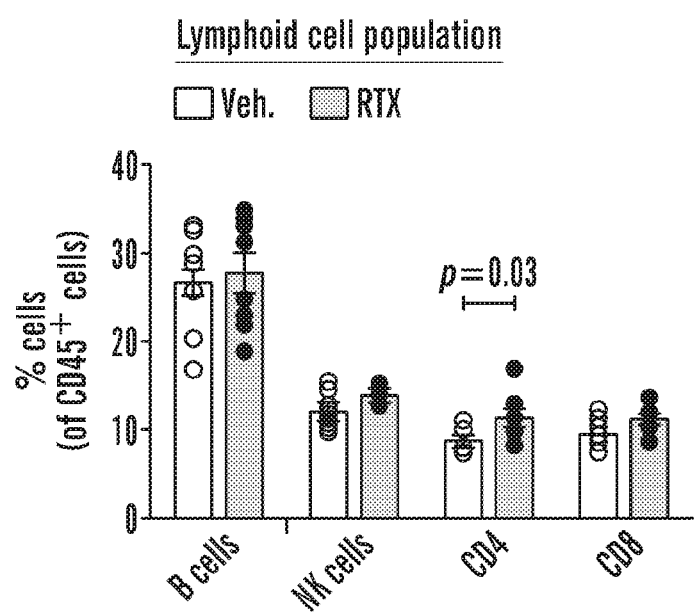
Figure 30C:
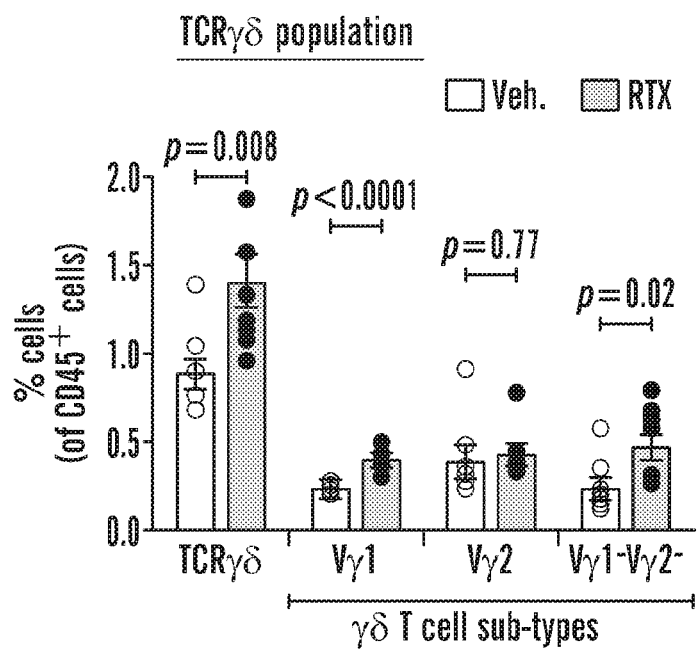
Figure 30D:
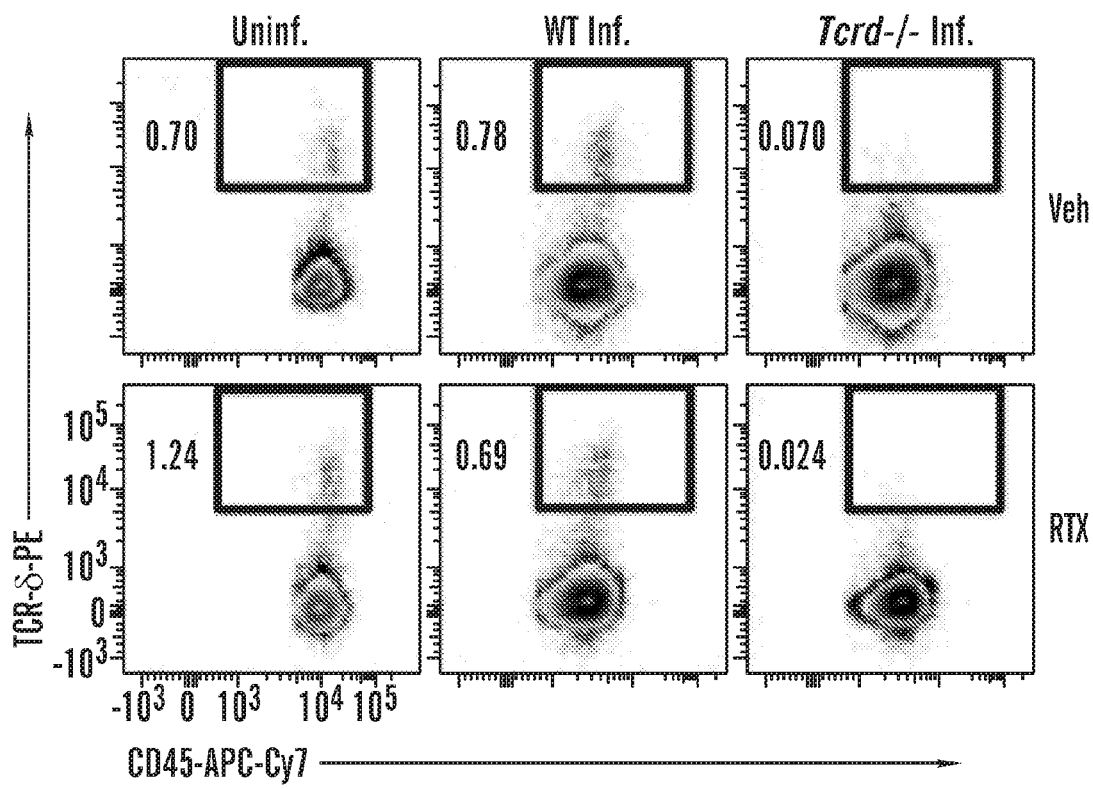
Figure 30E:
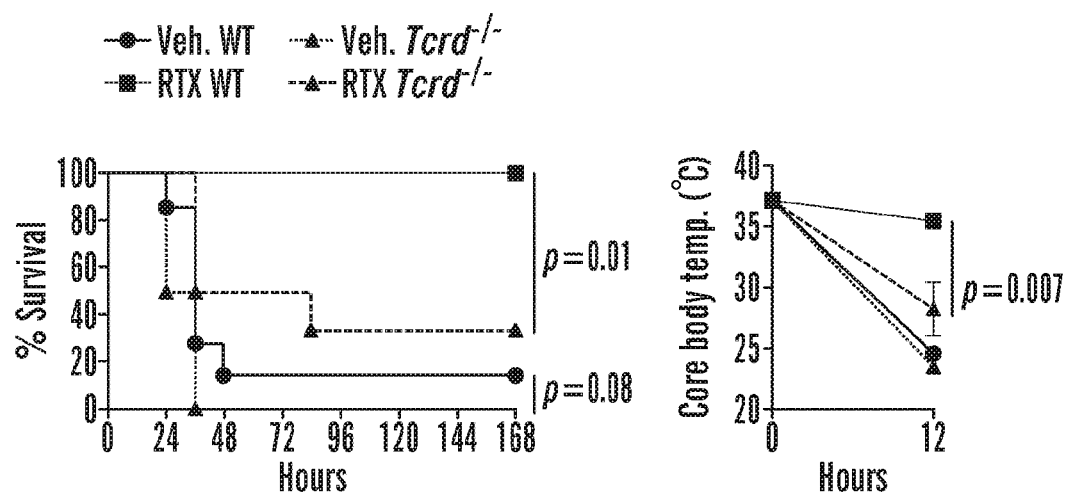
Figure 30F:
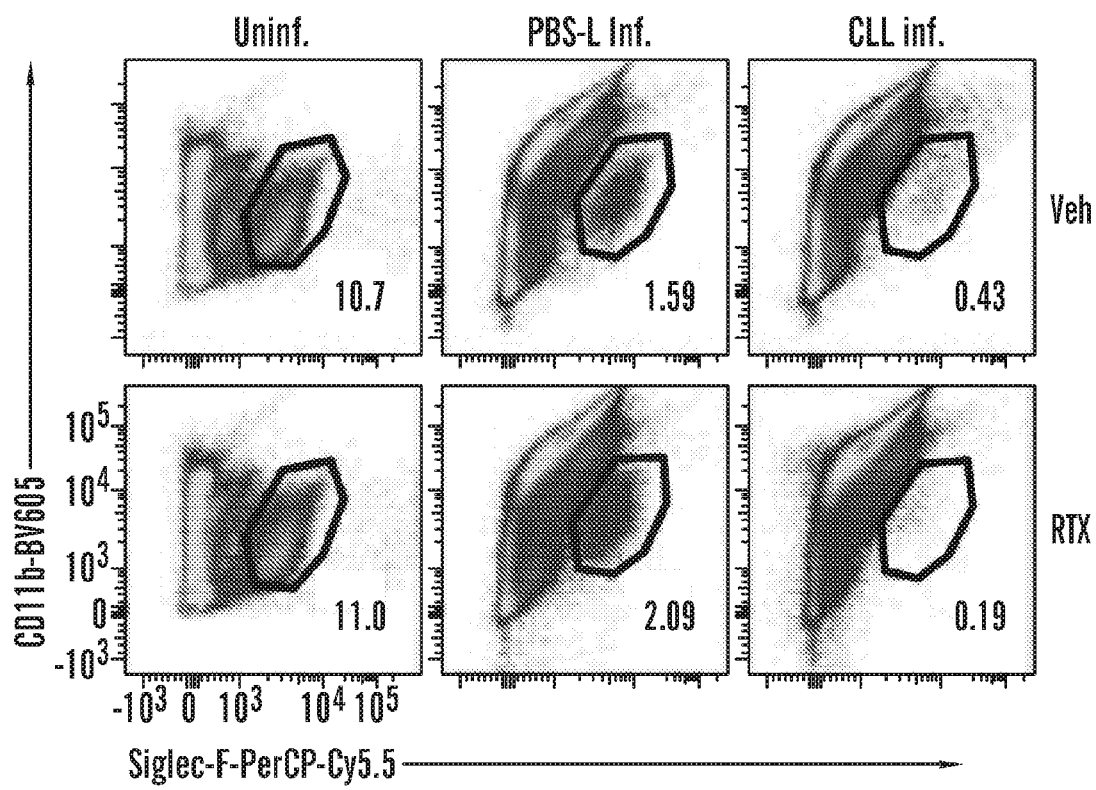

30A-30C and 30E (core body temp.) and FIG. 30F (core body temp.) are the mean±s.e.m.

FIG. 31A-31G present data that show vagal TRPV1 neurons and the neuropeptide CGRP regulate *S. aureus* pneumonia. (FIG. 31A) Diphtheria toxin (DT) or PBS alone was injected bilaterally into vagal ganglia of Trpv1-Dtr mice. Quantification of proportions of TRPV1+ and CGRP+ neurons in VG and DRGs (T1-T9) of vagal DT-injected mice (n=3) and PBS-injected littermate control (n=3) mice; Statistical analysis by two-tailed unpaired t-tests. (FIG. 31B) Left, Kaplan-Meier survival curves of PBS vagal ganglia-injected Trpv1-Dtr mice (n=9) compared to DT vagal injected Trpv1-Dtr mice (n=8) following lethal *S. aureus* lung infection ($1.3$-$1.4 \times 10^8$ CFU/mouse); Log-rank test, p=0.0003. Right, Core body temperature in PBS vagal-injected Trpv1-Dtr mice (n=4) compared to DT vagal-injected Trpv1-Dtr mice (n=4) following infection; Two-way RM ANOVA with Bonferroni post-tests (***p<0.0001). (FIG. 31C) CGRP levels in the BALF of uninfected mice, or 12 h after infection with WT USA300 *S. aureus* ($0.8 \times 10^8$ CFU/mouse) or Δagr USA300 *S. aureus* ($0.8 \times 10^8$ CFU/mouse); Uninfected (n=5), WT infected (n=5), and Δagr infected (n=5); Statistical analysis by one-way ANOVA with Bonferroni's post-tests. (FIG. 31D) CGRP levels in the BALF of RTX-treated mice (n=5), and vehicle-treated mice (n=5); or CGRP levels in vagal DT-treated (n=5) or PBS-treated Trpv1-Dtr mice (n=4) 12 h after WT *S. aureus* infection ($1.1$-$1.4 \times 10^8$ CFU/mouse); Statistical analysis by two-tailed unpaired t-test. (FIG. 31E) Production levels of TNF-α, IL-6 and CXCL-1 by whole lung cell cultures after infection with *S. aureus* at a multiplicity of infection (MOI) of 2 at 2 h, 6 h, 12 h, 20 h post-infection with or without CGRPα (100 nM). Statistical analysis by two-way ANOVA with Bonferroni's post-tests. (FIG. 31F) The CGRP receptor antagonist, $CGRP_{8-37}$ was administered systemically (i.p.) at 800 ng (256 pmoles) per dose dissolved in PBS at −24 h, −2 h, 12 h, 24 h, 36 h and 48 h relative to intra-tracheal *S. aureus* infection (0 h). Control mice received PBS injections i.p. at the same time points. (Left) Kaplan-Meier survival curves (PBS-treated, n=8; $CGRP_{8-37}$-treated, n=8) of mice following *S. aureus* lung infection; Log-rank test, p=0.04. (Right) Core body temperature measurements (PBS-treated, n=3; $CGRP_{8-37}$-treated, n=5) following *S. aureus* infection; Two-way RM ANOVA with Bonferroni post-tests (p=0.004 and *p=0.0002). (FIG. 31G) $CGRP_{8-37}$ was administered i.p. at 7.5 μg (2.4 nmoles) per dose in PBS at 4 h, 16 h and 24 h time points relative to intra-tracheal *S. aureus* infection (0 h). Control mice received PBS injections i.p. at same time points. Left, Kaplan-Meier survival curves for PBS-treated (n=20) and $CGRP_{8-37}$ treated (n=19) mice; Log-rank test, p=0.03. Right, Core body temperature of PBS-treated (n=12) and $CGRP_{8-37}$ treated (n=11) mice; Two-way RM ANOVA with Bonferroni post-tests (p=0.002 (16 h) and p=0.004 (24 h)). One experiment was performed with multiple biological replicates for FIGS. 31A, 31D, and 31F; two independent experiments were performed for FIGS. 31B, 31C, and 31E and three independent experiments were performed for FIG. 31G.

Figure 32A:
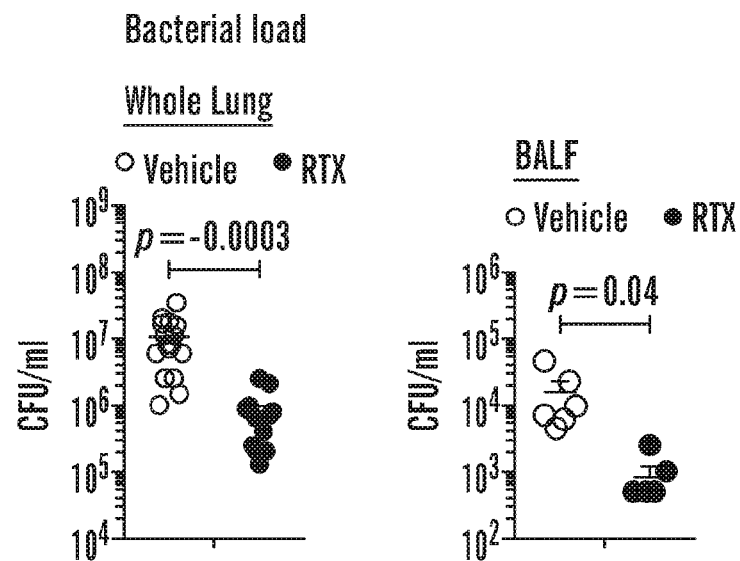
Figure 32B:
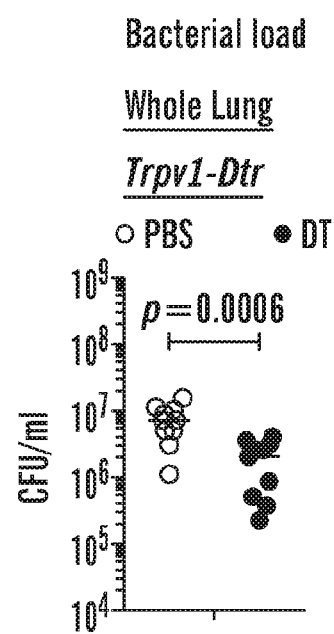

FIGS. 32A and 32C present data that show nociceptor neuron ablation leads to improved bacterial clearance following sub-lethal *S. aureus* lung infection. (FIG. 32A) Bacterial load recovery from whole lung lysates (Left) and broncho-alveolar lavage fluid (BALF, Right) from vehicle-treated mice or RTX-treated mice measured 12 h after infection with a sub-lethal dose of *S. aureus* ($2$-$4 \times 10^7$ CFU/mouse). For whole lung lysate analysis, data are from vehicle-treated mice (n=16) and RTX-treated mice (n=14) pooled from 3 independent experiments; For BALF analysis, data are from vehicle-treated mice (n=6) and RTX-treated mice (n=5) from one experiment. (FIG. 32B) Bacterial load recovery from whole lung lysates of PBS-treated Trpv1-Dtr mice (n=11) and DT-treated Trpv1-Dtr mice (n=12) determined 12 h post-infection with *S. aureus* ($2$-$4 \times 10^7$ CFU/mouse) pooled from two independent experiments. Statistical analysis throughout figure by two-tailed unpaired t-test, and data are plotted as the mean±s.e.m.

Figure 33A:
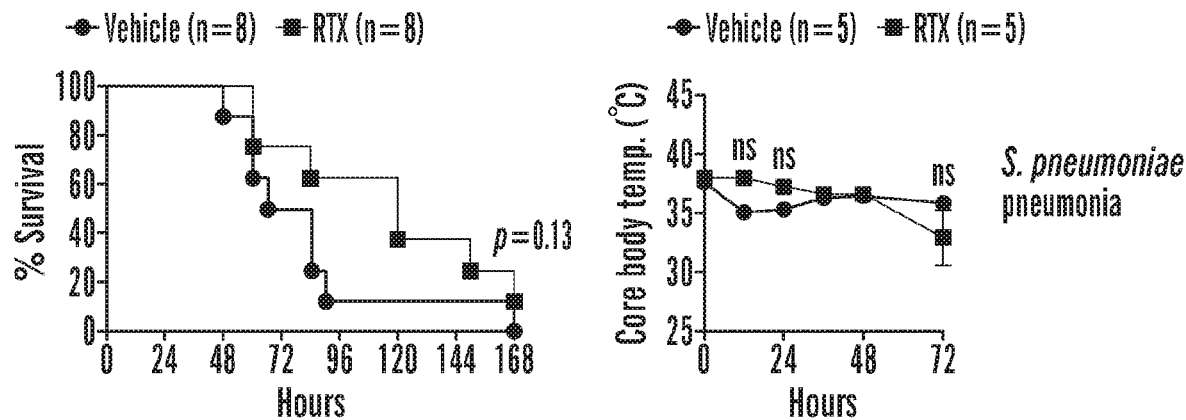
Figure 33B:
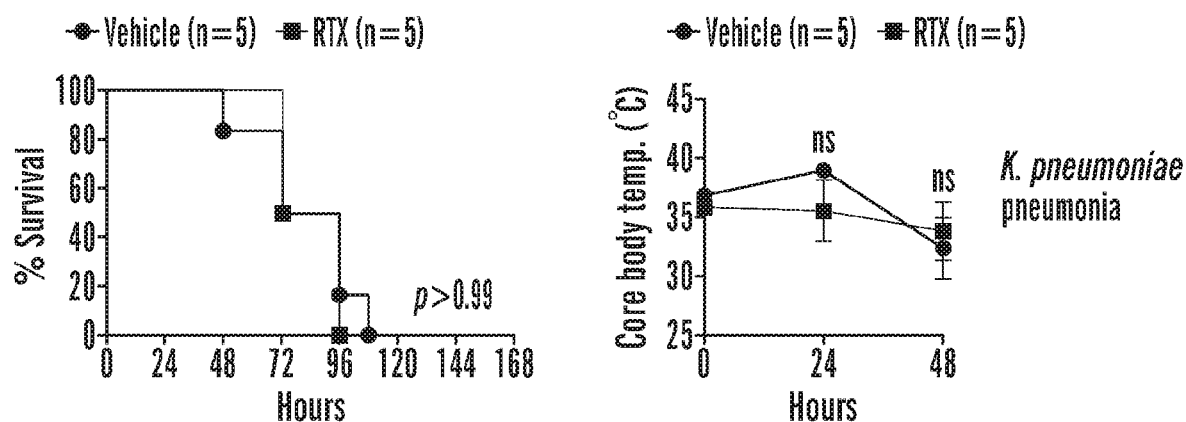
Figure 33C:
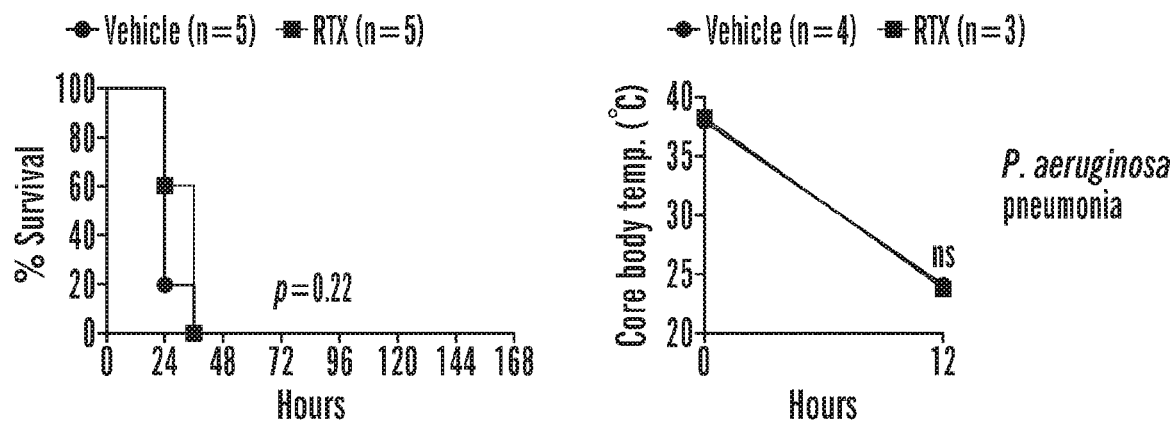

FIGS. 33A-33C present data that show role of TRPV1+ neurons in host defense against *S. pneumoniae*, *K. pneumoniae*, and *P. aeruginosa* lung infections. (FIG. 33A) Left, Kaplan-Meier survival curves of RTX-treated mice (n=8) and vehicle-treated mice (n=8) after infection with *Streptococcus pneumoniae* strain WU-2 ($5 \times 10^6$ CFU/mouse), analyzed by log-rank test (p=0.13). Right, Core body temperature measurements in RTX-treated (n=5) and vehicle-treated mice (n=5), analyzed by two-way RM ANOVA with Bonferroni post-tests (ns, not significant, p>0.05). (FIG. 33B) Left, Kaplan-Meier survival curves of RTX-treated (n=5) and vehicle-treated mice (n=5) after infection with *Klebsiella pneumoniae* ($10^4$ CFU/mouse), log-rank test (p>0.99). Right, Core body temperature measurements in RTX-treated (n=5) and Vehicle-treated (n=4) mice, two-way RM ANOVA with Bonferroni post-tests (ns, p>0.05). (FIG. 33C) Left, Kaplan-Meier survival curves of RTX-treated (n=5) and vehicle-treated (n=5) mice after infection with *Pseudomonas aeruginosa* strain PA01V ($7 \times 10^6$ CFU/mouse), log-rank test (p=0.22). Right, Core body temperature measurements in RTX-treated (n=3) and vehicle-treated (n=4) mice, analyzed by two-way RM ANOVA with Bonferroni post-tests (ns, p>0.05). Data shown in FIG. 33A and FIG. 33C are from two independent experiments, and in FIG. 33B from one experiment. Error bars throughout figure indicate mean±s.e.m.

Figure 34B:
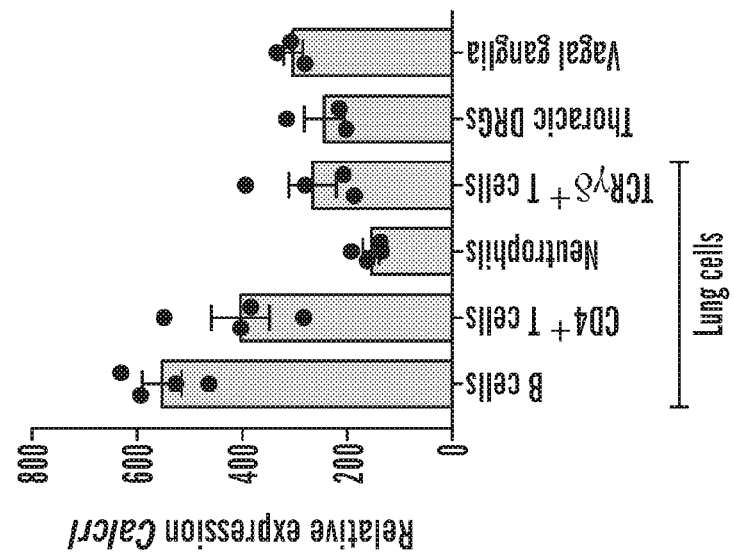
Figure 34A:
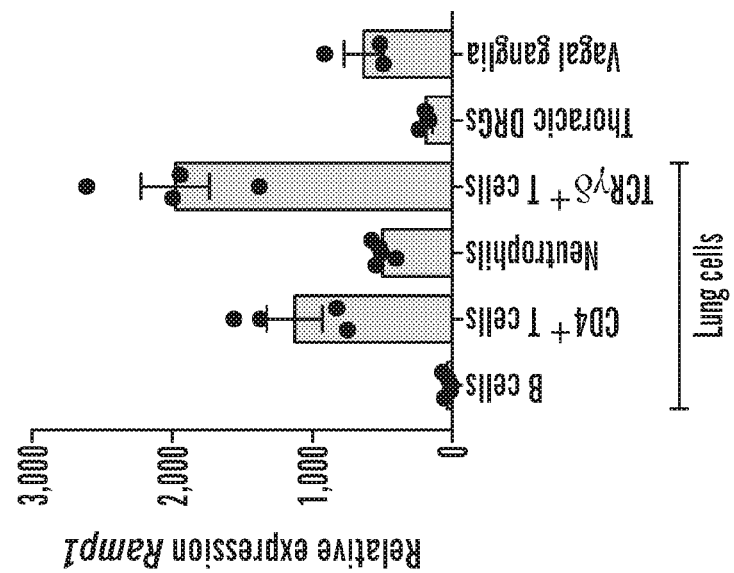

FIGS. 34A and 34B present data that show Ramp1 and Calcrl expression by lung immune cells and sensory ganglia. The indicated populations of lung immune cell populations (B cells, CD4+ T cells, neutrophils, TCRγδ+ cells), thoracic dorsal root ganglia (DRG), and vagal ganglia were isolated from C57BL/6 mice. Relative gene expression of Ramp1 (FIG. 34A) or Calcrl (FIG. 34B) were analyzed by quantitative real-time PCR using Taqman Assays. Data are from purified B cells (n=4), CD4+ T cells (n=4), Neutrophils (n=4), TCRγδ+ cells (n=4), thoracic DRG (n=3), and nodose ganglia (n=3) were analyzed. Error bars indicate mean±s.e.m.

Figure 35:
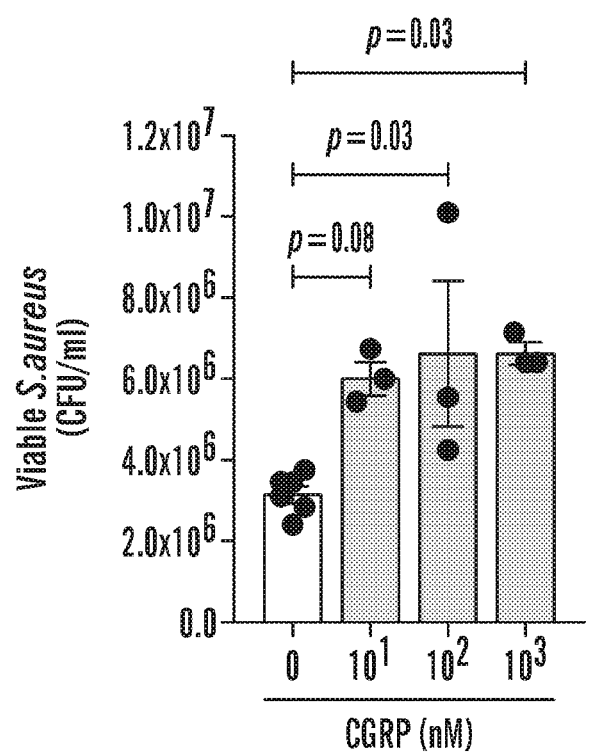

FIG. 35 presents data that show CGRP treatment of mouse neutrophils decreases *S. aureus* clearance in culture. Mouse neutrophils were co-cultured with *S. aureus* in the presence of different CGRP concentrations for 2 h (0 nM CGRP, n=6; 10 nM CGRP, n=3; 100 nM CGRP, n=3; 1000 nM CGRP, n=3). Each n represents an individual biological replicate of stimulation. Cells were treated with gentamycin to remove extracellular bacteria. Intracellular bacterial survival was quantified after lysing cells and plating of serial dilutions on TSA. Statistical analysis by one-way ANOVA with Bonferroni post-tests. Error bars indicate mean±s.e.m

DETAILED DESCRIPTION

The invention described herein relates to, in part, the discovery that microbes causing infection, e.g., infectious bacteria, are susceptible to treatment by antagonism of CGRP and CGRP receptor signaling. This antagonism enhances the immune response, which is normally inhibited by CGRP. Accordingly, described herein are methods and compositions for inhibiting CGRP for treating and/or preventing infection in a subject having, or at risk of having, an infection. One aspect described herein relates to a method for treating a microbial infection comprising administering to a subject in need thereof an agent that inhibits CGRP, e.g., at an amount and for a duration sufficient to treat a microbial infection. Another aspect described herein relates to a method for preventing a microbial infection comprising administering to a subject in need thereof an agent that inhibits CGRP, e.g., at an amount and for a duration sufficient to prevent a microbial infection.

CGRP (Calcitonin Gene-Related Peptide) is a 37 amino-acid neuropeptide, expressed by nociceptive sensory neurons that mediate pain. It is stored in the dense-core vesicles at both peripheral and central nerve terminals of nociceptive neurons. There are two known isoforms of CGRP, Alpha-CGRP and Beta-CGRP, that have substantially identical functions. CGRP is produced in neurons that functions in pain neurotransmission and neurogenic inflammation. CGRP is released by nociceptive neurons from nerve terminals upon calcium influx. CGRP binds to its receptor complex formed by RAMP1 and CALCRL, which is expressed by many cell types, including the vascular endothelial cells, innate and adaptive immune cells. Blocking CGRP from binding and activating CALCRL can lead to increased immune responses against bacterial pathogens. The action of CGRP on the vasculature induces acute vasodilation and blood flow, which is termed "neurogenic inflammation". It was found that CGRP potently acts on innate immune cells including neutrophils to suppress cytokine production and killing of bacteria, including both *S. pyogenes* and *S. aureus*. Therefore, CGRP inhibits the immune response against bacterial pathogens. As described herein, it was found that antagonism of CGRP receptors increases bacterial killing.

Method of Treating

In one aspect of the invention is a method of treating a microbial infection comprising administering to a subject in need thereof an agent that inhibits CGRP activity, release, or receptor signaling in an amount and for a duration sufficient to treat a microbial infection.

In one embodiment of any aspect described herein, Alpha-CGRP activity, release, or receptor signaling is inhibited. In another embodiment of any aspect described herein, Beta-CGRP activity, release, or receptor signaling is inhibited. In yet embodiment of any aspect described herein, Alpha-CGRP and Beta-CGRP activity, release, or receptor signaling are inhibited.

In one embodiment, the subject has previously been diagnosed with having a microbial infection. In one embodiment, prior to administration, the subject is diagnosed with having a microbial infection.

In one aspect of the invention is a method for treating a *Staphylococcus aureus* infection comprising administering to a subject in need thereof an agent that inhibits a nociception in an amount and for a duration sufficient to treat a *Staphylococcus aureus* infection.

Nociceptor neurons are the specific subset of peripheral sensory neurons that mediate pain, an unpleasant sensation that warns organisms of danger. In addition to transducing pain signals to the central nervous system, nociceptors release neuropeptides (e.g., CGRP) from their peripheral nerve terminals that can directly modulate inflammation. These neuropeptides bind to their cognate receptors on immune cells (e.g., CGRP receptor signaling), leading to changes in transcription, cytokine production, and immune phenotypic polarization (Pinho-Ribeiro et al., 2017).

In one embodiment, the agent is an inhibitor of TRPV1 or leads to denervation of TRPV1 expressing neurons. The Transient receptor potential vanilloid 1 (TRPV1) ion channel responds to capsaicin, protons, and heat stimuli. TRPV1 is expressed by many C-fibers (e.g., fibers that are unmyelinated and have a small diameter and low conduction velocity), including nociceptors that mediate thermal nociception and inflammatory hyperalgesia. TRPV1 functions to transduce painful thermos-stimuli in vivo. TRPV1 sequences are known for a number of species, e.g., human TRPV1 (NCBI Gene ID: 7442) and mRNA (NCBI Ref Seq NM_018727.5, and NCBI Ref Seq NP_061197.4). TRPV1 can refer to human TRPV1, including naturally occurring variants and alleles thereof. In some embodiments of any of the aspects, e.g., in veterinary applications, TRPV1 can refer to the TRPV1 of, e.g., dog, cat, cow, horse, pig, and the like. Homologs and/or orthologs of human TRPV1 are readily identified for such species by one of skill in the art, e.g., using the NCBI ortholog search function or searching available sequence data for a given species for sequence similar to a reference TRPV1 sequence.

Exemplary TRPV1 antagonists that can inhibit TRPV1 include A 425619, A 784168, AMG 21629, AMG 517, AMG 9810, Arachidonyl serotonin, BCTC, Capsazepine, GSK 2193874, HC 067047, 6-Iodonordihydrocapsaicin, 5'-Iodoresiniferatoxin, JNJ 17203212, L-R4W2, RN 1734, RN 9893 hydrochloride, SB 366791, SB 452533, α-Spinasterol, and Tranilast.

In one embodiment, the agent that inhibits TRPV1 and leads to TRPV1 neuron denervation is Resiniferatoxin (RTX). Resiniferatoxin is a TRPV1 agonist, that upon prolonged administration, results in its activation and the subsequent desensitization of TRPV1, resulting in a decrease in TRPV1 activity and/or function. Exemplary TRPV1 agonists that can function in the same manner include AM 404, Anandamide, Anandamide (in Tocrisolve™ 100), (E)-Capsaicin, 6'-Iodoresiniferatoxin, NADA, OLDA, Olvanil, and PPAHV.

In one embodiment, the subject has previously been diagnosed with having a *Staphylococcus aureus* infection. In one embodiment, prior to administration, the subject is diagnosed with having a *Staphylococcus aureus* infection.

Method of Preventing

In one aspect of the invention is a method of preventing a microbial infection comprising administering to a subject in need thereof an agent that inhibits CGRP activity, release, or receptor signaling in an amount and for a duration sufficient to treat a microbial infection.

In one embodiment, the subject has previously been diagnosed with having a microbial infection. In one embodiment, prior to administration, the subject is diagnosed with being at risk of having a microbial infection.

When provided prophylactically, an agent described herein can be administered to a subject in advance of any symptom of a lung disorder, e.g., fever, pain at infection site, or inflamed tissue. Accordingly, the prophylactic administration of an agent serves to prevent a microbial infection, as disclosed herein.

Microbial Infection

In one embodiment, the microbial infection is a bacterial infection, e.g, a gram-positive bacterial infection. Gram-positive bacteria display a cytoplasmic lipid membrane, a thick peptidoglycan layer forming its cell wall, and a smaller volume or periplasm than that of gram-negative bacteria. Gram-positive bacteria have teichoic acids and lipoids which serve as chelating agents and allow for certain types of adherence. Gram positive bacteria can be identified by one skilled in the art, for example using a gram stain test. Optionally, gram-positive bacteria can have a capsule formed by polysaccharides, or contain flagella. Gram-positive bacteria are divided into two major groups: bacilli, which contain for example *Corynebacterium, Clostridium, Listeria*, and *Bacillus*; and Cocci, which are further divided into two groups: 1) *Staphylococcus* and 2) *Streptococcus*.

In one embodiment, the microbial infection is a *Streptococcus* infection. Streptococci are spherical, chain-forming bacteria. Most Streptococci are oxidase-negative and catalase-negative. Streptococci are often facultative anaerobes, meaning they are capable of growing both aerobically and anaerobically. Over 50 species have been identified in the *Streptococcus* genus and are often found in the salivary microbiome. Streptococci are classified based on their hemolytic properties. Alpha-hemolytic species, such as S. pneumococci, cause oxidization of iron in hemoglobin molecules within red blood cells, giving it a greenish color on blood agar. Beta-hemolytic, such as *S. pyogenes*, cause complete rupture of red blood cells. On blood agar, this appears as wide areas clear of blood cells surrounding bacterial colonies. Gamma-hemolytic species cause no hemolysis. Beta-hemolytic streptococci are further classified by Lancefield grouping, a serotype describing specific carbohydrates present on the bacterial cell wall. The 20 described serotypes are named Lancefield groups A to V (excluding I and J).

In one embodiment, the *Streptococcus* infection is a Group A *Streptococcus* infection. Group A *Streptococcus* can cause infections of the throat (pharyngitis), skin and soft tissues (cellulitis), ranging from very mild conditions to severe, life-threatening diseases. Many virulence factors of Group A *Streptococcus* can influence the epigenetics of the host, and influence the disease acquired. Furthermore, persons with suppressed or compromised immune systems may be more susceptible to certain diseases caused by Group A *Streptococcus* than other persons with intact immune systems. Humans may also carry the Group A *Streptococcus* either on the skin or in the throat and show no symptoms. These carriers are less contagious than symptomatic carriers of the bacteria. Testing for non-symptomatic Group A *Streptococcus* is done for a subject at risk for infection, for example having a lowered immune system during pregnancy.

In one embodiment, the *Streptococcus* infection is a *S. pyogenes* infection. A common Group A *Streptococcus* species is *S. pyogenes*. *S. pyogenes* is a gram-positive pathogenic bacteria, and is the predominant species in Group A *Streptococcus*, causing an estimated 700 million infections a year world-wide, with a mortality rate of 25%. *S. pyogenes* has several virulence factors that enable it to attach to host tissues, evade the immune response, and spread by penetrating host tissue layers, for example a carbohydrate-bases bacterial capsule. *S. pyogenes* is the leading cause of necrotizing fasciitis, a life-threatening and highly invasive bacterial infection that may require surgical debridement or amputation. *S. pyogenes* also causes scarlet fever and rheumatic heart disease.

In one embodiment, the *Streptococcus* infection is a *Streptococcus pneumoniae* infection. *S. pneumoniae* is a leading cause of bacterial lung infections and pneumonia in neonates, the elderly and the immunocompromised.

In one embodiment, the *Streptococcus* infection is a Group B *Streptococcus* infection. Group B *Streptococcus* is a leading cause of bacterial meningitis in neonates and can cause developmental defects if infected in pregnant women.

In one embodiment, the microbial infection is a *Staphylococcus* infection. *Staphylococcus* is a genus of gram-positive bacteria. They are round bacteria (cocci) and form "grape-like" clusters. The *Staphylococcus* genus includes at least 40 species, with nine having two subspecies, one having three subspecies, and one having four subspecies. Staphylococci are often harmless and reside on skin and mucous membranes, in addition to being a small component of soil microbial flora. *Staphylococcus* species are facultative anaerobes. One important feature used to classify Staphylococci is their ability to produce coagulase. Staphylococci frequently colonize in the skin and upper respiratory tract, and are found often in mammals and birds.

In one embodiment, the *Staphylococcus* infection is a *Staphylococcus aureus* infection. *Staphylococcus aureus* (*S. aureus*) is frequently found in the nose, respiratory tract, and on the skin. It is often positive for catalase and nitrate reduction and is a facultative anaerobe that can grow without the need for oxygen. Although *S. aureus* is not always pathogenic, it is a common cause of skin infections including abscesses, respiratory infections such as sinusitis, and food poisoning. Pathogenic strains often promote infections by producing virulence factors such as potent protein toxins, and the expression of a cell-surface protein that binds and inactivates antibodies.

In one embodiment, the *Staphylococcus aureus* infection is a methicillin resistant *Staphylococcus aureus* infection.

In one embodiment, an agent described here is used to treat a *Cornyebacterium* infection, a *Listeria* infection, a *Clostridium* infection, a *Pseudomonas aerogeinosa* infection, an *Escherichia coli* infection, a *Klebsiella* infection, a *Aeromonas hydrophila* infection, or a *Neisseria gonorrhoeae* infection.

In one embodiment, a subject has a microbial infection localized to the skin, soft tissue, or subcutaneous infection. Non-limiting examples of skin, soft tissue, or subcutaneous infections include but are not limited to impetigo, bullous impetigo, scalded skin syndrome, folliculitis, furuncles, carbuncles, cellulitis, myositis, necrotizing fasciitis, streptococcal toxic shock, toxic shock syndrome, acne, and gangrene.

In one embodiment, a subject has a microbial infection localized to the respiratory tract or lung. Non-limiting examples of respiratory tract or lung infections include but are not limited to scarlet fever, bacterial respiratory tract infection, pneumonia, lethal pneumonia, acute lung injury, acute respiratory distress syndrome, bacterial sepsis, endotoxin shock, and bacterial meningitis, acute rhinosinusitis, acute bacterial rhinosinusitis, pharyngitis, bacterial tracheitis, and bronchitis.

In one embodiment, the subject further has a burn. In one embodiment, the burn comprises a microbial infection.

Non-limiting examples of bacterial infections that can be treated or prevented by administering an agent that inhibits CGRP activity, release, or receptor signaling includes but is not limited to *Aeromonas* infection, African tick bite fever, American tick bite fever (*Rickettsia parkeri* infection), *Arcanobacterium haemolyticum* infection, Bacillary angiomatosis, Bejel (endemic syphilis), Blastomycosis-like pyoderma (pyoderma vegetans), Blistering distal dactylitis, Botryomycosis, Briii-Zinsser disease, Brucellosis (Bang's disease, Malta fever, undulant fever), Bubonic plague, Bullous impetigo, Cat scratch disease (cat scratch fever, English-Wear infection, inoculation lymphoreticulosis, subacute regional lymphadenitis), Cellulitis, Chancre, Chancroid (soft chancre, ulcus molle), *Chlamydia* infection, Chronic lymphangitis, Chronic recurrent erysipelas, Chronic undermining burrowing ulcers (Meleney gangrene), Chromobacteriosis infection, Condylomata lata, Cutaneous actinomycosis, Cutaneous anthrax infection, Cutaneous *C. diphtheriae* infection (Barcoo rot, diphtheric desert sore, septic sore, Veldt sore), Cutaneous group B streptococcal infection, Cutaneous *Pasteurella* hemo/ytica infection, Cutaneous *Streptococcus iniae* infection, Dermatitis gangrenosa (gangrene of the skin), Ecthyma, Ecthyma gangrenosum, *Ehrlichiosis ewingii* infection, Elephantiasis nostras, Endemic typhus (murine typhus), Epidemic typhus (epidemic louse-borne typhus), Erysipelas (ignis sacer, Saint Anthony's fire), Erysipeloid of Rosenbach, Erythema marginatum, Erythrasma, External otitis (otitis externa, swimmer's ear), Felon, Flea-borne spotted fever, Flinders Island spotted fever, Flying squirrel typhus, Folliculitis, Fournier gangrene (Fournier gangrene of the penis or scrotum), Furunculosis (boil), Gas gangrene (clostridial myonecrosis, myonecrosis), Glanders (equinia, farcy, malleus), Gonococcemia (arthritis-dermatosis syndrome, disseminated gonococcal infection), Gonorrhea (clap) Gram-negative folliculitis, Gram-negative toe web infection, Granuloma inguinale (Donovanosis, granuloma genitoinguinale, granuloma inguinale tropicum, granuloma venereum, granuloma venereum genitoinguinale, lupoid form of groin ulceration, serpiginous ulceration of the groin, ulcerating granuloma of the pudendum, ulcerating sclerosing granuloma), Green nail syndrome, Group JK *Corynebacterium* sepsis, *Haemophilus influenzae* cellulitis, *Helicobacter* cellulitis, Hospital furunculosis, Hot tub folliculitis (*Pseudomonas aeruginosa* folliculitis), Human granulocytotropic anaplasmosis, Human monocytotropic ehrlichiosis, Impetigo contagiosa, Japanese spotted fever, Leptospirosis (Fort Bragg fever, pretibial fever, Weil's disease), Listeriosis, Ludwig's angina, Lupoid sycosis, Lyme disease (Afzelius' disease, Lyme borreliosis), Lymphogranuloma venereum (climatic bubo, Durand-Nicolas-Favre disease, lymphogranuloma inguinale, poradenitis inguinale, strumous bubo), Malakoplakia (malacoplakia), Mediterranean spotted fever (Boutonneuse fever), Melioidosis (Whitmore's disease), Meningococcemia, Missouri Lyme disease, *Mycoplasma* infection, Necrotizing fasciitis (flesh-eating bacteria syndrome), Neonatal toxic shock-like exanthematous disease, Nocardiosis, Noma neonatorum, North Asian tick typhus, Ophthalmia neonatorum, Oroya fever (Carrion's disease), Pasteurellosis, Perianal cellulitis (perineal dermatitis, streptococcal perianal disease), Periapical abscess, Pinta, Pitted keratolysis (keratolysis plantare sulcatum, keratoma plantare sulcatum, ringed keratolysis), Plague, Primary gonococcal dermatitis, Pseudomonal pyoderma, *Pseudomonas* hot-foot syndrome, Pyogenic paronychia, Pyomyositis, Q fever, Queensland tick typhus, Rat-bite fever, Recurrent toxin-mediated perineal erythema, Rhinoscleroma, *Rickettsia aeschlimannii* infection, Rickettsialpox, Rocky Mountain spotted fever, Saber shin (anterior tibial bowing), Saddle nose, *Salmonellosis*, Scarlet fever, Scrub typhus (Tsutsugamushi fever), Shigellosis, Staphylococcal scalded skin syndrome (pemphigus neonatorum, Ritter's disease), Streptococcal intertrigo, Superficial pustular folliculitis (impetigo of Bockhart, superficial folliculitis), Sycosis vulgaris (barber's itch, sycosis barbae), Syphilid, Syphilis (lues) Tick-borne lymphadenopathy, Toxic shock syndrome (streptococcal toxic shock syndrome, streptococcal toxic shock-like syndrome, toxic streptococcal syndrome), Trench fever (five-day fever, quintan fever, urban trench fever), Tropical ulcer (Aden ulcer, jungle rot, Malabar ulcer, tropical phagedena), Tularemia (deer fly fever, Ohara's disease, Pahvant Valley plague, rabbit fever), Verruga peruana, *Vibrio vulnificus* infection, Yaws (bouba, frambOsie, parangi, pian), Aquarium granuloma (fish-tank granuloma, swimming-pool granuloma), Borderline lepromatous leprosy, Borderline leprosy, Borderline tuberculoid, leprosy, Buruli ulcer (Bairnsdale ulcer, Searl ulcer, Searle's ulcer), Erythema induratum (Bazin disease), Histoid leprosy, Lepromatous leprosy, Leprosy (Hansen's disease), Lichen scrofulosorum (tuberculosis cutis lichenoides), Lupus vulgaris (tuberculosis luposa), Miliary tuberculosis (disseminated tuberculosis, tuberculosis cutis acuta generalisata, tuberculosis cutis disseminata), *Mycobacterium avium*-intracellulare complex infection, *Mycobacterium haemophilum* infection, *Mycobacterium kansasii* infection, Papulonecrotic tuberculid, Primary inoculation *tuberculosis* (cutaneous primary complex, primary tuberculous complex, tuberculous chancre), Rapid-growing *Mycobacterium* infection, Scrofuloderma (tuberculosis cutis colliquativa), Tuberculosis cutis orificialis (acute tuberculous ulcer, orificial tuberculosis), *Tuberculosis verrucosa* cutis (lupus verrucosus, prosector's wart, warty tuberculosis), Tuberculous cellulitis, Tuberculous gumma (metastatic tuberculous abscess, metastatic tuberculous ulcer), Tuberculoid leprosy, and sexually transmitted diseases caused by bacteria.

In one embodiment, the microbial infection is meningitis. Meningitis is the inflammation of brain and spinal cord membranes caused by an infection.

In one embodiment, the microbial infection is scarlet fever. Scarlet fever is a disease caused by a group A *Streptococcus* infection. Non-limiting examples of scarlet fever symptoms include sore throat, fever, and swollen lymph nodes.

In one embodiment, the microbial infection is a urinary tract infection. As used herein, a "urinary tract infection" refers to an infection of the urinary system, kidneys, bladder, or urethra.

In one embodiment, the microbial infection is a sexually transmitted disease. Sexually transmitted diseases are typically found in the reproductive tract, comprising internal and external sex organs of the male and female. Non-limiting examples of sexually transmitted diseases that comprise a microbial infection include Chancroid, *Chlamydia*, Gonorrhea, Lymphogranuloma Venereum, *Mycoplasma Genitalium*, Nongonococcal Urethritis, Pelvic Inflammatory Disease, Syphilis, vaginitis, bacterial vaginitis, yeast vaginitis, yeast infection.

In one embodiment, the infection is fungal. Non-limiting examples of infectious fungi causing fungal infections that are contemplated for use with the combinatorial therapeutic compositions and methods described herein include, but are not limited to: *Candida* spp.; *Cryptococcus* spp.; *Aspergillus* spp.; *Microsporum* spp.; *Trichophyton* spp.; *Epidermophyton* spp.; *Trichosporon* spp.; *Tinea versicolor; Tinea barbae; Tinea corporis; Tinea cruris; Tinea manuum; Tinea pedis; Tinea unguium; Tinea faciei; Tinea imbricate; Tinea incognito; Epidermophyton floccosum; Microsporum canis; Microsporum audouinii; Trichophyton interdigitale; Trichophyton mentagrophytes; Trichophyton tonsurans; Trichophyton schoenleini; Trichophyton rubrum; Hortaea werneckii; Piedraia hortae; Malasserzia furfur; Coccidioides immitis; Coccidioides posadasii; Histoplasma capsulatum; Histoplasma duboisii; Lacazia loboi; Paracoccidioides brasiliensis; Blastomyces dermatitidis; Sporothrix schenckii; Penicillium marneffei; Candida albicans; Candida glabrata; Candida tropicalis; Candida lusitaniae; Candida jirovecii; Exophiala jeanselmei; Fonsecaea pedrosoi; Fonsecasea compacta; Phialophora verrucosa; Geotrichum candidum; Pseudallescheria boydii; Rhizopus oryzae; Muco indicus; Absidia corymbifera; Syncepiasastrum racemosum; Basidiobolus ranarum; Conidiobolus coronatus;*

*Conidiobolus incongruous; Cryptococcus neoformans; Enterocytozoan bieneusi; Encephalitozoon intestinalis*; and *Rhinosporidium seeberi.*

Non-limiting examples of disorders/diseases caused by fungal infections or toxins produced during fungal infections, and for which the compositions and methods described herein are applicable in various aspects and embodiments, include, but are not limited to, infection of a surface wound or burn; infection of a mucosal surface; respiratory infection; infections of the eyes, ears, nose, or throat; or infection of an intestinal pathogen. In other embodiments, the fungal infection is an infection of soft tissue or skin, such as a superficial mycosis; a cutaneous mycosis; a subcutaneous mycosis; a vaginal mycosis; a systemic mycosis; or is an infected wound or burn.

In one embodiment, the microbial infection is chronic. In one embodiment, the microbial infection is acute. An acute infection is a short term infection, persisting less than 2 weeks, while a chronic infection is long term, and persists longer than two weeks. The method for treating an acute infection can be the same method used to treat a chronic infection. In contrast, a different method can be used to treat an acute and chronic infection.

In some embodiments of any of the aspects, the microbial infection is a systemic infection. As described herein, "systemic infection" refers to an infection that has spread throughout the body, for example, an infection that is present in the blood. Non-limiting examples of systemic infections include bacterial sepsis and endotoxin shock.

Antibiotic Resistance

The emergence of antibiotic-resistant strains of *S. aureus* such as methicillin-resistant *S. aureus* (MRSA) is a worldwide problem in clinical medicine. In one embodiment, the microbial infection has a bacterium which is resistant to at least one or more antibiotics. As used herein, "resistant" refers to a bacterium that is unaffected, e.g., can tolerate (e.g., continue to grow and divide) the presence of a given antibiotic. A "resistant" bacterium can continue to grow and divide at a slower rate in the presence of an antibiotic as compared to the growth in the division of the bacterium that is not in the presence of a given antibiotic. In one embodiment, a microbial infection comprises a bacterium which is resistant to multiple antibiotics. In one embodiment, the bacterium is resistant to at least 1, 2, 3, 4, 5, 6, 7, 8, 9, 10, or more antibiotics.

In one embodiment, the infection has *S. aureus* that is resistant to antibiotics. In one embodiment, *S. aureus* is resistant to methicillin. Methicillin-resistant *S. aureus* is commonly found in settings with large populations living within close proximity, for example a college dormitory, prison, and hospitals. A non-limiting example of another antibiotic *S. aureus* has developed resistance to is Vancomycin.

Non-limiting examples of bacteria that have adapted a resistance to current standard of care treatments include Methicillin-resistant *Staphylococcus aureus*, vancomycin-resistant Enterococci, vancomycin-resistant *Staphylococcus aureus*, drug-resistant *Streptococcus pneumoniae*, Drug-Resistant *Mycobacterium tuberculosis*, carbapenem-resistant Enterobacteriaceae, Multiple drug-resistant *Pseudomonas Aeruginosa*, extended-spectrum beta-lactamase (ESBL)-producing Enterobacteriaceae, and drug-resistant *Neisseria gonorrhoeae.*

Antibiotic resistance can be assessed by a skilled practicioner using anti microbial susceptibility assays. Antimicrobial susceptibility testing is used to determine the effectiveness of particular antimicrobials against particular microbes, whether the microbes are resistant to selected antimicrobials, and/or to identify antimicrobial resistance patterns.

Identification of Microbial Infection

In one embodiment, a subject is diagnosed with having a microbial infection prior to administration of an agent described herein. There are various tests known to those skilled in the art that are performed in a laboratory to establish or confirm the diagnosis of a microbial infection, as well as to identify the causative microbial species. Culturing of the microbial species with antimicrobial sensitivity testing is considered the gold standard laboratory test. Skin samples can be collected in the following ways: 1) dry sterile cotton-tip swab rubbed on the suspicious skin site, e.g., blistered or dry skin lesions or pustules; 2) moist swab taken from a mucosal surface, such as inside the mouth; 3) aspiration of fluid/pus from a skin lesion using a needle and syringe; and 4) skin biopsy: a small sample of skin removed under local anesthetic. Culturing of, e.g., bacteria is most commonly done by brushing the skin swab on sheep blood agar plates and exposing them to different conditions. The species of microbe that grow depend on the medium used to culture the specimen, the temperature for incubation, and the amount of oxygen available. An obligate aerobe can only grow in the presence of oxygen, while an obligate anaerobe cannot grow at all in the presence of oxygen.

A gram stain uses a series of stains on a sample, followed by inspection under a light microscope to detect and identify bacteria as gram positive or gram negative. A gram stain can be done on the original sample, but it is usually done on cultured bacteria after transferring a colony of bacteria from the agar plate to a glass microscope slide. A gram-positive bacterium appears purple due to crystal violet dye adhering to the cell wall. A gram-negative bacterium appears red due to the red dye used to counterstain. The gram stain also identifies the bacterium's shape and behavior; cocci are round in shape, bacilli are rod shaped, and some bacteria form clusters versus chains.

The coagulase test detects coagulase, which is an enzyme produced by certain bacteria that converts fibrinogen to fibrin and is observed as clumping of cells in plasma. The coagulase test differentiates coagulase-positive *Staphylococcus aureus* from coagulase-negative staphylococci.

The catalase test detects catalase, an enzyme that degrades hydrogen peroxide into hydrogen and oxygen. The bacterial sample is added to a test tube of hydrogen peroxide. The production of bubbles (oxygen) indicates a positive result. The catalase test differentiates catalase-positive staphylococci and micrococci from catalase-negative streptococci.

Blood tests require a sample of blood accessed by a needle from a vein. Non-limiting examples of tests for bacterial infection include: 1) full blood count, bacterial infection often raises the white cell count with increased neutrophils (neutrophilia); 2) C-reactive protein (CRP), CRP is often elevated>50 in serious bacterial infections; 3) procalcitonin, a marker of generalized sepsis due to bacterial infection, 3) serology, tests 10 days apart to determine immune response to a particular organism; 4) Rapid Plasma Reagin (RPR) test, if syphilis is suspected; and 4) blood culture to detect bacteria if high fever>100.4° F.

Polymerase chain reaction (PCR) involves isolating and amplifying lengths of bacterial DNA from a sample of skin, blood or other tissue. The DNA is compared to bacterial DNA from known organisms, thus identifying the species. This test is useful for slow-growing bacteria such as anaerobic bacteria and mycobacteria (*tuberculosis* and atypical mycobacteria), or bacteria that cannot be cultured by standard methods.

Agents

In one embodiment, an agent inhibits CGRP activity. In one embodiment, an agent inhibits CGRP release. In another embodiment, an agent inhibits CGRP receptor signaling.

In one aspect, an agent that inhibits CGRP (e.g., CGRP activity, release, or receptor signaling) is administered to a subject in need thereof to treat a microbial infection.

In another aspect, an agent that inhibits CGRP (e.g., CGRP activity, release, or receptor signaling) is administered to a subject in need thereof to prevent a microbial infection.

An agent can inhibit e.g., the transcription, or the translation of CGRP in the cell. An agent can inhibit the activity or alter the activity (e.g., such that the activity no longer occurs, or occurs at a reduced rate) of CGRP in the cell (e.g., CGRP's expression).

In one embodiment, an agent that inhibits the level and/or activity of CGRP by at least 10%, by at least 20%, by at least 30%, by at least 40%, by at least 50%, by at least 60%, by at least 70%, by at least 80%, by at least 90%, by at least 100% or more as compared to an appropriate control. As used herein, an "appropriate control" refers to the level and/or activity of CGRP prior to administration of the agent, or the level and/or activity of CGRP in a population of cells that was not in contact with the agent.

In one embodiment, an agent that inhibits the release of CGRP by at least 10%, by at least 20%, by at least 30%, by at least 40%, by at least 50%, by at least 60%, by at least 70%, by at least 80%, by at least 90%, by at least 100% or more as compared to an appropriate control. As used herein, an "appropriate control" refers to the release of CGRP prior to administration of the agent, or the release of CGRP in a population of cells that was not in contact with the agent.

In one embodiment, an agent that inhibits the receptor signaling of CGRP by at least 10%, by at least 20%, by at least 30%, by at least 40%, by at least 50%, by at least 60%, by at least 70%, by at least 80%, by at least 90%, by at least 100% or more as compared to an appropriate control. As used herein, an "appropriate control" refers to the receptor signaling of CGRP prior to administration of the agent, or the receptor signaling of CGRP in a population of cells that was not in contact with the agent.

The agent may function directly in the form in which it is administered. Alternatively, the agent can be modified or utilized intracellularly to produce something which inhibits CGRP (e.g., CGRP activity, release, or receptor signaling), such as introduction of a nucleic acid sequence into the cell and its transcription resulting in the production of the nucleic acid and/or protein inhibitor of CGRP within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property or can be identified from a library of diverse compounds.

In one embodiment, the agent that is a botulinum neurotoxin. Botulinum neurotoxins (BoNTs), also known as botulinum toxin, is a neurotoxic protein produced by the bacterium *Clostridium botulinum* and related species (e.g., other *Clostridium* species). It functions by preventing the release of the neurotransmitter acetylcholine from axon endings at the neuromuscular junction, leading to flaccid paralysis and reduced muscle tone. Infection with the bacterium causes botulism, an often fatal illness that may be acquired, for example, as a foodborne illness. However, while the toxin is acutely lethal at an LD50 of 1.3-2.1 ng/kg (intramuscularly), sub-lethal doses have been developed for use in fields such as cosmetics (e.g., Botox®).

Botulinum toxin is released from the bacterium as a single polypeptide and is proteolytically cleaved into a 100 kDa heavy chain and a 50 kDa light chain, which are joined by a disulfide bond. The heavy domain mediates binding to presynaptic nerve terminals while the light chain contains a metalloprotease that cleaves host SNARE proteins (e.g., SNAP-25), which are responsible for neurotransmitter vesicle fusion. Cleavage of SNAP-25 abrogates the release of neuropeptides such as CGRP, or neurotransmitters such as acetylcholine from axon endings. The toxin exists in seven serotypes: BoNT/A, BoNT/B, BoNT/C, BoNT/D, BoNT/E, BoNT/F, and BoNT/G. Each serotype has a different tertiary structure, primary sequence, and distinct receptors and/or SNARE targets. The botulinum toxins used in this invention may be modified, such as with a chemical moiety (e.g., peptide, sugar, nucleic acid, toxin, ligand, linker, polymer or targeting factor) and may contain amino acid substitutions such that the peptide still has significant homology to a BoNT (e.g., at least 50%, 60%, 70%, 80%, 90%, 95%, 98%, 99%, 99.5%, or 100% homology). For example, the receptor binding moieties of BoNTs may be engineered so that they target specific or different cell-types, or a particular subset of neurons. This may be achieved, for example, by chemical modification with a short peptide or a receptor ligand. Furthermore, any full-length botulinum neurotoxin polypeptide or fragment thereof may be used with the methods described herein.

Modified BoNTs are described, for example in US Publication No. 2011/0294747, the disclosure of which is herein incorporated by reference. Other examples of modified or engineered BoNTs are described, for example, in U.S. Pat. No. 9,598,685, U.S. Provisional Application Nos. 62/138, 818, 62/336,958, 62/410,558, and 62/378,967, Taiwanese Publication No. 105109524, and PCT Publication No. WO2016/154534, the disclosures of which are herein incorporated by reference.

Botulinum toxins may be modified with oligopeptides (e.g., daxibotulinumtoxinA), as described in PCT Publication Nos. WO2017/075468 and WO2006/094193, or pegylated, as described in U.S. Pat. No. 8,003,601, the disclosures of each of which are herein incorporated by reference as they pertain to modified botulinum toxins. Additionally, chimeric toxins may be used, such as those described in PCT Publication No. WO2005/068494, the disclosure of which is herein incorporated by reference. Furthermore, the botulinum toxins of the present invention may be modified as described in Pickett et al. ("Towards new uses of botulinum toxin as a novel therapeutic tool." Toxins 3.1 (2011): 63-81), the disclosure of which is herein incorporated in its entirety.

In one embodiment, the botulinum neurotoxins is any serotype (e.g., botulinum neurotoxin serotype A, botulinum neurotoxin serotype B, botulinum neurotoxin serotype C, botulinum neurotoxin serotype D, botulinum neurotoxin serotype E, botulinum neurotoxin serotype F, and botulinum neurotoxin serotype G). The toxin may be chemically modified, such as with a peptide or a receptor ligand. Other modified botulinum neurotoxins suitable for use in the methods of the invention are described herein.

In one embodiment, the agent is an inhibitor of a nociceptive neuron. In one embodiment, nociception is inhibited via the inhibition of TRPV1 expressing neurons. In one embodiment, the agent that inhibits TRPV1 neurons is Resiniferatoxin (RTX). RTX, an analog of capsaicin, activates TRPV1 in a sub-population of primary afferent sensory neurons involved in nociception, resulting in excess calcium influx. RTX-mediated activation of TRPV1 and subsequent calcium influx can result in the denervation of the neuron due to nerve ending death when a high enough dose is administered. In one embodiment, an RTX analog is administered to a subject in need thereof to treat or prevent a microbial infection. It is contemplated that RTX will be administered in an amount sufficient to induce denervation and inhibit CGRP release. Uses thereof, dosages of RTX that cause denervation, and RTX analogs are further described in, e.g., U.S. Pat. No. 5,290,816; U.S. Application No. US2008/013,964; U.S. Application No. US2003/027,064; U.S. Application No. US2009/0,209,633; which are incorporated herein by reference in their entireties.

In some embodiments of any of the aspects, an agent that inhibits CGRP is a competitive inhibitor of CGRP. In some embodiments of any of the aspects, the agent is an antagonist of CGRP receptors. Exemplary CGRP receptor antagonists are further described in Patent No.: WO2007/047577; CA2,378,428; WO2007/141275; and CA2,654,047; which are incorporated herein by reference in their entireties.

In some embodiments, the agent that inhibits CGRP lowers expression of CGRP. One skilled in the art can determine if the levels of CGRP are reduced, for example by detecting CGRP levels with a CGRP antibody (ab47027, Abeam; Cambridge, Mass.) via western blotting or PCR-based assays, and comparing CGRP protein or mRNA levels, respectively, prior to and after administration of the agent.

In some embodiments, the agent interferes with CGRP function. One skilled in the art can assess CGRP function, for example by assessing the activity of downstream targets.

In one embodiment, the agent that inhibits CGRP (e.g., CGRP activity, release, or receptor signaling) is an anti-CGRP antibody or antibody reagent.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, CDRs, and domain antibody (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

Exemplary anti-CGRP antibodies are described in Patent Application No.: WO 2012/162,257, which is incorporated herein by reference in its entirety. In one embodiment, the anti-CGRP antibody is ALD403, LY2951742, AMG 334, or TEV-48125. These therapeutic anti-CGRP antibodies have all been shown to be effective in treating and preventing migraines in patients during clinical trials, with little to no side effects presenting in the patients. In some embodiments of any of the aspects, the antibody or antibody reagent can compete for binding of CGRP or the CGRP receptor with an antibody of Table 1.

Table 1 shows the targets of the known CGRP antibodies.

TABLE 1

Known CGRP therapeutic antibodies.

| Name | Target | Manufacturer | Use |
| --- | --- | --- | --- |
| ALD403 | CGRP with humanized antibody | Alder Biopharmaceuticals | Episodic and chronic migraines. |
| LY2951742 | CGRP with humanized antibody | Eli Lily Pharmaceuticals | |
| AMG 334 | CGRP receptor with humanized antibody | Amgen | |
| TEV-48125 | CGRP with fully humanized antibody | Teva Pharmaceuticals | |

In one embodiment, the antibody or antibody reagent binds to an amino acid sequence that corresponds to the amino acid sequence encoding an CGRP isoform, e.g., alpha-CGRP or beta-CGRP (SEQ ID NO: 1 or 2).

SEQ ID NO: 1 is an amino acid sequence encoding Alpha-CGRP.

```
                                         (SEQ ID NO: 1)
Ala-Cys-Asp-Thr-Ala-Thr-Cys-Val-Thr-His-Arg-Leu-

Ala-Gly-Leu-Leu-Ser-Arg-Ser-Gly-Gly-Val-Val-Lys-

Asn-Asn-Phe-Val-Pro-Thr-Asn-Val-Gly-Ser-Lys-Ala-

Phe
```

SEQ ID NO: 2 is an amino acid sequence encoding Beta-CGRP.

```
                                         (SEQ ID NO: 2)
Ala-Cys-Asn-Thr-Ala-Thr-Cys-Val-Thr-His-Arg-Leu-

Ala-Gly-Leu-Leu-Ser-Arg-Ser-Gly-Gly-Met-Val-Lys-

Ser-Asn-Phe-Val-Pro-Thr-Asn-Val-Gly-Ser-Lys-Ala-

Phe
```

In another embodiment, the anti-CGRP antibody or antibody reagent binds to an amino acid sequence that comprises the sequence of SEQ ID NO: 1 or 2; or binds to an amino acid sequence that comprises a sequence with at least 80%, at least 85%, at least 90%, at least 95%, at least 96%, at least 97%, at least 98%, at least 99% or greater sequence identity to the sequence of SEQ ID NO: 1 or 2. In one embodiment, the anti-CGRP antibody or antibody reagent binds to an amino acid sequence that comprises the entire sequence of SEQ ID NO: 1 or 2. In another embodiment, the antibody or antibody reagent binds to an amino acid sequence that comprises a fragment of the sequence of SEQ ID NO: 1 or 2, wherein the fragment is sufficient to bind its target, e.g., CGRP, and result in a reduction in the severity of the microbial infection.

In one embodiment, the agent is a compound that inhibits CGRP receptors. In some embodiments of any of the aspects, an agent can be a small molecule inhibitor of CGRP receptors. Non-limiting examples of a small molecule inhibitor of CGRP receptors are BIBN4096, olcegepant, telcagepant, ubrogepant, tacagepant, Avitriptan, eletriptan, naratriptan, rizatriptan, sumatriptan, zolmitriptan, galcanezumab, eptinezumab, erenumab, rimegepant (Zydis), NXN-118, fremanezumab, (piperidin-1-yl)piperidin-1-yl) propan-2-yl)piperidine-1-carboxamide (BMS 694153), atogepant, and MK-3207.

In one embodiment, the agent inhibits the CGRP receptor. In one embodiment, the CGRP receptor is RAMP1/CALCRL. The protein encoded by the Ramp1 gene is a member of the RAMP family of single-transmembrane-domain proteins, called receptor calcitonin activity modifying proteins (RAMPs). RAMPs are type I transmembrane proteins with an extracellular N terminus and a cytoplasmic C terminus. RAMPs are required to transport calcitonin-receptor-like receptor (CALCRL) to the plasma membrane. CALCRL, a receptor with seven transmembrane domains, can function as either a calcitonin gene-related peptide (CGRP) receptor or an adrenomedullin receptor, depending on which members of the RAMP family are expressed. In combination with the RAMP1 protein, CALCRL functions as the CGRP receptor.

CALCRL sequences are known for a number of species, e.g., human CALCRL (NCBI Gene ID: 10203) and mRNA (NCBI Ref Seq NM_001271751). CALCRL can refer to human CALCRL, including naturally occurring variants and alleles thereof. In some embodiments of any of the aspects, e.g., in veterinary applications, CALCRL can refer to the CALCRL of, e.g., chimpanzee, monkey, wolf, cow, horse, and the like. Homologs and/or orthologs of human CALCRL are readily identified for such species by one of skill in the art, e.g., using the NCBI ortholog search function or searching available sequence data for a given species for sequence similar to a reference CALCRL sequence.

RAMP1 sequences are known for a number of species, e.g., human RAMP1 (NCBI Gene ID: 10267) and mRNA (NCBI Ref Seq NM_001308353.1). RAMP1 can refer to human RAMP1, including naturally occurring variants and alleles thereof. In one embodiment, e.g., in veterinary applications, RAMP1 can refer to the RAMP1 of, e.g., chimpanzee, monkey, wolf, cow, and horse and the like. Homologs and/or orthologs of human RAMP1 are readily identified for such species by one of skill in the art, e.g., using the NCBI ortholog search function or searching available sequence data for a given species for sequence similar to a reference RAMP1 sequence.

In one embodiment, the agent is a nucleic acid that encodes an inhibitor of CGRP, e.g., human $CGRP_{8-37}$ peptide. In one embodiment, the agent is a polypeptide that competitively inhibits CGRP binding to its receptor. In some embodiments of any of the aspects, the polypeptide is human $CGRP_{8-37}$ peptide, or a mutein thereof. In one embodiment, the polypeptide consists of or consists essentially of human $CGRP_{8-37}$ or a mutein thereof. Muteins of the human $CGRP_{1-7}$ peptide, including have been shown to inhibit CGRP activity and are described in U.S. Pat. No. 7,030,081, which is incorporated herein by reference in its entirety.

In one embodiment, the agent that inhibits CGRP (e.g., CGRP activity, release, or receptor signaling) is an antisense oligonucleotide. As used herein, an "antisense oligonucleotide" refers to a synthesized nucleic acid sequence that is complementary to a DNA or mRNA sequence, such as that of a microRNA. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under cellular conditions to a gene, e.g., CGRP. Thus, oligonucleotides are chosen that are sufficiently complementary to the target, i.e., that hybridize sufficiently well and with sufficient specificity in the context of the cellular environment, to give the desired effect. For example, an antisense oligonucleotide that inhibits CGRP may comprise at least 5, at least 10, at least 15, at least 20, at least 25, at least 30, or more bases complementary to a portion of the coding sequence of a human CGRP isoform, e.g., Alpha-CGRP or Beta-CGRP (e.g., SEQ ID NO: 3 or 4), respectively.

SEQ ID NO: 3 is a nucleic acid encoding Alpha-CGRP.

(SEQ ID NO: 3)

```
001    gcctctctga tccaagccac ctcccgccag agaggtgtca tgggcttcca aaagttctcc 061    cccttcctgg ctctcagcat cttggtcctg ttgcaggcag gcagcctcca tgcagcacca 121    ttcaggtctg ccctggagag cagcccagca gacccggcca cgctcagtga ggacgaagcg 181    cgcctcctgc tggctgcact ggtgcaggac tatgtgcaga tgaaggccag tgagctggag 241    caggagcaag agagagaggg ctccagcctg gacagcccca gatctaagcg gtgcggtaat 301    ctgagtactt gcatgctggg cacatacacg caggacttca acaagtttca cacgttcccc 361    caaactgcaa ttggggttgg agcacctgga aagaaaaggg atatgtccag cgacttggag 421    agagaccatc gccctcataa tcattgccca gaagagagcc tgtgacactg ccacctgtgt 481    gactcatcgg ctggcaggct tgctgagcag atcaggggggt gtggtgaaga acaactttgt 541    gcccaccaat gtgggttcca aagcctttgg caggcgccgc agggaccttc aagcctgagc
```

```
-continued
601    agctgaatga ctcaagaagg tcacaataaa gctgaactcc ttttaatgtg taatgaaagc 661    aatttgtagg aaaggctcca t
```

SEQ ID NO: 4 is a nucleic acid encoding Beta-CGRP.

```
                                                              (SEQ ID NO: 4)
001    gcaggtgtgg tgttcatccc gggtcgaccg gccgctcgcg ctgccctgaa actctagtcg 061    ccagagaggc ggcatgggtt tccggaagtt ctcccccttc ctggctctca gtatcttggt 121    cctgtaccag gcgggcagcc tccaggcggc gccattcagg totgocctgg agagcagccc 181    agacccggcc acactcagta aagaggacgc gcgcctcctg ctggctgcac tggtgcagga 241    ctatgtgcag atgaaggcca gtgagctgaa gcaggagcag gagacacagg gctccagctc 301    cgctgcccag aagagagcct gcaacactgc cacctgtgtg actcatcggc tggcaggctt 361    gctgagcaga tcagggggca tggtgaagag caacttcgtg cccaccaatg tgggttccaa 421    agcctttggc aggcgccgca gggaccttca agcctgagca gatgaatgac tccaggaaga 481    aggttatcat gaaactgaac tcaccatttc tattaatttc tgttggtaag aacttggtga 541    gaatgccccg tggaagatac acatgtttgc atcctaagat actgaaaaaa gggcaccttt 601    gtcacttgaa aggaatgaaa ctgaatgcaa aataagctaa ttccatattt gctgtgcatc 661    atttttatat ttaattctat gtccagtaaa agtgatggca tctctcattg acttatctgg 721    tagcaaactg gttctttcgg agccatcctg ttgatcatgc agctccacca aaccttaggg 781    ggacgtgaaa tcactgcctg ttgtggtctc cgaggacaca tggtaatggt gatgctgtgc 841    cttgttatct aagaacatga ttgtataatt tgtttaagaa aatgtcaata ttgtgccatt 901    tgtgaacttc atcaagatta aaagcatatt ttgggtacat ttgtttcaaa accttggtga 961    tgcattacaa cttgttttct tatgtaataa taatgatgat gatgatgata ataataaata 1021   tttttgagtg c
```

In one embodiment, the agent is an inhibitory nucleic acid. Inhibitors of the expression of a given gene can be an inhibitory nucleic acid. In some embodiments of any of the aspects, the inhibitory nucleic acid is an inhibitory RNA (iRNA). Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target.

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of the expression and/or activity of a target, e.g. CGRP. In certain embodiments, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA.

In one embodiment, the agent is siRNA that inhibits CGRP. In one embodiment, the agent is shRNA that inhibits CGRP. In one embodiment, the agent is miRNA that inhibits CGRP.

In one embodiment, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments of any of the aspects, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

In one embodiment, CGRP is depleted from the cell's genome using any genome editing system including, but not limited to, zinc finger nucleases, TALENS, meganucleases, and CRISPR/Cas systems. In one embodiment, the genomic editing system used to incorporate the nucleic acid encoding one or more guide RNAs into the cell's genome is not a CRISPR/Cas system; this can prevent undesirable cell death in cells that retain a small amount of Cas enzyme/protein. It is also contemplated herein that either the Cas enzyme or the sgRNAs are each expressed under the control of a different inducible promoter, thereby allowing temporal expression of each to prevent such interference.

When a nucleic acid encoding one or more sgRNAs and a nucleic acid encoding an RNA-guided endonuclease each need to be administered in vivo, the use of an adenovirus associated vector (AAV) is specifically contemplated. Other vectors for simultaneously delivering nucleic acids to both components of the genome editing/fragmentation system (e.g., sgRNAs, RNA-guided endonuclease) include lentiviral vectors, such as Epstein Barr, Human immunodeficiency virus (HIV), and hepatitis B virus (HBV). Each of the components of the RNA-guided genome editing system (e.g., sgRNA and endonuclease) can be delivered in a separate vector as known in the art or as described herein.

In one embodiment, the agent inhibits CGRP by RNA inhibition. Inhibitors of the expression of a given gene can be an inhibitory nucleic acid. In some embodiments of any of the aspects, the inhibitory nucleic acid is an inhibitory RNA (iRNA). The RNAi can be single stranded or double stranded.

The iRNA can be siRNA, shRNA, endogenous microRNA (miRNA), or artificial miRNA. In one embodiment, an iRNA as described herein effects inhibition of the expression and/or activity of a target, e.g. CGRP. In some embodiments of any of the aspects, the agent is siRNA that inhibits CGRP. In some embodiments of any of the aspects, the agent is shRNA that inhibits CGRP.

One skilled in the art would be able to design siRNA, shRNA, or miRNA to target CGRP, e.g., using publically available design tools. siRNA, shRNA, or miRNA is commonly made using companies such as Dharmacon (Layfayette, Colo.) or Sigma Aldrich (St. Louis, Mo.).

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions The RNA of an iRNA can be chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference.

In one embodiment, the agent is miRNA that inhibits CGRP. microRNAs are small non-coding RNAs with an average length of 22 nucleotides. These molecules act by binding to complementary sequences within mRNA molecules, usually in the 3' untranslated (3'UTR) region, thereby promoting target mRNA degradation or inhibited mRNA translation. The interaction between microRNA and mRNAs is mediated by what is known as the "seed sequence", a 6-8-nucleotide region of the microRNA that directs sequence-specific binding to the mRNA through imperfect Watson-Crick base pairing. More than 900 microRNAs are known to be expressed in mammals. Many of these can be grouped into families on the basis of their seed sequence, thereby identifying a "cluster" of similar microRNAs. A miRNA can be expressed in a cell, e.g., as naked DNA. A miRNA can be encoded by a nucleic acid that is expressed in the cell, e.g., as naked DNA or can be encoded by a nucleic acid that is contained within a vector.

The agent may result in gene silencing of the target gene (e.g., CGRP), such as with an RNAi molecule (e.g. siRNA or miRNA). This entails a decrease in the mRNA level in a cell for a target by at least about 5%, about 10%, about 20%, about 30%, about 40%, about 50%, about 60%, about 70%, about 80%, about 90%, about 95%, about 99%, about 100% of the mRNA level found in the cell without the presence of the agent. In one preferred embodiment, the mRNA levels are decreased by at least about 70%, about 80%, about 90%, about 95%, about 99%, about 100%. One skilled in the art will be able to readily assess whether the siRNA, shRNA, or miRNA effective target e.g., CGRP, for its downregulation, for example by transfecting the siRNA, shRNA, or miRNA into cells and detecting the levels of a gene or protein (e.g., CGRP) found within the cell via PCR-based assay or western blotting, respectively.

An agent described herein may be contained in and thus further include a vector. Many such vectors useful for transferring exogenous genes into target mammalian cells are available. The vectors may be episomal, e.g. plasmids, virus-derived vectors such as cytomegalovirus, adenovirus, etc., or may be integrated into the target cell genome, through homologous recombination or random integration, e.g. retrovirus-derived vectors such as MMLV, HIV-1, ALV, etc. In some embodiments, combinations of retroviruses and an appropriate packaging cell line may also find use, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "expression vector" refers to a vector that directs expression of an RNA or polypeptide (e.g., a CGRP inhibitor) from nucleic acid sequences contained therein linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

Integrating vectors have their delivered RNA/DNA permanently incorporated into the host cell chromosomes. Non-integrating vectors remain episomal which means the nucleic acid contained therein is never integrated into the host cell chromosomes. Examples of integrating vectors include retroviral vectors, lentiviral vectors, hybrid adenoviral vectors, and herpes simplex viral vector.

One example of a non-integrative vector is a non-integrative viral vector. Non-integrative viral vectors eliminate the risks posed by integrative retroviruses, as they do not incorporate their genome into the host DNA. One example is the Epstein Barr oriP/Nuclear Antigen-1 ("EBNA1") vector, which is capable of limited self-replication and known to function in mammalian cells. As containing two elements from Epstein-Barr virus, oriP and EBNA1, binding of the EBNA1 protein to the virus replicon region oriP maintains a relatively long-term episomal presence of plasmids in mammalian cells. This particular feature of the oriP/EBNA1 vector makes it ideal for generation of integration-free iPSCs. Another non-integrative viral vector is adenoviral vector and the adeno-associated viral (AAV) vector.

Another non-integrative viral vector is RNA Sendai viral vector, which can produce protein without entering the nucleus of an infected cell. The F-deficient Sendai virus vector remains in the cytoplasm of infected cells for a few passages, but is diluted out quickly and completely lost after several passages (e.g., 10 passages).

Another example of a non-integrative vector is a minicircle vector. Minicircle vectors are circularized vectors in which the plasmid backbone has been released leaving only the eukaryotic promoter and cDNA(s) that are to be expressed.

As used herein, the term "viral vector" refers to a nucleic acid vector construct that includes at least one element of viral origin and has the capacity to be packaged into a viral vector particle. The viral vector can contain a nucleic acid encoding a polypeptide as described herein in place of non-essential viral genes. The vector and/or particle may be utilized for the purpose of transferring nucleic acids into cells either in vitro or in vivo. Numerous forms of viral vectors are known in the art.

Compositions

One aspect of the invention is a composition for the treatment of a microbial infection comprising any of the agents described herein. In one embodiment, any composition described herein further comprises a second therapeutic agent. In one embodiment, the second therapeutic agent is an antibiotic or antimicrobial agent.

One aspect of the invention is a composition for the prevention of a microbial infection comprising any of the agents described herein. In one embodiment, any composition described herein further comprises a second therapeutic agent. In one embodiment, the second therapeutic agent is an antibiotic or antimicrobial agent.

The pharmaceutical composition can be formulated with a pharmaceutically acceptable carrier or excipient. A pharmaceutically acceptable carrier or excipient refers to a carrier (e.g., carrier, media, diluent, solvent, vehicle, etc.) which does not significantly interfere with the biological activity or effectiveness of the active ingredient(s) of a pharmaceutical composition and which is not excessively toxic to the host at the concentrations at which it is used or administered. Other pharmaceutically acceptable ingredients can be present in the composition as well. Suitable substances and their use for the formulation of pharmaceutically active compounds are well-known in the art (see, for example, Remington: The Science and Practice of Pharmacy. 21st Edition. Philadelphia, Pa. Lippincott Williams & Wilkins, 2005, for additional discussion of pharmaceutically acceptable substances and methods of preparing pharmaceutical compositions of various types).

A pharmaceutical composition is typically formulated to be compatible with its intended route of administration. For topical application, a pharmaceutical composition may be formulated in a suitable ointment, lotion, gel, or cream containing the active components suspended or dissolved in one or more pharmaceutically acceptable carriers suitable for use in such compositions. For some applications, the composition is formulated as a solid (e.g., lyophilized), liquid, gel, or hydrogel and may contain additives such as surfactants, buffers (e.g., succinate), salts (e.g., sodium chloride), polymers (e.g., polysaccharides, hyaluronic acid), proteins (e.g., albumin, human serum albumin), or amino acids (e.g., methionine).

Examples of BoNT formulations are described, for example, in U.S. Pat. Nos. 9,629,904; 9,480,731; 9,220,780; 9,144,692; 9,050,336; 9,044,477; 8,617,568; 8,216,591; and 8,713,138, and US Publication Nos. 20160051646; 20140302008; 20150297684; 20140302007; 20120141532; 20120039862; and 20160256532, the disclosures of each of which are herein incorporated by reference as they pertain to BoNT formulations.

Combination Therapy

In one embodiment, the agent described herein is used as a monotherapy. In one embodiment, the agents described herein can be used in combination with other known agents and therapies for a microbial infection. Administered "in combination," as used herein, means that two (or more) different treatments are delivered to the subject during the course of the subject's affliction with the infection, e.g., the two or more treatments are delivered after the subject has been diagnosed with the infection and before the infection has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The agents described herein and the at least one additional therapy can be administered simultaneously, in the same or in separate compositions, or sequentially. For sequential administration, the agent described herein can be administered first, and the additional agent can be administered second, or the order of administration can be reversed. The agent and/or other therapeutic agents, procedures or modalities can be administered during periods of active disorder, or during a period of remission or less active disease. The agent can be administered before another treatment, concurrently with the treatment, post-treatment, or during remission of the disorder.

In some embodiments, the methods and compositions described herein further comprise administering a second therapeutic agent to a subject. In one embodiment, the second therapeutic agent is an antifungal. In one embodiment, the second therapeutic agent is an antibiotic. Examples of suitable antibiotics include, but are not limited to Aknilox, Ambisome, Amoxycillin, Ampicillin, Augmentin, Avelox, Azithromycin, Bactroban, Betadine, Betnovate, Blephamide, Cefaclor, Cefadroxil, Cefdinir, Cefepime, Cefix, Cefixime, Cefoxitin, Cefpodoxime, Cefprozil, Cefuroxime, Cefzil, Cephalexin, Cephazolin, Ceptaz, Chloramphenicol, Chlorhexidine, Chloromycetin, Chlorsig, Ciprofloxacin, Clarithromycin, Clindagel, Clindamycin, Clindatech, Cloxacillin, Colistin, Co-trimoxazole, Democlocycline, Diclocil, Dicloxacillin, Doxycycline, Duricef, Erythromycin, Flamazine, Floxin, Framycetin, Fucidin, Furadantin, Fusidic, Gatifloxacin, Gemifloxacin, Gemifloxacin, llosone, Iodine, Levaquin, Levofloxacin, Lomefloxacin, Maxaquin, Mefoxin, Meronem, Minocycline, Moxifloxacin, Myambutol, Mycostatin, Neosporin, Netromycin, Nitrofurantoin, Norfloxacin, Norilet, Ofloxacin, Omnicef, Ospamox, Oxytetracycline, Paraxin, Penicillin, Pneumovax, Polyfax, Povidone, Rifadin, Rifampin, Rifaximin, Rifinah, Rimactane, Rocephin, Roxithromycin, Seromycin, Soframycin, Sparfloxacin, Staphlex, Targocid, Tetracycline, Tetradox, Tetralysal, tobramycin, Tobramycin, Trecator, Tygacil, Vancocin, Velosef, Vibramycin, Xifaxan, Zagam, Zitrotek, Zoderm, Zymar, and Zyvox.

In one embodiment, the second therapeutic agent is an anti-bacterial agent. Examples of anti-bacterial agents include, but is not limited to aminoglycosides (e.g., amikacin (Amikin®), gentamicin (Garamycin®), kanamycin (Kantrex®), neomycin (Mycifradin®), netilmicin (Netromycin®), tobramycin (Nebcin®), Paromomycin (Humatin®)), ansamycins (e.g., geldanamycin, herbimycin), carbacephem (e.g., loracarbef (Lorabid®), Carbapenems (e.g., ertapenem (Invanz®), doripenem (Doribax®), imipenem/cilastatin (Primaxin®), meropenem (Merrem®), cephalosporins (first generation) (e.g., cefadroxil (Duricef®), cefazolin (Ancef®), cefalotin or cefalothin (Keflin®), cefalexin (Keflex®), cephalosporins (second generation) (e.g., cefaclor (Ceclor®), cefamandole (Mandol®), cefoxitin (Mefoxin®), cefprozil (Cefzil®), cefuroxime (Ceftin®, Zinnat®)), cephalosporins (third generation) (e.g., cefixime (Suprax®), cefdinir (Omnicef®, Cefdiel®), cefditoren (Spectracef®), cefoperazone (Cefobid®), cefotaxime (Ciaforan®), cefpodoxime (Vantin®), ceftazidime (Fortaz®), ceftibuten (Cedax®), ceftizoxime (Cefizox®), ceftriaxone (Rocephin®)), cephalosporins (fourth generation) (e.g., cefepime (Maxipime®)), cephalosporins (fifth generation) (e.g., ceftobiprole (Zeftera®)), glycopeptides (e.g., teicoplanin (Targocid®), vancomycin (Vancocin®), telavancin (Vibativ®)), lincosamides (e.g., clindamycin (Cieocin®), lincomycin (Lincocin®)), lipopeptide (e.g., daptomycin (Cubicin®)), macrolides (e.g., azithromycin (Zithromax®, Sumamed®, Zitrocin®), clarithromycin (Biaxin®), dirithromycin (Dynabac®), erythromycin (Erythocin®, Erythroped®), roxithromycin, troleandomycin (Tao®), telithromycin (Ketek®), spectinomycin (Trobicin®)), monobactams (e.g., aztreonam (Azactam®)), nitrofurans (e.g., furazolidone (Furoxone®), nitrofurantoin (Macrodantin®, Macrobid®)), penicillins (e.g., amoxicillin (Novamox®, Amoxil®), ampicillin (Principen®), azlocillin, carbenicillin (Geocillin®), cloxacillin (Tegopen®), dicloxacillin (Dynapen®), flucloxacillin (Floxapen®), mezlocillin (Mezlin®), methicillin (Staphcillin®), nafcillin (Unipen®), oxacillin (Prostaphlin®), penicillin G (Pentids®), penicillin V (Pen-Vee-K®), piperacillin (Pipracil®), temocillin (Negaban®), ticarcillin (Ticar®)), penicillin combinations (e.g., amoxicillin/clavulanate (Augmentin®), ampicillin/sulbactam (Unasyn®), piperacillin/tazobactam (Zosyn®), ticarcillin/clavulanate (Timentin®)), polypeptides (e.g., bacitracin, colistin (Coly-Mycin-S®), polymyxin B, quinolones (e.g., ciprofloxacin (Cipro®, Ciproxin®, Ciprobay®), enoxacin (Penetrex®), gatifloxacin (Tequin®), levofloxacin (Levaquin®), lomefloxacin (Maxaquin®), moxifloxacin (Avelox®), nalidixic acid (Neggram®), norfloxacin (Noroxin®), ofloxacin (Fioxin®, Ocuflox®), trovafloxacin (Trovan®), grepafloxacin (Raxar®), sparfloxacin (Zagam®), temafloxacin (Omniflox®)), sulfonamides (e.g., mafenide (Sulfamylon®), sulfonamidochrysoidine (Prontosil®), sulfacetamide (Sulamyd®, Bleph-10®), sulfadiazine (Micro-Sulfon®), silver sulfadiazine (Silvadene®), sulfamethizole (Thiosulfil Forte®), sulfamethoxazole (Gantanol®), sulfanilimide, sulfasalazine (Azulfidine®), sulfisoxazole (Gantrisin®), trimethoprim (Proloprim®), Trimpex®), trimethoprim-sulfamethoxazole (co-trimoxazole) (TMP-SMX) (Bactrim®, Septra®)), tetracyclines (e.g., demeclocycline (Declomycin®), doxycycline (Vibramycin®), minocycline (Minocin®), oxytetracycline (Terramycin®), tetracycline (Sumycin®, Achromycin® V, Steclin®)), drugs against mycobacteria (e.g., clofazimine (Lamprene®), dapsone (Avlosulfon®), capreomycin (Capastat®), cycloserine (Seromycin®), ethambutol (Myambutol®), ethionamide (Trecator®), isoniazid (I.N.H.®), pyrazinamide (Aidinamide®), rifampin (Rifadin®, Rimactane®), rifabutin (Mycobutin®), rifapentine (Priftin®), streptomycin), and others (e.g., arsphenamine (Salvarsan®), chloramphenicol (Chloromycetin®), fosfomycin (Monurol®), fusidic acid (Fucidin®), linezolid (Zyvox®), metronidazole (Fiagyl®), mupirocin (Bactroban®), platensimycin, quinupristin/ dalfopristin (Synercid®), rifaximin (Xifaxan®), thiamphenicol, tigecycline (Tigacyl®), and tinidazole (Tindamax®, Fasigyn®).

When administered in combination, the agent and the additional therapeutic (e.g., second or third therapeutic), or all, can be administered in an amount or dose that is higher, lower or the same as the amount or dosage of each agent used individually, e.g., as a monotherapy. In certain embodiments, the administered amount or dosage of the agent, the additional agent (e.g., second or third agent), or all, is lower (e.g., at least 20%, at least 30%, at least 40%, or at least 50%) than the amount or dosage of each agent used individually. In other embodiments, the amount or dosage of agent, the additional agent (e.g., second or third agent), or all, that results in a desired effect (e.g., treatment of an autoimmune disease) is lower (e.g., at least 20%, at least 30%, at least 40%, or at least 50% lower) than the amount or dosage of each agent individually required to achieve the same therapeutic effect.

A second or further therapeutic agent can be administered in an admixture with the inhibitor of CGRP described herein. Alternatively, the second or further therapeutic agent can be administered separately, e.g., via a second route or site or at a second time, then the inhibitor of CGRP described herein.

Dosages Forms and Administration

The dosages of compositions comprising an agent that inhibits CGRP that treat and/or prevent microbial infection can be determined by one of ordinary skill in the art depending on the clinical severity of the disorder (e.g., antibiotic resistant bacterial infection), the age and weight of the patient, and other pharmacokinetic factors generally understood in the art. The interrelationship of dosages for animals of various sizes and species and humans based on mg/m$^3$ of surface area is described by E. J. Freireich et al., "Quantitative Comparison of Toxicity of Anticancer Agents in Mouse, Rat, Hamster, Dog, Monkey and Man," Cancer Chemother. Rep. 50: 219-244 (1966). Adjustments in the dosage regimen can be made to optimize the therapeutic response. Doses can be divided and administered on a daily basis or the dose can be reduced proportionally depending on the therapeutic situation.

The dosage range depends upon the potency, and includes amounts large enough to produce the desired effect, e.g., a decrease in microbial infection. The dosage should not be so large as to cause unacceptable adverse side effects. Generally, the dosage will vary with the type of agent (e.g., a CGRP antibody, a small molecule inhibitor of CGRP or its receptor signaling, antibiotic, or antimicrobial), and with the age, and condition of the patient. The dosage can be determined by one of skill in the art and can also be adjusted by the individual physician in the event of any complication. Typically, the dosage will range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In some embodiments of any of the aspects, the dose range is from 5 µg/kg body weight to 30 µg/kg body weight. Alternatively, the dose range will be titrated to maintain serum levels between 5 µg/mL and 30 m/mL.

Sub-lethal doses may be administered systemically (e.g., intravenously). Botulinum toxin has a median lethal dose (LD50) of 1.3-2.1 ng/kg when administered intravenously or intramusculuarly, and 10-13 ng/kg when inhaled.

Common dosages of botulinum neurotoxins known in the art are described in terms of units (e.g., Botox is 20 u and Dysport is 50 u). Units are defined by the biological activity of the neurotoxin in blocking SNARE fusion and may correspond to a number of BoNT molecules, but are not necessarily identical between different manufacturers. BoNTs may be administered in a dose of between about 0.01 and 10,000 units (e.g., 0.01 u-0.1 u, e.g., 0.02 u, 0.03 u, 0.04 u, 0.05 u, 0.06 u, 0.07 u, 0.08 u, 0.09 u, 0.1 u, e.g., 0.1 u-1 u, e.g., 0.2 u, 0.3 u, 0.4 u, 0.5 u, 0.6 u, 0.7 u, 0.8 u, 0.9 u, 1 u, e.g., 1 u-10 u, 1 u, 2 u, 3 u, 4 u, 5 u, 6 u, 7 u, 8 u, 9 u, 10 u, e.g., 10 u-100 u, e.g., 20 u, 30 u, 40 u, 50 u, 60 u, 70 u, 80 u, 90 u, 100 u, e.g., 100 u-1000 u, e.g., 200 u, 300 u, 400 u, 500 u, 600 u, 700 u, 800 u, 900 u, 1,000 u, e.g., 1000 u-10,000 u, e.g., 2000 u, 3000 u, 4000 u, 5000 u, 6000 u, 7000 u, 8000 u, 9000 u, 10,000 u). In some instances, 1 unit is defined as the peritoneal LD50 of mice. The dosage may also be defined as a unit per kg subject.

These agents can be administered orally, and they can be administered in conventional pill or liquid form. If administered in pill form, they can be administered in conventional formulations with excipients, fillers, preservatives, and other typical ingredients used in pharmaceutical formations in pill form. Typically, the agents are administered in a conventional pharmaceutically acceptable formulation, typically including a carrier. Conventional pharmaceutically acceptable carriers known in the art can include alcohols, e.g., ethyl alcohol, serum proteins, human serum albumin, liposomes, buffers such as phosphates, water, sterile saline or other salts, electrolytes, glycerol, hydroxymethylcellulose, propylene glycol, polyethylene glycol, polyoxyethylenesorbitan, other surface active agents, vegetable oils, and conventional anti-bacterial or anti-fungal agents, such as parabens, chlorobutanol, phenol, sorbic acid, thimerosal, and the like. A pharmaceutically-acceptable carrier within the scope of the present invention meets industry standards for sterility, isotonicity, stability, and non-pyrogenicity.

The pharmaceutically acceptable formulation can also be in pill, tablet, or lozenge form as is known in the art, and can include excipients or other ingredients for greater stability or acceptability. For the tablets, the excipients can be inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc, along with the substance for autophagy modulation and other ingredients.

The agents can also be administered in liquid form in conventional formulations that can include preservatives, stabilizers, coloring, flavoring, and other generally accepted pharmaceutical ingredients. Typically, when the agents are administered in liquid form, they will be in aqueous solution. The aqueous solution can contain buffers, and can contain alcohols such as ethyl alcohol or other pharmaceutically tolerated compounds.

Alternatively, the agents can be administered by subcutaneous injection by one of several routes well known in the art. Agents can additionally be formulated for topical administration by one skilled in the art. Agents that inhibit CGRP and additional therapeutic agents can be administered parenterally. The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation.

In one embodiment, the agent is administered locally, e.g., at the site of the infection, or the predicted site of a possible infection. In one embodiment, the agent is administered systemically.

In some embodiments, a therapeutically effective amount of an agent that inhibits CGRP (e.g., CGRP activity, release, or receptor signaling) is administered using intrapulmonary administration, such as an intranasal or intratracheal route. In one embodiment, a therapeutically effective amount of the agent or composition comprising an agent is administered using a systemic, such as an intraperitoneal or intravenous route. In one embodiment, a therapeutically effective amount of the agent is administered using both intrapulmonary and intraperitoneal administration. These methods are particularly aimed at therapeutic and prophylactic treatments of human subjects having, or at risk of having, a microbial infection, e.g., of the lung. As defined herein, "intrapulmonary" administration or delivery refers to all routes of administration whereby an agent is administered in a way that results in direct contact of the agent with the airways of a subject, including, but not limited to, transtracheal, intratracheal, and intranasal administration. In some such embodiments, the agent is injected into the nasal passages or trachea. In some embodiments, the agent is directly inhaled by a subject. In some embodiments, intrapulmonary delivery of the agent includes administration methods whereby the agent is administered to an intubated subject via a tube placed in the trachea or "tracheal intubation." As used herein, "tracheal intubation" refers to the placement of a flexible tube, such as a plastic tube, into the trachea. The most common tracheal intubation, termed herein as "orotracheal intubation" is where, with the assistance of a laryngoscope, an endotracheal tube is passed through the mouth, larynx, and vocal cords, into the trachea. A bulb is then inflated near the distal tip of the tube to help secure it in place and protect the airway from blood, vomit, and secretions. In some embodiments, an agent is administered to a subject having "nasotracheal intubation," which is defined as a tracheal intubation where a tube is passed through the nose, larynx, vocal cords, and trachea.

The agents can be administered from once per day to up to at least five times per day, depending on the severity of the disease, the total dosage to be administered, and the judgment of the treating physician. The agent can be administered, for example, every minute, hour, day, week, month, or year. The composition can be administered for a specific duration (e.g., 1 minute, 1 hour, 1 day, 1 week, 1 month, or 1 year). In some cases, the agents need not be administered on a daily basis, but can be administered every other day, every third day, or on other such schedules. However, it is generally preferred to administer the agents daily.

In some embodiments of any of the aspects, the inhibitor of CGRP described herein is administered as a monotherapy, e.g., another treatment for the microbial infection is not administered to the subject. In some embodiments of any of the aspects, the inhibitor of CGRP is administered to the site of the microbial infection and/or to the site of a nerve affected by the microbial infection (e.g., a nerve interposed between the site of the infection and the central nervous system). In some embodiments of any of the aspects, the subject is a subject not diagnosed as having, or not in need of treatment for headaches or migraines. In some embodiments of any of the aspects, the inhibitor of CGRP is not administered to the central nervous system.

In some embodiments, the technology described herein relates to a pharmaceutical composition comprising an inhibitor of CGRP as described herein, and optionally a pharmaceutically acceptable carrier. In some embodiments, the active ingredients of the pharmaceutical composition comprise an inhibitor of CGRP as described herein. In some embodiments, the active ingredients of the pharmaceutical composition consist essentially of an inhibitor of CGRP as described herein. In some embodiments, the active ingredients of the pharmaceutical composition consist of CGRP as described herein.

Controlled and Delayed Release Dosage Forms

In some embodiments of the aspects described herein, an agent is administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) blue uced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of formula (I)'s onset of action, duration of action, plasma levels within the therapeutic window, and peak blood levels. In particular, controlled- or extended-release dosage forms or formulations can be used to ensure that the maximum effectiveness of an agent is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with any agent described herein. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, DUO-LITE® A568 and DUOLITE® AP143 (Rohm&Haas, Spring House, Pa. USA).

Efficacy Measurement

The efficacy of a given treatment or prevention of a microbial infection can be determined by the skilled clinician. However, a treatment is considered "effective treatment," as the term is used herein, if any one or all of the signs or symptoms of, as but one example, fever, or other clinically accepted symptoms or markers of the infection are improved or ameliorated, e.g., by at least 10% following treatment with a composition comprising an agent that inhibits CGRP described herein. Efficacy can also be measured by failure of an individual to worsen as assessed by need for medical interventions (e.g., progression of infection is halted or at least slowed). Methods of measuring these indicators are known to those of skill in the art and/or described herein. Example methods are described above herein. Treatment includes any treatment of the infection in an individual or an animal (some non-limiting examples include a human, or a mammal) and includes: (1) inhibiting the infection, e.g., arresting, or slowing symptoms of the infection, for example fever and inflamed tissue; or (2) relieving the infection, e.g., causing regression of symptoms, reducing the symptoms by at least 10%; and (3) preventing future microbial infection.

An effective amount for the treatment of a microbial infection means that amount which, when administered to a mammal in need thereof, is sufficient to result in effective treatment as that term is defined herein, for that infection. Efficacy of the composition can be determined by a physician by assessing physical indicators of microbial infection, such as e.g., fever and inflamed tissue.

The term "effective amount" as used herein refers to the amount of an agent that inhibits CGRP described herein needed to alleviate at least one or more symptom of a microbial infection and relates to a sufficient amount of pharmacological composition to provide the desired effect. The term "therapeutically effective amount" therefore refers to an amount of a composition that is sufficient to provide a particular effect when administered to a typical subject. An effective amount as used herein, in various contexts, would also include an amount sufficient to delay the development of a symptom of the infection, alter the course of a symptom (for example but not limited to, slowing the progression of a symptom of the infection), or reverse a symptom of the infection. Thus, it is not generally practicable to specify an exact "effective amount." However, for any given case, an appropriate "effective amount" can be determined by one of ordinary skill in the art using only routine experimentation. The term "effective amount" is used interchangeably with the term "therapeutically effective amount" and refers to the amount of at least one agent at dosages and for periods of time necessary to achieve the desired therapeutic result, for example, to reduce or stop at least one symptom of a microbial infection, in the subject.

Effective amounts, toxicity, and therapeutic efficacy of drug agents, e.g., for formulations or treatments using antimicrobials in addition to CGRP inhibitory agents, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$. Compositions and methods that exhibit large therapeutic indices are preferred. A therapeutically effective dose can be estimated initially from in vivo assays. Also, a dose can be formulated in animal models to achieve a circulating plasma concentration range that includes the $IC_{50}$ (i.e., the concentration of the active ingredient, which achieves a half-maximal inhibition of symptoms). Levels in plasma can be measured, for example, by high performance liquid chromatography or other appropriate technique. The effects of any particular dosage can be monitored by a suitable bioassay. The dosage can be determined by a physician and adjusted, as necessary, to suit observed effects of the treatment.

Kit

In one aspect is a kit comprising an agent that inhibits CGRP (e.g., CGRP activity, release, or receptor signaling) as described herein in the amount sufficient to treat a microbial infection.

In one aspect is a kit comprising an agent that inhibits CGRP (e.g., CGRP activity, release, or receptor signaling) as described herein in the amount sufficient to prevent a microbial infection.

A kit is any manufacture (e.g., a package or container) comprising at least one reagent, e.g., the agent being promoted, distributed, or sold as a unit for performing the methods described herein. The kits described herein can optionally comprise additional components useful for performing the methods described herein, e.g., needles, tubing, etc useful for administration by the desired route. By way of example, the kit can comprise fluids (e.g., buffers) suitable for use with the agents described herein, an instructional material which describes performance of a method as described herein, and the like. A kit can further comprise devices and/or reagents for delivery of the composition as described herein. Additionally, the kit may comprise an instruction leaflet and/or may provide information as to dosages, administration frequency, etc.

The kits of the invention comprise one or more packages or containers containing the agent in combination with a set of instructions, generally written instructions, relating to the use and dosage of the emulsion. The kits may further comprise additional containers containing one or more second therapeutic agent that may be added to the agent prior to administration. The packages containing the agent may be in the form of unit doses or pharmacy bulk packages. The doses may be packaged in a format such that each dose is associated, for example, with a day of the week. There may also be associated with the kit a notice in the form prescribed by a governmental agency regulating the manufacture, use or sale of biological products, which notice reflects approval by the agency of manufacture, use or sale for human or animal administration.

One aspect of the invention is the use of any of the kits or compositions described herein for the treatment of a microbial infection.

One aspect of the invention is the use of any of the kits or compositions described herein for the prevention of a microbial infection.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only and is not intended to limit the scope of the present invention, which is defined solely by the claims.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the technology described herein can be defined according to any of the following numbered paragraphs:

1. A method for treating a microbial infection in a subject, the method comprising; administering to a subject in need thereof an agent that inhibits Calcitonin gene-related peptide (CGRP) activity, CGRP release, and/or CGRP receptor signaling in an amount and for a duration sufficient to treat a microbial infection.
2. A method for preventing a microbial infection in a subject, the method comprising; administering to a subject at risk of a microbial infection an agent that inhibits Calcitonin gene-related peptide (CGRP) activity, CGRP release, and/or CGRP receptor signaling in an amount and for a duration sufficient to prevent a microbial infection.
3. The method of paragraphs 1 or 2, wherein the agent is a botulinum neurotoxin.
4. The method of paragraph 3, wherein the botulinum neurotoxin is selected from the group consisting of: botulinum neurotoxin serotype A, botulinum neurotoxin serotype B, botulinum neurotoxin serotype C, botulinum neurotoxin serotype D, botulinum neurotoxin serotype E, botulinum neurotoxin serotype F, and botulinum neurotoxin serotype G.
5. The method of paragraphs 1 or 2, wherein the agent is an inhibitor of Transient Receptor Potential Vanilloid 1 (TRPV1)-expressing neurons.
6. The method of paragraph 5, wherein the inhibitor of TRPV1-expressing neurons is Resiniferatoxin (RTX).
7. The method of paragraphs 1 or 2, wherein the agent comprises a competitive inhibitor of CGRP.
8. The method of paragraphs 1 or 2, wherein the agent comprises an antagonist of CGRP receptors and their signaling.
9. The method of paragraphs 1 or 2, wherein the agent comprises an anti-CGRP antibody or antibody reagent.
10. The method of paragraph 7, wherein the anti-CGRP antibody is ALD403, LY2951742, AMG 334, or TEV-48125.
11. The method of paragraphs 1 or 2, wherein the agent is a compound that inhibits CGRP activity, release, or receptor signaling.
12. The method of paragraphs 1 or 2, wherein the agent inhibits the expression of CGRP.
13. The method of paragraph 12, wherein the agent inhibits the expression of CGRP at least 10%, at least 20%, at least 30%, at least 40%, at least 50%, at least 60%, at least 70%, at least 80%, at least 90%, or more as compared to an appropriate control.
14. The method of paragraphs 1 or 2, wherein the agent inhibits with the function of CGRP.
15. The method of paragraph 14, wherein the agent inhibits the function of CGRP at least 10%, at least 20%, at least 30%, at least 40%, at least 50%, at least 60%, at least 70%, at least 80%, at least 90%, or more as compared to an appropriate control.
16. The method of paragraphs 1 or 2, wherein the agent comprises a small molecule that inhibits CGRP.
17. The method of paragraph 16, wherein the small molecule is selected from the group consisting of: olcegepant, obrogepant, tacagepant, Avitriptan, eletriptan, naratriptan, rizatriptan, sumatriptan, zolmitriptan, galcanezumab, eptinezumab, erenumab, fremanezumab, (piperidin-1-yl)piperidin-1-yl)propan-2-yl)piperidine-1-carboxamide (BMS 694153), atogepant, and MK-3207.
18. The method of paragraphs 1 or 2, wherein the agent inhibits a CGRP receptor.
19. The method of paragraphs 1 or 2, wherein the CGRP receptor is RAMP1/CALCRL.
20. The method of paragraphs 1 or 2, wherein the agent comprises a nucleic acid that encodes an inhibitor of CGRP.
21. The method of paragraphs 1 or 2, wherein the agent comprises a polypeptide that inhibits CGRP.
22. The method of paragraph 21, wherein the polypeptide comprises $CGRP_{8-37}$ peptide.
23. The method of paragraphs 1 or 2, wherein the agent comprises siRNA that inhibits CGRP activity, release, or receptor signaling.
24. The method of paragraphs 1 or 2, wherein the agent comprises shRNA that inhibits CGRP activity, release, or receptor signaling.
25. The method of paragraphs 1 or 2, wherein the agent comprises miRNA that inhibits CGRP activity, release, or receptor signaling.
26. The method of paragraphs 1 or 2, wherein the microbial infection comprises a bacterium which is resistant to at least one antibiotic.
27. The method of paragraphs 1 or 2, wherein the microbial infection comprises a bacterium which is resistant to at least two antibiotics.
28. The method of paragraphs 1 or 2, wherein the microbial infection comprises a gram-positive bacterial infection.
29. The method of paragraphs 1 or 2, wherein the microbial infection comprises a *Streptococcus* infection.
30. The method of paragraph 29, wherein the *Streptococcus* infection comprises Group A *Streptococcus*.
31. The method of paragraph 29, wherein the *Streptococcus* infection comprises Group B *Streptococcus*.
32. The method of paragraph 29, wherein the *Streptococcus* infection comprises *Streptococcus pneumoniae*.
33. The method of paragraph 29, wherein the *Streptococcus* infection comprises *Streptococcus pyogenes*.
34. The method of paragraphs 1 or 2, wherein the microbial infection comprises a *Staphylococcus* infection.
35. The method of paragraph 34, wherein the *Staphylococcus* infection comprises *Staphylococcus aureus*.
36. The method of paragraph 35, wherein *Staphylococcus aureus* is methicillin resistant *Staphylococcus aureus*.

37. The method of paragraphs 1 or 2, wherein the microbial infection is selected from the group consisting of: a *Corynebacterium* infection, a *Listeria* infection, a *Clostridium* infection, a *Pseudomonas aeruginosa* infection, an *Escherichia coli* infection, a *Klebsiella* infection, an *Aeromonas* infection, and a *Neisseria* infection.
38. The method of any one of paragraphs 1-37, wherein the microbial infection is a skin, soft tissue, or subcutaneous infection.
39. The method of paragraph 38, wherein the skin, soft tissue, or subcutaneous infection is selected from a group consisting of: impetigo, bullous impetigo, scalded skin syndrome, folliculitis, furuncles, carbuncles, cellulitis, myositis, necrotizing fasciitis, streptococcal toxic shock, toxic shock syndrome, acne, and gangrene.
40. The method of any one of paragraphs 1-37, wherein the microbial infection is a respiratory tract or lung infection.
41. The method of paragraph 40, wherein the respiratory tract or lung infection is selected from a group consisting of: scarlet fever, bacterial respiratory tract infection, pneumonia, lethal pneumonia, acute lung injury, acute respiratory distress syndrome, bacterial sepsis, endotoxin shock, and bacterial meningitis, acute rhinosinusitis, acute bacterial rhinosinusitis, pharyngitis, bacterial tracheitis, and bronchitis.
42. The method of any one of paragraphs 1-41, wherein the microbial infection is a systemic infection.
43. The method of paragraph 42, wherein the systemic infection is bacterial sepsis or endotoxin shock.
44. The method of any one of paragraphs 1-37, wherein the microbial infection is meningitis.
45. The method of any one of paragraphs 1-37, wherein the microbial infection is encephalitis.
46. The method of any one of paragraphs 1-37, wherein the microbial infection is scarlet fever.
47. The method of any one of paragraphs 1-37, wherein the microbial infection is a urinary tract infection.
48. The method of any one of paragraphs 1-37, wherein the microbial infection is a sexually transmitted disease.
49. The method of any one of paragraphs 1-37, wherein the microbial infection comprises a fungal infection.
50. The method of any one of paragraphs 1-49, wherein the subject further has a burn.
51. The method of paragraph 50, wherein the burn comprises a microbial infection.
52. The method of any one of paragraphs 1-51, wherein the microbial infection is acute or chronic.
53. The method of any one of paragraphs 1-51, further comprising administering to a subject a second therapeutic agent.
54. The method of paragraph 53, wherein the second therapeutic agent is an antibiotic, antifungal, or antimicrobial agent.
55. The methods of any one of paragraphs 1-54, wherein the subject has previously been diagnosed with having an infection.
56. The method of paragraph 1, further comprising, prior to administering, diagnosing a subject with a microbial infection.
57. A method for treating a microbial infection in a subject, the method comprising; administering to a subject in need thereof a botulinum neurotoxin in an amount and for a duration sufficient to treat a microbial infection.
58. A method for preventing a microbial infection in a subject, the method comprising; administering to a subject at risk of a microbial infection a botulinum neurotoxin in an amount and for a duration sufficient to prevent a microbial infection.
59. The method of paragraphs 57 or 58, wherein the botulinum neurotoxin is selected from the group consisting of: botulinum neurotoxin serotype A, botulinum neurotoxin serotype B, botulinum neurotoxin serotype C, botulinum neurotoxin serotype D, botulinum neurotoxin serotype E, botulinum neurotoxin serotype F, and botulinum neurotoxin serotype G.
60. A method for treating a *Staphylococcus aureus* infection in a subject, the method comprising; administering to a subject in need thereof an agent that inhibits nociception in an amount and for a duration sufficient to treat a microbial infection.
61. The method of paragraph 60, wherein the agent inhibits Transient receptor potential vanilloid 1 (TRPV1)-expressing neurons.
62. The method of paragraph 60, wherein the agent that inhibits TRPV1-expressing neurons is Resiniferatoxin (RTX).
63. The method of any one of paragraphs 60-62, wherein the *Staphylococcus aureus* is methicillin resistant *Staphylococcus aureus*.
64. The method of any one of paragraphs 60-63, wherein the *Staphylococcus aureus* is resistant to at least 2 antibiotics.
65. The method of any one of paragraphs 60-64, wherein the *Staphylococcus aureus* infection is a skin, soft tissue, subcutaneous respiratory tract, and/or lung infection.
66. The method of any one of paragraphs 60-65, wherein the *Staphylococcus aureus* infection is a systemic infection.
67. The method of any one of paragraphs 60-66, further comprising administering to a subject a second therapeutic agent.
68. The method of paragraph 67, wherein the second therapeutic agent is an antibiotic, antifungal, or antimicrobial agent.
69. The methods of any one of paragraphs 60-67, wherein the subject has previously been diagnosed with having a *Staphylococcus aureus* infection.
70. The method of paragraph 60, further comprising, prior to administering, diagnosing a subject with a *Staphylococcus aureus* infection.
71. A composition for treating a microbial infection in a subject, the composition comprising; an amount of a CGRP inhibitory agent sufficient to treat a microbial infection.
72. A composition for preventing a microbial infection in a subject, the composition comprising; an amount of a CGRP inhibitory agent sufficient to prevent a microbial infection.
73. The composition of any one of paragraphs 71 and 72, further comprising a pharmaceutically acceptable carrier.
74. The composition of any one of paragraphs 71 and 72, further comprising a second therapeutic agent.
75. The composition of paragraph 74, wherein the second therapeutic agent is an antibiotic or antimicrobial agent.

76. A kit for treating a microbial infection in a subject, the kit comprising; an amount of an agent that inhibits CGRP activity, CGRP release, and/or CGRP receptor signaling sufficient to treat a microbial infection.
77. A kit for preventing a microbial infection in a subject, the kit comprising; an amount of an agent that inhibits CGRP activity, CGRP release, and/or CGRP receptor signaling sufficient to prevent a microbial infection.
78. The kit of any one of paragraphs 76 and 77, further comprising a second therapeutic agent.
79. Use of the composition or kit of any one of paragraphs 71-78 for the treatment of a microbial infection.
80. Use of the composition or kit of any one of paragraphs 71-78 for the prevention of a microbial infection.

EXAMPLES

Example 1

Difficult-to-treat antibiotic resistant infections by bacteria are increasingly prevalent in both community and hospital settings. It is proposed that targeting CGRP and its receptor signaling using 1) Neutralizing antibodies against CGRP and 2) antagonists of CGRP receptor signaling could be novel approaches to treat severe bacterial infections, including bacterial and viral respiratory infections, acute respiratory distress syndrome (ARDS), lethal bacterial pneumonia, bacterial sepsis, and bacterial meningitis.

It was found that bacteria directly activate neurons to induce neuronal secretion of CGRP. CGRP then suppresses the ability of the immune system to fight bacterial infections by inhibiting cytokine production and neutrophil killing of bacteria. Targeting CGRP using neutralizing antibodies, or RAMP1/CALCRL receptor signaling using pharmacological inhibitors could significantly increase survival and the outcome of severe bacterial infections including pneumonia, sepsis and meningitis. As a proof of principle, it was found that blocking CGRP signaling enhances innate immune host defenses and survival in lethal bacterial pneumonia caused by methicillin-resistant *Staphylococcus aureus* (MRSA) intratracheal infections.

Example 2

Botulinum Toxin (BoNT/A) Injection Significantly Inhibited Necrotic Lesion Formation in a Mouse Model of Necrotizing Fasciitis Cause by *Streptococcus pyogenes*.

Figures 1A, 1B:
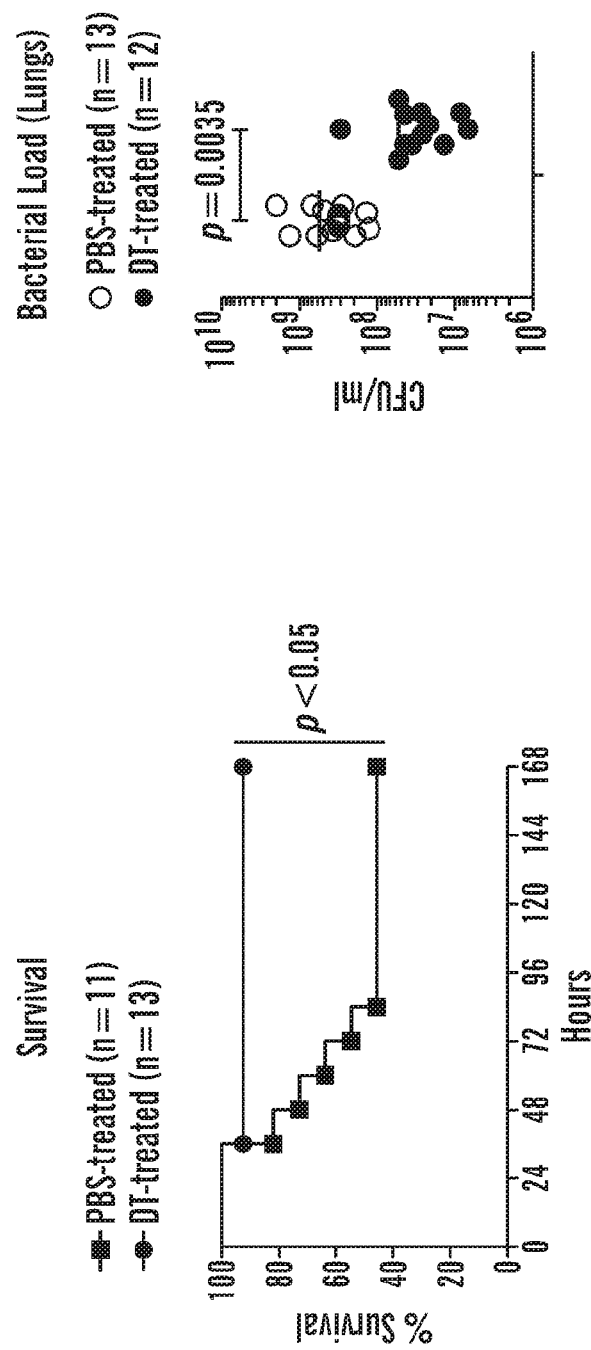
FIGS. 1A-1D show that TRPV1+ nociceptors expressing CGRP suppress survival and bacterial clearance in MRSA lethal pneumonia. TRPV1-DTR mice are transgenic mice where the diphtheria toxin receptor is driven under the promoter of the ion channel TRPV1, thus marking nociceptive neurons. TRPV1-DTR mice were injected with Diptheria Toxin to ablate nociceptive neurons, or PBS as a control. Mice were infected intratracheally with methicillin-resistant $S.\ aureus$ to induce lethal pneumonia.
Figure 1D:
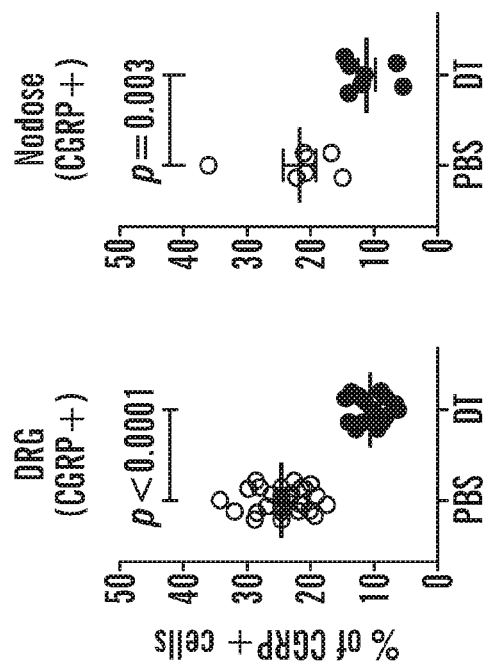
Figure 1C:
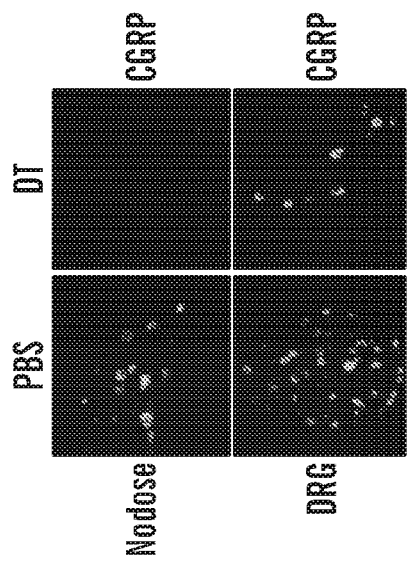

A mouse model of *S. pyogenes* infection was developed that resembles necrotizing fasciitis. Mice were infected with a human clinical isolate of *S. pyogenes* (Strain 854 M1T1) in the flank skin, which lead to development of large necrotizing lesions. Botulinum Neurotoxin A (BoNT/A) pre-treatment by local injection lead to significantly decreased development of dermonecrotic lesions, and they resolve much quicker than vehicle injected mice (FIG. 1).

It was determined that BoNT/A treatment could prevent development of dermonecrotic lesions caused by *S. pyogenes*. Mice were shaved on the flank, and either injected with 100 uL of vehicle or 100 uL of Botulinum Toxin (25 pg, BoNT/A) prior to subcutaneous infection with $5\times10^6$ colony forming units (CFU) *S. pyogenes* (Strain 854 M1T1 clinical isolate from a human patient). BoNT/A treatment prevented development of dermonecrotic lesions over the next 14 days. As shown in FIG. 1A, *S. pyogenes* lesions existed at day 8 post-infection in a vehicle injected mouse and a BoNT/A injected mouse. As shown in FIG. 1B, necrotizing lesions were measured using a micrometer, and the area of dermonecrosis was plotted daily over time to compare BoNT/A treated vs. Vehicle treated mice. BoNT/A treatment significantly reduced the formation of lesions ($P<0.0001$, interaction by Two-Way RM ANOVA with Bonferroni post-tests at each time point, *, $P<0.05$; , $P<0.01$; *, $P<0.001$). N=10 mice per group.

Example 3

Botulinum toxin (BoNT/A) treatment significantly inhibited abscess formation caused by *S. pyogenes* infection. Abscess sizes formed by $5\times10^6$ CFU *S. pyogenes* (854 M1T1 strain) in mice are significantly decreased with prior treatment by 100 uL of subcutaneous BoNT/A injection (25 pg) compared to vehicle injected mice. The area of abscess was measured using a micrometer daily during the time course of infection. $P<0.0001$ by Two-way RM ANOVA with Bonferroni post-tests at each time point (*, $P<0.05$; , $P<0.01$; **, $P<0.0001$). N=10 mice per group. It was observed that development of abscesses at the site of infection are significantly smaller in size and resolve quicker in mice injected subcutaneously with BoNT/A. (FIG. 2)

Example 4

Figure 3:
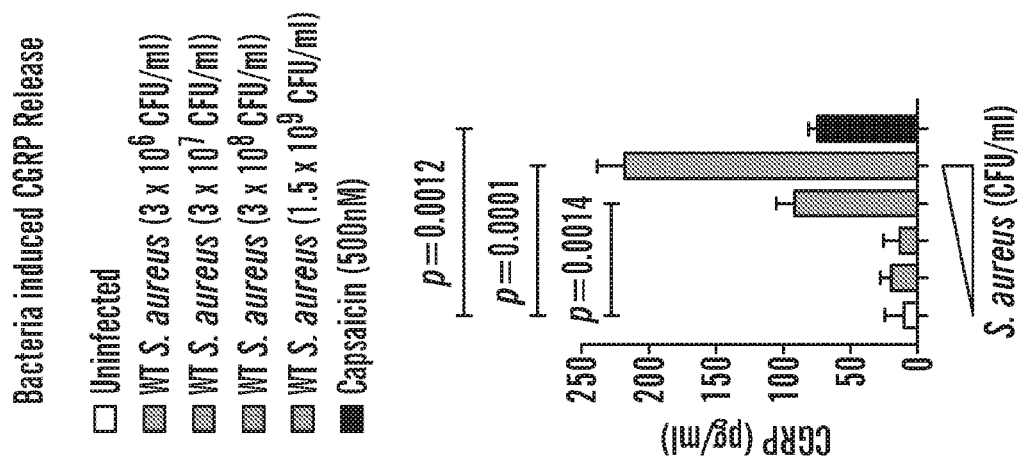
FIG. 3 shows that bacteria directly activate CGRP release from sensory neurons, Methicillin-resistant $S.\ aureus$ was applied at different concentrations on cultured mouse DRG neurons. CGRP levels measured by EIA show bacteria induces release in a dose dependent manner. Capsaicin was used as a positive control.

Botulinum toxin (BoNT/A) treatment significantly inhibits weight loss caused by *S. pyogenes* infection. Weight loss was measured as a percentage of starting weight following subcutaneous infection with $5\times10^6$ CFU *S. pyogenes* (854 M1T1 strain) in mice pretreated with 25 pg of BoNT/A (N=5) vs. vehicle injection (N=6). BoNT/A treated mice show significantly less weight loss overtime: $P<0.0001$ by Two-Way RM ANOVA with Bonferroni post-tests at each time point: **, $P<0.01$. Weight loss, which is a measure of morbidity following infection, was significantly less and improved in BoNT/A treated mice following *S. pyogenes* infection than in vehicle treated mice (FIG. 3).

Example

Figure 4:
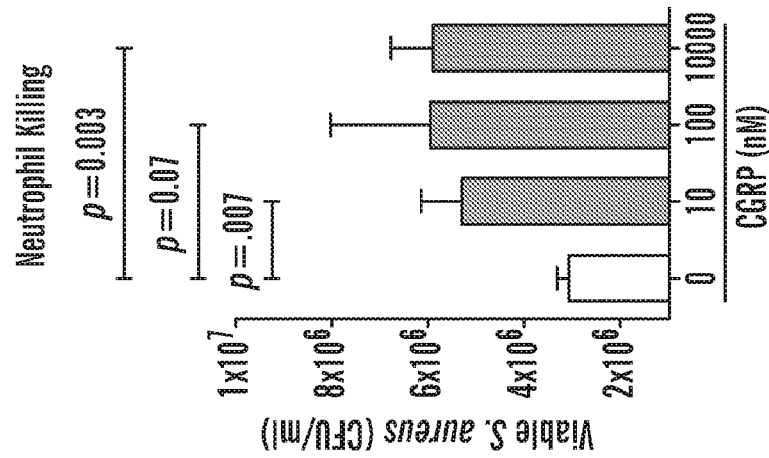
FIG. 4 shows that CGRP inhibits neutrophil killing of bacteria. Primary neutrophils, a key immune cell type in host defense against bacteria, show inhibition of killing of co-cultured Methicillin resistant $S.\ aureus$ in the presence of increasing doses of CGRP (0-1000 nM).

Intrathecal injection of BoNT/A prevented pain development after *S. pyogenes* infection. Next, the goal was to determine if BoNT/A had effects on pain during infection. Mice were injected intrathecally with 25 pg BoNT/A or vehicle prior to subcutaneous infection with *S. pyogenes*. As show in FIG. 4A, acute nocifensive pain (over 1 hr) following infection was significantly decreased in BoNT/A injected mice. *, $P<0.001$ by t-test. As shown in FIG. 4B, left panel, BoNT/A injected mice showed significantly less thermal hyperalgesia (Hargreaves' test) than vehicle injected mice. As shown in FIG. 4B, right panel, BoNT/A injected mice showed significantly less mechanical hyperalgesia (von Frey test) than vehicle injected mice as measured by Two-way RM ANOVA with Bonferroni post-tests: , $P<0.01$; *, $P<0.001$; **, $P<0.001$. It was found that intrathecal injection of BoNT/A prior to infection completely abrogated nocifensive pain, thermal hyperalgesia, and mechanical hyperalgesia, indicating effective pain block.

Example 6

Figure 5B:
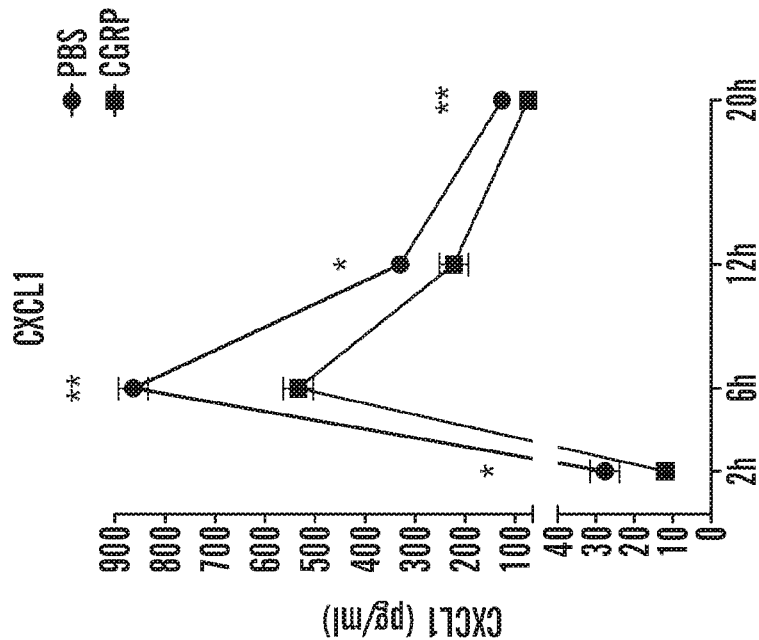
FIGS. 5A and 5B show that CGRP inhibits TNF-α and CXCL1 secretion by lung cells infected with $S.\ aureus$. Lung cells were dissociated enzymatically from mice and cultured with $S.\ aureus$ and control or CGRP (100 nM). Supernatant was collected at different timepoints and levels of TNF-α (FIG. 5A) or CXCL1 analyzed (FIG. 5B). CGRP significantly reduces expression of both cytokines compared to PBS treated cells, indicating an inhibition of these key innate immune cytokines in lung cells.
Figure 5A:
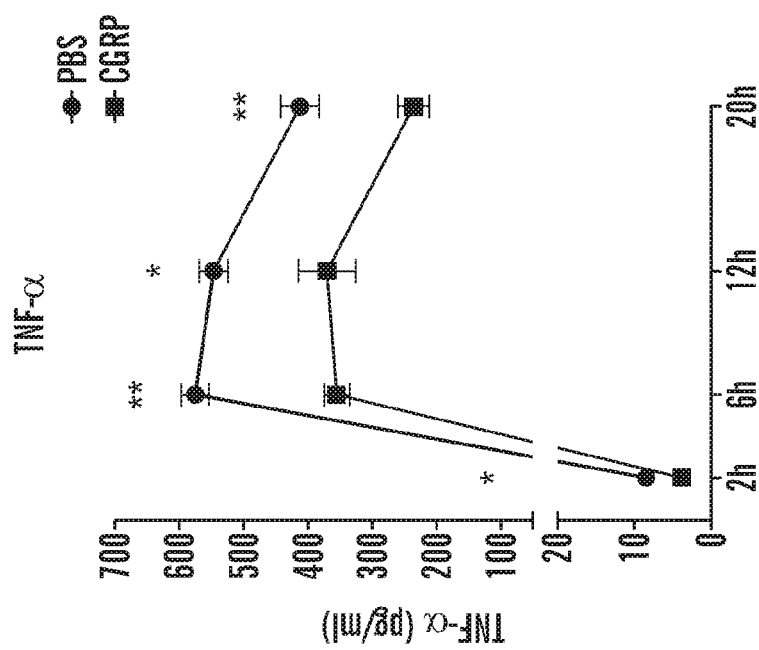

Subcutaneous injection of BoNT/A did not affect pain after *S. pyogenes* infection. Mice were injected subcutaneously with 25 pg BoNT/A or vehicle locally prior to subcutaneous infection with *S. pyogenes* in the hind paw. As show in FIG. 5A, acute nocifensive pain (over 1 hr) following infection was not significantly different between groups. In FIG. 5B, thermal hyperalgesia (left) and mechanical hyperalgesia (right) did not differ between groups post-infection (Two-Way RM ANOVA). Local subcutaneous BoNT/A injection did not block pain, though it did significantly improve lesion development.

Example 7

Figures 6A, 6B:
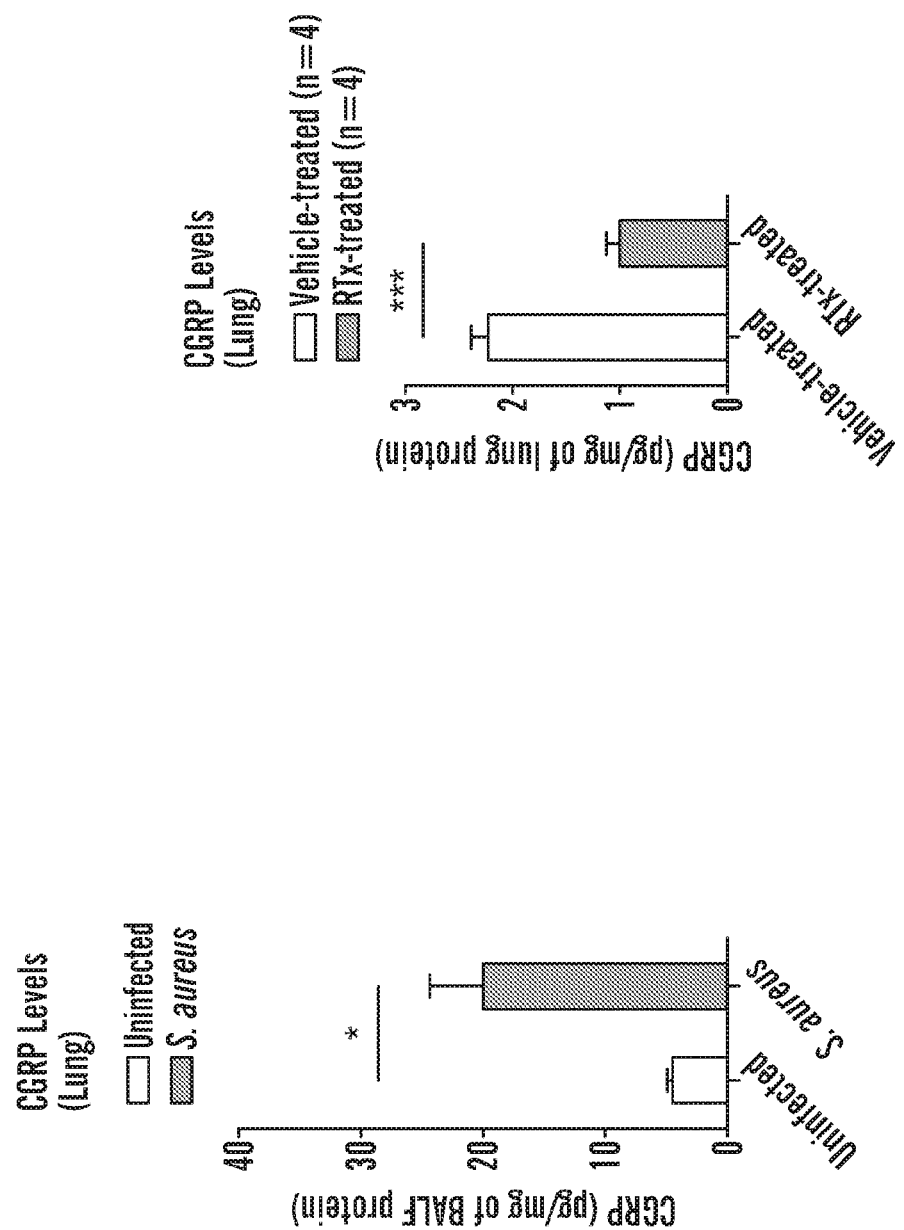

Botulinum Toxin (BoNT/A) acts by preventing neuronal release of CGRP, which is increased in infection and inhibits bacterial killing. Mouse primary dorsal root ganglia (DRG) sensory neurons were cultured in 96 well-plates (5000 DRG neurons/well) for 7 days (FIG. 6A). They were treated with 20 μL of supernatant from *S. pyogenes* bacterial cultures ($5\times10^8$ CFU) of WT, or those lacking sagA (ΔsagA) or complemented with sagA. The last column are neurons pretreated with BoNT/A 24 hr before stimulation with WT *S. pyogenes* supernatant. Levels of CGRP were measured by EIA. BoNT/A treatment significantly decreased the induction of CGRP by WT *S. pyogenes* (*, $P<0.05$; **, $P<0.01$ by t-test). Skin and subcutaneous tissue was isolated from *S. pyogenes* infected mice, incubated in media, and levels of CGRP measured (FIG. 6B). Significant CGRP was released during infection at 7 hr compared to the 0 hour time point (*, $P<0.05$ by t-test). Human whole blood or purified mouse neutrophils were incubated together with *S. pyogenes* in the presence of different concentrations of CGRP (FIG. 6C). Following incubation, cells were lysed and plated on blood agar to detect presence of bacteria. 100 nM CGRP significantly enhanced the growth of bacteria, indicating inhibition of killing of bacteria by this neuropeptide.

Example 8

The skin is a major barrier tissue that is exposed to external insults and microbial invasion. The somatosensory nervous system densely innervates the skin, detecting noxious and environmental stimuli to mediate pain, itch, thermosensation, and mechanosensation (Abraira and Ginty, 2013; Basbaum et al, 2009). Somatosensory neurons actively communicate with the immune system in pain and inflammatory conditions (Pinho-Ribeiro et al., 2017). However, the role of the sensory nervous system in host defense is not well understood. Work described herein finds that *Streptococcus pyogenes*, an invasive bacterial pathogen, activates sensory neurons to produce pain and to induce neural suppression of the immune system to enhance its survival during infection.

Necrotizing fasciitis (also known as "flesh-eating disease") is a life-threatening, aggressive bacterial infection of the subcutaneous tissue and underlying fascia. A cardinal manifestation of this infection is "pain out of proportion" to physical findings at early time points (Borschitz et al., 2015). *S. pyogenes* (or group A *Streptococcus*) is a gram-positive bacterial pathogen and the leading cause of necrotizing fasciitis (Leitch et al., 2000). *S. pyogenes* also frequently causes pharyngitis (or "strep throat"), a painful infection that affects 600 million people annually (Ralph and Carapetis, 2013). Necrotizing fasciitis is difficult to treat and has a mortality rate of 24-32% in developed countries (Cole et al., 2011). Due to its rapid progression, disfiguring surgical debridement or limb amputation is often required to prevent mortality. Despite the importance of pain in the diagnosis of necrotizing fasciitis, the role of pain in *S. pyogenes* invasion is unclear.

A critical role for the nervous system in the regulation of host defense during *S. pyogenes* invasive infection is identified herein. In mouse models of necrotizing fasciitis established using *S. pyogenes* clinical isolates, it was found that bacteria directly activate $TRPV1^+$ neurons to produce pain through the action of the secreted pore-forming toxin SLS. Nociceptors release CGRP, a neuropeptide that suppresses the recruitment and bactericidal activity of neutrophils essential for host defense. Silencing nerve fibers and their signaling to immune cells via administration of botulinum neurotoxin A (BoNT/A) or a CGRP antagonist halts bacterial invasion, showing that targeting the nervous system could be a strategy to enhance host defense and treat invasive bacterial infections.

Results

*S. pyogenes* induces pain independently of the inflammatory response. To study the role of pain fibers in bacterial invasion, a mouse model of *S. pyogenes* infection was adapted to mimic pathologic features of human necrotizing fasciitis (Ashbaugh et al., 1998). Two *S. pyogenes* strains from human infections were used: 1) 854 M-type 1 (M1), a clinical isolate representative of the dominant clonal group among isolates from contemporary invasive infections (Gryllos et al., 2008), and (2) 950771 M-type 3 (M3), a clinical isolate from a child with necrotizing fasciitis (Ashbaugh et al., 1998).

Subcutaneous infection of the mouse hind paw was initiated, which is densely innervated and well suited for the study of pain reflex behaviors. Both bacterial strains induced progressive edema and dermonecrotic lesions (FIG. 12A), necrosis in the subcutaneous tissues, overlying dermis, and thrombosis of the arterioles and venules, resembling human necrotizing fasciitis (FIG. 12B). Body weight loss and mortality occurred over time, associated with bacterial proliferation (FIGS. 19A, 20A-20C). While M3 produced lethality at all doses, M1 only caused death at the highest dose (FIG. 19B).

Pain behavioral analysis showed that both *S. pyogenes* M1 and M3 bacterial strains evoked dose-dependent and robust, spontaneous lifting/licking and flinching pain reflexes of the infected paw within minutes of injection (FIGS. 12C, 19D-19E). M1 and M3 strains also produced dose-dependent mechanical hyperalgesia (increased sensitivity to noxious stimuli) within 1 h that continued for 48 h post-injection (FIG. 12D). At lower doses, M1 infection induced stronger mechanical hyperalgesia than M3 infection. Heat hyperalgesia was also robustly produced by *S. pyogenes* M1 and M3 in a similar time course as mechanical hyperalgesia. Because mechanical and heat sensitivity returned towards baseline at 48 h after infection (FIG. 12D), it was determined if this transition was correlated with neural damage. At 48 h and 72 h post-infection, significant changes in the proportions of TRPV1+, CGRP+, or NF200+ cell bodies were not detected in the L4-L6 dorsal root ganglia (DRG) (FIG. 19F). However, loss of sensory nerve fibers innervating the footpad was detected in mice infected with M1 *S. pyogenes* at 72 h. At the center of infected lesions, there was complete loss of CGRP+ and PGP9.5+ nerves, with some intact nerves at lesion borders, whereas nerves remained unaffected in areas remote from the lesion (FIG. 19G). Thus, *S. pyogenes* infection induces significant spontaneous pain and hyperalgesia at early time points, as well as subsequent local loss of sensory nerves.

It was next determined whether inflammatory mediators or immune cells drove the early intense hyperalgesia during *S. pyogenes* infection. Ibuprofen, which blocks cyclo-oxygenase mediated prostaglandin synthesis, had no effect on mechanical or heat hyperalgesia (FIG. 20A). It was next found that mice deficient in caspase-1 (Casp1$^{-/-}$, which mediates IL-1β production, or mice deficient in myeloid derived factor 88 (Myd88$^{-/-}$), which mediates toll-like receptor and IL-1R signaling, developed hyperalgesia similar to wild-type mice following S. pyogenes infection (FIG. 20A). Neither depletion of neutrophils (Gr1 antibody treatment), nor deficiency in recombination activating gene 2 (Rag2$^{-/-}$), which mediates T and B cell development, altered the development of hyperalgesia after infection (FIG. 20A). These data, together with the observation that S. pyogenes induces pain within minutes, indicate that bacteria can directly interact with neurons independent of the immune response.

Figure 12A:
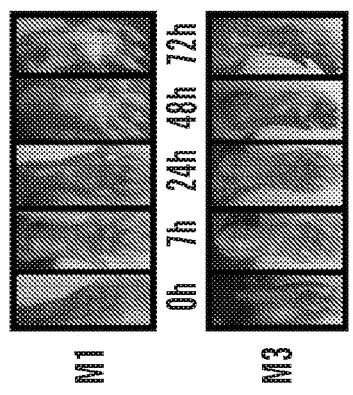
Figure 12B:
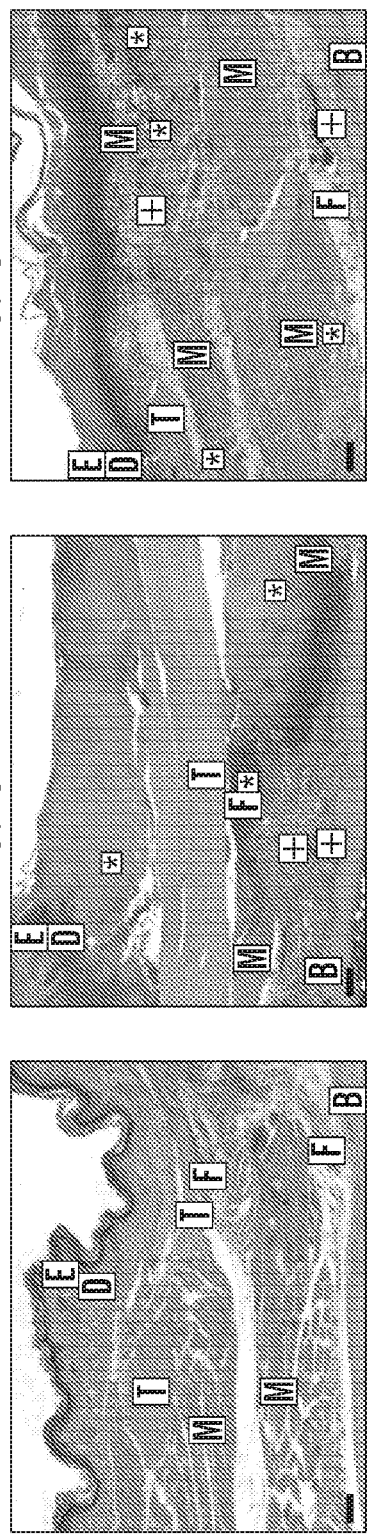
Figure 12C:
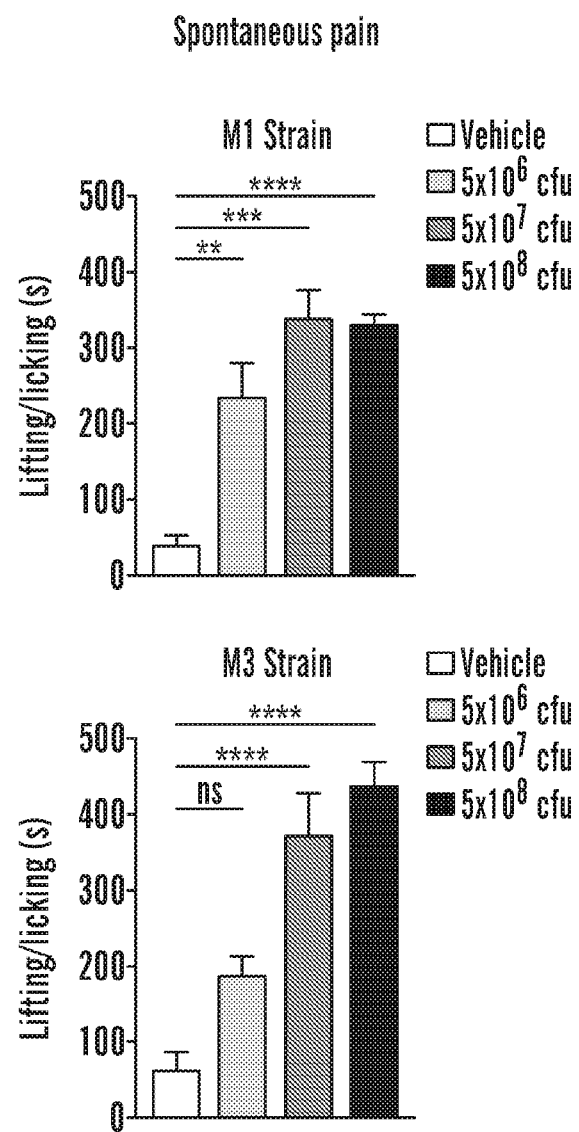
Figure 12D:
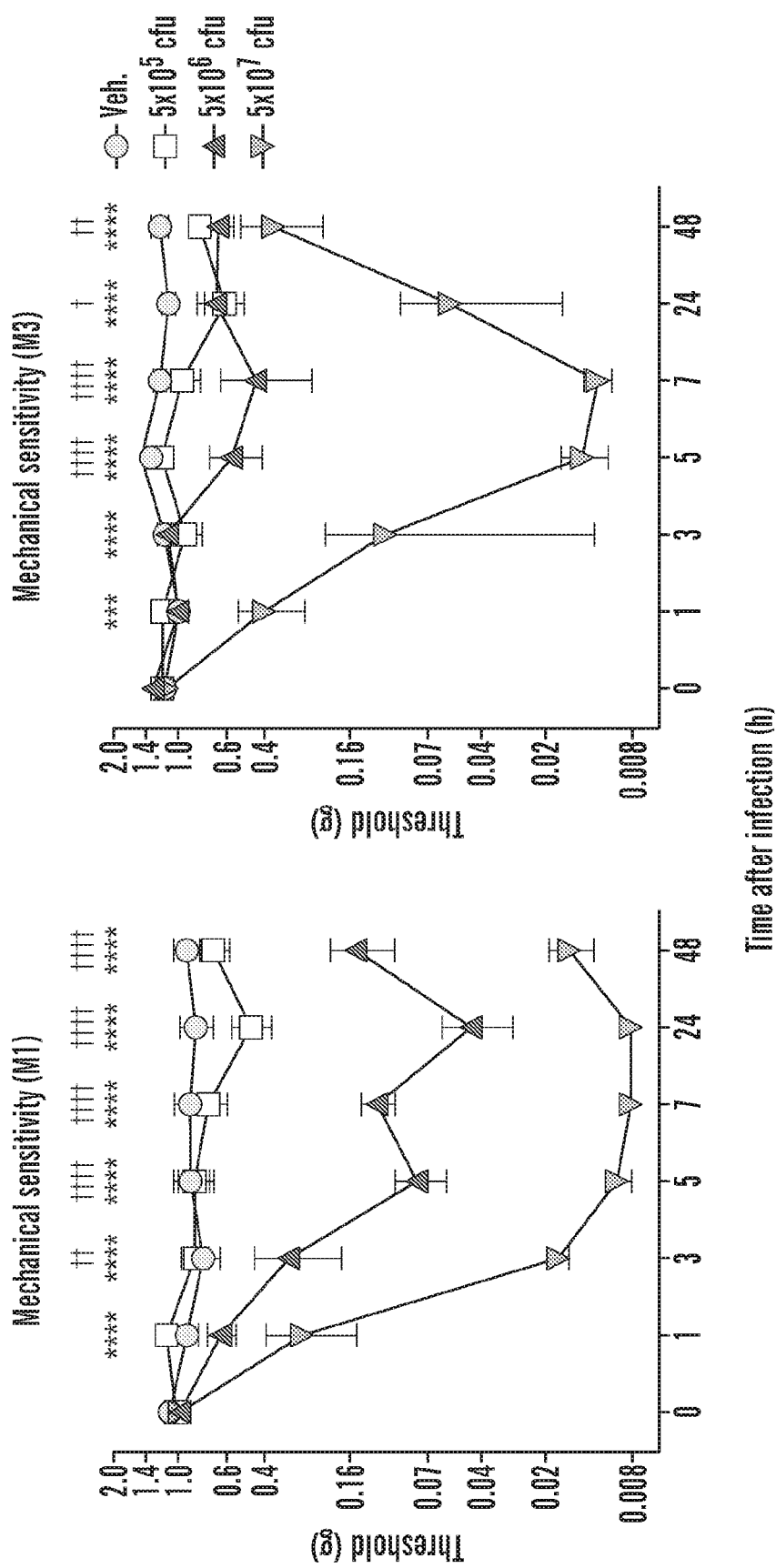
Figure 12E:
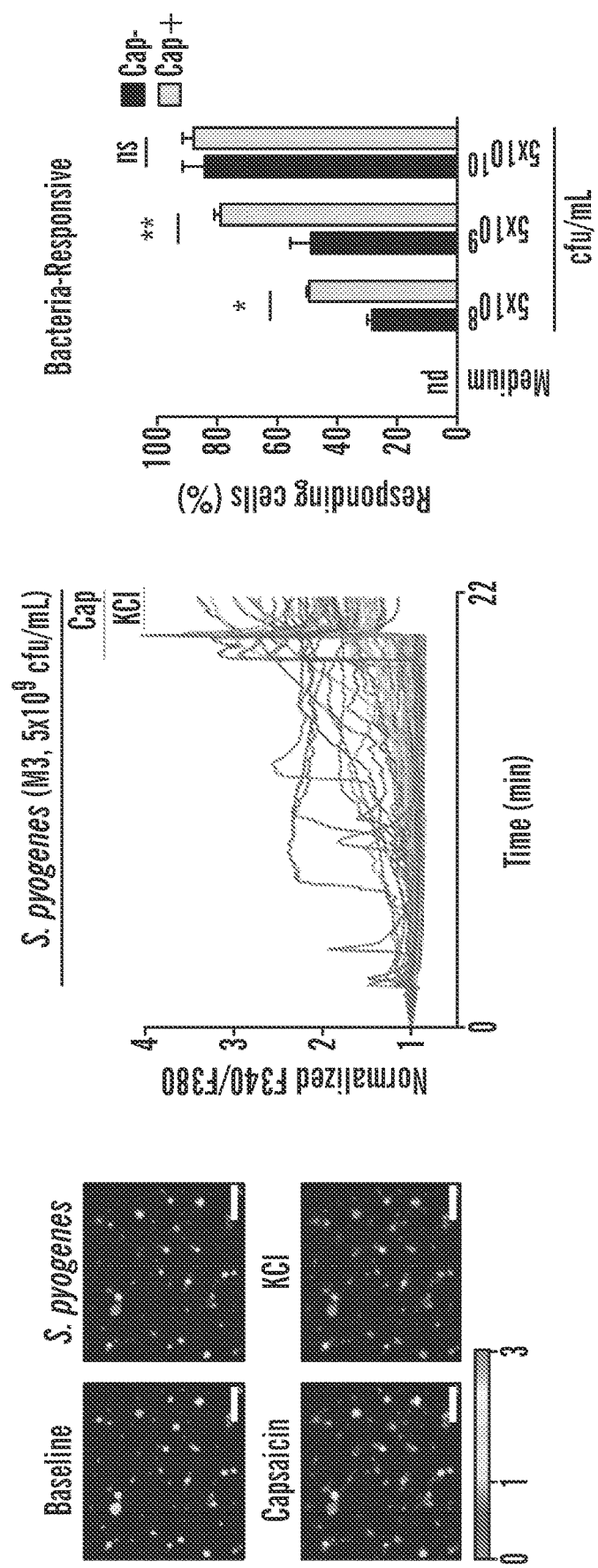
Figure 12F:
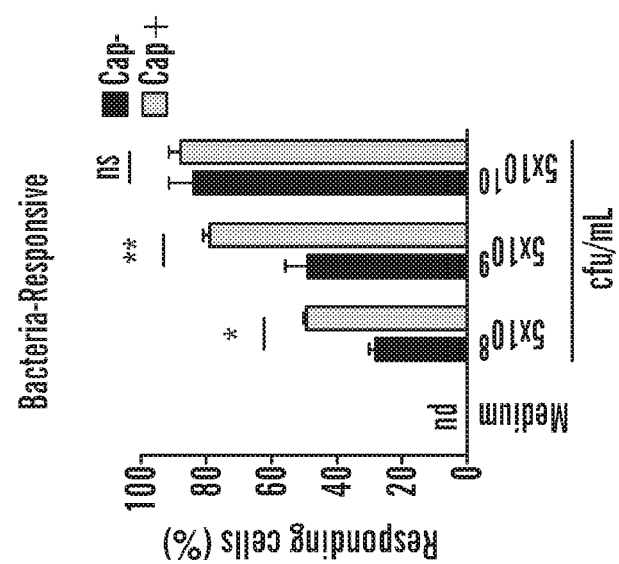
Figure 12F:
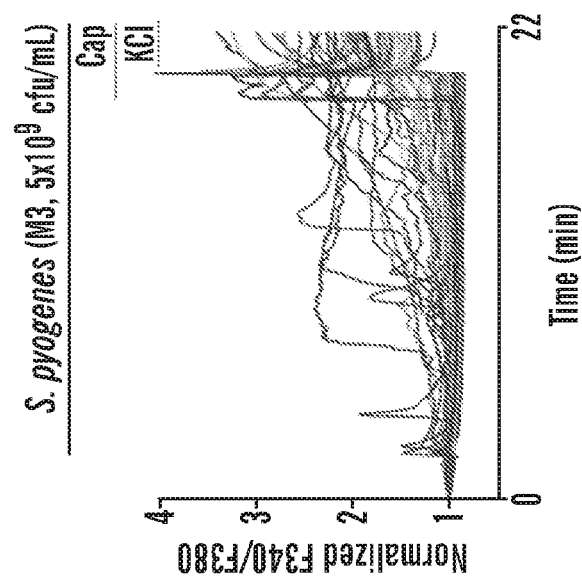
Figure 12F:
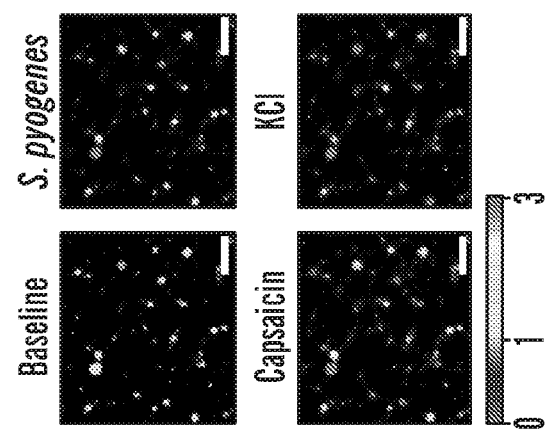
Figure 13A:
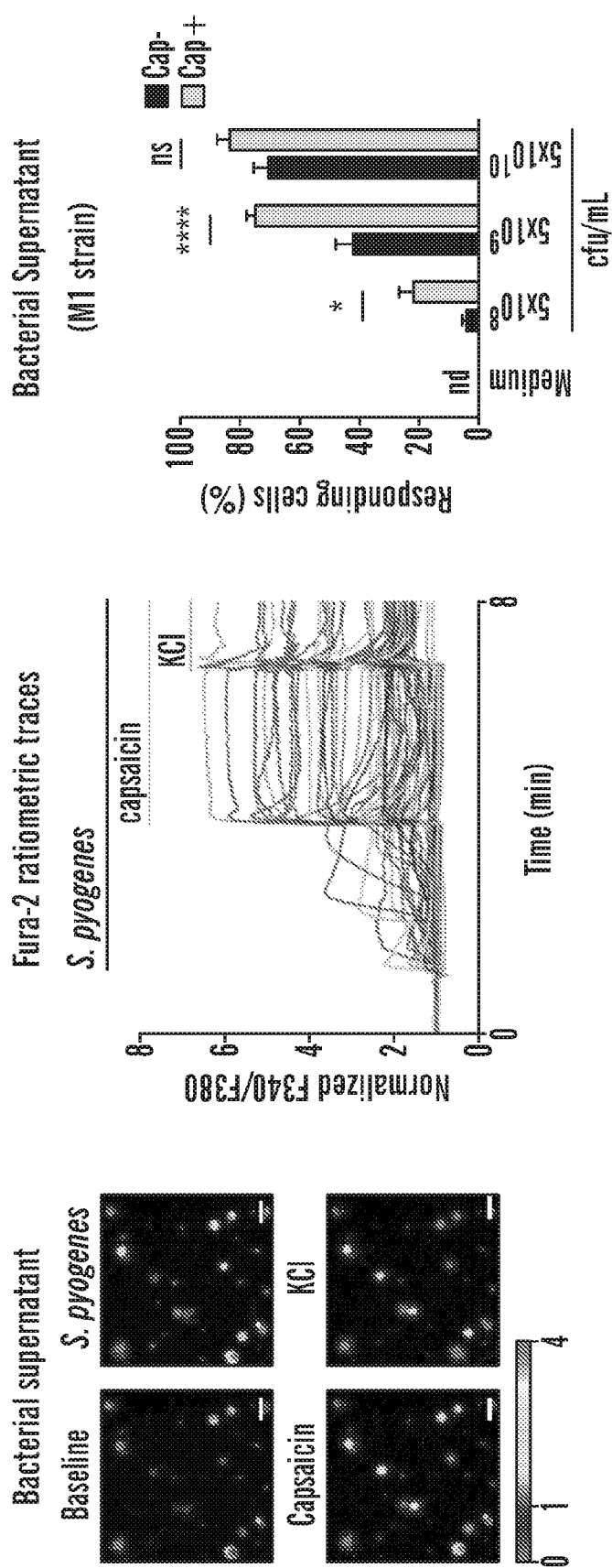
Figure 23A:
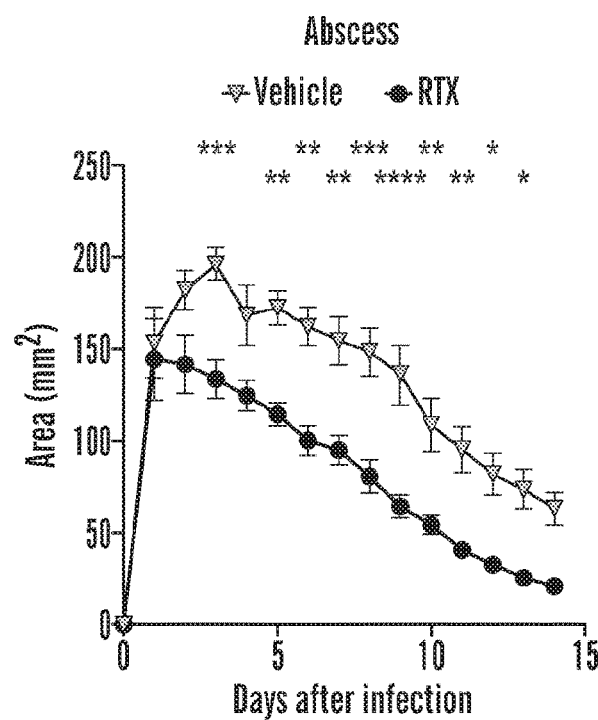

S. pyogenes directly activates nociceptor neurons through SLS. It was next determined whether S. pyogenes could directly act on sensory neurons to produce pain. Live M3 S. pyogenes induced robust calcium influx in DRG neurons in vitro within minutes of application (FIG. 12E). Bacteria-responsive neurons also frequently responded to capsaicin, a ligand for TRPV1, a heat-sensitive ion channel expressed by many nociceptors. At lower bacterial concentrations ($5 \times 10^8$-$5 \times 10^9$ cfu/mL), more capsaicin-responsive (Cap+) neurons were activated by S. pyogenes than capsaicin-unresponsive (Cap-) neurons. At $5 \times 10^{10}$ cfu/mL, the majority of DRG neurons were activated (FIG. 12E). Bacteria-free filtered supernatant from M1 S. pyogenes cultures also induced calcium influx in DRG neurons in a dose-dependent manner (FIG. 23A). Similar to responses to live bacteria, Cap+ nociceptors were more responsive to supernatants from lower density bacterial cultures than were Cap- neurons (FIG. 13A). DRG neurons with smaller cell body areas were observed to be more sensitive to activation by bacterial supernatant than larger-sized neurons (FIG. 20B).

Figure 13C:
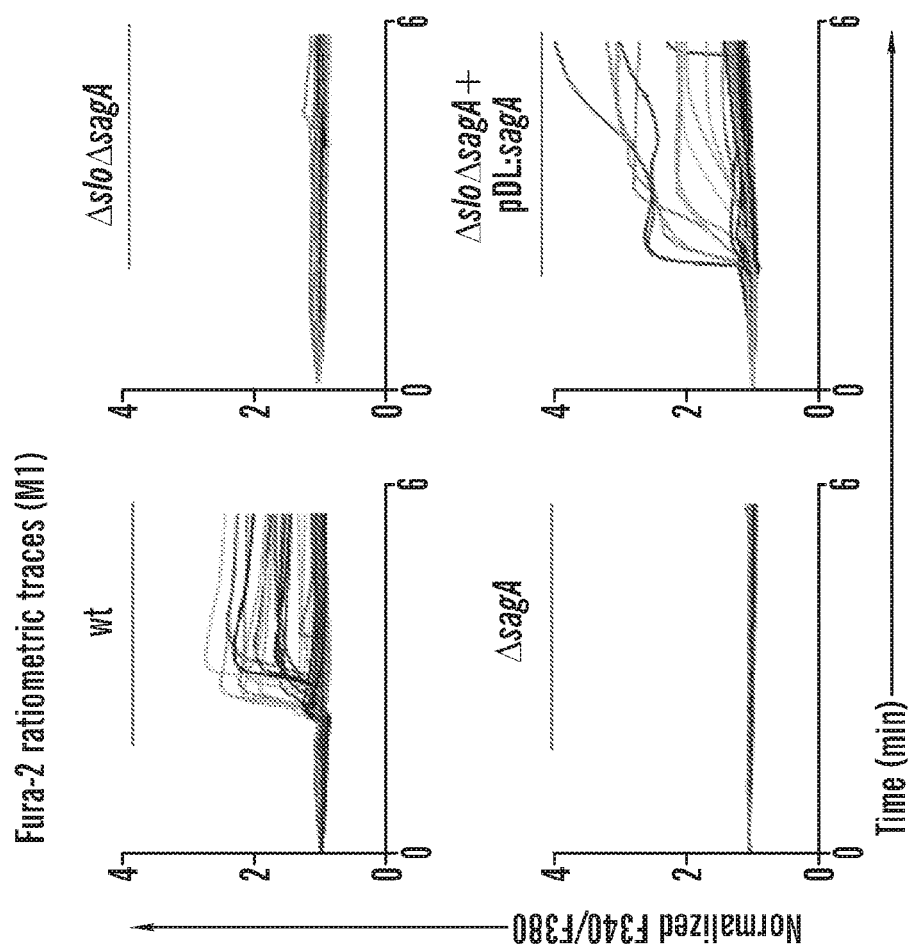
Figure 13B:
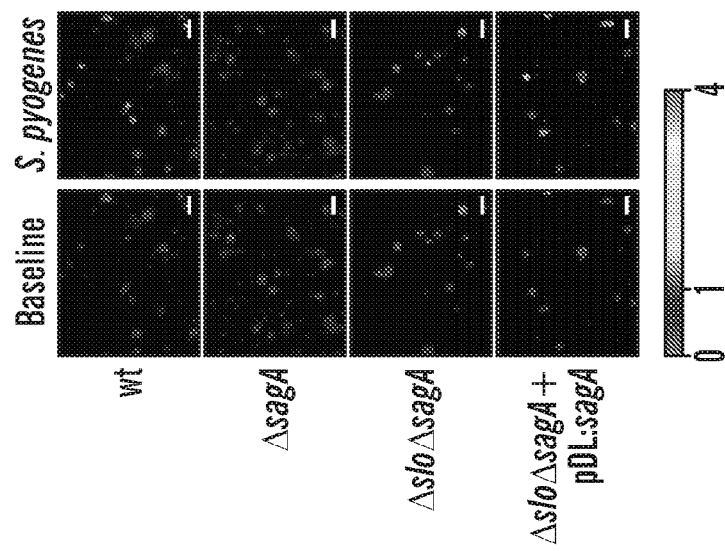
Figure 13E:
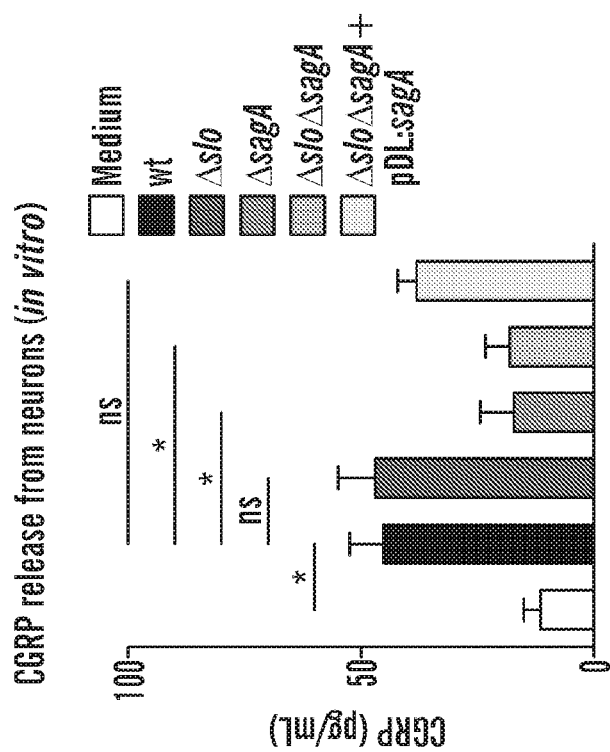
Figure 13D:
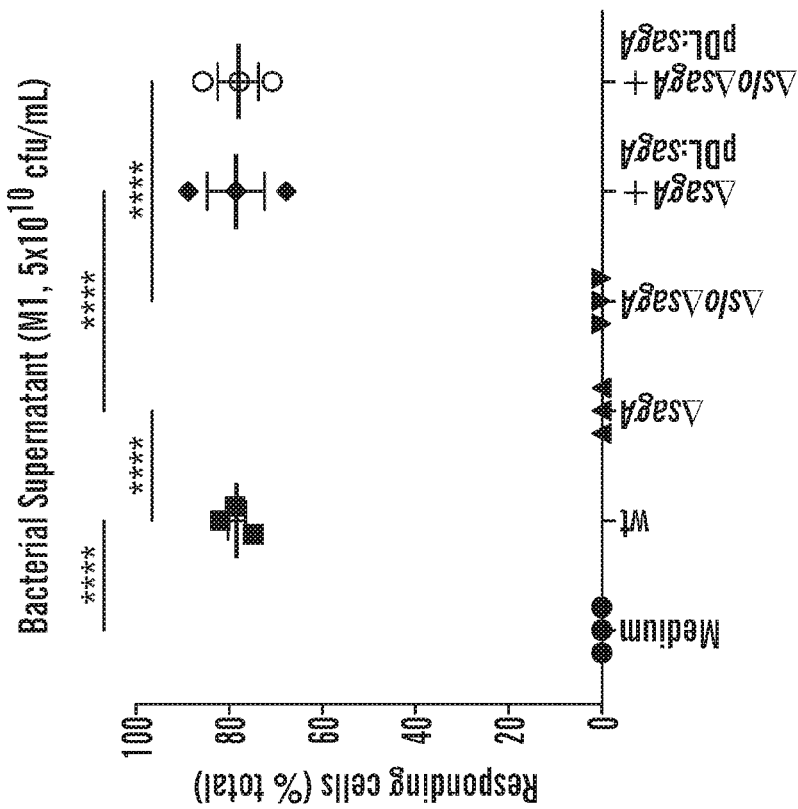
Figure 20C:
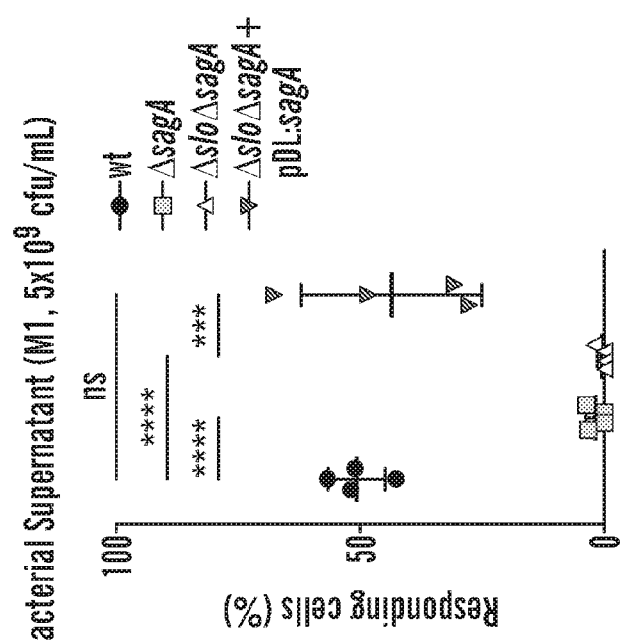
Figure 21B:
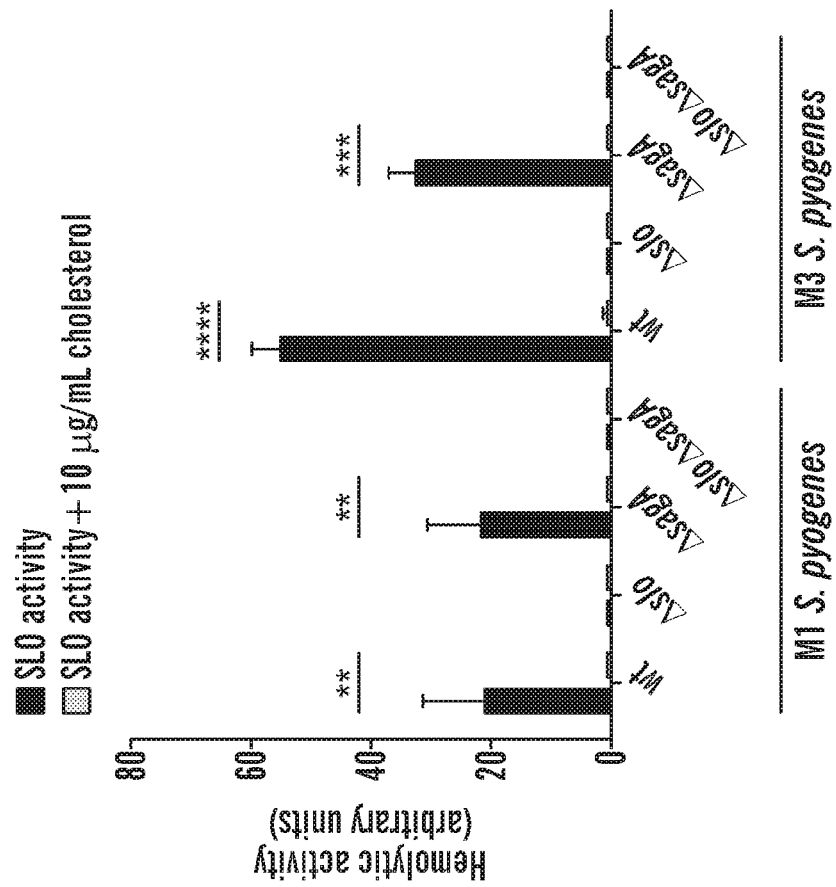
Figure 21A:
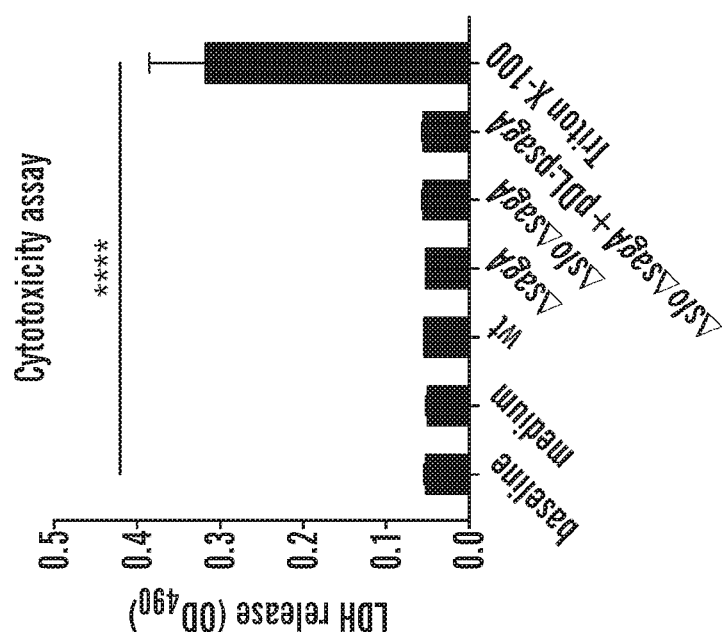

Without wishing to be bound by a particular theory, it was hypothesized that S. pyogenes pore-forming toxins (PFT) could be molecular candidates for mediators of neuronal activation, due to their capacity to induce cation influx in mammalian cells (Bentley et al., 2005). S. pyogenes produces two PFTs, streptolysin O (SLO) and SLS. M1 and M3 isogenic mutant strains that lacked expression of SLO (Δslo), SLS (ΔsagA), or both toxins (ΔsloΔsagA) were generated. Supernatant from bacteria deficient in SLS (ΔsagA and ΔsloΔsagA) did not induce calcium influx in DRG neurons (FIG. 13B-13D). Plasmid complementation of SLS (pDL:sagA) into SLS mutant bacteria (ΔsagA+pDL:saga and ΔsagAΔslo+pDL:sagA) restored the ability of S. pyogenes to activate neurons at similar levels as wt bacteria (FIG. 13B-13D). SLS (sagA) was required for S. pyogenes mediated neuronal activation at both low and high bacterial concentrations for Cap- and Cap+ cellular subsets (FIG. 13D, 20C-20D). It was also found that S. pyogenes mediated release of the neuropeptide CGRP by DRG neurons in a SLS-dependent manner (FIG. 13E). LDH release assays showed that this neuropeptide release was unrelated to cell lysis (FIG. 21A). SLO activity was intact in wt and sagA mutant strains, indicating these effects were specific to SLS (FIG. 21B).

Figure 14A:
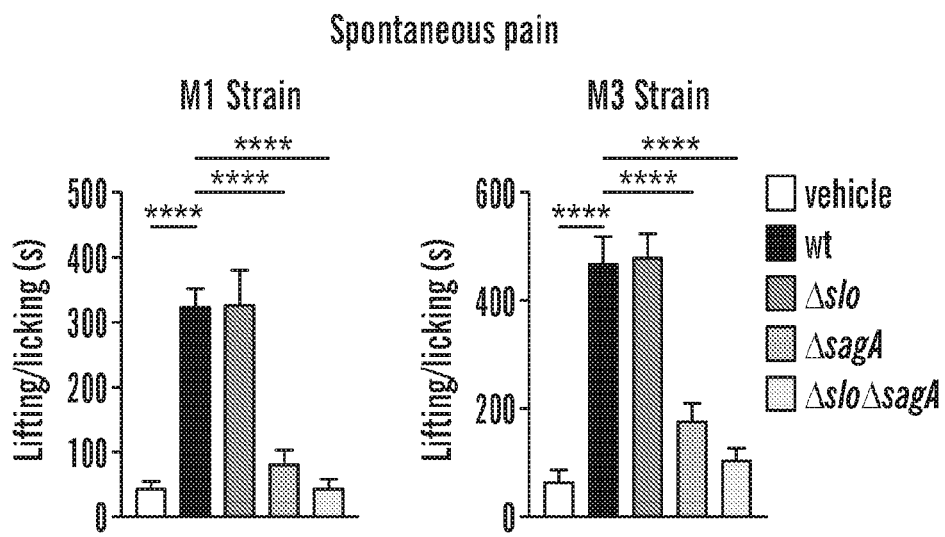
Figure 14B:
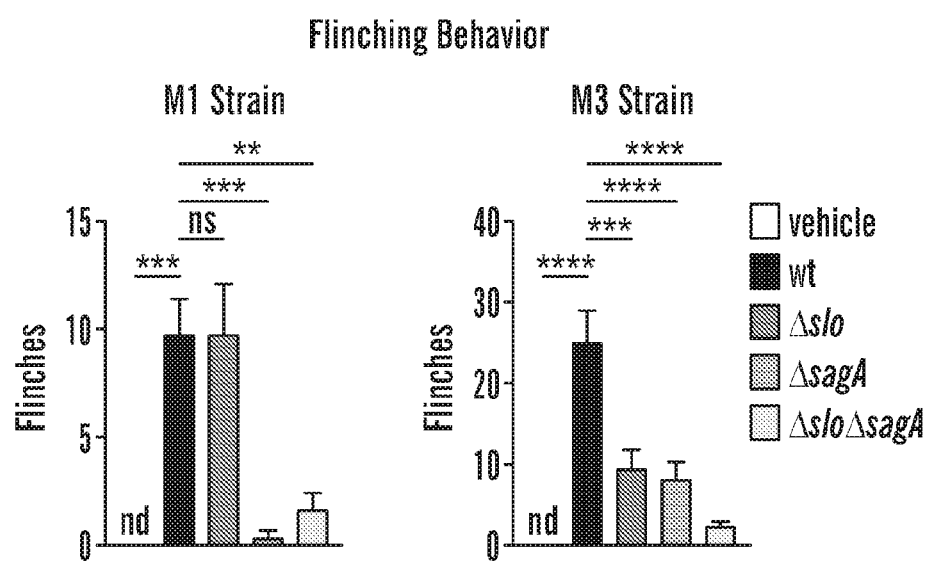
Figure 21C:
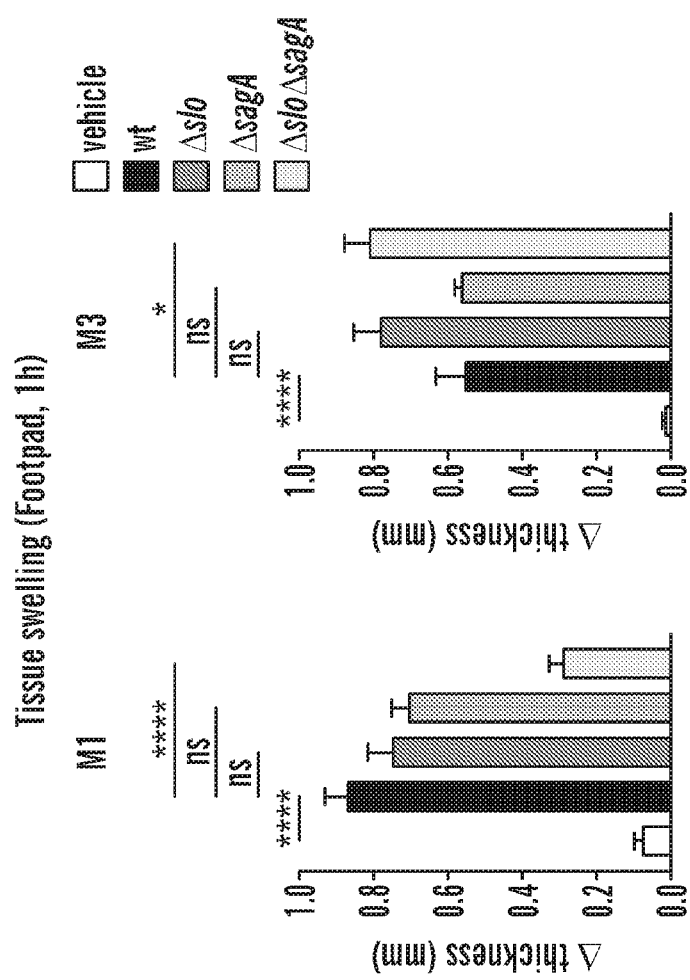
Figures 21D, 21E:

SLS is critical for S. pyogenes-induced pain and pathogenesis. To determine the role of SLS in pain in vivo, mice were infected with wt or mutant S. pyogenes strains. Spontaneous lifting/licking pain behaviors were abrogated in mice infected with SLS-deficient bacteria (ΔsagA and ΔsloΔsagA) on both M1 and M3 S. pyogenes strain backgrounds, but not in mice infected with bacteria deficient in SLO alone (Δslo) (FIG. 14A). Spontaneous flinches were abrogated in mice infected with SLS deficient strains (FIG. 14B). Paw swelling and bacterial load recovery after infection did not vary between wt and mutant strains post-infection at the 1 hour time point after analysis of spontaneous pain behaviors (FIG. 21C-21D).

Figure 14D:
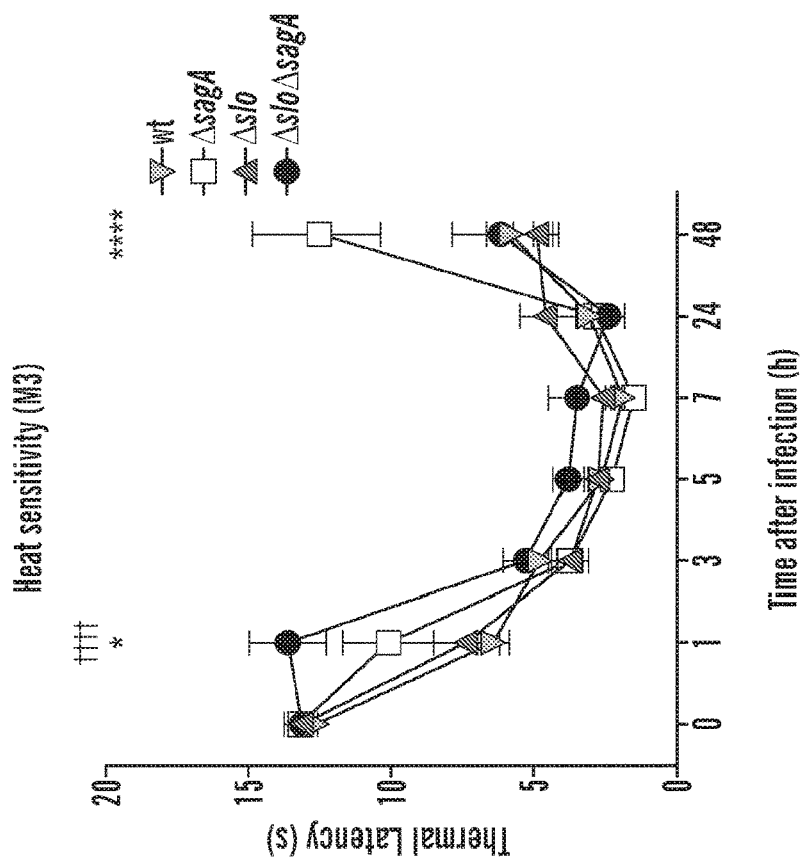
Figure 14C:
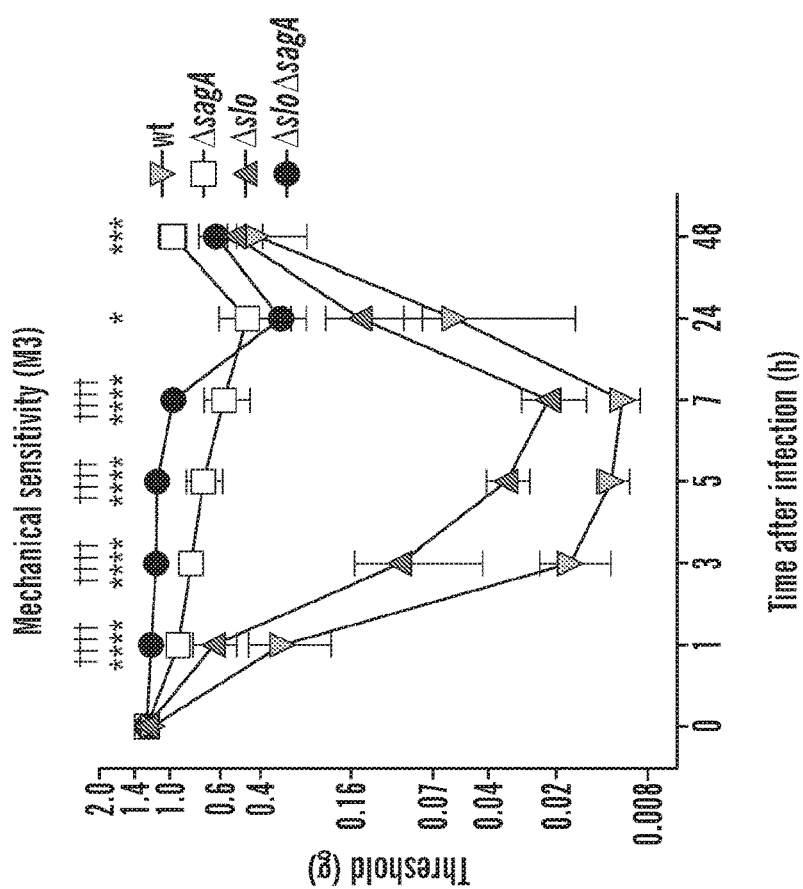
Figure 14E:
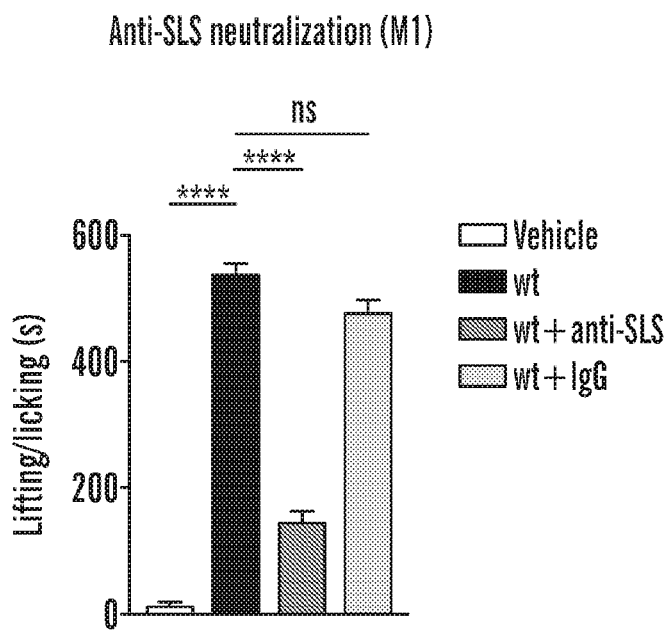
Figure 14F:
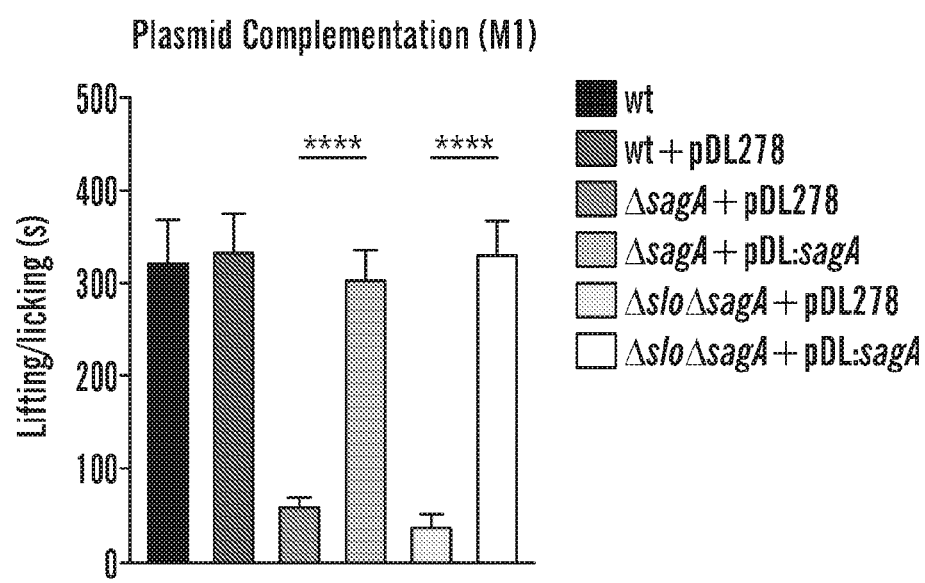

It was next found that mice infected with SLS mutants (ΔsagA or ΔsloΔsagA) did not develop mechanical hyperalgesia, while wt and Δslo strains induced significant mechanical hyperalgesia (FIG. 14C). Heat hyperalgesia was not significantly altered by deficiencies in SLS or SLO (FIG. 14D). It was next determined whether antibody neutralization of SLS affected S. pyogenes-induced pain. Mice were treated with a polyclonal antibody against a synthetic peptide encoded by sagA (Dale et al., 2002). Anti-SLS, but not control IgG, blocked spontaneous pain behaviors following M3 S. pyogenes infection (FIG. 14E, 21E). Plasmid complementation with a functional copy of sagA (pDL:sagA) fully restored spontaneous pain reflexes induced by mutant SLS strains (FIG. 14F).

Figure 22C:
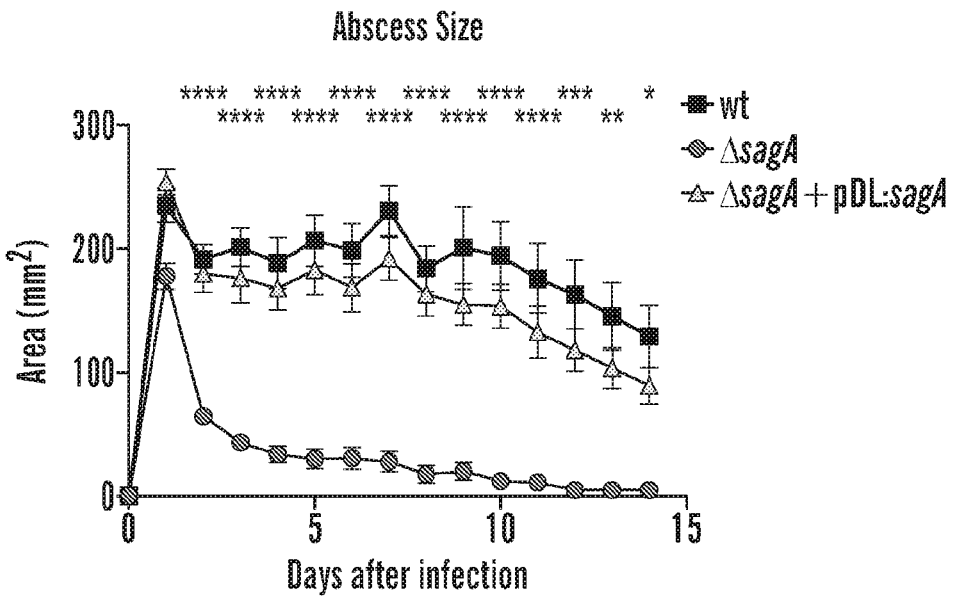
Figure 22D:
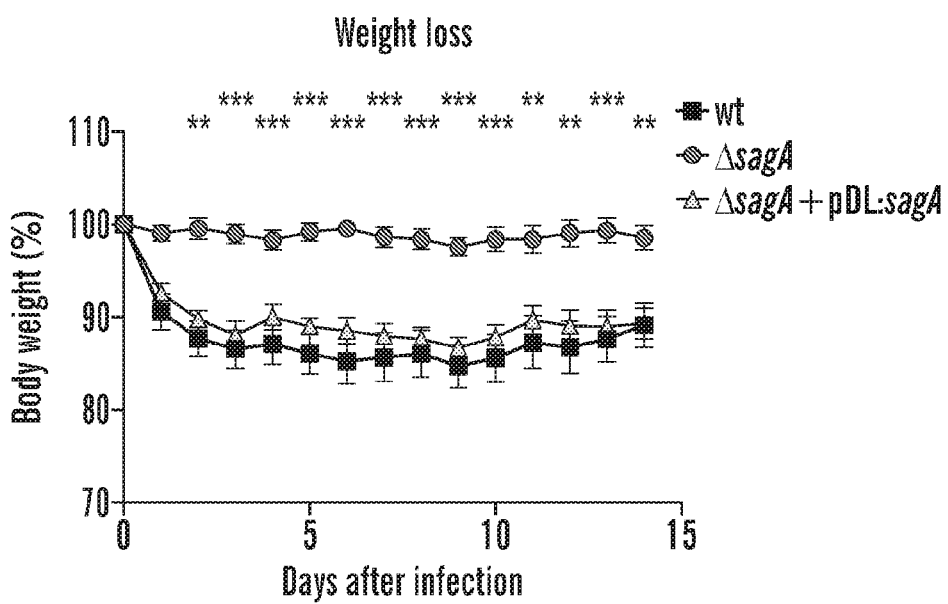

To investigate the role of SLS in mediating S. pyogenes pathogenesis during soft tissue infection, infection was initiated by subcutaneous injection of M1 S. pyogenes ($5 \times 10^6$ cfu) into the flank, a model that allows serial measurement of skin lesions over time (Ashbaugh et al., 1998). Dermonecrotic lesions appeared 1 day after injection of wt strain, peaked at day 9, and began to decrease after day 10, while mice infected with ΔsagA bacteria did not develop dermonecrotic lesions (FIG. 22A). No bacteria were recovered at day 9 from mice infected with ΔsagA S. pyogenes (FIG. 22B). Local abscesses resolved faster in mice infected with ΔsagA bacteria, and weight loss was also dependent on SLS (FIG. 22C-22D). Plasmid complementation of ΔsagA bacteria with pDL:sagA restored dermonecrosis, bacterial proliferation, abscess formation and weight loss to similar levels as wt bacteria (FIG. 22A-22D).

Figure 15A:
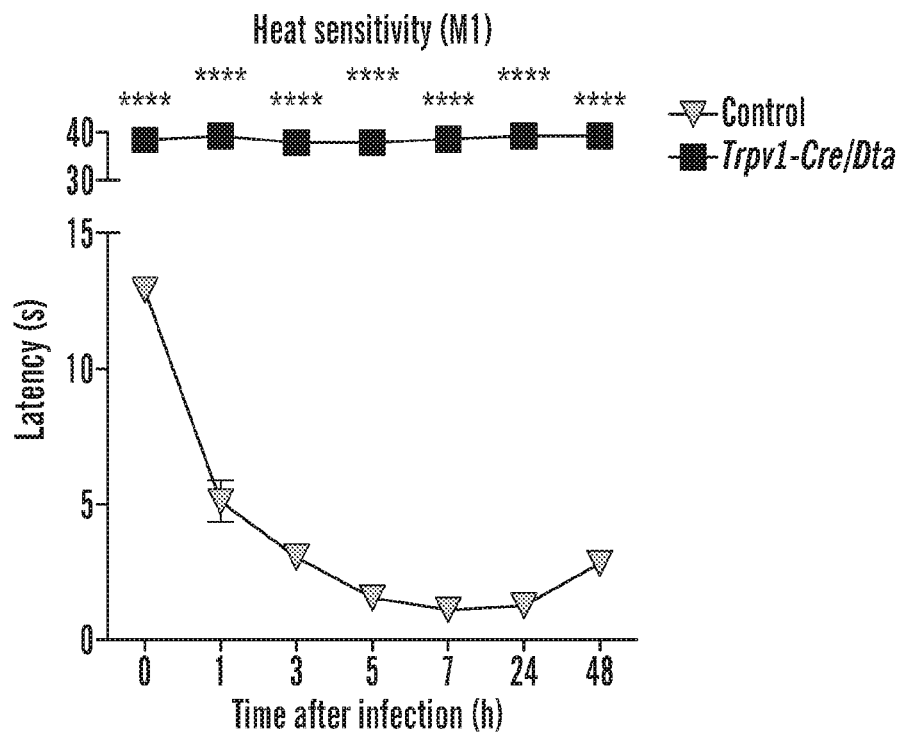
Figure 15B:
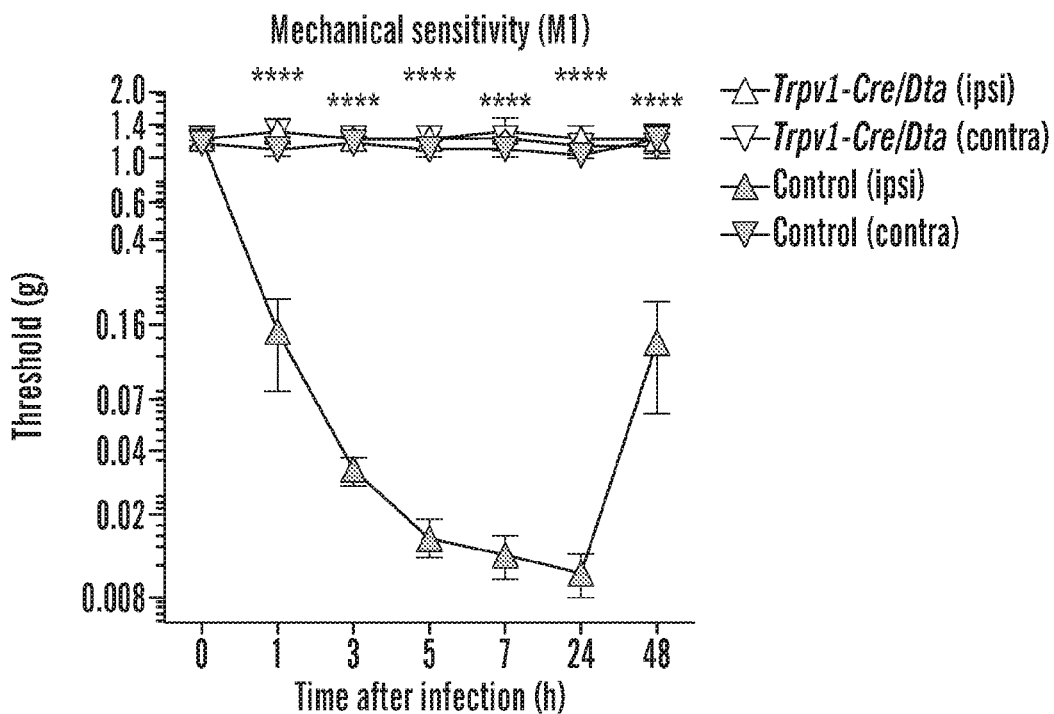
Figure 15C:
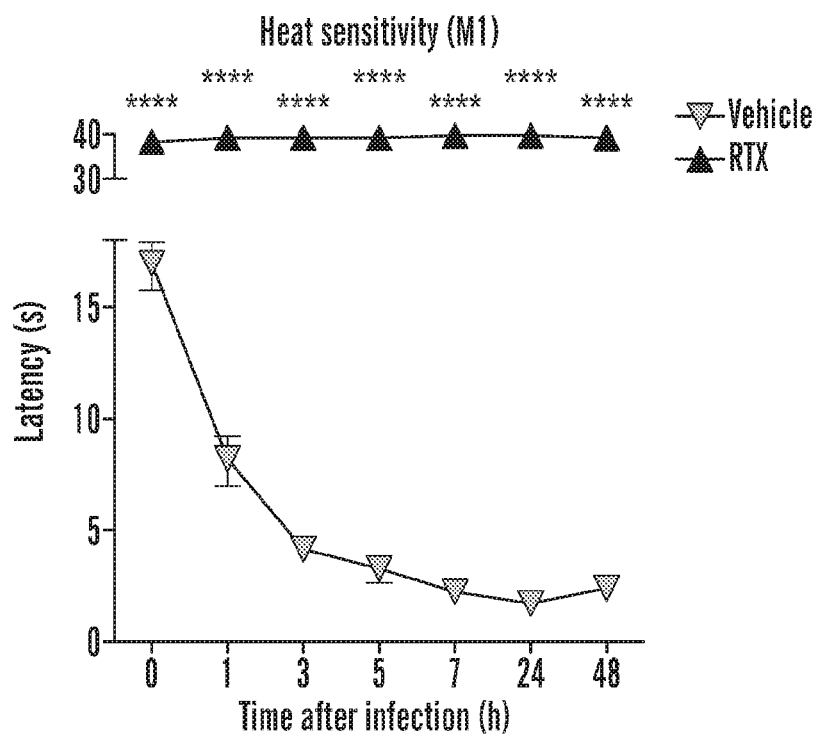
Figure 15D:
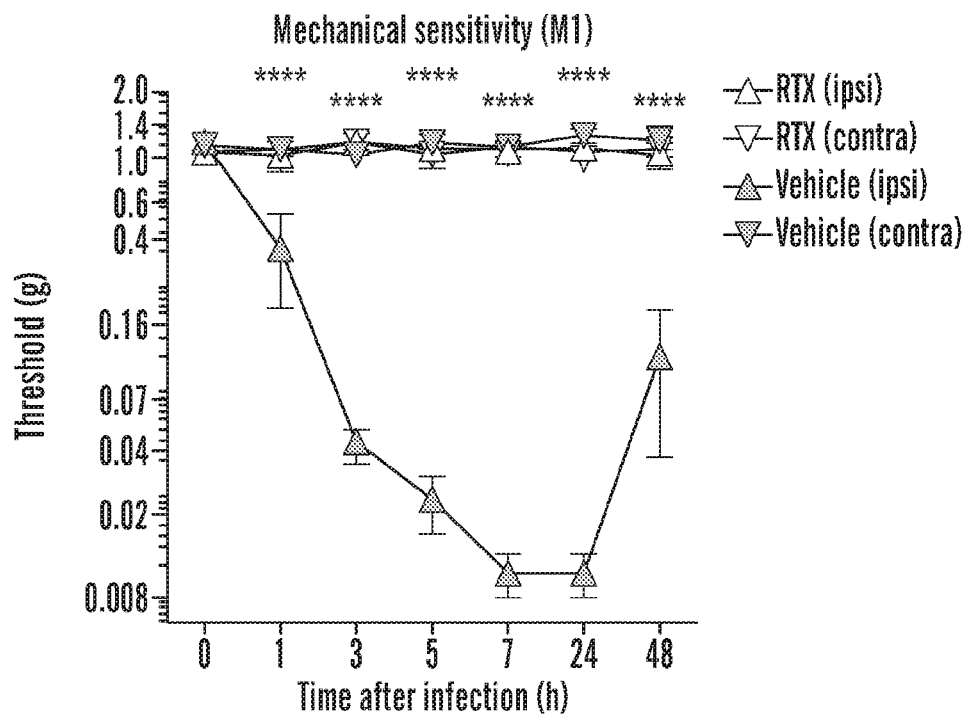
Figures 22E, 22F, 22G, 22H:
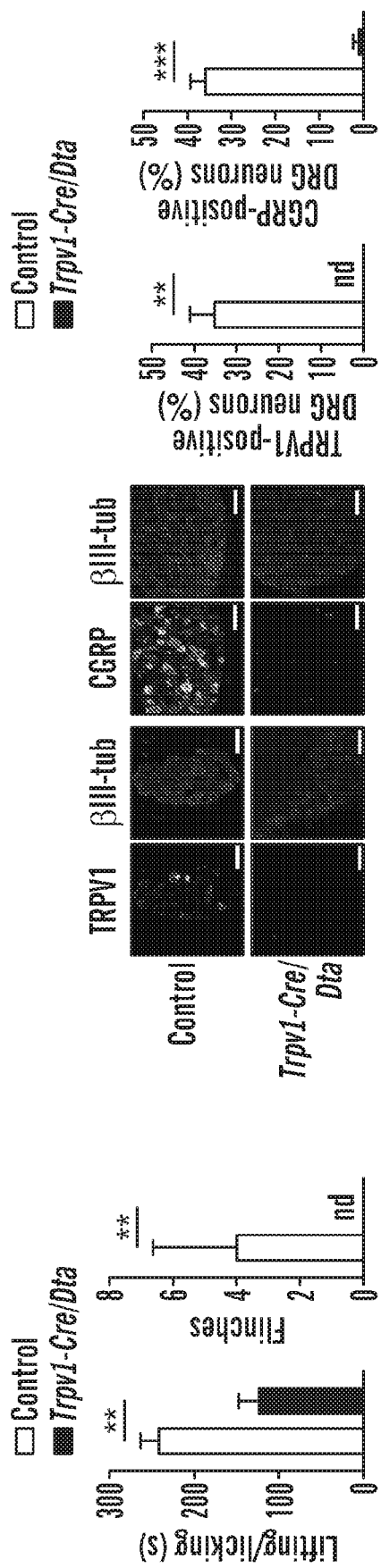

Ablation of nociceptor neurons improves host control of S. pyogenes invasion. Since nociceptor neurons responded directly to SLS, which was crucial for S. pyogenes pathogenesis, it was investigated whether pain fibers played a role in the outcome of infection. Specifically, TRPV1 neurons were ablated by crossing Trpv1-Cre mice with diphtheria toxin A reporter (Dta) mice, which ablates TRPV1-lineage neurons. Heat and mechanical hyperalgesia induced by M1 S. pyogenes was eliminated in Trpv1-Cre/Dta mice compared to control littermates (FIG. 15A-15B). Infection-induced spontaneous pain reflexes were also reduced in these mice (FIG. 22E). Loss of TRPV1+ and CGRP+DRG neurons was confirmed by immunostaining (FIG. 22F).

Figure 15E:
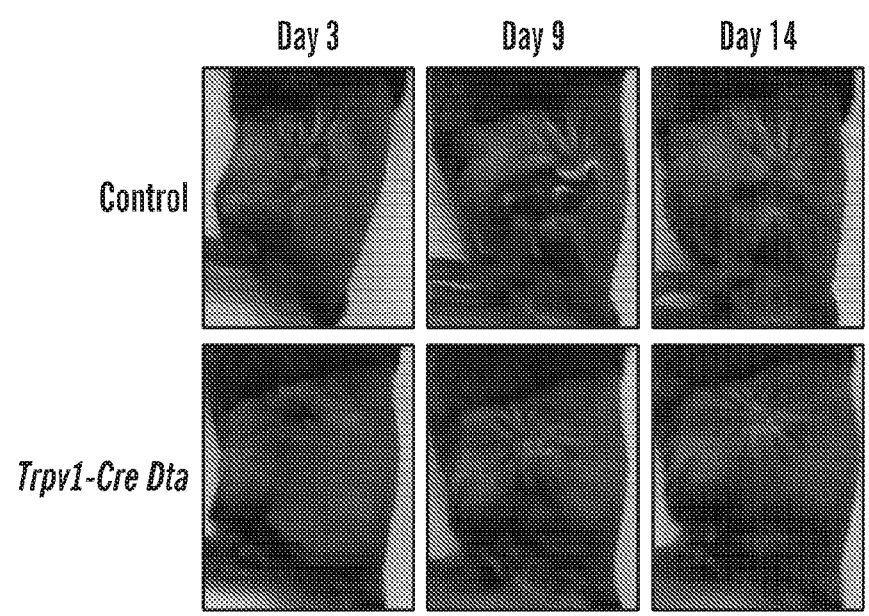
Figure 15F:
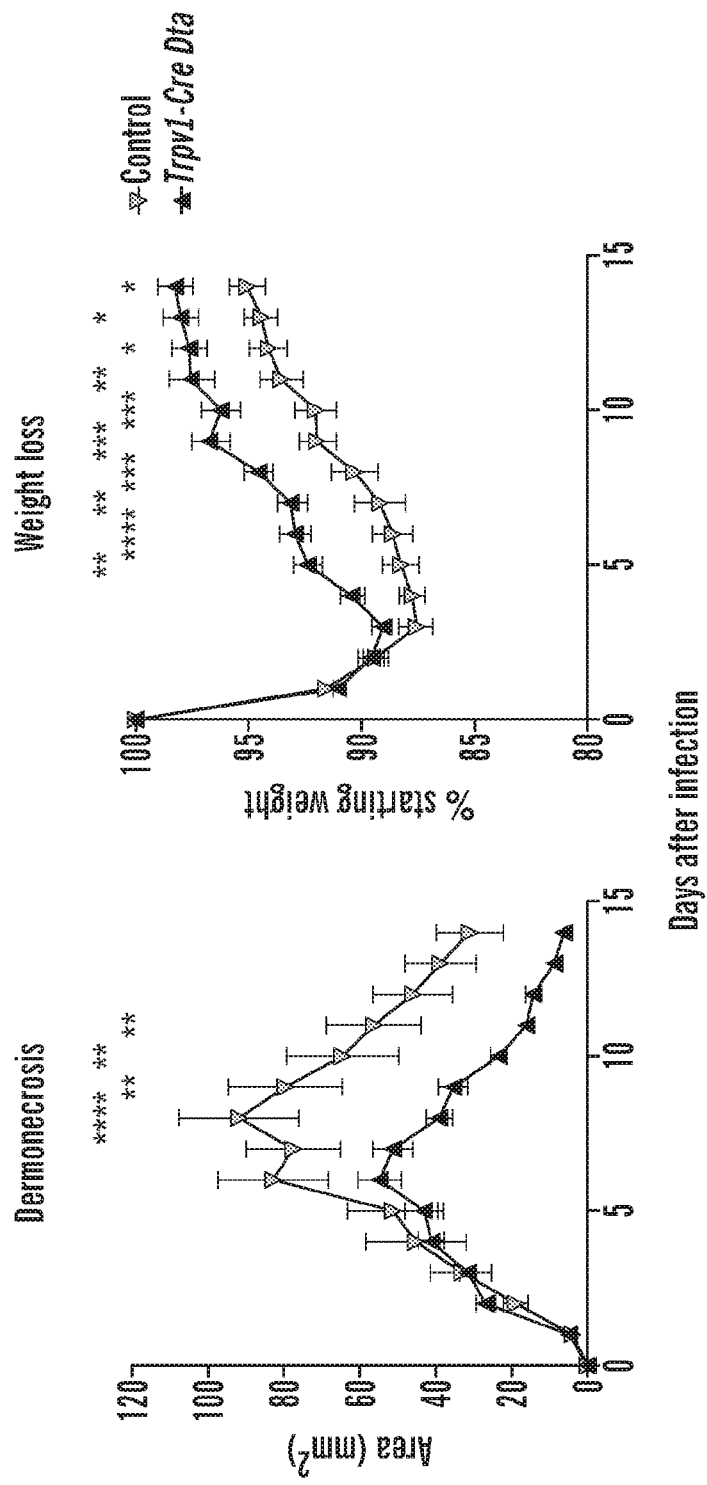
Figure 15G:
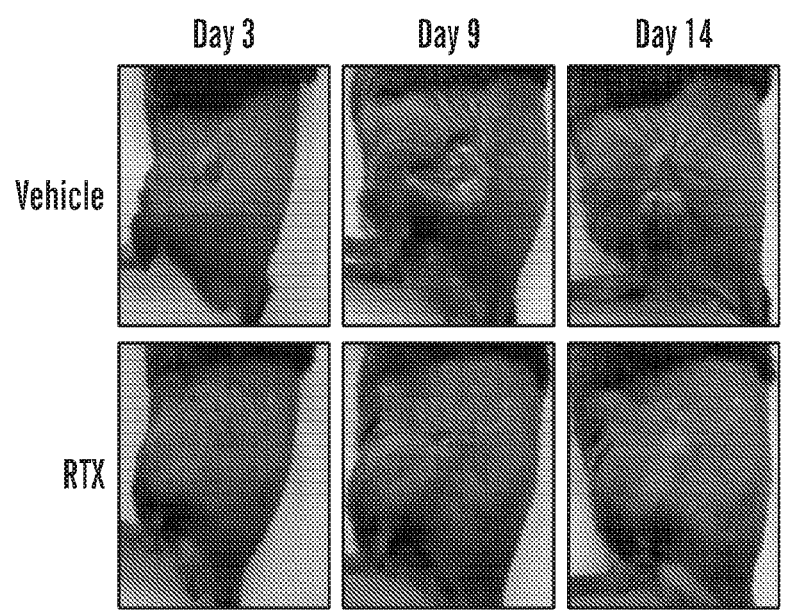
Figure 15H:
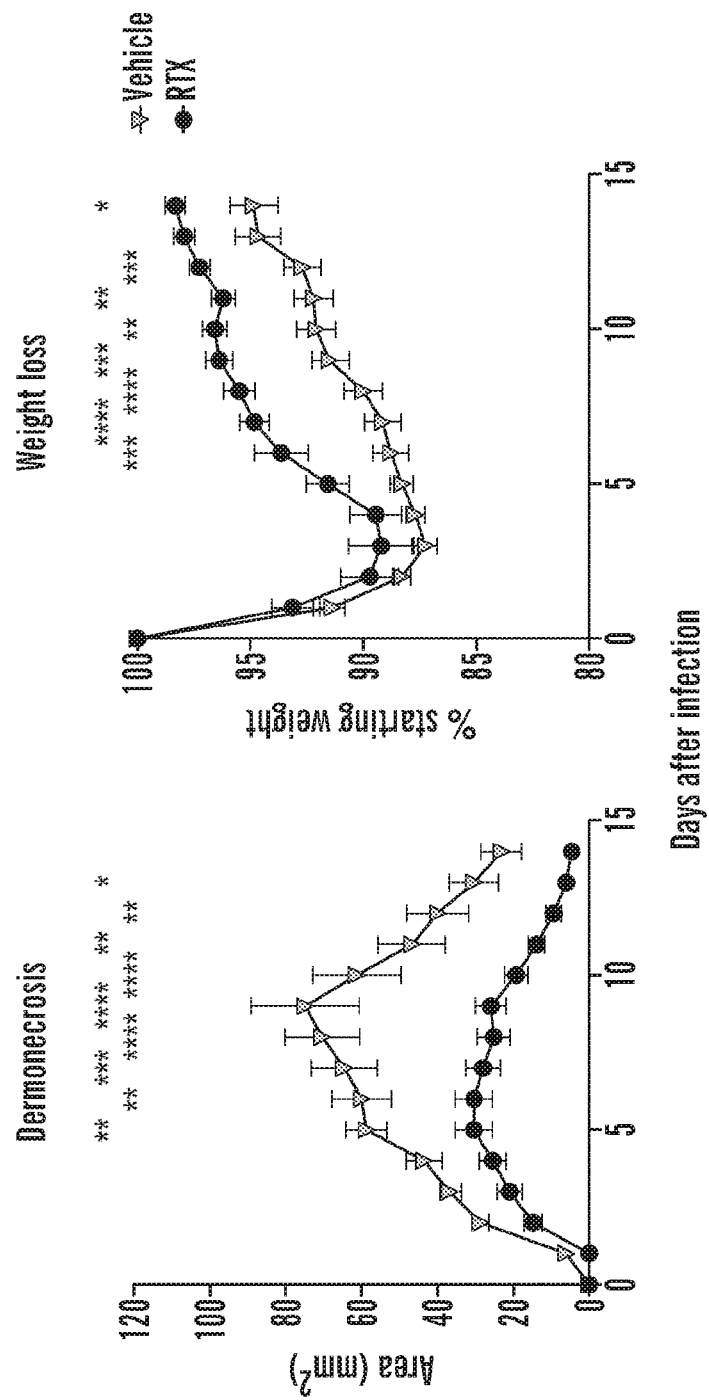
Figure 16A:
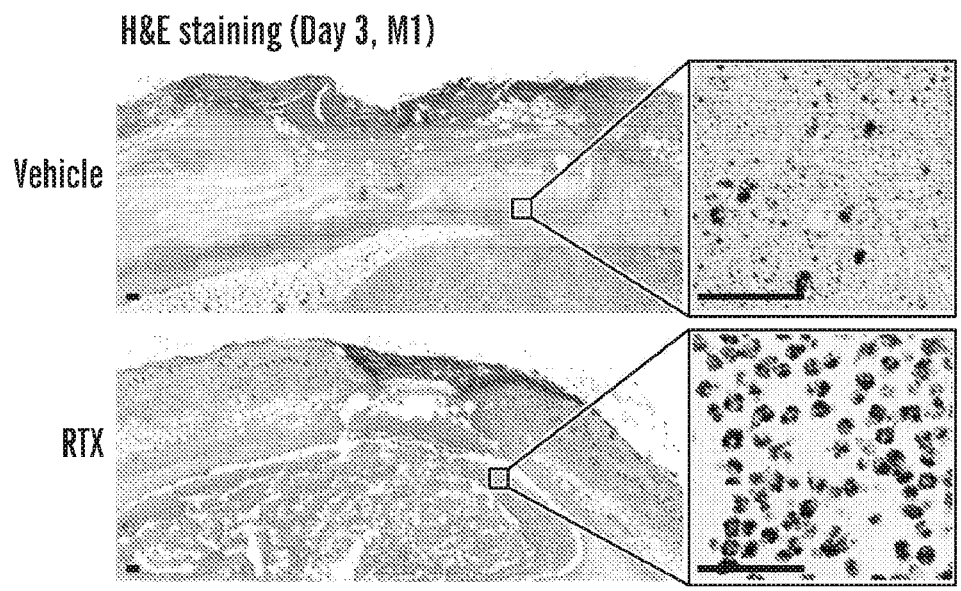
Figure 23B:
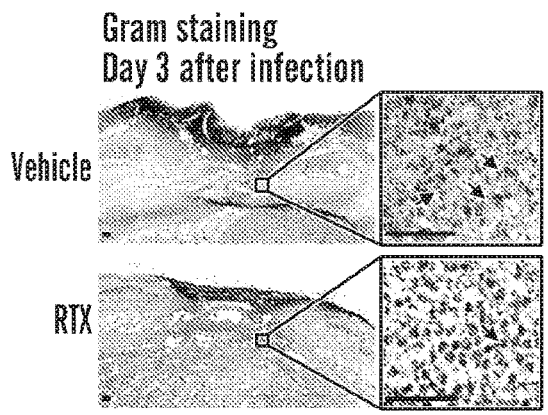

It was next found that Trpv1-Cre/Dta mice developed significantly smaller dermonecrotic lesions and faster weight recovery compared to controls following S. pyogenes flank infection (FIG. 15E-15F). In a second approach to ablate nociceptors, mice were treated with resiniferatoxin (RTX), a high affinity TRPV1 agonist (Sándor et al., 2009). RTX treatment abrogated spontaneous pain behaviors, mechanical and heat hyperalgesia induced by S. pyogenes infection (FIG. 15C-15D, 22G), and led to loss of TRPV1+ and CGRP+ neurons (FIG. 22H). RTX-treated mice developed significantly less dermonecrosis and regained body weight faster than vehicle-treated mice following infection (FIG. 15G-15H). Skin abscess sizes in RTX-treated mice also resolved faster (FIG. 23A). Histopathologic analysis of skin from RTX-treated mice revealed containment of the bacterial infection within a circumscribed abscess containing polymorphonuclear leukocytes, whereas vehicle-treated animals showed necrosis of the subcutaneous tissues with abundant bacteria and relatively few leukocytes (FIG. 16A, 23B). Quantitative cultures confirmed log-fold reductions of

Figure 16B:
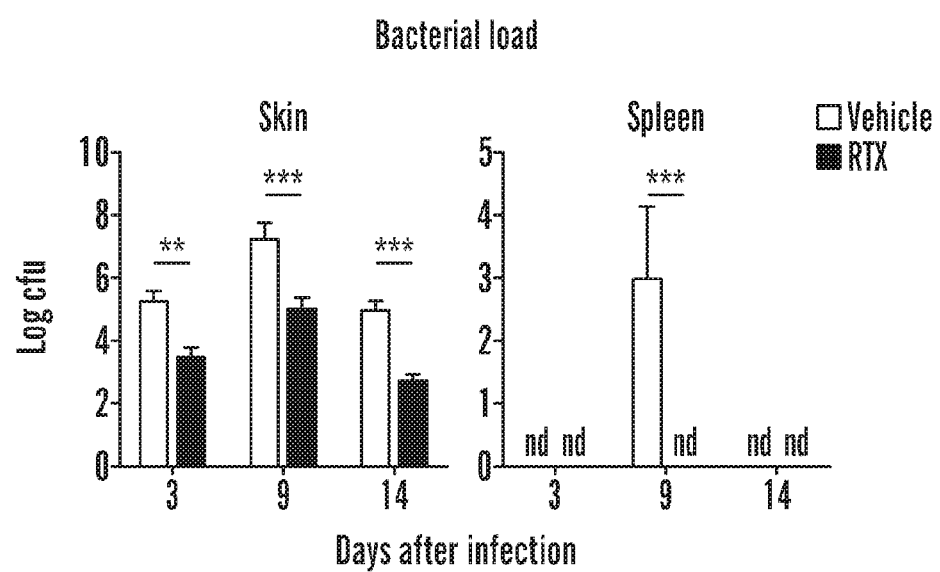
Figure 23C:
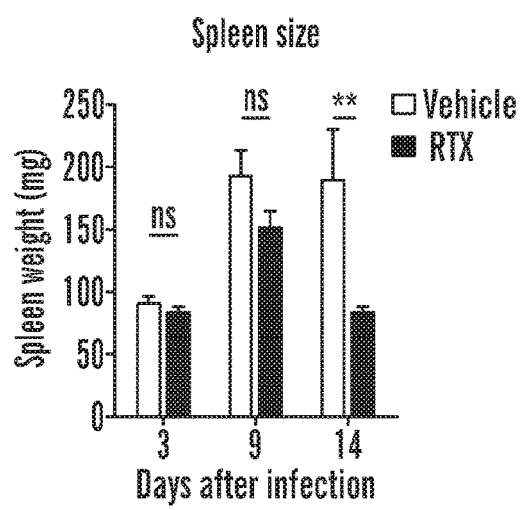

*S. pyogenes* in lesions of RTX-treated mice compared to vehicle controls (FIG. 16B). *S. pyogenes* was cultured from spleens of vehicle-treated mice on day 9, whereas spleens of RTX-treated mice did not yield detectable bacteria (FIG. 16B). Spleen size increased during infection in vehicle-treated mice, but not in RTX-treated mice (FIG. 23C).

Figure 16C:
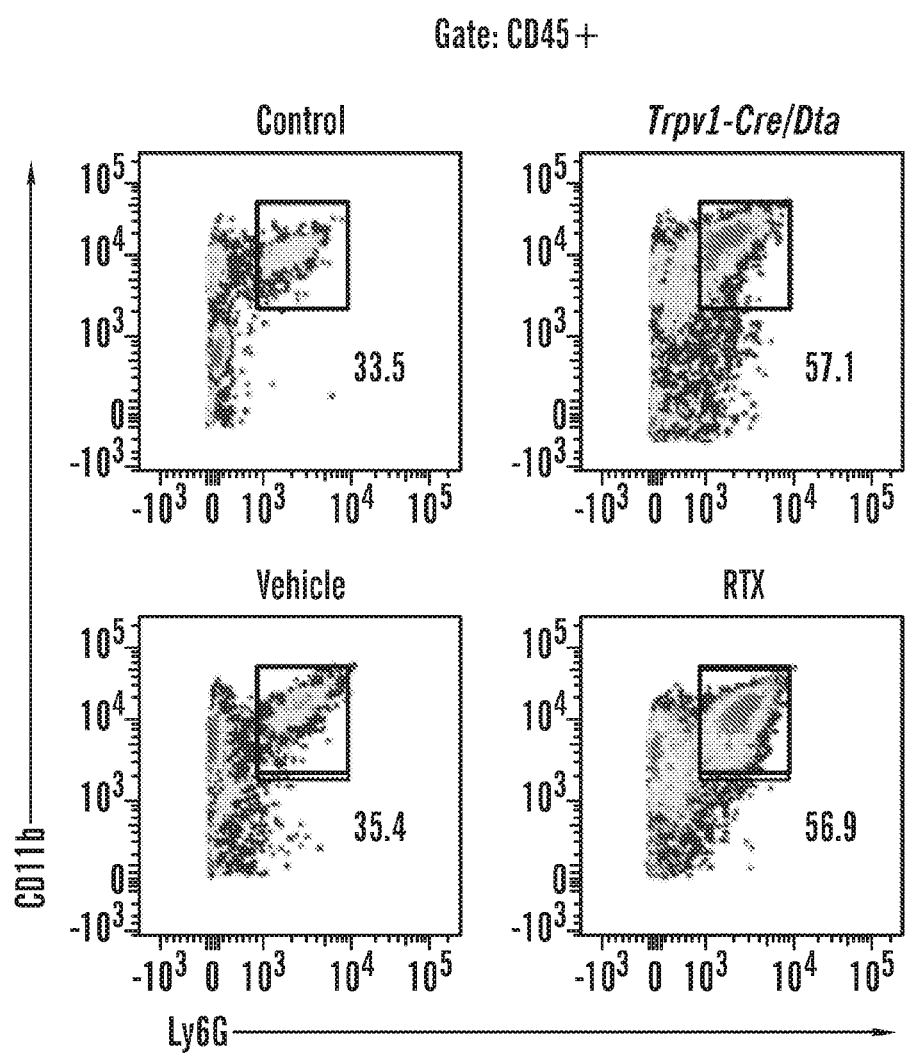
Figure 16E:
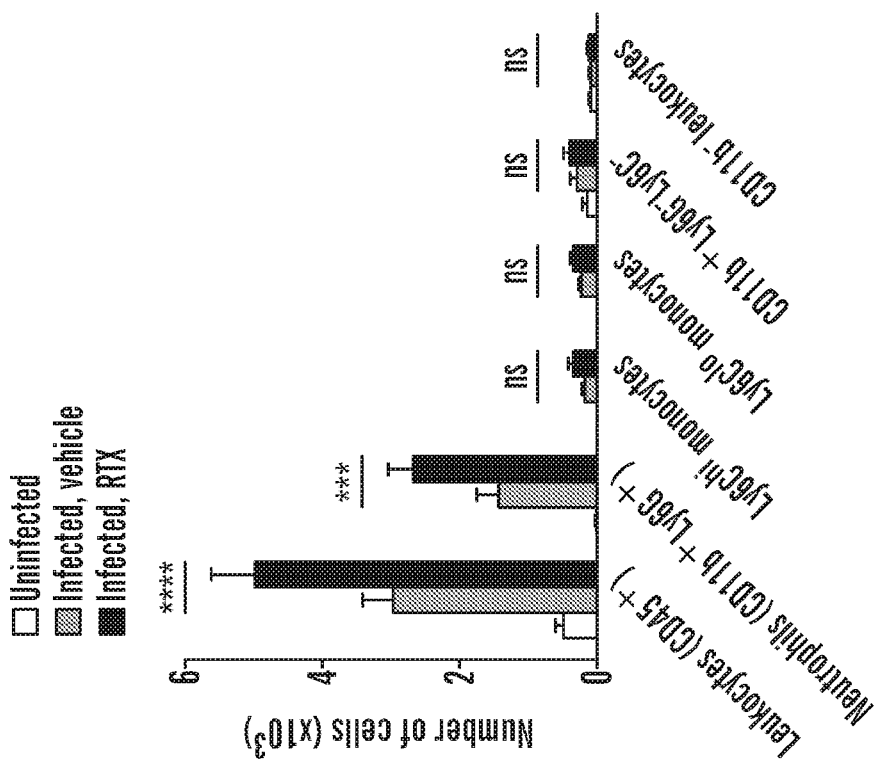
Figure 16D:
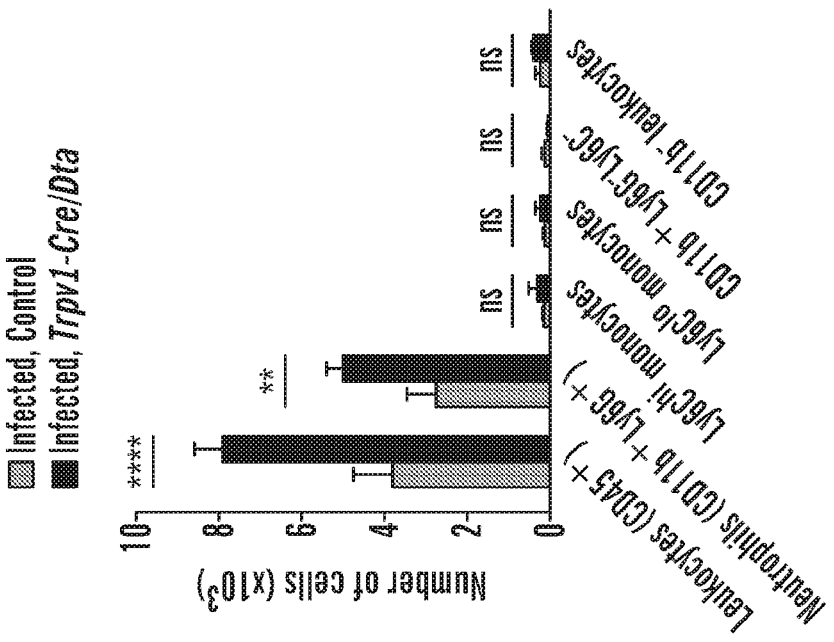
Figure 23D:
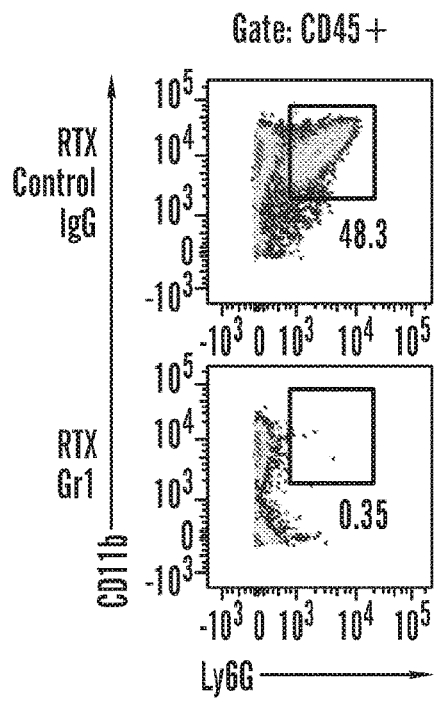
Figure 23E:
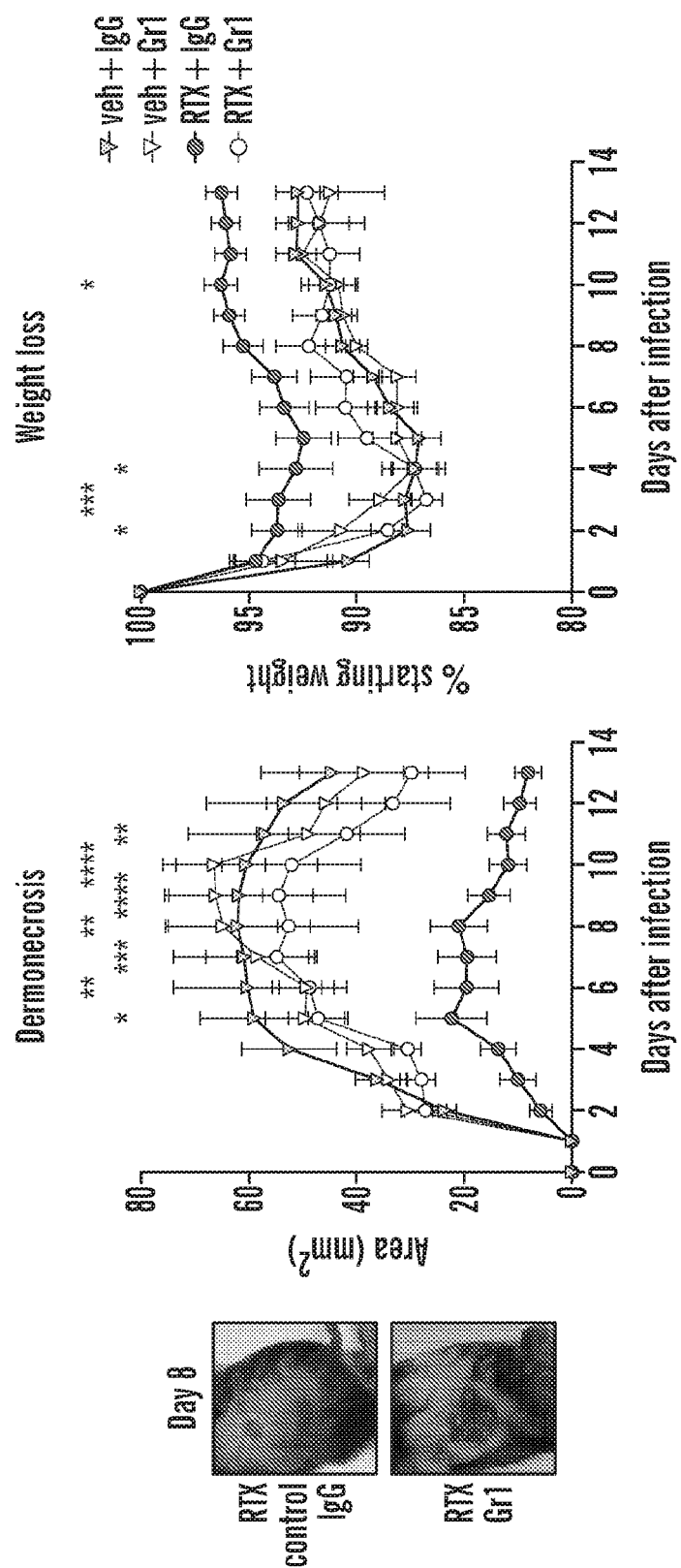
Figure 23F:
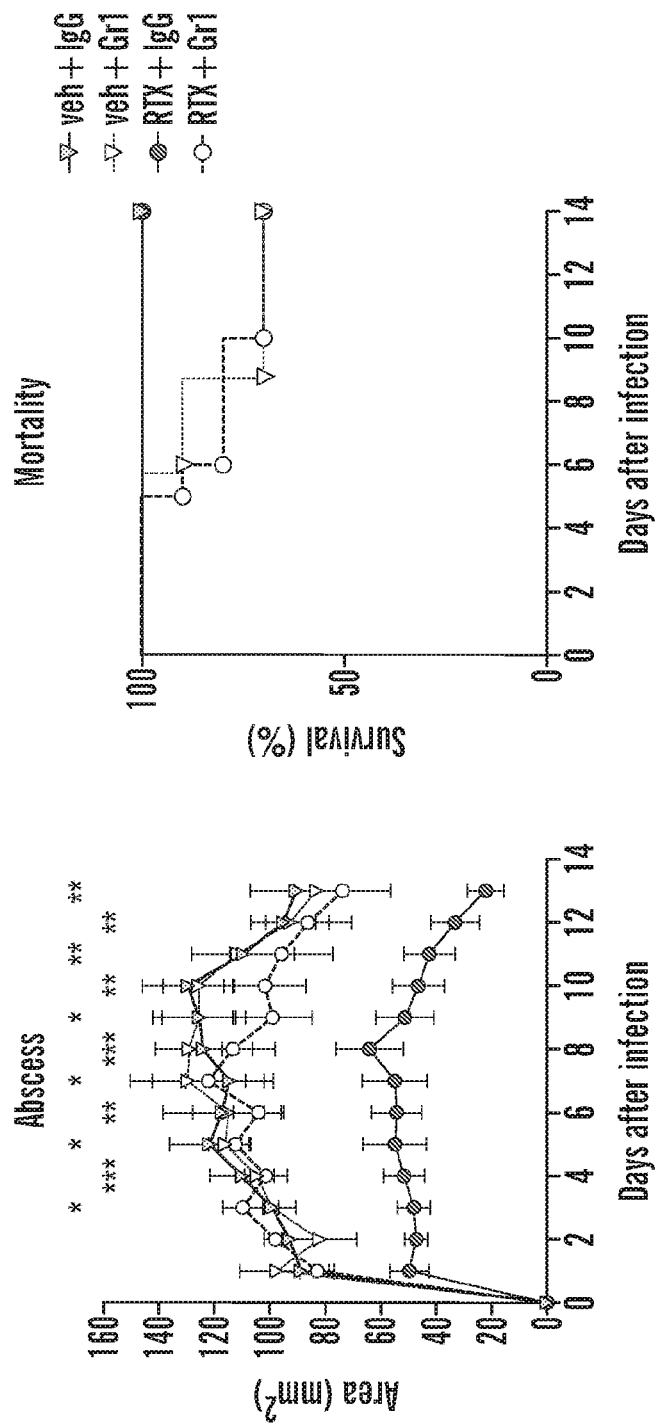

Neutrophils are essential for *S. pyogenes* clearance and prevention of bacterial dissemination (Hidalgo-Grass et al., 2006). FACS analysis of infected tissues indicated that more CD11b$^+$Ly6G$^+$ neutrophils were recruited in Trpv1-Cre/Dta mice compared to controls (FIG. 16C-16D). A similar increase was observed in RTX-treated mice compared to vehicle-treated mice (FIG. 16C, 16E). By contrast, significant differences in Cd11b$^+$Ly6G$^-$Ly6C$^{hi}$ monocytes, CD11b$^+$Ly6G$^-$Ly6C$^{lo}$ monocytes, Cd11b$^+$Ly6G$^-$Ly6C$^-$ myeloid cells, or CD11b$^-$Cd45$^+$ leukocytes were not detected (FIG. 16D-16E). The host protective effect of RTX-treatment was eliminated by GR1-mediated neutrophil ablation, causing mice to develop dermonecrotic lesions, abscesses, and weight loss similar to controls (FIG. 23D-23F).

Figures 16F, 16G, 16H:
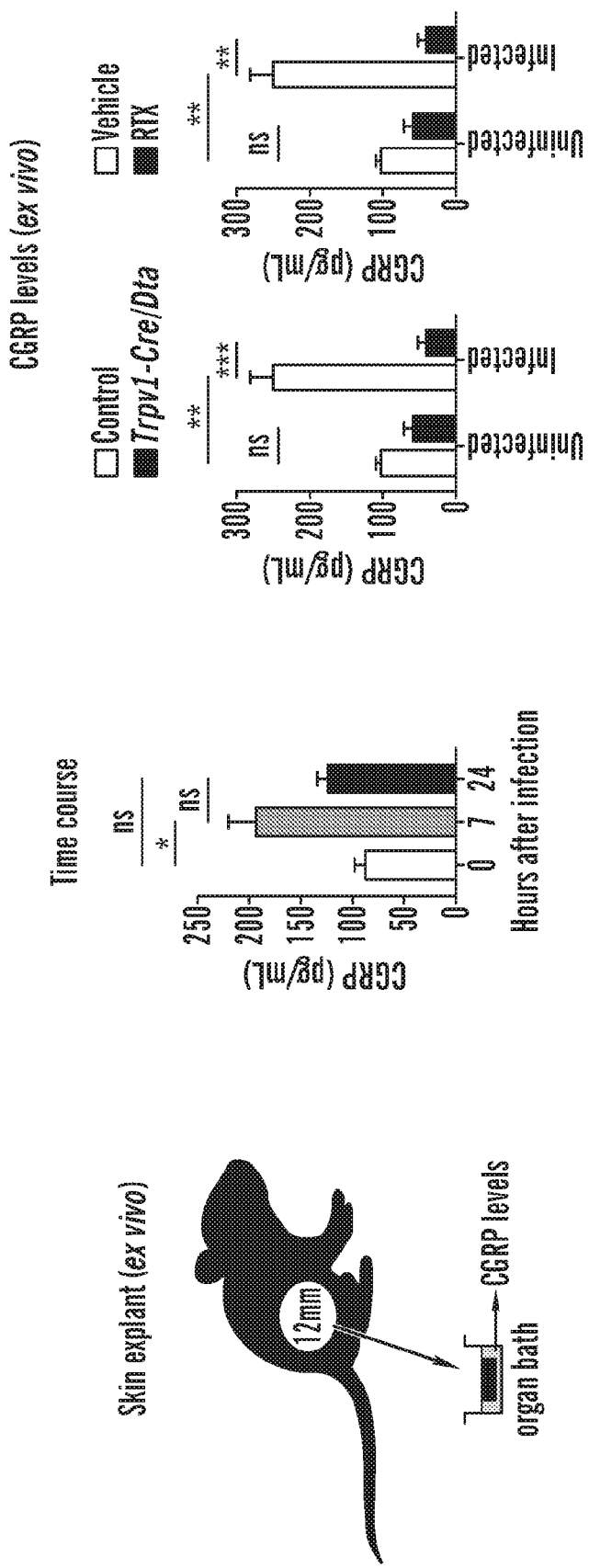

TRPV1 neurons release CGRP into infected tissues. Given the observation that *S. pyogenes* induced CGRP release by cultured nociceptor neurons in vitro through SLS (FIG. 13E), it was next determined whether bacterial invasion also induced CGRP release at the infection site using an ex vivo organ culture of skin explants (FIG. 16F). A significant increase in CGRP levels was observed from biopsies collected 7 h after *S. pyogenes* infection, returning to baseline levels at 24 h (FIG. 16G). This CGRP release was TRPV1 neuron dependent, as Trpv1-Cre/Dta mice showed reduced CGRP release after *S. pyogenes* infection compared to littermate controls (FIG. 16H), and RTX-treated mice showed lower CGRP release in infected tissues compared to vehicle-treated controls (FIG. 16H).

BoNT/A dissociates pain perception from neural regulation of host defense. Botulinum neurotoxin A (BoNT/A) is a bacterial toxin that cleaves SNAP-25, a component of the SNARE complex required for neuronal vesicle release (Binz et al., 1994). Two different protocols of BoNT/A treatment (subcutaneous vs. intrathecal) were used to dissociate the effects of peripheral neuropeptide release from central pain transmission, to understand the roles of each neuronal process in bacterial infection.

Figure 17A:
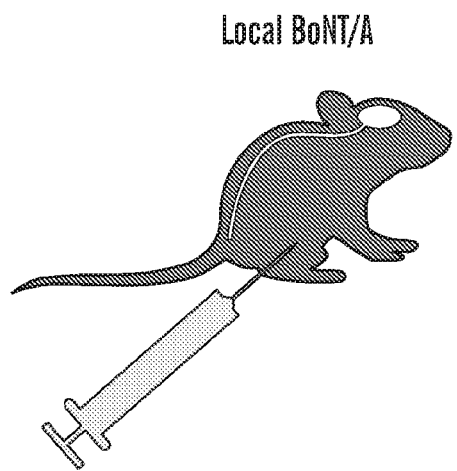
Figure 17B:
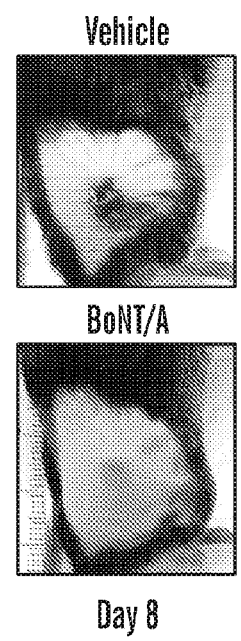
Figure 17C:
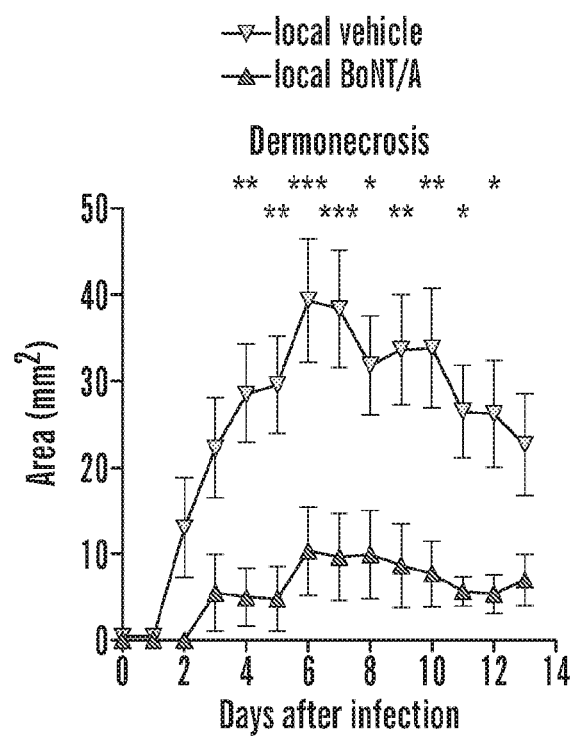
Figure 17D:
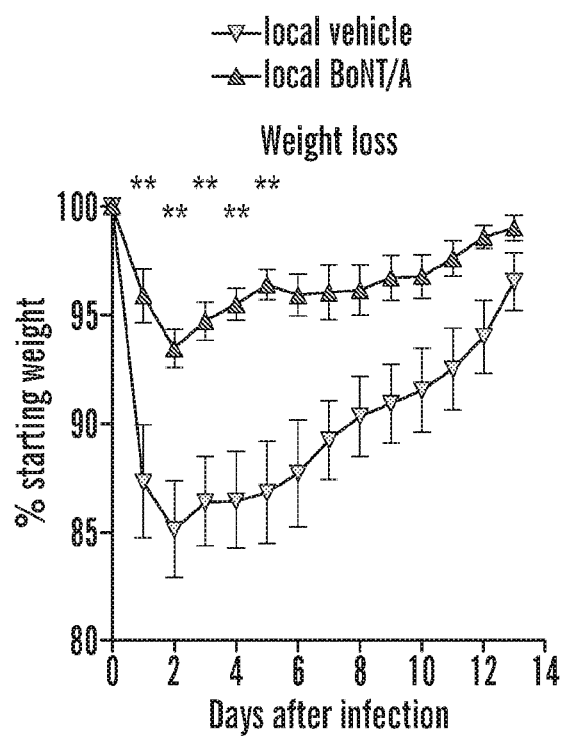
Figures 24A, 24B:
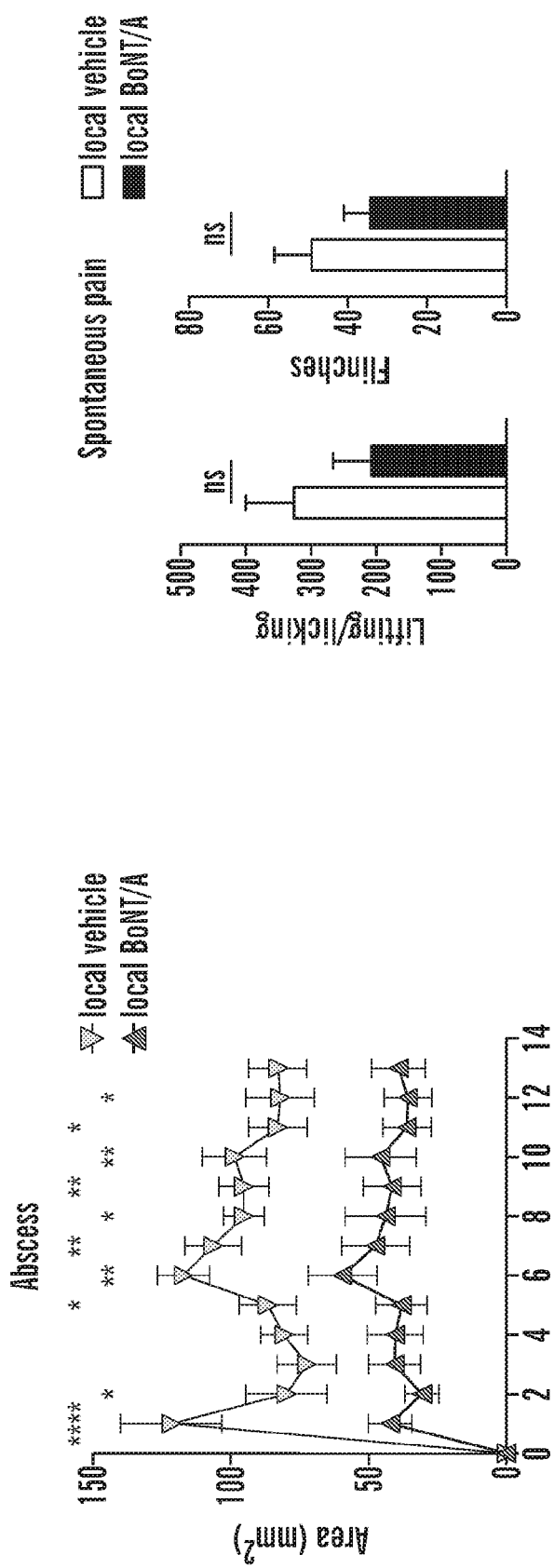
Figure 24C:
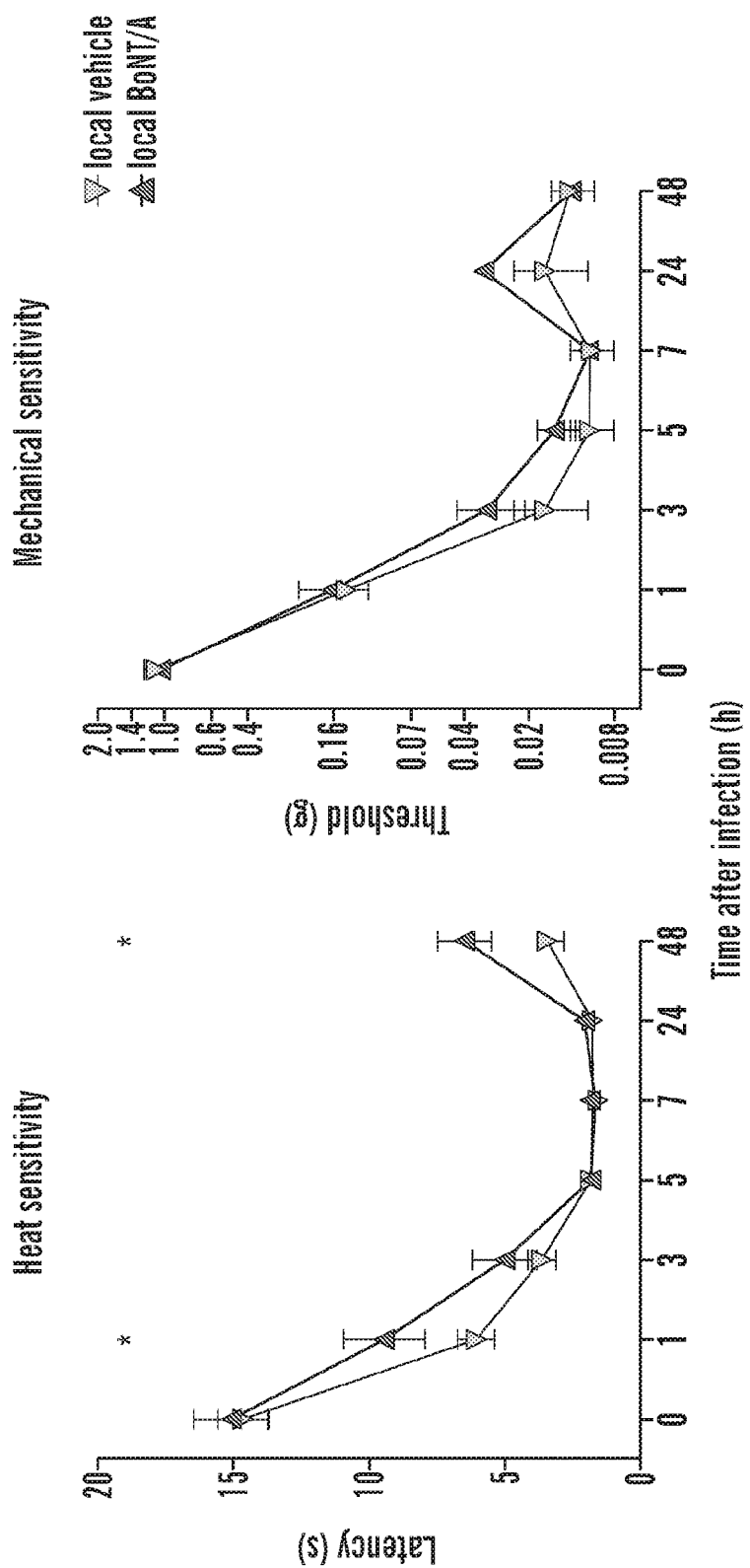
Figure 24D:
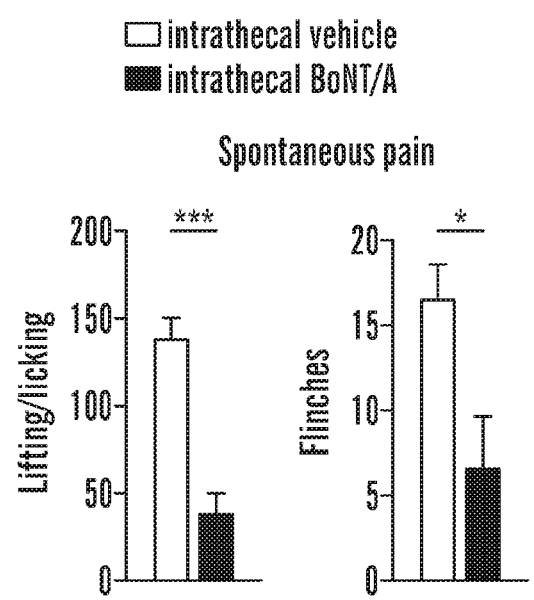
Figure 24E:
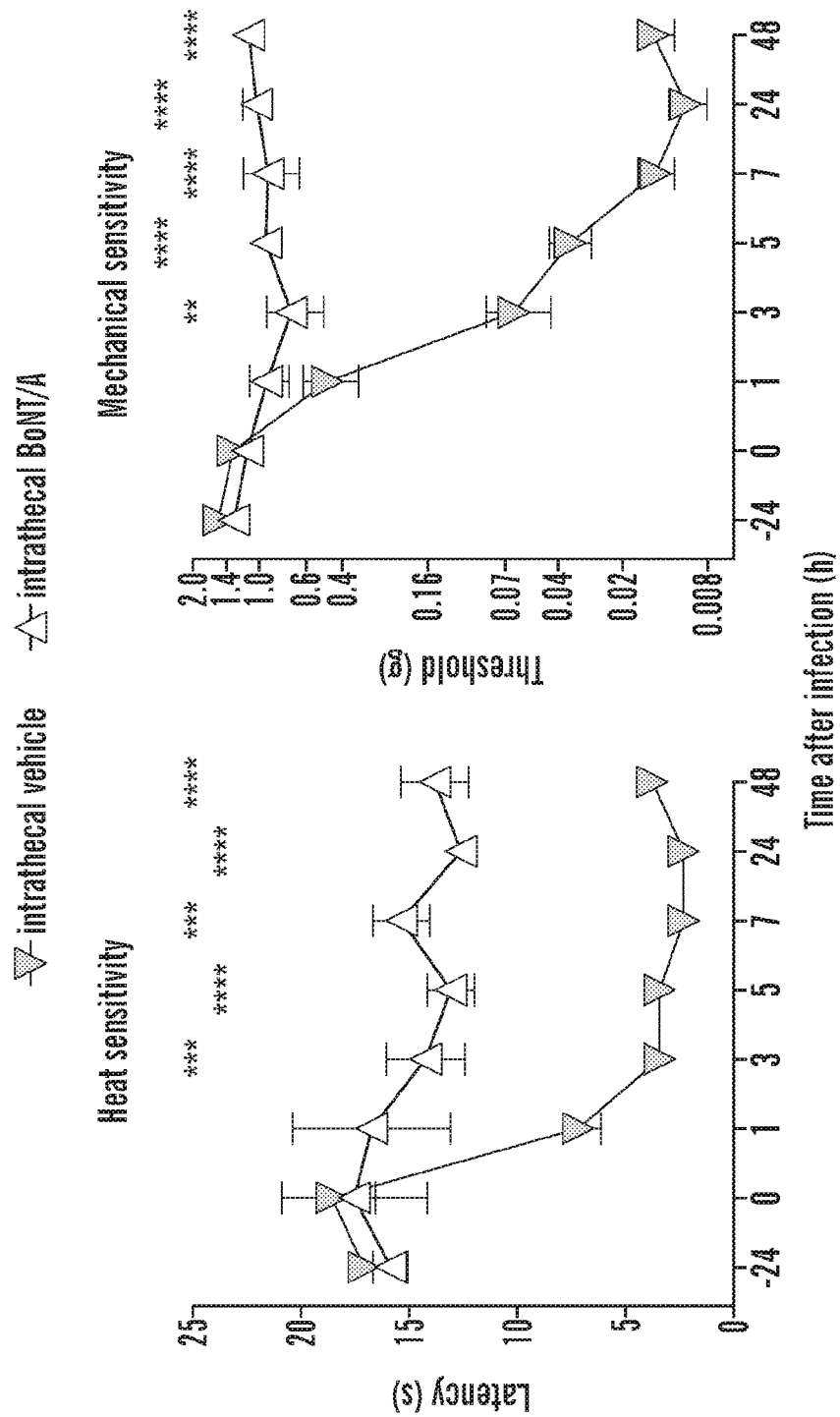
Figure 24F:
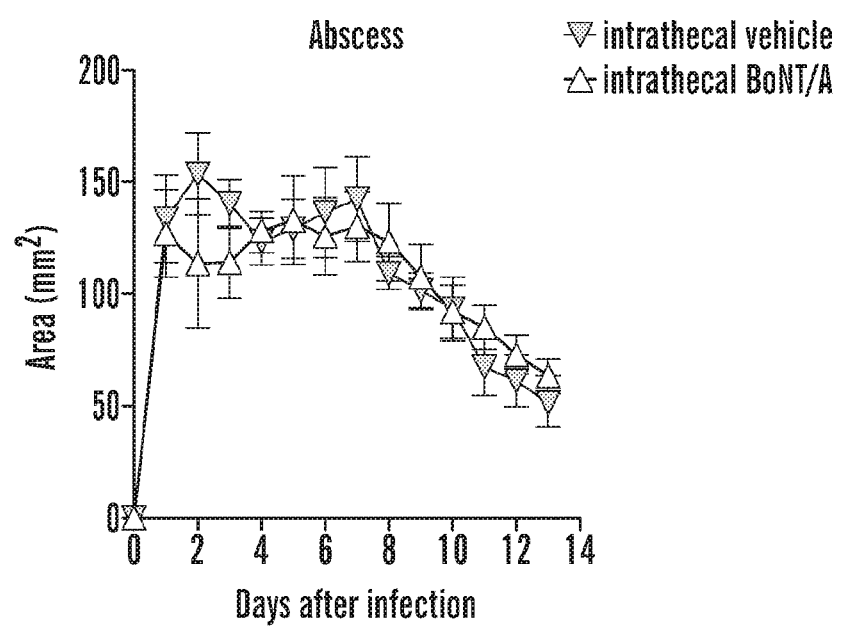

BoNT/A was first injected subcutaneously at the anticipated site of infection 6 days prior to the bacterial inoculum. BoNT/A local treatment dramatically prevented the development of dermonecrotic lesions caused by *S. pyogenes* infection (FIG. 17A-17C), with significantly reduced abscess formation (FIG. 24A) and body weight loss (FIG. 17D). Local BoNT/A treatment had no effect on spontaneous pain and hyperalgesia during infection (FIG. 24B-24C).

Figure 17I:
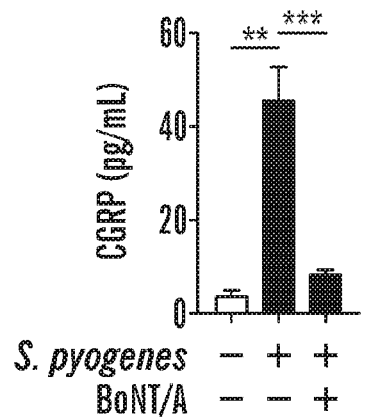
Figure 17J:
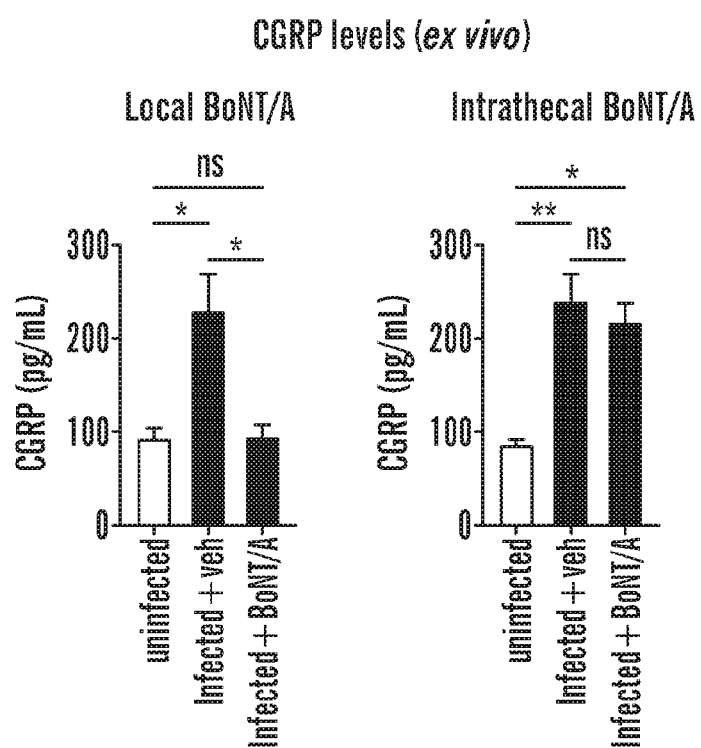

By contrast, intrathecal injection of BoNT/A (FIG. 17E) efficiently blocked both spontaneous pain and hyperalgesia caused by *S. pyogenes* infection (FIG. 24D-24E), but had no effect on dermonecrotic lesions, abscess size, or body weight loss (FIG. 17F-17H, 24F). BoNT/A inhibited *S. pyogenes*-induced CGRP release when applied to cultured DRG neurons (FIG. 17I). While subcutaneous BoNT/A treatment inhibited infection-induced CGRP release, intrathecal BoNT/A treatment did not alter this CGRP release (FIG. 17J). These results indicate that rather than central pain neurotransmission, peripheral neuropeptide release is likely a key modulator of host defense.

Figure 25B:
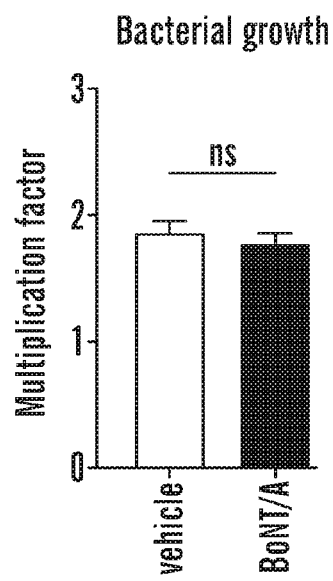
Figure 25C:
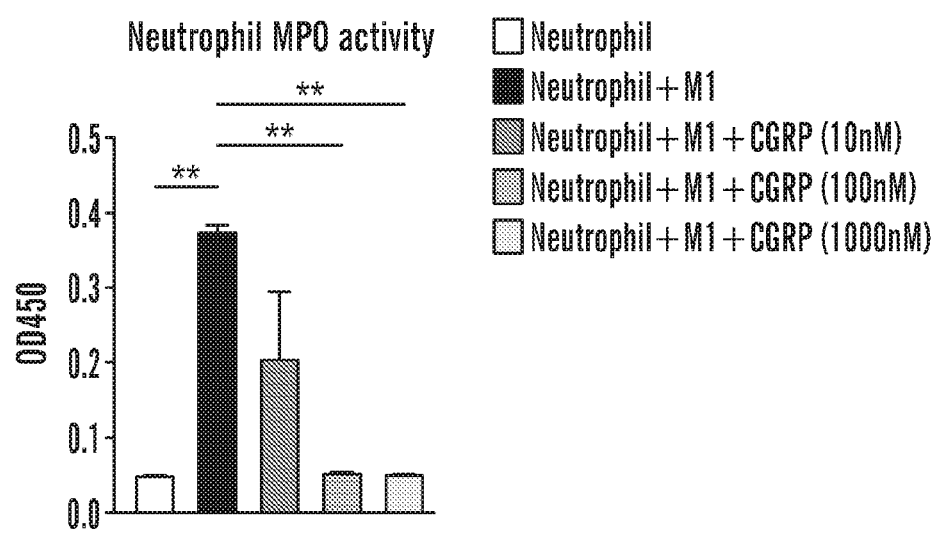
Figure 25D:
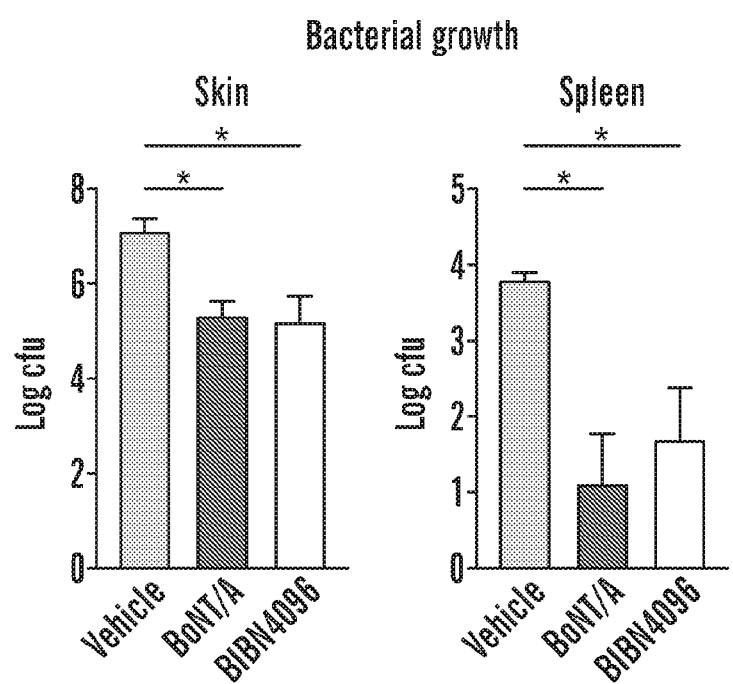

CGRP released by neurons inhibits neutrophil-mediated killing of bacteria. It was next determined whether nociceptor neurons could affect the opsonophagocytic killing of *S. pyogenes* by mouse neutrophils. In the presence of cultured nociceptors, the killing of *S. pyogenes* by mouse neutrophils was significantly inhibited (FIG. 18A). Pre-treatment of neurons with BoNT/A reversed the suppressive effect of DRG neurons on the capacity of neutrophils to kill *S. pyogenes* (FIG. 18A). CGRP receptor antagonists CGRP$_{8-37}$ and BIBN4096, when added to DRG neurons together with neutrophils, each prevented the suppressive effects of DRG neurons on neutrophil killing of *S. pyogenes*. BoNT/A, CGRP$_{8-37}$, and BIBN4096 did not have direct effects on *S. pyogenes* growth or viability, indicated that they acted on neural-immune signaling (FIG. 25A-25B). It was also observed that mouse CGRP inhibited murine neutrophil killing of *S. pyogenes* (FIG. 18B), and human CGRP inhibited the killing of *S. pyogenes* by human whole blood (FIG. 18C). CGRP inhibited the activity of the bactericidal enzyme myeloperoxidase (MPO) in neutrophil supernatants in a dose-dependent manner in the presence of *S. pyogenes* (FIG. 25C).

Figure 25E:
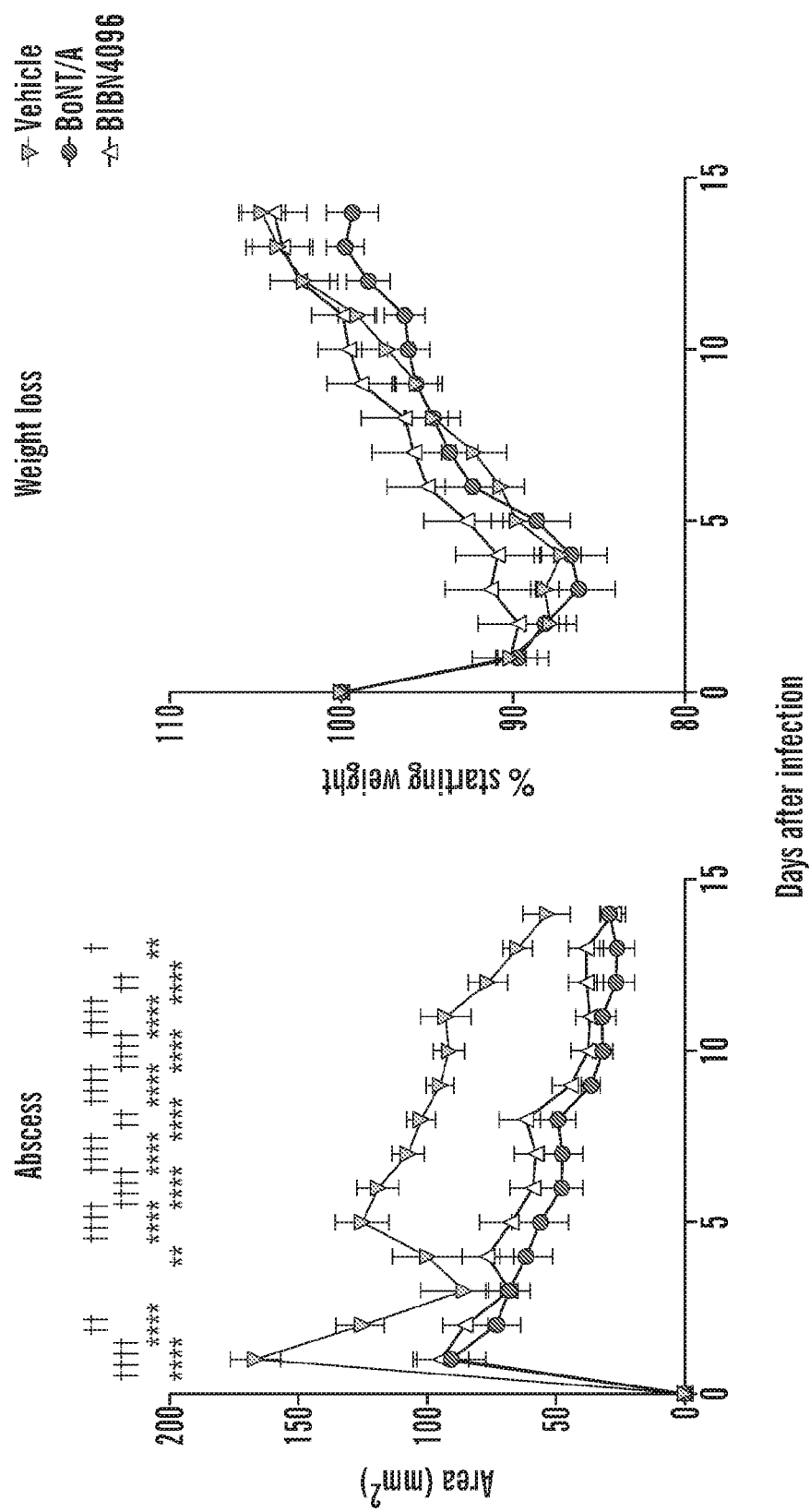
Figure 25G:
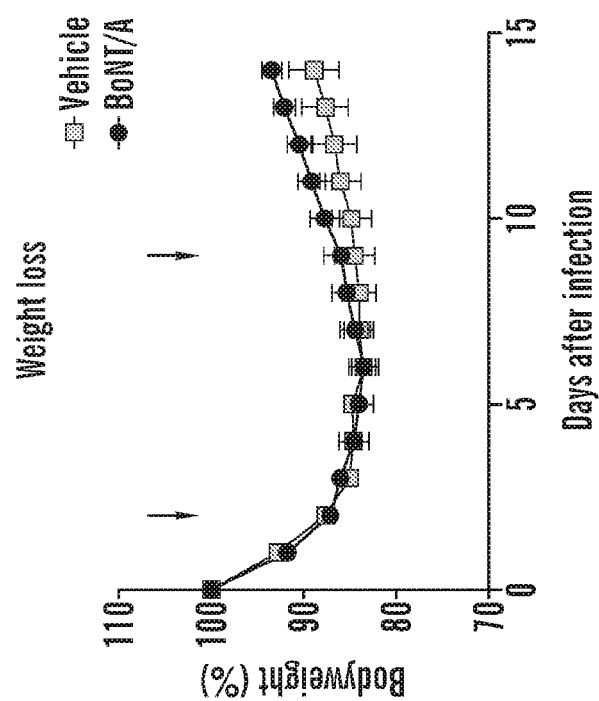
Figure 25F:
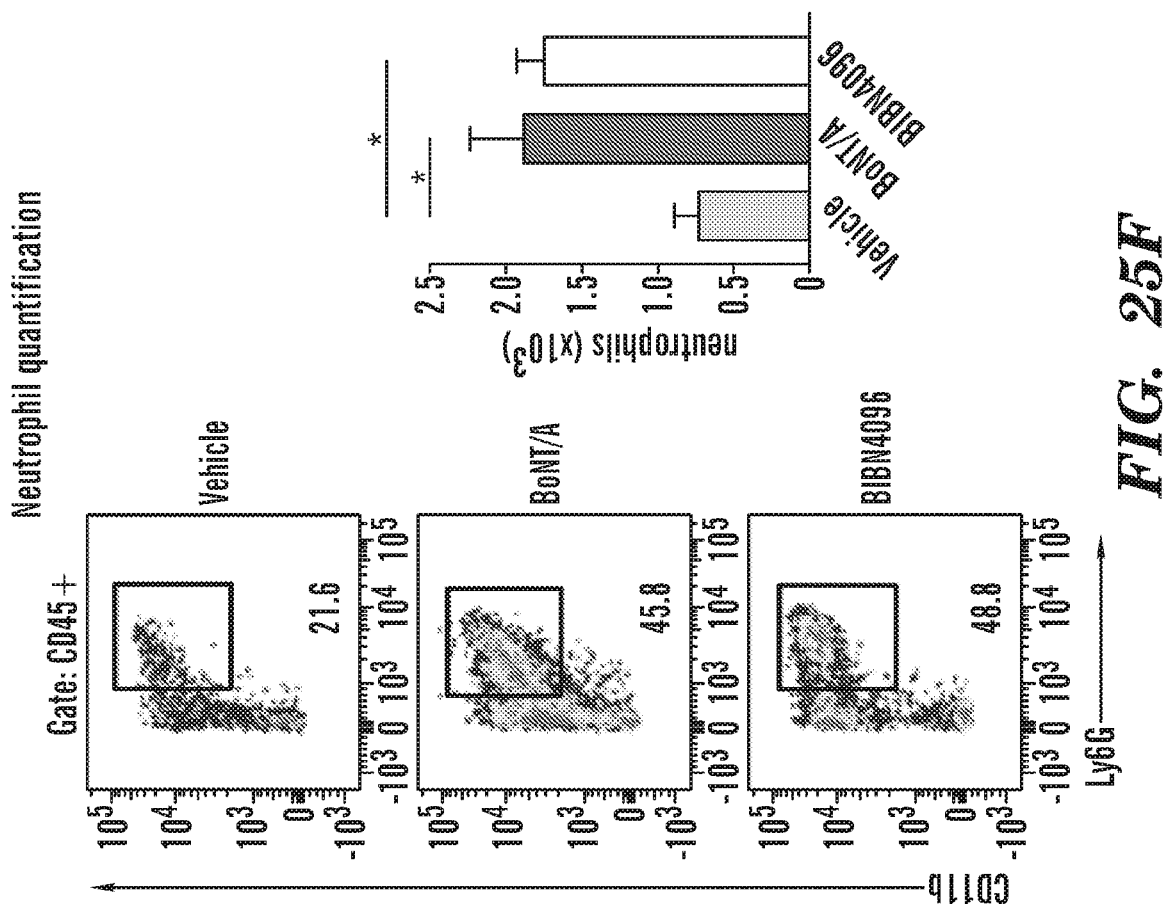

BoNT/A injection and CGRP receptor antagonism treats infection. Next, the therapeutic potential of BoNT/A treatment and CGRP receptor antagonism for *S. pyogenes* invasive infection was determined. Local BoNT/A or systemic BIBN4096 treatments, when administrated 2 h after infection, were associated with increased bacterial clearance in the skin (FIG. 25D), smaller dermonecrotic lesions (FIG. 18D) and reduced abscesses compared to mice treated with vehicle alone (FIG. 25E). BoNT/A or BIBN4096 increased the recruitment of neutrophils to the infected area compared to infected, untreated mice (FIG. 25F).

Figure 18F:
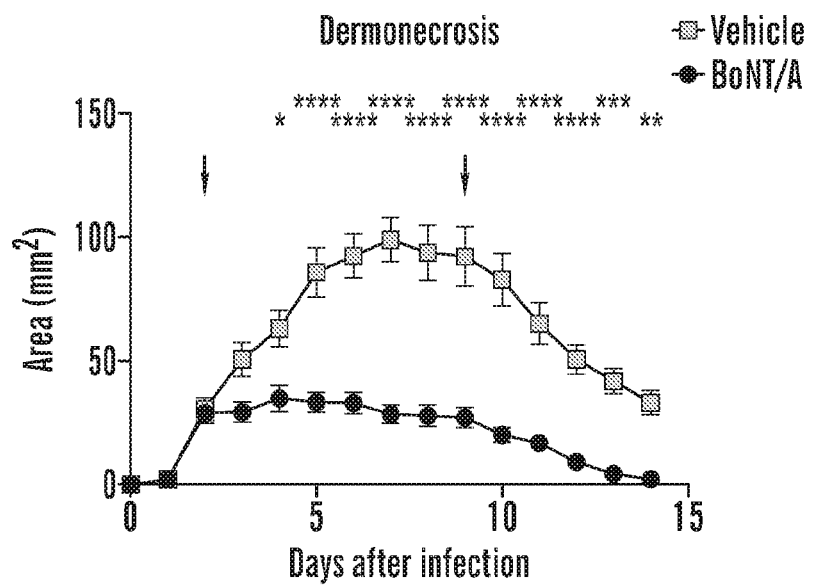
Figure 18G:
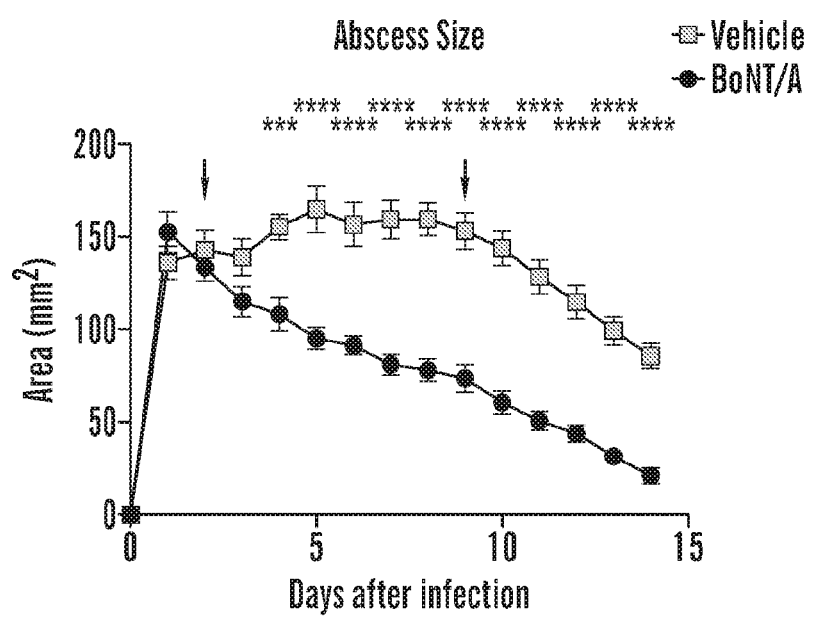
Figure 19A:
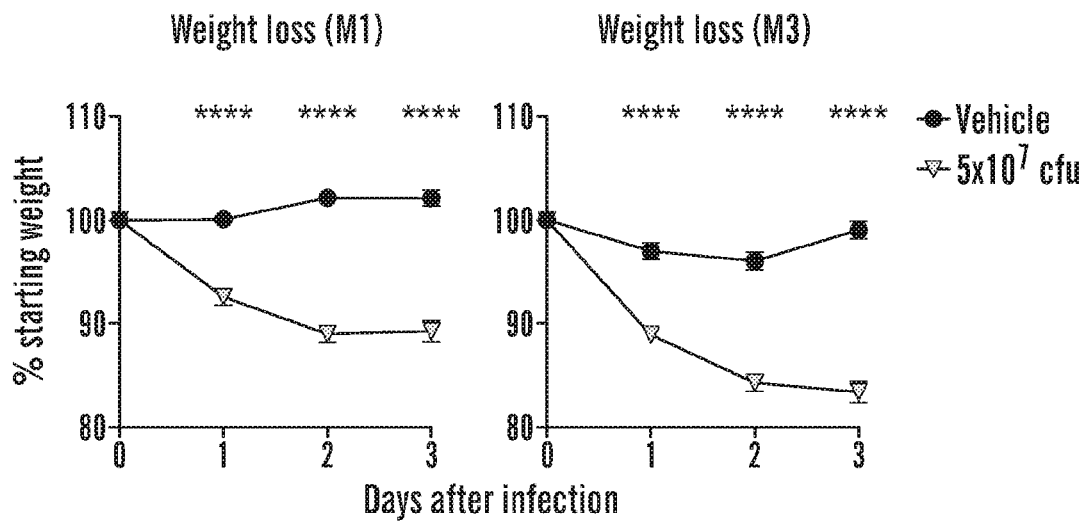
Figure 19B:
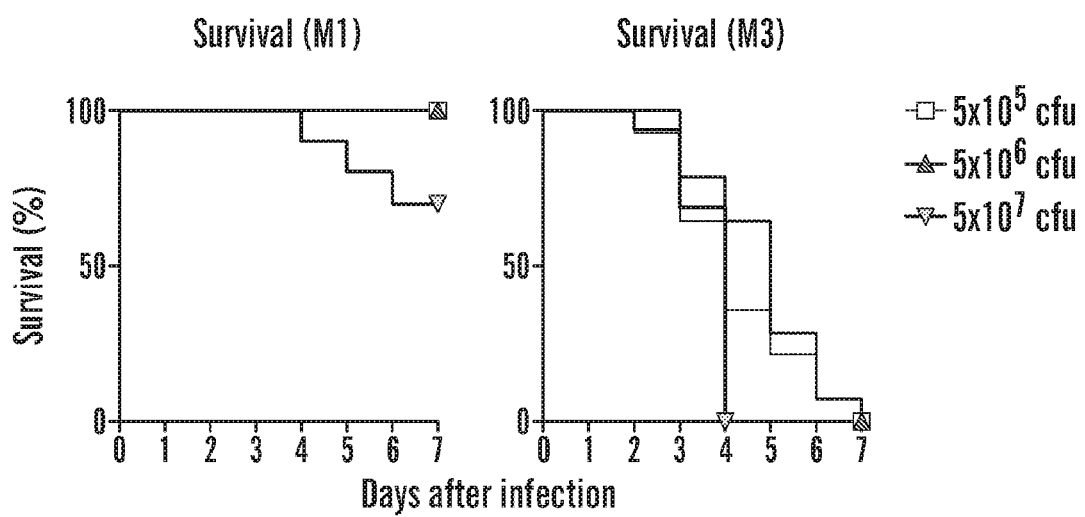
Figure 19C:
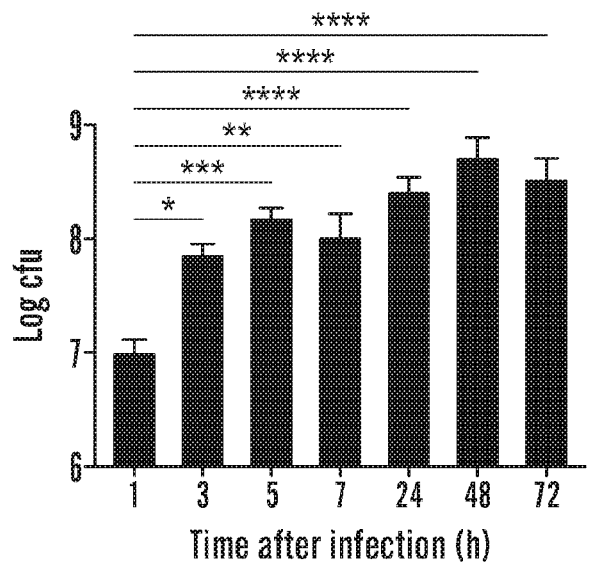
Figure 19D:
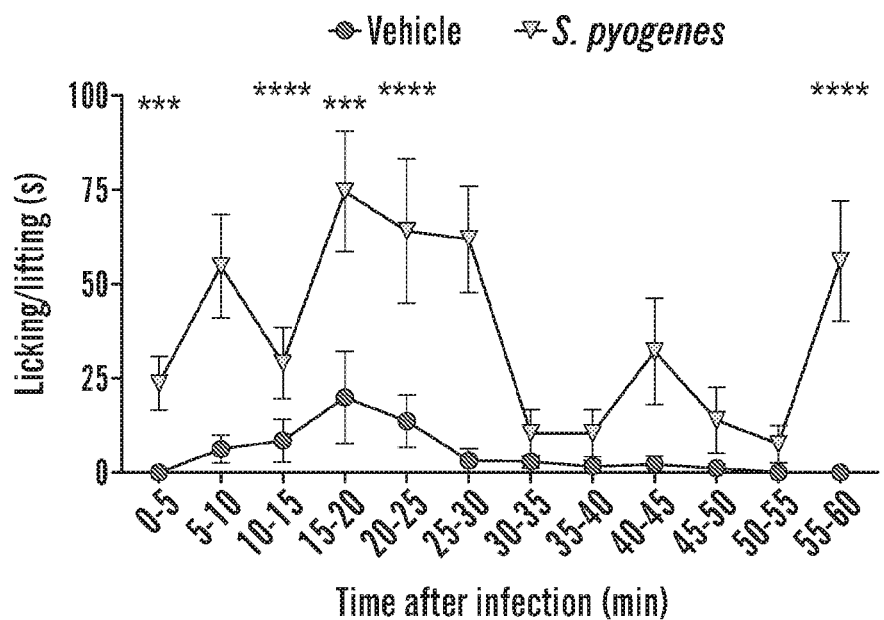
Figure 19E:
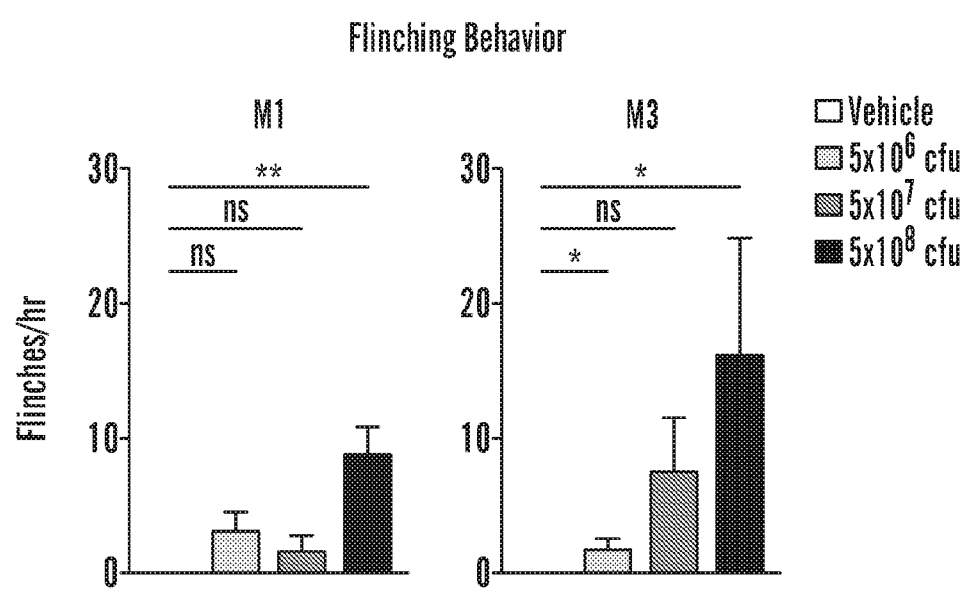
Figure 19F:
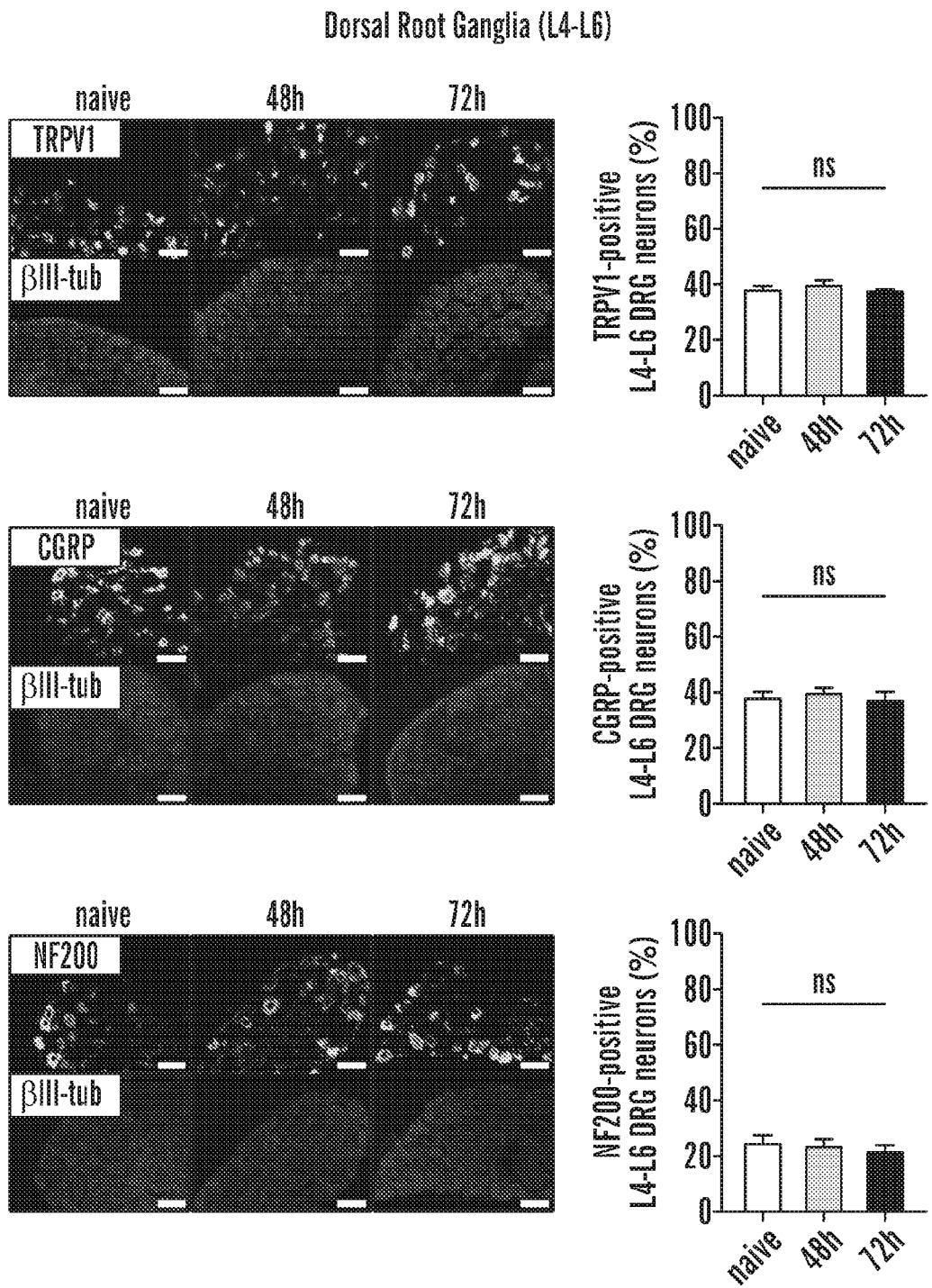
Figure 19G:
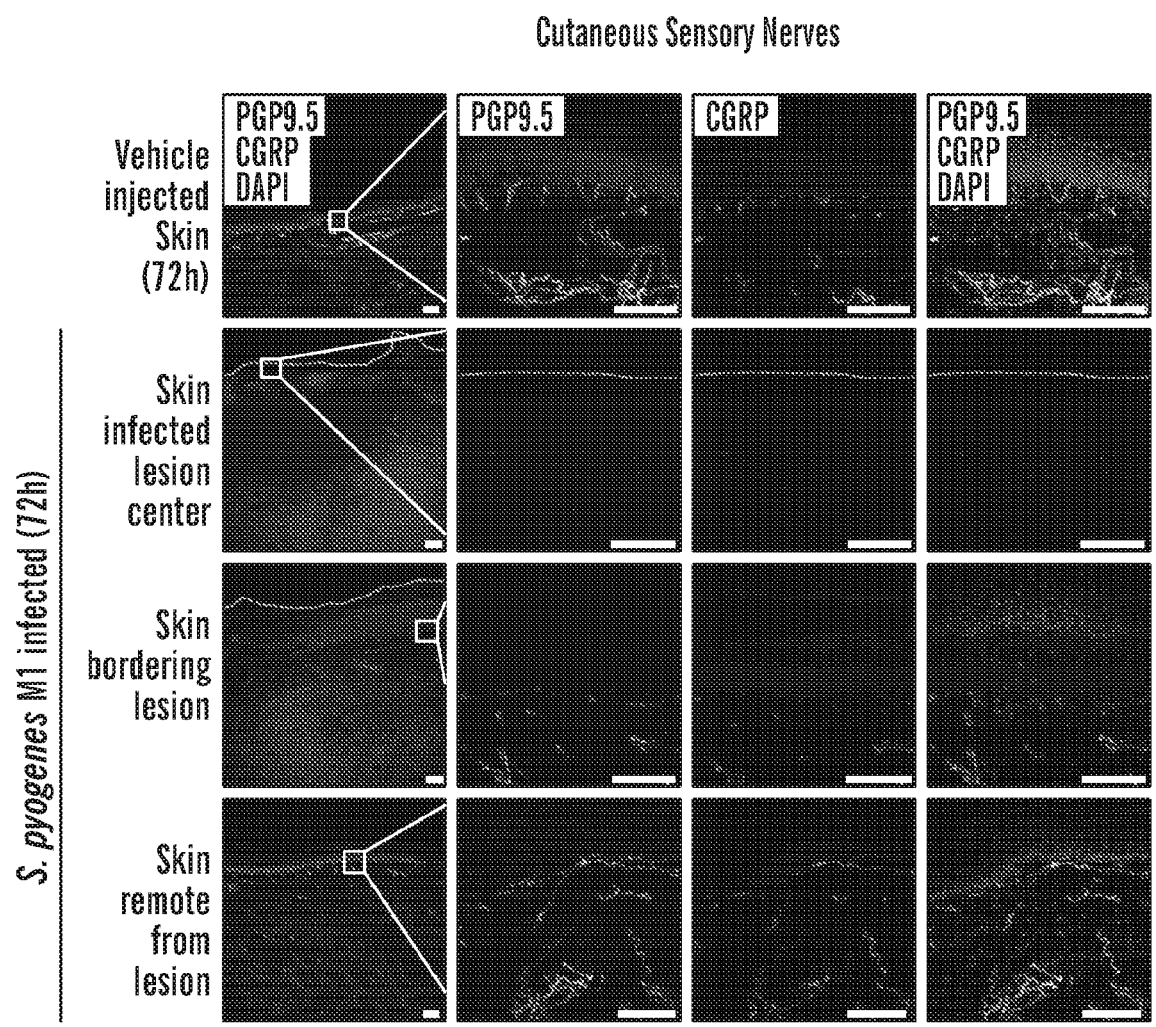

It was next determined if BoNT/A administration at later time points could treat infection. At the 48 h time point, when large lesions were evident, mice were injected with BoNT/A or vehicle at sites around the lesion (FIG. 18E). These injections halted the progression of *S. pyogenes* invasion, leading to less dermonecrosis and a rapid decrease in abscess size (FIG. 18F-18G). A second BoNT/A injection at day 9 post-infection did not appear to further accelerate resolution of dermonecrotic lesions or abscesses but may have a beneficial effect on weight recovery (FIG. 25G).

Discussion

The goals of the present investigation were to determine mechanisms of pain associated with *S. pyogenes* invasion and role of neurons in host defense. It was found that pain during infection depended on bacterial production of the toxin SLS. SLS triggered neural release of CGRP into infected tissues, which inhibited neutrophil recruitment and bactericidal activity, facilitating *S. pyogenes* survival. These data indicate that *S. pyogenes* hijacks pain and neural modulation of immunity to drive bacterial invasion. Blocking neuro-immunological signaling using BoNT/A or a CGRP antagonist were identified as strategies to treat infections.

The molecular basis of pain in necrotizing fasciitis. "Pain out of proportion" to physical findings is a hallmark of necrotizing fasciitis. In a survey of clinical parameters, pain was the best predicting factor for distinguishing necrotizing fasciitis from cellulitis (Borschitz et al., 2015). Though pain correlates with disease severity, its underlying mechanisms were unknown. It was determined herein that SLS critically mediates pain in mouse models of *S. pyogenes* necrotizing fasciitis. This role was revealed using several strategies: 1) comparison of pain produced by wt and isogenic mutant strains lacking SLS (sagA) from two clinical isolates; 2) antibody-mediated neutralization of SLS; and 3) plasmid complementation of SLS in isogenic mutants to restore neuronal activation. SLS-mediated spontaneous pain reflexes in mice maybe analogous to stabbing, sporadic pain experienced by humans during infection. SLS-mediated mechanical hyperalgesia maybe analogous to pressure-induced pain of infected tissues. SLS did not contribute to heat hyperalgesia, a pain modality that requires further investigation.

SLO and SLS are both implicated in S. pyogenes evasion of host defenses (Flaherty et al., 2015; Lin et al., 2009; Sierig et al., 2003). SLS is a small oxygen-stable, pore-forming peptide from the thiazole/oxazole-modified microcin family and member of a class of post-translationally modified virulence peptides that occur across several species of pathogenic bacteria (Nizet et al., 2000). SLO, by contrast, is a relatively large oxygen-labile toxin and member of cholesterol-dependent cytolysins (Tweten et al., 2015). It was shown herein that SLS, but not SLO, is responsible for the pain of necrotizing fasciitis. It was also found that SLS showed more selectivity for TRPV1 neurons at lower bacterial concentrations but activated most DRG neurons at higher concentrations. A recent study showed that SLS activates Band3, an anion exchanger in erythrocytes (Higashi et al, 2015). Band3 in sensory neurons in transcriptional datasets was not found (Chiu et al, 2014). Thus, the basis of SLS selectivity for TRPV1 neurons remain unclear.

S. pyogenes infection induced significant nerve loss within the lesion site but not the loss of DRG cell bodies. This finding may relate to necrotizing fasciitis, where intense early pain transitions to local loss of sensation at later time points (Buchanan and Haserick, 1970; Wilson and Haltalin, 1973). The degree of pain and nerve loss is likely a balance between SLS activity and membrane repair. Host cells activate membrane repair processes like microvesicle shedding and lysosomal fusion in response to streptolysins and other PFTs (Romero et al, 2017). Given that SLS is a highly damaging molecule, it may be evolutionarily beneficial for nociceptors to detect SLS and produce pain.

Nociceptor neurons suppress immunity and bacterial killing. Neuro-immune interactions at barrier surfaces play a major role in tissue inflammation (Veiga-Fernandes and Mucida, 2016). In the skin, crosstalk between sensory neurons, keratinocytes and immune cells mediate itch in atopic and contact dermatitis (Oetjen et al., 2017; Wilson et al., 2013a, b; Liu et al., 2013). Nociceptors mediate dermal dendritic cell activation in host defense against C. albicans (Kashem et al., 2015), and in a mouse model of psoriasis (Gilbert and Ward, 2014; Riol-Blanco et al., 2014). Lung-innervating sensory neurons modulate innate lymphoid cells and T cells to drive allergic airway inflammation (Caceres et al., 2009; Talbot et al., 2015). In the gut, enteroendocrine cells sense bacterial metabolites and signal to sensory neurons (Bellono et al., 2017). Gut-intrinsic enteric neurons and extrinsic sympathetic neurons also crosstalk with muscularis macrophages to regulate gut motility and macrophage tissue-specific programming (Muller et al, 2014; Gabanyi et al., 2016).

Herein it was found that nociceptors suppress neutrophil recruitment and function to drive the progression of S. pyogenes invasive infection. Neutrophils are the most abundant leukocytes in the blood where they remain in a mature state, poised to migrate towards tissues to control pathogen spread. S. pyogenes virulence relies on its capacity to inhibit or resist neutrophils (Okumura and Nizet, 2014). The extent of neutrophil infiltration during human necrotizing fasciitis is variable. A study of biopsies from patients with S. pyogenes soft tissue infections showed positive correlation between bacterial load and neutrophil density (Thulin et al., 2006), but surgical exploration in necrotizing fasciitis sometimes revealed thin grayish "dishwater" fluid with few neutrophils despite the presence of large numbers of bacteria (Stevens and Bryant, 2017). S. pyogenes produces the proteases ScpC (or SpyCEP) and ScpA to cleave chemotactic factors that mediate neutrophil recruitment, such as CXCL8/IL-8 and C5a. S. pyogenes strains lacking expression of these proteases have profoundly attenuated virulence due increased neutrophilic influx (Ji et al., 1996; Kurupati et al., 2010). SLO also silences neutrophil function by damaging phagolysosomal membranes and inducing cell death (Sierig et al., 2003). The observation that SLS drives pain and neuromodulation of neutrophil killing indicates a functional synergism between these toxins in defeating neutrophil function.

Neural suppression of immunity during bacterial invasion may seem counterproductive for host defense. As pain accompanies inflammation, neuromodulation of immunity evolved can be a feedback mechanism to limit injury from excessive inflammation. In the case of S. pyogenes infection, SLS hijacks this neuro-immune communication by stimulating neuropeptide release and consequently blocking host defense.

A potential strategy to treat S. pyogenes invasion and necrotizing fasciitis. Necrotizing fasciitis is a life-threatening condition in which treatment with surgical debridement, antibiotic therapy, and intensive supportive care have only limited efficacy, and mortality remains unacceptably high. Work described herein identifies three approaches as potential therapies: 1) Neutralizing SLS with a specific antibody, 2) BoNT/A to inhibit CGRP release, and 3) BIBN4096 to inhibit CGRP receptor signaling. BoNT/A is currently used in cosmetic dermatology and treatment of migraine (Grando and Zachary, 2017). Neutralizing anti-CGRP antibodies and CGRP receptor antagonists are also being developed for migraine (Petersen et al., 2005; Tso and Goadsby, 2017).

BoNT/A has been shown previously to act on nociceptors to block pain transmission (reviewed in Matak and Lacković, 2014). It is found herein that BoNT/A can also block neuronal suppression of the local immune response, unrelated to pain perception. It is important to note that BoNT/A could also act on other cell-types including skin-innervating cholinergic and sympathetic neurons (Grando and Zachary, 2017), that may in turn modulate immune function (Chavan et al., 2017). BoNT/A may also target epithelial cells and skin immune cells (Grando and Zachary, 2017).

CGRP could similarly mediate functions in S. pyogenes infection beyond suppression of neutrophil function. In the skin, the CGRP receptor complex (Ramp1/Calcrl) is expressed by vascular endothelial cells, smooth muscle cells, keratinocytes, fibroblasts, and some immune cells (Granstein et al., 2015; Pinho-Ribeiro et al., 2017). CGRP acts on vascular cells to induce vasodilation, mediates keratinocyte proliferation to accelerate wound healing, and modulates Langerhans cells and dermal dendritic cells to polarize Th2 responses. It remains to be determined whether these other cell-types contribute to neural suppression of host defense.

It is found herein that BoNT/A injections after the development of dermonecrosis blunted the progression of S. pyogenes invasion in mice. There are important differences in S. pyogenes pathogenesis between mouse and human (Olsen and Musser, 2010), as humans are the only natural hosts of S. pyogenes. Despite this limitation, mouse models of soft tissue infection have been utilized to demonstrate the role of major virulence determinants such as surface M protein and the hyaluronic acid capsular polysaccharide (Ashbaugh et al, 1998; Schrager et al., 1996). Of particular relevance to the work described herein, soft tissue infection models in mice support a role in virulence for SLS (Betschel et al., 1998; Datta et al., 2005). SLS also mediates infection of human oropharyngeal keratinocytes and macrophages (Bastiat-Sempe et al., 2014; O'Seaghdha and Wessels, 2013).

In conclusion, neurons and their signaling to the immune system have a major impact on the outcome of bacterial soft tissue infection. BoNT/A and CGRP antagonists may be repurposed for treatment of infections due to S. pyogenes and perhaps other bacterial pathogens. Targeting the peripheral nervous system provides therapeutic approaches in invasive infections including necrotizing fasciitis.

Materials and Methods

Human blood donors. Blood samples were collected by a trained phlebotomist from three healthy adult volunteers of either sex at Boston Children's Hospital with approval from the hospital's Institutional Review Board (protocol X04-01-008). Written informed consent was obtained from all volunteers. No further demographic data was collected from the volunteers. Blood collected was from a single donor per experiment and was not pooled.

Animals. All animal experiments were approved by the Institutional Animal Care and Use Committee (IACUC) at Harvard Medical School and were conducted in accordance with National Institutes of Health (NIH) animal research guidelines. C57BL6/J, B6(Cg)-Rag2$^{tm1.1Cgn}$/J, B6N.129S2-Casp1$^{tm1Flv}$/J, B6.129P2(SJL)-Myd88$^{tm1.1Defr}$/J, B6.129-Trpv1$^{tm1(cre)Bdm}$/J, B6.129P2-Gt(ROSA)26Sor$^{tm1(DTA)Lky}$/J, and B6.129X1-Tr1$^{tm1Jul}$/J mice were purchased from Jackson Laboratories (Bar Harbor, Me.). Mice were bred and housed in individually ventilated micro isolator cages within a full barrier, specific pathogen-free animal facility at Harvard Medical School under a 12 h light/dark cycle with ad libitum access to food and water. B6.129-Trpv1$^{tm1(cre)Bbm}$J heterozygous (+/−) mice were bred with B6.129P2-Gt (ROSA)26Sor$^{tm1DTALky}$/J homozygous (+/+) mice to generate nociceptor-ablated Trpv1-Cre/Dta (Trpv1-Cre$^{+/-}$/Dta$^{+/-}$) mice and control littermates (Trpv1-Cre$^{-/-}$/Dta$^{+/-}$). Both male and female age-matched mice from 6 to 14 weeks of age were used for all experiments in this study. Male and female mice were similarly susceptible to Streptococcus pyogenes infection. Individual animal health status was routinely monitored by Harvard Center for Comparative Medicine veterinary staff. Additionally, one cage containing two sentinel animals was maintained on each rack. These sentinel cages were supplied with pooled samples of soiled bedding from regular colony animals at every cage change. All cage changes were performed in Class II biosafety change stations. Animal sentinels were tested quarterly for pinworms, fur mites, Sendai virus, Pneumonia virus of mice, Mouse hepatitis virus, GD-7 virus, Minute virus of mice, Mycoplasma pulmonis, Mouse parvovirus, Epizootic diarrhea of infant mice, Reo-3 virus, and annually for ectromelia virus and lymphocytic choriomeningitis virus. Only healthy animals were used for experiments. Euthanasia was performed by $CO_2$ inhalation.

Bacterial strains and culture. All procedures related to bacterial strains and infectious disease work were approved by the Committee on Microbiological Safety (COMS) at Harvard medical school and were conducted under Biosafety Level 2 protocols and guidelines. All Streptococcus pyogenes strains used in this study are listed in the Key Resources Table. S. pyogenes 854 M-type 1 was originally isolated from a patient with retroperitoneal abscess (Gryllos et al, 2008). S. pyogenes 950771 M3 serotype strain is a clinical isolate obtained from a patient with necrotizing fasciitis and sepsis (Ashbaugh et al, 1998). These founder bacterial strains were mutated to generate isogenic mutant strains (see Methods Details). Bacteria were grown on Tryptic Soy Agar (TSA) plates supplemented with 5% Sheep Blood (BD Biosciences, Cat #221239), or grown in liquid culture in Todd-Hewitt Broth (Sigma, Cat #T1438) supplemented with 0.2% yeast extract (Sigma, Cat #Y1625) (THY broth) at 37° C. with 5% $CO_2$. When required, THY broth was supplemented with spectinomycin (50 µg/mL, Sigma, Cat #S4014). For storage, bacterial glycerol frozen stocks (20% glycerol, Sigma, Cat #G5516) of S. pyogenes strains were prepared and kept at −80° C. until use.

Primary cells. Murine DRG neurons were obtained from healthy naïve animals as described in Dorsal root ganglia neuron dissection and culture. Mouse neutrophils were isolated from mouse bone marrow as described in Neutrophil isolation and killing assays.

DRG neurons were maintained under sterile conditions in a humidified incubator at 37° C. and 5% $CO_2$. For calcium imaging experiments, DRG neurons were incubated for 12-24 h in 35 mm laminin (20 µg/mL, Thermo Fisher, Cat #23017015)-coated sterile cell culture dishes (VWR International, Cat #10062-888) containing 2 mL of neurobasal-A medium (Thermo Fisher, Cat #21103049), B-27 supplement (Thermo Fisher, Cat #1704044), penicillin/streptomycin (100 units/mL and 100 µg/mL, Thermo Fisher, Cat #15140122), L-glutamine (2 mM, Thermo Fisher, Cat #25030081) and mouse NGF (50 ng/mL, Thermo Fisher, Cat #50385MNAC50).

For the experiments involving in vitro CGRP release assays by neurons, or co-incubation of DRG neurons with neutrophils, DRG neurons were first incubated for one week in laminin (20 µg/mL, Thermo Fisher, Cat #23017015)-coated sterile flat bottom 96-wells plates (Thermo Fisher, Cat #08-772-53) containing 200 µL of neurobasal-A medium (Thermo Fisher, Cat #21103049), B-27 supplement (Thermo Fisher, Cat #1704044), penicillin/streptomycin (100 units/mL and 100 µg/mL, Thermo Fisher, Cat #15140122), L-glutamine (2 mM, Thermo Fisher, Cat #25030081), mouse NGF (50 ng/mL, Thermo Fisher, Cat #50385MNAC50), and cytosine arabinoside (10 µM, Sigma, Cat #C6645). Half of the medium was replaced with fresh media every two days. At day 7, neurons were stimulated for CGRP assays or co-cultured with neutrophils for experiments as described in Neuronal stimulation and CGRP release and in Neutrophil isolation and killing assays sections.

Skin biopsies. Skin punch biopsies were collected as described in the section "CGRP release assay from skin explants" from the flank area injected with vehicle or bacteria. Samples were collected under sterile conditions, rapidly transferred to sterile 24-well cell culture plates (Genesee Scientific, Cat #25-107) containing 1 mL of DMEM (Thermo Fisher, Cat #11995073) at 32° C. and immediately used for experiments.

Generation of isogenic mutant S. pyogenes strains The slo-negative derivatives of the S. pyogenes 854 and 950771 were generated by allelic exchange as described previously (Love et al., 2012; Bricker et al., 2002). Genomic DNA for use as a PCR template was prepared from an overnight culture of S. pyogenes as follows: Cells from a 10 mL overnight culture were harvested by centrifugation at 10,000 rpm and resuspended in 1 mL of STE buffer (100 mM NaCl, 10 mM EDTA, 10 mM Tris, pH 8.0) containing mutanolysin (50 µg, Sigma). This suspension was incubated at 37° C. with agitation for 2 h at which point DNase-free RNase (10

μg; Sigma) and N-Lauroylsarcosine (0.5% (v/v), Sigma) were added. After a further 10 min incubation at 37° C., pronase was added (10 mg, Sigma) and the mixture was incubated at 37° C. for a further 10 min. *S. pyogenes* genomic DNA was precipitated by mixing with an equal volume of phenol:chloroform (1:1), followed by centrifugation at 12,000 rpm. The pellet was washed with ice-cold ethanol and then washed and dissolved in TE buffer (10 mM Tris, pH 8.0, 1 mM EDTA). For PCR, 1 μL of genomic DNA template in a 50 μL PCR reaction mixture was used. PCR products corresponding to the 5' and 3' ends of slo were produced using the primer pairs 5'-CCC TCTAGAGGTAACCTTGTTACTGCTAATGC-3' (SEQ ID NO: ) and 5'-CCC GGATCCCAGTGACAGAGTCAATGATGG-3' (SEQ ID NO: ) (441 bp product) and 5'-CCC GAATTCGCGGGTGTCAATAACAGAACTG-3' (SEQ ID NO: ) and 5'-CCC GGTACCCCATATGGGCTCAGGGTTGATC-3' (SEQ ID NO: ) (367 bp product), respectively.

All PCR reactions were performed using Phusion High-Fidelity PCR Master Mix (New England Biolabs). The products were directionally cloned into the temperature-sensitive shuttle vector pJRS233 (provided by June Scott) (Perez-Casal et al., 1993) using unique XbaI, BamHI, EcoRI and Asp718 restriction endonuclease sites (underlined) incorporated into the PCR primers. The final construct representing the slo sequence with an 818 bp internal deletion was cloned into pJRS233 at the XbaI and Asp718 sites. The resultant plasmid, pJsloΔ was verified by DNA sequencing (Genewiz) using the primers pJRSseqF (5'-GGGATGTGCTGCAAGGCG-3') (SEQ ID NO: ) and pJRSseqR (5'-ACGACAGGTTTCCCGACTG-3') (SEQ ID NO: ), which recognize regions outside the 5' and 3' termini of the pJRS233 multiple cloning site.

The pJsloΔ plasmid was introduced into competent *E. coli* DH5a cells (New England Biolabs) by transformation according to the manufacturer's instructions. This plasmid was purified using the Plasmid midi- or maxi-prep kits (Qiagen) and transformed into electrocompetent *S. pyogenes* cells. Plasmid integration followed by allelic exchange was allowed to occur at the permissive temperature (Perez-Casal et al., 1993). Mutants were verified by PCR of the slo gene using the first and forth primers listed above and Phusion® High-Fidelity PCR Master Mix (New England Biolabs).

SLS was inactivated in *S. pyogenes* 854 and 950771 by deletion of sagA (Sierig et al., 2003). DNA fragments corresponding to regions at the 5' (359 bp) and 3' (392 bp) termini of sagA were generated using the primer pairs 5'-CGCGGTACCCACATAGTTATTGATAGAAT-3' (SEQ ID NO: ) and 5'-TCCAGGAGCAACTTGAGTTG-3' (SEQ ID NO: ) (5') and 5'-CAACTCAAGTTGCTCCTGGACAAGGTGGTAGCG-GAAGTTA-3' (SEQ ID NO: ) and 5'-GCG AAGCTTGTAATCCGATAAGGACAAGT-3' (3') (SEQ ID NO: ). These fragments have overlapping ends at the 3' and 5' ends, respectively to permit a subsequent overlap PCR, using the first and fourth primers listed above. The resultant PCR product harbored an internal 60-bp deletion in sagA. This product was directionally cloned into pJRS233 using the unique BamHI and HindIII restriction endonuclease sites included in the PCR primers (underlined), to generate pJsagAΔ in *E. coli* strain DH5a. Plasmid pJsagAΔ was purified and used to generate 950771ΔsagA and 854ΔsagA as described above for Δslo. Mutants were identified by their lack of beta hemolysis on blood agar and verified by PCR analysis of the sagA locus. To generate ΔsloΔsagA mutants, pJsagAΔ was introduced to 950771Δslo or 854Δslo by allelic replacement as described above.

For complementation studies, the sagA gene including a 780 bp promoter region upstream (Nizet et al., 2000) was cloned using the primer pair 5'-CCG GAATTCGGCCCAAGAACGGAGTGTAT-3' (SEQ ID NO: ) and 5'-GGA GCATGCTTATTTACCTGGCGTATAACTTCCG-3' (SEQ ID NO: ). This product was directionally cloned using EcoRI and SphI (underlined in primer sequence) into pDL278, to generate pSagA. Plasmid pSagA was purified and introduced into ΔsagA and ΔsloΔsagA backgrounds by electroporation and maintained by selection using spectinomycin (Sigma). Positive transformants were verified by PCR and their restoration of beta hemolysis on blood agar medium.

Streptolysin 0 activity. SLO activity was measured by determination of hemolytic titers of bacterial supernatants of *S. pyogenes* taken at early stationary phase. Supernatants were filtered through a 0.45 mm membrane, Dithiothreitol added at 6 mM and incubated at 37° C. for 30 min. Sheep erythrocytes was prepared by diluting fresh defibrinated sheep blood (Northeast Lab Services) in PBS and the suspension was added to each bacterial culture sample. After 30 min incubation at 37° C., cell mixtures were centrifuged, and absorbance measured at 550 nm. Hemolytic units correspond to the reciprocal of the dilution of supernatant that yielded 50% lysis, where 100% lysis corresponds to that caused by 1% Triton X-100. Hemolytic activities were also determined after pre-treatment of samples with the SLO inhibitor, cholesterol (cholesterol-methyl-β-cyclodextrin, Sigma) at a concentration of 250 μg/mL (estimated cholesterol concentration, 10 μg/mL).

General experimental design. All in vivo experiments were performed in both male and female age-matched littermates. Pain behavioral tests were performed by blinded observers that were unaware of treatment groups and genotypes. Treatment groups of mice were randomized and evenly distributed across littermates in cages. Treatments were performed by blinded investigators unaware of the contents of syringes or other administration devices. In experiments involving transgenic mice, littermates with different genotypes were cohoused for the duration of experiments. Quantification and analysis of microscopy images were performed by a blinded investigator unaware of groups and genotypes. Animal numbers for experiments were estimated based on pilot studies of *S. pyogenes* infections in the lab and based on standard numbers used in the field based on publications on pain and bacterial infection work. For pain behavioral tests, at least 4 mice per group were used. For pain behavioral experiments, mice that did not survive the entire time-course of analysis were excluded from analysis. For bacterial infections and analysis (demornecrotic lesion size, abscess size, and weight loss following infection), at least 5 mice per group were used. For histology, bacterial load recovery analysis, flow cytometry, ex vivo, and in vitro experiments, at least 3 biological replicates per group were used. All statistical analysis was performed using Graphpad Prism (v. 7.02). For specific numbers of replicates used for each experiment, please see the section Quantification and Statistical Analysis.

Bacterial infections. *S. pyogenes* strains were grown overnight on TSA plates supplemented with 5% Sheep Blood (BD Biosciences, Cat #221239) at 37° C. with 5% $CO_2$. The next morning, bacterial colonies were picked and inoculated into THY broth (Todd-Hewitt Broth, Sigma, Cat #T1438, with 0.2% yeast extract, Sigma, Cat #Y1625), incubated for 3 h at 37° C. without shaking until growth reached mid-exponential phase, and resuspended in fresh medium to $A_{600\,nm}$ of 0.6. Bacterial cells were collected by centrifugation at 800 g for 15 min, washed once in PBS, and then resuspended in PBS at different estimated concentrations for injection. Before injection of bacteria, mice were lightly anesthetized by inhalation of isoflurane (Patterson Veterinary) 3% in oxygen using a precision vaporizer. For hind paw infections, a single dose of $5 \times 10^5$-$5 \times 10^8$ cfu of S. pyogenes in 20 µL PBS was administered by intraplantar injection of the right hind paw using a 0.5 cc syringe fitted with a 31-gauge needle (BD Biosciences). For flank infections, $5 \times 10^6$ cfu of S. pyogenes in 50 µL PBS was injected subcutaneously into the flank previously shaved using a hair clipper (Patterson Veterinary). In some cases, hair removal cream (Nair) was also applied for hair removal prior to infection. The bacterial suspension was kept on ice until use, and the inoculum was confirmed by quantitative culture of an aliquot of the final suspension prior to injection. Injections of bacteria or vehicle were performed by an investigator blinded to the content of syringes. Syringes were previously assigned to specific animals by an investigator aware of the groups in order to distribute groups across multiple cages.

Bacterial load recovery analysis. Mice were euthanized by $CO_2$ inhalation and rapidly used for tissue dissection. During necropsy of mice, total hind paw tissues including epidermis, dermis, and subcutaneous tissue to the tendons, or flank tissue encompassing the injection site including epidermis, dermis, and subcutaneous tissue, or spleens were dissected and weighed. Tissues were then transferred to 2 mL eppendorf tubes containing 5 mm stainless steel beads (Qiagen, Cat #69989) and 1 mL of ice-cold sterile distilled water. Tissues were homogenized using a TissueLyser II (Qiagen) for 10 min at 30 Hz. To determine bacterial load recovery, serial dilutions were made and plated on TSA plates with 5% Sheep Blood plates (BD Biosciences, Cat #221239), and colonies were counted after overnight incubation at 37° C. with 5% $CO_2$.

Pain behavioral tests. Spontaneous pain behaviors were evaluated by quantifying the time that mice spent 1) lifting/licking the hind paw and 2) the number of paw flinches that occurred over a 1 h time period immediately after infection. Data was collected in 5-minute intervals. For mechanical and heat hyperalgesia tests, mice were allowed to habituate to the apparatus during 2 h and for three consecutive days before the beginning of measurements. After habituation, baseline measurements were obtained on two consecutive days prior to infection. Pain intensity to mechanical stimulus (mechanical hyperalgesia) was measured using von Frey monofilaments. Briefly, mice were placed on an elevated wire framework and a series of von Frey monofilaments with different pressure intensities (from 0.007 g to 4 g) were applied to the plantar surface of the infected hind paw. The threshold of pain was determined as the lowest pressure filament that induced a response (paw withdrawal) in five out of ten applications. To measure pain sensitivity to a heat stimulus (heat hyperalgesia), mice were placed on the temperature-controlled (29° C.) glass plate of a Hargreaves apparatus (Model 390G, IITC Life Science). A radiant heat source (active intensity 23%) was used to stimulate the infected paw by gradually increasing the temperature of the plantar surface. The threshold of pain was determined as the latency (in seconds) to evoke a response of paw withdrawal. The mean of three measurements was determined for each animal at each time point. An exposure limit of 40 s was used to prevent tissue damage. Data from mice that did not survive until the end of the tests were not included in the analysis. Pain behavior tests were performed by blinded observers that were unaware of the treatments, groups, and genotypes.

Lesion size measurement. One day prior to subcutaneous injection with S. pyogenes, mice were lightly anesthetized by inhalation of isoflurane (Patterson Veterinary) 3% in oxygen using a precision vaporizer, and the flank area was shaved using a hair clipper. Abscess sizes and dermonecrotic skin lesions were measured daily with a digital caliper (VWR International, Cat #62379-531) for 14 days after injection, and area calculated with the formula $A=(\pi/2)$(length)(width). Mice were also anesthetized with isoflurane 3% in oxygen during the measurements. Data from mice that did not survive until the end of the tests were not included in the analysis.

In vivo BoNT/A and BIBN4096 treatments. Botulinum neurotoxin A (BoNT/A, List Biological Labs, Cat #130B) intrathecal or local subcutaneous pre-treatments were used that were able to distinguish the contribution of pain perception from peripheral neuropeptide release. Mice were subsequently infected with M1 S. pyogenes in the footpad for pain behavioral assays or in the flank for dermonecrotic lesion measurements. For intrathecal pre-treatments, BoNT/A (25 pg in 5 µL PBS) or vehicle (5 µL PBS) was injected at the level of L4-L6 segments of spinal cord 24 h before infection with S. pyogenes. For local pre-treatments, different groups of mice received a subcutaneous BoNT/A injection (25 pg in 5 µL PBS) or vehicle (5 µL PBS) in the footpad, or they received BoNT/A (25 pg in 100 µL PBS) or vehicle (100 µL PBS) in the for flank skin at the anticipated site of infection 6 days before infection. It was also evaluated whether BoNT/A or CGRP antagonist (BIBN4096, Tocris, Cat #4561) was able to treat S. pyogenes infection. For these experiments, mice were infected in the flank skin with S. pyogenes M1. 2 h after infection, subcutaneous injection of BoNT/A (25 pg in 50 µL PBS) were performed at the site of infection or intraperitoneal injection of CGRP receptor antagonist BIBN4096 (30 mg/kg). In another set of experiments to determine therapeutic potential, BoNT/A or vehicle was administered locally in mice infected with S. pyogenes at day 2 after flank skin infection, and again at day 9 after infection. For this experiment, BoNT/A (25 pg in 100 µL PBS) or vehicle (100 µL PBS) was distributed in 5 applications of 20 uL each around the borders of the lesion at day 2 and at day 9. The injection sites were marked using a blue marker at each day of injection. BoNT/A was administered using a Hamilton syringe (Hamilton Company, Cat #7636-01) fitted with a 32 gauge needle (Hamilton Company, Cat #7803-04). S. pyogenes M1 wt was used at the following doses for the experiments described above: $5 \times 10^6$ cfu for flank infections and lesion size measurements, $5 \times 10^7$ cfu for foot pad infections and hyperalgesia studies, and $5 \times 10^8$ cfu for foot pad infections and spontaneous lifting/licking/flinching tests.

Histology. Mice were euthanized by $CO_2$ inhalation and intracardially perfused with 30 mL of ice-cold PBS, followed by 30 mL of PBS/4% paraformaldehyde (PFA, Sigma, Cat #P6148). Infected hind paw and flank lesion samples were dissected, post-fixed for 12 h at 4° C. in PBS/4% paraformaldehyde solution, embedded in paraffin, sectioned, and stained using hematoxylin and eosin (H&E) or Brown and Brenn Gram stains by the Harvard Medical School Rodent Histopathology Core. Stained sections were imaged by light microscopy on an Eclipse Ti-S/L100 inverted microscope (Nikon), and images collected by NIS-Elements AR software.

Immunostaining and microscopy. For immunofluorescence staining, hind paw skin tissues and dorsal root ganglion (DRG) tissues were dissected from mice previously euthanized by $CO_2$ inhalation and intracardially perfused with 30 mL of PBS, followed by 30 mL of PBS/4% PFA (Sigma, Cat #P6148). Samples were post-fixed in PBS/4% PFA solution at 4° C. for 12 h, cryoprotected in PBS/30% sucrose (Sigma, Cat #S0389) for 3 days at 4° C., embedded in Optimal Cutting Temperature (OCT, Sakura Finetek, Cat #4583), and stored at −80° C. until processing. Cryosections (20 µm for DRG, 40 min for skin) were cut onto Superfrost Plus slides (Thermo Fisher) before immunostaining. Hind paw skin or DRG sections were stained with mouse or rabbit anti-beta III tubulin (Tuj 1, Abeam, 1:500), rabbit anti-CGRP (Sigma, 1:10,000), mouse anti-NF200 (MilliporeSigma, 1:1000), mouse anti-PGP9.5 (Abeam, 1:500), or guinea pig anti-TRPV1 (MilliporeSigma, 1:1000), followed by Alexa 594 donkey anti-mouse IgG (Abeam, 1:500), DyLight 488 donkey anti-rabbit IgG (Abeam, 1:500) or goat anti-guinea pig IgG (Sigma, 1:500). Stained sections were mounted in Vectashield mounting medium (Vector Labs, Cat #H1000), with addition of DAPI (BioLegend, Cat #422801) for skin samples. Fluorescence imaging was performed using a FV1000 laser-scanning confocal microscope (Olympus). Data were collected using Olympus Fluoview software. Samples were imaged with z-stacks of 1 µm steps and 20 min (for DRG) or 40 µm (for skin) total thickness; maximum projection images were exported for analysis.

Quantification of DRG neurons. DRG samples were collected, sectioned, stained, and imaged as described in the section Immunostaining and microscopy. Maximum projection images (3 fields per sample) obtained for each channel were exported for analysis. The number of TRPV1, CGRP, or NF200 positive neurons, and the total number of neurons (βIII-tubulin positive) field were quantified by an investigator blinded for the groups. Percentage of TRPV1, CGRP, or NF200 positive neurons out of the total neurons (βIII-tubulin positive) was determined for each sample as the average of 3 fields.

RTX mediated ablation of nociceptor neurons. Resiniferatoxin (RTX, Sigma-Aldrich), a potent capsaicin analog, was used to deplete TRPV1-positive nociceptors. Male and female 4-week-old C57BL/6 mice were lightly anesthetized by inhalation of isoflurane (Patterson Veterinary) 3% in oxygen using a precision vaporizer. Three RTX escalating doses (30 µg/kg, 70 µg/kg, 100 µg/kg, diluted in PBS with 1.2% DMSO and 0.06% Tween-80) were subcutaneously injected over the flank of anesthetized mice on three consecutive days, as adapted from established protocols (Sándor et al., 2009; Riol-Blanco et al., 2014). Control littermates were injected with vehicle solution on the same days (PBS with 1.2% DMSO and 0.06% Tween-80). Mice were used for infection experiments four weeks after the last injection of RTX. Vehicle and RTX treated mice were housed together before and during the experiments. Efficiency of RTX treatment in depleting TRPV1-positive nociceptors was confirmed by counting the number of TRPV1-positive neurons in the DRG by microscopy. DRG samples were collected, sectioned, and stained as described in the section Immunostaining and microscopy, and quantified as described in the section Quantification of DRG neurons.

Dorsal root ganglia neuron dissection and culture. Adult, 7-13 wk old male and female mice were euthanized by $CO_2$ inhalation. Dorsal root ganglia (DRG) were dissected from all segments of the spinal cord and transferred to neurobasal medium (Thermo Fisher) supplemented with B-27 (Thermo Fisher) and penicillin/streptomycin (Thermo Fisher). DRGs were enzymatically dissociated by incubating in 2 mL of HEPES-buffered saline (Sigma) containing collagenase A (1 mg/kg, Sigma) and dispase II (2.4 U/mL, Roche Applied Sciences) for 20 min at 37° C. Supernatant was carefully removed, replaced with 2 mL of fresh collagenase A/dispase II solution and incubated for 20 min at 37° C. again. Cells were transferred to a tube containing 10 mL of DMEM/10% FBS (Thermo Fisher), centrifuged for 1 min at 200 g at 4° C., and resuspended in 800 µL of DMEM/10% FBS containing DNase I (150 U/mL, Thermo Fisher). DRG cells were dissociated with fire-polished glass Pasteur pipettes (VWR International) with decreasing tip diameters to create single-cell suspensions. Cells were resuspended in 2 mL of neurobasal medium (Life Technologies), and then centrifuged (260 g, 10 min) after overlaying on a 10% bovine serum albumin (BSA) gradient (diluted in Neurobasal medium from a 30% BSA solution in PBS, Sigma). Supernatant was removed and resulting pellet resuspended in neurobasal medium for plating. For calcium imaging, cells were plated onto 35 mm laminin-coated (Thermo Fisher) cell culture dishes (2,000 cells per dish) in neurobasal-A medium plus 50 ng/mL nerve growth factor (Thermo Fisher); DRG neurons were used for calcium imaging 12-24 h after plating. For co-incubation with neutrophils and CGRP release experiments, 5,000 DRG neurons were seeded per well in laminin-coated flat bottom 96-wells plates and incubated with neurobasal-A medium plus 50 ng/mL nerve growth factor (Thermo Fisher) and cytosine arabinoside (10 µM, Sigma) for one week; half of the medium was replaced with fresh media every two days.

Calcium imaging and data analysis. Cultured DRG neurons were washed and loaded with 5 µM Fura-2 AM (Thermo Fisher) in Neurobasal-A medium for 30 min at 37° C., then washed twice and imaged in Krebs-Ringer solution (Boston BioProducts). DRG neurons were imaged using an Eclipse Ti-S/L100 inverted microscope (Nikon) and Zyla sCMOS camera (Andor). An ultraviolet light source (Lambda XL lamp, Sutter Instrument) was used for excitation of Fura-2-AM by alternating 340 nm and 380 nm wavelengths. NIS-elements software (Nikon) was used to image, process and analyze 340/380 ratiometric images from neurons. An increase in 340/380 ratio of 10% or more from baseline levels was considered a positive response to a ligand. For calcium imaging experiments, cell size for individual DRG neurons (measured as area in $\mu m^2$) was determined using NIS-elements software by marking individual cells using the Region of Interest tool in combination with the Automated Measurement tool (Nikon). The percentage of bacteria-responsive cells or bacteria-unresponsive cells from 3 separate neuronal fields/condition was determined and binned into four groups for analysis based on their cell body area (<149, 150-249, 250-349, and >350 $\mu m^2$).

S. pyogenes supernatant for neuronal stimulation. S. pyogenes strains were grown overnight on TSA plates with 5% sheep blood (BD Biosciences) at 37° C. in 5% $CO_2$. Bacterial colonies were picked and inoculated into liquid cultures of THY broth, grown for 3 h at 37° C. without shaking until mid-exponential phase, and bacterial density estimated by $A_{600\ nm}$. Bacterial cells were collected by centrifugation, washed, and then resuspended ($5 \times 10^8$-$5 \times 10^{10}$ cfu per mL) in phenol red-free neurobasal-A medium plus 6% BSA (Sigma) and incubated at 37° C. for 1 h, centrifuged for 15 min at 800 g, and the supernatant filtered with a 20 µm cell strainer. For calcium imaging, DRG neurons were stimulated with 200

µL of the filtrate, representing bacterial supernatant. For CGRP release assay, 50 µL of bacterial supernatant was used.

Neuronal stimulation and CGRP release. DRG neurons (5,000 per well) were cultured for one week in Neurobasal-A medium containing 50 ng/mL nerve growth factor and cytosine arabinoside as described in the sections Dorsal root ganglia neuron dissection and culture. One group of neurons was treated with 25 pg (in 200 uL of Neurobasal-A medium) of Botulinum neurotoxin A (BoNT/A) for 24 h prior to neuronal stimulation. The neuronal culture medium was removed from all wells, and 200 µL of fresh neurobasal-A medium was added to the wells. Filtered supernatants from S. pyogenes M1 854 strain or isogenic mutant strains were collected at the day of the test as described in the section S. pyogenes supernatant for neuronal stimulation. Immediately before stimulation, 50 µL of cell culture supernatant was removed and 50 µL of bacterial supernatant or control medium (neurobasal-A medium+6% BSA) was added to the wells. Cells were incubated for 30 min at 37° C. and with 5% of $CO_2$ and then 50 µL of supernatant were collected to determine CGRP concentration. A CGRP Enzyme Linked Immunosorbent kit (Cayman Chemical) was used to quantify CGRP according to manufacturer's instructions.

Neutrophil isolation and killing assays. Following euthanasia, femurs and tibias were dissected from mice. Bone marrow cells were flushed out using PBS/1 mM EDTA (Sigma) in a syringe and a 21 gauge needle. Cells were then strained through a 100 µm cell strainer, centrifuged for 5 min at 300 g, resuspended in 3 mL of red blood cell lysis buffer (eBioscience) and incubated for 15 min at room temperature. PBS (22 mL) was added and the cells were centrifuged for 5 min at 300 g. Supernatant was removed, and the cells were resuspended in neurobasal-A medium (Thermo Fisher) with 10% fetal bovine serum (FBS) at a maximum concentration of $1 \times 10^8$ cells/mL. Neutrophils were isolated using an immune magnetic negative selection kit according to manufacturer's instructions (EasySep mouse neutrophil enrichment kit and EasySep Magnet, StemCell). Half of the final neutrophil suspension solution was saved to collect the supernatant. This supernatant was added to the conditions where neutrophils were absent (control conditions) instead of fresh media to control for effects of used cell media on bacterial growth.

For opsonophagocytic killing assays, mouse neutrophils were used immediately after isolation. S. pyogenes ($5 \times 10^3$ cfu) M1 wt strain was mixed with mouse neutrophils ($5 \times 10^5$ cells per well) in 200 µL of neurobasal-A medium containing 10% of fresh mouse serum. As described before, neutrophil filtered supernatant was added to the control conditions (without neutrophils). CGRP (1 µM, GenScript) or the antagonists $CGRP_{8-37}$ (1 µM, GenScript) or BIBN4096 (1 µM, Tocris) were added to the cultures immediately before S. pyogenes. For neuron-neutrophil co-incubation experiments, neutrophils and bacteria were added to the plates containing $5 \times 10^3$ DRG neurons and incubated under the same conditions. One group of DRG neurons was treated with 25 pg (200 µL) of BoNT/A 24 h before the assay. Some wells of neuron-neutrophil co-cultures were treated with the antagonists $CGRP_{8-37}$ (1 GenScript) or BIBN4096 (1 Tocris) at the time of neutrophil addition.

For all conditions described for neutrophil opsonophagocytic killing assays, plates were incubated for 1 h at 37° C. with gently shaking (150 rpm). The amount of extracellular and intracellular bacteria was determined after resuspension in ice-cold $ddH_2O$ by serial dilution plating on TSA plates with sheep blood agar (BD Biosciences), and bacterial colonies were counted after overnight incubation at 37° C. in 5% $CO_2$. The multiplication factor of net bacterial growth was calculated as the number of cfu recovered/number of cfu added to wells.

Neutrophil myeloperoxidase activity (MPO) assay. Mouse neutrophils were isolated from mouse bone marrow using EasySep mouse neutrophil enrichment kit and EasySep Magnet according to manufacturer's instructions (StemCell). These neutrophils ($5 \times 10^5$ cells per well) were then treated with CGRP (0.01-1 GenScript) or vehicle (PBS), immediately prior to mixture with S. pyogenes ($5 \times 10^3$ cfu) M1 wt strain or vehicle (PBS) in 200 µL of neurobasal-A medium containing 10% of fresh mouse serum. Serum was obtained after coagulation of whole mouse blood. Plates were incubated for 30 min at 37° C. with gently shaking (150 rpm), and supernatant collected for MPO activity measurements. Supernatants (50 µL) were added to 200 µL, of 50 mM phosphate buffer solution (pH 6.0) containing 0.167 mg/mL of peroxidase substrate o-dianisidine dihydrochloride (Santa Cruz Biotech) and 0.05% hydrogen peroxide (Santa Cruz Biotech) and incubated for 30 min at room temperature. MPO activity was determined spectrophotometrically by measuring the increase in absorbance at 450 nm.

Lancefield assay. Human blood phagocytosis assays (Lancefield bactericidal test) were performed as described previously with slight modifications (Gryllos et al., 2008). S. pyogenes M1 wt strain was cultured to $OD_{600}$ of 0.15 in L3 medium at 37° C. with 5% $CO_2$ and diluted in sterile PBS. Quantitative cultures of the bacterial suspension were performed to allow precise quantification of the starting inoculum. Whole human blood (10 mL/tube) was collected into heparin-containing tubes (BD Vacutainer™, Fisher Scientific) Approximately 20-200 S. pyogenes cfu were inoculated into heparinized whole blood obtained from three healthy donors supplemented with human CGRP (10 or 100 nM) and incubated for 3 h at 37° C. with end-over-end rotation. Bacterial survival was quantified as multiplication factor of number of surviving colonies relative to the starting inoculum. Each condition was tested in triplicate.

CGRP release assay from skin explants. Skin punch biopsies (12 mm) were collected from the uninfected or infected flank skin samples of euthanized mice, and rapidly transferred to 24-well plates containing 1 mL of DMEM. Explants were incubated at 32° C. with gentle shaking (150 rpm) for 30 min. After incubation, the bath supernatant from the organ cultures was collected, and assayed to determine CGRP concentration with the CGRP EIA kit (Cayman Chemical) according to manufacturer's instructions.

Flow cytometry. Flank tissue samples of dermonecrotic lesions were dissected 24 h after infection, minced and incubated for 2 h (37° C., shaking) in 2 mL of HEPES-buffered saline (Sigma) containing collagenase A (1 mg/kg, Roche Applied Sciences) and dispase II (2.4 U/mL, Roche Applied Sciences). After incubation, cells were gently dissociated using a 16G needle attached to a 10 mL sterile syringe, filtered through a 70 µm mesh, and mixed with 20 mL of washing buffer constituted by HBSS (Thermo Fisher) and 0.5% BSA (Sigma). Cells were centrifuged for 5 min at 300 g, supernatant was discarded, and the pellet was resuspended in 500 µL, of washing buffer. The cell suspension was incubated on ice with mouse FcR Blocking Reagent (Miltenyi Biotec) for 10 min, and then incubated for 30 min on ice with the following antibodies: anti-CD45-APC/Cy7 (1:200, Biolegend), anti-Ly6G-A488 (1:200, Biolegend), anti-Ly6C-PercP/Cy5.5 (1:200, Biolegend), anti-CD11b-

BV605 (1:200, Biolegend), and Fixable Viability Dye eFluor-506 (1:1,200, Thermo Fisher). Cells were centrifuged for 5 min at 300 g and the pellet resuspended in 500 µL, of washing buffer/2% PFA. Flow cytometry was performed on a LSR II flow cytometer (BD Biosciences). Flow cytometry data were collected and exported using BD FACSDiva software (BD Biosciences). FACS data were analyzed and plotted using FlowJo software (FlowJo LLC).

References for Example 8

Abraira, V. E., and Ginty, D. D. (2013). The Sensory Neurons of Touch. Neuron 79, 618-639.

Ashbaugh, C. D., Warren, H. B., Carey, V. J., and Wessels, M. R. (1998). Molecular analysis of the role of the group A streptococcal cysteine protease, hyaluronic acid capsule, and M protein in a murine model of human invasive soft-tissue infection. J. Clin. Invest. 102, 550-560.

Bastiat-Sempe, B., Love J. F., Lomayesva, N., and Wessels, M. R. (2014). Streptolysin 0 and NAD-glycohydrolase prevent phagolysosome acidification and promote group A *Streptococcus* survival in macrophages. MBio 5, e01690-14.

Basbaum, A. I., Bautista, D. M., Scherrer, G., and Julius, D. (2009). Cellular and molecular mechanisms of pain. Cell 139, 267-284.

Bellono, N. W., Bayrer, J. R., Leitch, D. B., Castro, J., Zhang, C., O'Donnell, T. A., Brierley, S. M., Ingraham, H. A., and Julius, D. (2017). Enterochromaffin Cells Are Gut Chemosensors that Couple to Sensory Neural Pathways. Cell 170, 185-198.e16.

Bentley, C. C., Hakansson, A., Christianson, J., and Wessels, M. R. (2005). Extracellular group A *Streptococcus* induces keratinocyte apoptosis by dysregulating calcium signalling. Cell. Microbiol. 7, 945-955.

Betschel, S. D., Borgia, S. M., Barg, N. L., Low, D. E., and De Azavedo, J. C. S. (1998). Reduced Virulence of Group A Streptococcal Tn916 Mutants That Do Not Produce Streptolysin S. Infect. Immun. 66, 1671-1679.

Binshtok, A. M., Wang, H., Zimmermann, K., Amaya, F., Vardeh, D., Shi, L., Brenner, G. J., Ji, R.-R., Bean, B. P., Woolf, C. J., et al. (2008). Nociceptors are interleukin-1beta sensors. J. Neurosci. 28, 14062-14073.

Binz, T., Blasi, J., Yamasaki, S., Baumeister, A., Link, E., Südhof, T. C., Jahn, R., and Niemann, H. (1994). Proteolysis of SNAP-25 by types E and A botulinal neurotoxins. J. Biol. Chem. 269, 1617-1620.

Borschitz, T., Schlicht, S., Siegel, E., Hanke, E., von Stebut, E., and Goldberg, E. (2015). Improvement of a Clinical Score for Necrotizing Fasciitis: "Pain Out of Proportion" and High CRP Levels Aid the Diagnosis. PLoS One 10, e0132775.

Bricker, A. L., Cywes, C., Ashbaugh, C. D., and Wessels, M. R. (2002). NAD+-glycohydrolase acts as an intracellular toxin to enhance the extracellular survival of group A streptococci. Mol. Microbiol. 44, 257-269.

Buchanan, C. S. and Haserick, J. R. (1970). Necrotizing fasciitis due to group A beta-hemolytic streptococci. Arch. Dermatol. 101, 664-668.

Caceres, A. I., Brackmann, M., Elia, M. D., Bessac, B. F., del Camino, D., D'Amours, M., Witek, J. S., Fanger, C. M., Chong, J. a, Hayward, N. J., et al. (2009). A sensory neuronal ion channel essential for airway inflammation and hyperreactivity in asthma. Proc. Natl. Acad. Sci. U.S.A. 106, 9099-9104.

Chavan, S. S., Pavlov, V. A., and Tracey, K. J. (2017). Mechanisms and Therapeutic Relevance of Neuro-immune Communication. Immunity 46, 927-942.

Chiu, I. M., Heesters, B. A., Ghasemlou, N., Von Hehn, C. A., Zhao, F., Tran, J., Wainger, B., Strominger, A., Muralidharan, S., Horswill, A. R., et al. (2013). Bacteria activate sensory neurons that modulate pain and inflammation. Nature 501, 52-57.

Chiu, I. M., Barrett, L. B., Williams, E. K., Strochlic, D. E., Lee, S., Weyer, A. D., Lou, S., Bryman, G. S., Roberson, D. P., Ghasemlou, N., et al. (2014). Transcriptional profiling at whole population and single cell levels reveals somatosensory neuron molecular diversity. Elife 3.

Cole, J. N., Barnett, T. C., Nizet, V., and Walker, M. J. (2011). Molecular insight into invasive group A streptococcal disease. Nat. Rev. Microbiol. 9, 724-736.

Dale, J. B., Chiang, E. Y., Hasty, D. L., and Courtney, H. S. (2002). Antibodies against a synthetic peptide of SagA neutralize the cytolytic activity of streptolysin S from group A streptococci. Infect. Immun. 70, 2166-2170.

Datta, V., Myskowski, S. M., Kwinn, L. A., Chiem, D. N., Varki, N., Kansal, R. G., Kotb, M., and Nizet, V. (2005). Mutational analysis of the group A streptococcal operon encoding streptolysin S and its virulence role in invasive infection. Mol. Microbiol. 56, 681-695.

Flaherty, R. A., Puricelli, J. M., Higashi, D. L., Park, C. J., and Lee, S. W. (2015). Streptolysin S Promotes Programmed Cell Death and Enhances Inflammatory Signaling in Epithelial Keratinocytes during Group A *Streptococcus* Infection. Infect. Immun. 83, 4118-4133.

Gabanyi, I., Muller, P. A., Feighery, L., Oliveira, T. Y., Costa-Pinto, F. A., and Mucida, D. (2016). Neuro-immune Interactions Drive Tissue Programming in Intestinal Macrophages. Cell 164, 378-391.

Gilbert E, W. N. (2014). Efficacy of botulinum neurotoxin type A for treating recalcitrant plaque psoriasis. J. Drugs Dermatol. 13, 1407-1408.

Grando, S. A., and Zachary, C. B. (2017). THE NON-NEURONAL AND NON-MUSCULAR EFFECTS OF BOTULINUM TOXIN: A Graceful Opportunity for a Deadly Molecule to Treat a Human Disease in the Skin and Beyond. Br. J. Dermatol.

Granstein, R. D., Wagner, J. A., Stohl, L. L., and Ding, W. (2015). Calcitonin gene-related peptide: key regulator of cutaneous immunity. Acta Physiol. (Oxf). 213, 586-594.

Gryllos, I., Tran-Winkler, Cheng, M.-F., Chung, H., Bolcome, R., Lu, W., Lehrer, R. I., Wessels, M. R., and Wessels, M. R. (2008). Induction of group A *Streptococcus* virulence by a human antimicrobial peptide. Proc. Natl. Acad. Sci. U.S.A. 105, 16755-16760.

Higashi, D. L., Biais, N., Donahue, D. L., Mayfield, J. A., Tessier, C. R., Rodriguez, K., Ashfeld, B. L., Luchetti, J., Ploplis, V. A., Castellino, F. J., et al. (2016). Activation of band 3 mediates group A *Streptococcus* streptolysin S-based beta-haemolysis. Nat. Microbiol. 1, 15004.

Hou, Q., Barr, T., Gee, L., Vickers, J., Wymer, J., Borsani, E., Rodella, L., Getsios, S., Burdo, T., Eisenberg, E., et al. (2011). Keratinocyte expression of calcitonin gene-related peptide β: Implications for neuropathic and inflammatory pain mechanisms. Pain 152, 2036-2051.

Hunskaar, S., Fasmer, O. B., and Hole, K. (1985). Formalin test in mice, a useful technique for evaluating mild analgesics. J. Neurosci. Methods 14, 69-76.

Ji, Y., McLandsborough, L., Kondagunta, A., and Cleary, P. P. (1996). C5a peptidase alters clearance and trafficking of group A streptococci by infected mice. Infect. Immun. 64, 503-510.

Kashem, S. W., Riedl, M. S., Yao, C., Honda, C. N., Vulchanova, L., and Kaplan, D. H. (2015). Nociceptive Sensory Fibers Drive Interleukin-23 Production from CD301b+ Dermal Dendritic Cells and Drive Protective Cutaneous Immunity. Immunity 43, 515-526.

Kramer, H. H., Angerer, C., Erbguth, F., Schmelz, M., and Birklein, F. (2003). Botulinum Toxin A reduces neurogenic flare but has almost no effect on pain and hyperalgesia in human skin. J. Neurol. 250, 188-193.

Kurupati, P., Turner, C. E., Tziona, I., Lawrenson, R. A., Alam, F. M., Nohadani, M., Stamp, G. W., Zinkernagel, A. S., Nizet, V., Edwards, R. J., et al. (2010). Chemokine-cleaving *Streptococcus pyogenes* protease SpyCEP is necessary and sufficient for bacterial dissemination within soft tissues and the respiratory tract. Mol. Microbiol. 76, 1387-1397.

Lee, W.-H., Shin, T. J., Kim, H. J., Lee, J.-K., Suh, H.-W., Lee, S. C., and Seo, K. (2011). Intrathecal Administration of Botulinum Neurotoxin Type A Attenuates Formalin-Induced Nociceptive Responses in Mice. Anesth. Analg. 112, 228-235.

Leitch, H. A., Palepu, A., and Fernandes, C. M. (2000). Necrotizing fasciitis secondary to group A *streptococcus*. Morbidity and mortality still high. Can. Fam. Physician 46, 1460-1466.

Lin, A., Loughman, J. A., Zinselmeyer, B. H., Miller, M. J., and Caparon, M. G. (2009). Streptolysin S inhibits neutrophil recruitment during the early stages of *Streptococcus pyogenes* infection. Infect. Immun. 77, 5190-5201.

Liu, B., Escalera, J., Balakrishna, S., Fan, L., Caceres, A. I., Robinson, E., Sui, A., McKay, M. C., McAlexander, M A., Herrick, C. A., et al. (2013). TRPA1 controls inflammation and pruritogen responses in allergic contact dermatitis. FASEB J. 27, 3549-3563.

Love, J. F., Tran-Winkler, H. J., and Wessels, M. R. (2012). Vitamin D and the human antimicrobial peptide LL-37 enhance group a *streptococcus* resistance to killing by human cells. MBio 3, e00394-12.

Martinon, F., Burns, K., and Tschopp, J. (2002). The inflammasome: a molecular platform triggering activation of inflammatory caspases and processing of proIL-beta. Mol. Cell 10, 417-426.

Meng, J., Wang, J., Lawrence, G., and Dolly, J. O. (2007). Synaptobrevin I mediates exocytosis of CGRP from sensory neurons and inhibition by botulinum toxins reflects their anti-nociceptive potential. J. Cell Sci. 120, 2864-2874.

Mishra, S. K., Tisel, S. M., Orestes, P., Bhangoo, S. K., and Hoon, M. A. (2011). TRPV1-lineage neurons are required for thermal sensation. EMBO J. 30, 582-593.

Molloy, E. M., Cotter, P. D., Hill, C., Mitchell, D. A., and Ross, R. P. (2011). Streptolysin S-like virulence factors: the continuing sagA. Nat. Rev. Microbiol. 9, 670-681.

Muller, P. A., Koscso B., Rajani G. M., Stevanovic, K., Berres, M. L., Hashimoto, D., Mortha, A., Leboeuf, M., Li, X. M., Mucida, D., et al (2014). Crosstalk between muscularis macrophages and enteric neurons regulates gastrointestinal motility. Cell. 158, 300-313.

Nizet, V. (2002). Streptococcal beta-hemolysins: genetics and role in disease pathogenesis. Trends Microbiol. 10, 575-580.

Nizet, V., Beall, B., Bast, D. J., Data, V., Kilburn, L., Low, D. E., and De Azavedo, J. C. (2000). Genetic locus for streptolysin S production by group A *streptococcus*. Infect. Immun. 68, 4245-4254.

Oetjen, L. K., Mack, M. R., Feng, J., Whelan, T. M., Niu, H., Guo, C. J., Chen, S., Trier, A. M., Xu, A. Z., Tripathi, S. V., et al. (2017). Sensory Neurons Co-opt Classical Immune Signaling Pathways to Mediate Chronic Itch. Cell 171, 217-228.e13.

Olsen, R. J., and Musser, J. M. (2010). Molecular Pathogenesis of Necrotizing Fasciitis. Annu. Rev. Pathol. Mech. Dis. 5, 1-31.

O'Seaghdha, M. and Wessels, M. R (2013). Streptolysin 0 and its co-toxin NAD-glycohydrolase protect group A *Streptococcus* from Xenophagic killing. PLoS Pathog. 9, e1003394.

Okumura, C. Y. M., and Nizet, V. (2014). Subterfuge and Sabotage: Evasion of Host Innate Defenses by Invasive Gram-Positive Bacterial Pathogens. Annu. Rev. Microbiol. 68, 439-458.

Perez-Casal, J., Price, J. A., Maguin, E., and Scott, J. R. (1993). An M protein with a single C repeat prevents phagocytosis of *Streptococcus pyogenes*: use of a temperature-sensitive shuttle vector to deliver homologous sequences to the chromosome of *S. pyogenes*. Mol. Microbiol. 8, 809-819.

Petersen, K. A., Lassen, L. H., Birk, S., Lesko, L., and Olesen, J. (2005). BIBN4096BS Antagonizes Human $\alpha$-calcitonin Gene Related Peptide-induced Headache and Extracerebral Artery Dilatation*. Clin. Pharmacol. Ther. 77, 202-213.

Pinho-Ribeiro, F. A., Verri, W. A., and Chiu, I. M. (2017). Nociceptor Sensory Neuron-Immune Interactions in Pain and Inflammation. Trends Immunol. 38.

Ralph, A. P., and Carapetis, J. R. (2013). Group a streptococcal diseases and their global burden. Curr. Top. Microbiol. Immunol. 368, 1-27.

Riol-Blanco, L., Ordovas-Montanes, J., Perro, M., Naval, E., Thiriot, A., Alvarez, D., Paust, S., Wood, J. N., and von Andrian, U. H. (2014). Nociceptive sensory neurons drive interleukin-23-mediated psoriasiform skin inflammation. Nature 510, 157-161.

Rainsford, K. D. (2013). Fifty years of ibuprofen: advancing pain and fever management. Int. J. Clin. Pract. 67, 1-2.

Romero, M., Keyel, M., Shi, G., Bhattacharjee, P., Roth, R., Heuser, I. E., and Keyel, P. A. (2017). Intrinsic repair protects cells from pore-forming toxins by microvesicle shedding. Cell Death Differ. 24, 798-808.

Schrager, H. M., Rheinwald, J. G., and Wessels, M. R. (1996). Hyaluronic acid capsule and the role of streptococcal entry into keratinocytes in invasive skin infection. J. Clin. Invest. 98, 1954-1958.

Shinkai, Y., Rathbun, G., Lam, K. P., Oltz, E. M., Stewart, V., Mendelsohn, M., Charron, J., Datta, M., Young, F., and Stall, A. M. (1992). RAG-2-deficient mice lack mature lymphocytes owing to inability to initiate V(D)J rearrangement. Cell 68, 855-867.

Sierig, G., Cywes, C., Wessels, M. R., and Ashbaugh, C. D. (2003). Cytotoxic effects of streptolysin o and streptolysin s enhance the virulence of poorly encapsulated group a streptococci. Infect. Immun. 71, 446-455.

Stevens, D. L., and Bryant, A. E. (2017). Necrotizing Soft-Tissue Infections. N. Engl. J. Med. 377, 2253-2265.

Takahashi, K., Nakanishi, S., and Imamura, S. (1993). Direct effects of cutaneous neuropeptides on adenylyl cyclase activity and proliferation in a keratinocyte cell line: Stimulation of cyclic AMP formation by CGRP and VIP/PHM, and inhibition by NPY through G protein-coupled receptors. J. Invest. Dermatol. 101, 646-651.

Talbot, S., Abdulnour, R.-E. E., Burkett, P. R., Lee, S., Cronin, S. J. F., Pascal, M. A., Laedermann, C., Foster, S.

L., Tran, J. V., Lai, N., et al. (2015). Silencing Nociceptor Neurons Reduces Allergic Airway Inflammation. Neuron 87, 341-354.

Thulin, P., Johansson, L., Low, D. E., Gan, B. S., Kotb, M., McGeer, A., and Norrby-Teglund, A. (2006). Viable group A streptococci in macrophages during acute soft tissue infection. PLoS Med. 3, 371-379.

Tso, A. R., and Goadsby, P. J. (2017). Anti-CGRP Monoclonal Antibodies: the Next Era of Migraine Prevention? Curr. Treat. Options Neurol. 19, 27.

Tweten, R. K., Hotze, E. M., and Wade, K. R. (2015). The Unique Molecular Choreography of Giant Pore Formation by the Cholesterol-Dependent Cytolysins of Gram-Positive Bacteria. Annu. Rev. Microbiol. 69, 323-340.

Veiga-Fernandes, H., and Mucida, D. (2016). Neuro-Immune Interactions at Barrier Surfaces. Cell 165, 801-811.

Wilson, H. D., and Haltalin, K. C. (1973). Acute necrotizing fasciitis in childhood. Report of 11 cases. Am. J. Dis. Child. 125, 591-595.

Wilson, S. R., Thé, L., Batia, L. M., Beattie, K., Katibah, G. E., McClain, S. P., Pellegrino, M., Estandian, D. M., and Bautista, D. M. (2013a). The Epithelial Cell-Derived Atopic Dermatitis Cytokine TSLP Activates Neurons to Induce Itch. Cell 155, 285-295.

Wilson, S. R., Nelson, A. M., Batia, L., Morita, T., Estandian, D., Owens, D. M., Lumpkin, E. A., and Bautista, D. M. (2013b). The Ion Channel TRPA1 Is Required for Chronic Itch. J. Neurosci. 33, 9283-9294.

Yamamoto, M., Sato, S., Hemmi, H., Hoshino, K., Kaisho, T., Sanjo, H., Takeuchi, O., Sugiyama, M., Okabe, M., Takeda, K., et al. (2003). Role of Adaptor TRIF in the MyD88-Independent Toll-Like Receptor Signaling Pathway. Science 301, 640-643.

Example 9

The lung represents a major barrier surface that interfaces with the environment and is often prone to infection. A highly coordinated immune response protects the respiratory tract from pathogens and other external insults. The role of the nervous system in regulating pulmonary host defense is not well defined. Pulmonary infections and lethal pneumonia are major public health problems, frequently causing death in children, the immunocompromised, and elderly1. *Staphylococcus aureus* is a gram-positive human bacterial pathogen that is the leading cause of hospital-acquired infections, in particular respiratory tract infections and ventilator-associated pneumonia 1-4. The increased prevalence of multi-drug resistant bacteria including methicillin-resistant *S. aureus* (MRSA) strains necessitates non-antibiotic approaches to treatment. Targeting neuro-immune signaling could be a novel approach to boost host immunity against lung pathogens.

The trachea, bronchi and airways are innervated by peripheral sensory afferents originating from vagal and spinal sensory neurons, whose cell bodies reside within the vagal ganglia (VG) and dorsal root ganglia (DRG), respectively 5-7. Nociceptor neurons are the subset of these neurons that respond to noxious stimuli including heat, protons, ATP, mechanical injury, inflammation, and chemical irritants 8. Upon activation, nociceptors induce pain, cough, and bronchoconstriction 5, 8-10. Recent work has shown that nociceptors crosstalk with immune cells in the respiratory tract to drive allergic responses and bronchoconstriction in mouse models of asthma 5, 11, 12. Work described herein investigates a previously unexplored role for sensory neurons in pulmonary host defenses against bacterial invasion and lethal pneumonia.

Results

Transient receptor potential vanilloid 1 (TRPV1+) neurons mediate survival and bacterial clearance in pneumonia. Without being bound by a particular theory, it was hypothesized that lung-innervating nociceptors are poised to detect bacterial invasion and coordinate pulmonary immunity. The Transient receptor potential vanilloid 1 (TRPV1) ion channel responds to capsaicin, protons, and heat stimuli 8, 13. TRPV1 is expressed by many C-fibers, including nociceptors that mediate thermal nociception and inflammatory hyperalgesia 14-16. TRPV1+ neurons were found to drive allergic airway hypersensitivity 5.

A genetic approach was first used to determine the role of TRPV1+ neurons in host defense 5, 16. Trpv1-Dtr mice express the human diphtheria toxin receptor (DTR) under control of mouse TRPV1 regulatory sequences 16. Mouse cells are normally resistant to diphtheria toxin (DT)-induced apoptosis, but are rendered susceptible by expression of DTR. Daily injections of DT were performed into 5-7 week old Trpv1-Dtr mice to selectively ablate TRPV1+ neurons 5, 16. DT treatment significantly ablated TRPV1+ neurons in both DRG and VG compared to PBS-treated Trpv1-Dtr mice (data not shown). CGRP is expressed by many peptidergic c-fiber nociceptors 16, 17. CGRP+ neurons were significantly reduced in DT-treated Trpv1-Dtr mice compared to PBS-treated controls (Supplementary FIG. 26A-26F). By contrast, NF-200+ neurons, which include A-fibers, increased in proportion in DT-treated Trpv1-Dtr mice. A loss of CGRP+ nerves around the airways of DT-treated were also observed compared to PBS-treated Trpv1-Dtr mice (data not shown). Trpv1-Dtr mice showed reduced noxious heat responses in hot plate and tail-flick assays compared to PBS-treated controls (data not shown 3).

Next, whether TRPV1+ neurons impacted pulmonary host defenses was determined. Trpv1-Dtr mice recovered 7 days after DT or PBS treatment, and were subsequently intra-tracheally inoculated with a lethal dose of the MRSA strain USA300 (1.3-1.4×108 colony forming units, CFU) (FIG. 26A). Trpv1-Dtr mice treated with DT showed significantly increased survival and better maintenance of core body temperature following MRSA pneumonia compared to PBS-treated Trpv1-Dtr mice (FIG. 26B). DT-treated Trpv1-Dtr mice also had a 10-fold reduction in bacterial burdens recovered from lungs at 12 h post-infection compared to PBS treated controls (FIG. 26C).

Resiniferatoxin (RTX) was utilized as a second strategy to target TRPV1+ neurons. RTX is a high-affinity TRPV1 ligand that can be used to chemically denervate and ablate nociceptors 15, 18. Mice were subcutaneously treated with RTX at 4 weeks of age for consecutive days with escalating doses (30, 70, 100 µg/kg) according to established protocols 19, 20. RTX-treated mice showed increased latency to noxious heat in hot plate and tail-flick assays, and loss of TRPV1+ and CGRP+ neurons in DRG and VG compared to vehicle-treated mice (data not shown). 4 weeks after RTX injection, mice were intra-tracheally inoculated with MRSA (0.8-1×108 CFU) (FIG. 26D). While most vehicle-treated mice succumbed to pneumonia (80% mortality), the majority of RTX-treated mice survived (FIG. 26E). RTX-treated mice showed improved maintenance of core-body temperature (FIG. 26E), and showed reduced lung bacterial burdens compared to vehicle-treated mice (FIG. 26F). Trpv1-Dtr mediated ablation and RTX-treatment enhanced protection of mice infected with a sub-lethal dose of *S. aureus* (2-4×107 CFU), as measured by bacterial load recovery (FIG. 32A-

32B). As nociceptors may regulate peripheral resistance of the cardiovascular and pulmonary systems to infection, vital signs were measured. Oxygen saturation, heart rate, perfusion and respiratory rates did not differ between RTX-treated and vehicle-treated mice at steady state; respiratory rates also did not differ post-infection (data not shown).

Next, it was determined whether nociceptors modulated host defense against bacterial pathogens other than *S. aureus*. RTX-treated and vehicle-treated mice were infected with lethal doses of *Streptococcus pneumoniae, Klebsiella pneumoniae*, or *Pseudomonas aeruginosa*. RTX-treated mice showed similar drops in core body temperature after infection with all three pathogens as vehicle-treated mice (FIG. 33A-33C). Nociceptor deficiency showed a modest but non-significant protective effect (P=0.13) for survival during *S. pneumoniae* infection (FIG. 33A-33C). Nociceptor deficiency did not impact death caused by *K. pneumoniae* or *P. aeruginosa* pneumonia (FIG. 33A-33C).

Nav1.8 is a voltage-gated sodium channel expressed by a large subset of nociceptors that overlap with but are distinct from TRPV1+ neurons 16, 21. Nav1.8-cre+/− mice were bred with diphtheria toxin A (DTA) reporter mice to generate animals deficient in Nav1.8-lineage neurons (Nav1.8-Cre+/−/Dta) 21. Following MRSA infections, a trend towards increased survival (p=0.09) and decreased bacterial burdens (p=0.07) in Nav1.8-Cre+/−/Dta mice was observed compared to control littermates (data not shown). However, the beneficial effects of Nav1.8 neuron ablation were considerably smaller than those observed for Trpv1 neuron ablation (FIG. 26A-26F).

TRPV1 ion channel does not mediate pulmonary host defense. It was next determined whether the TRPV1 ion channel itself was involved in host defense. Trpv1−/− mice were previously found to have exaggerated physiologic responses in a model of polymicrobial sepsis 22. Following *S. aureus* lung infections, significant differences in survival, core body temperature measurements, or lung bacterial burdens in Trpv1−/− mice compared to Trpv1+/− or Trpv1+/+ control littermates was not observed (data not shown). Post-infection induction of cytokines (IL-17A, IL-6, IL-23) in lung lysates of Trpv1−/− mice was similar compared to control littermates (data not shown). The role of TRPA1 was also examined, which mediates airway inflammation in a mouse model of asthma 11. Trpa1−/− mice did not show differences in bacterial burdens compared to Trpa1+/+ littermates following lethal or sub-lethal *S. aureus* infections (data not shown).

TRPV1 and Nav1.8 neurons regulate bacterial dissemination. It was next determined whether nociceptors mediated the spread of bacterial pathogens from the lung to extra-pulmonary sites. DT-treated Trpv1-Dtr mice showed increased bacterial numbers in the blood (p=0.01) following lethal MRSA infection compared to controls (data not shown). RTX-treated mice also showed increased blood dissemination compared to vehicle-treated controls (data not shown). At a sub-lethal dose of infection, both Trpv1-Dtr ablation and RTX-treatment increased MRSA dissemination to the blood and spleen (data not shown). In Nav1.8-Cre+/−/Dta mice, significant bacterial dissemination to the blood compared to control littermates was observed, accompanied by increased spleen size (data not shown). It was investigated whether nociceptor ablation affected lung barrier permeability. RTX-treated mice showed increased leakage of FITC-dextran to the blood following intra-tracheal inoculation compared to vehicle-treated mice, indicating a role for nociceptors in maintaining barrier integrity (data not shown).

TRPV1 neurons regulate lung inflammation and cytokine induction. Histological analysis of lungs were performed at different time points to analyze pulmonary inflammation following *S. aureus* infection. RTX-treated mice showed an increased cellular immune influx compared to lungs of vehicle-treated mice at 12 h and 24 h post-infection by H&E (FIG. 27A). Without wishing to be bound by a particular theory, it was hypothesized that early increases in immune cells could correlate with improved bacterial clearance in RTX-treated mice. Brown and Brenn staining showed many gram-positive bacterial colonies in vehicle-treated lungs at 12 h and 24 h post-infection (FIG. 27B). By contrast, RTX-treated mice showed few bacterial colonies (FIG. 27B). It was next determined whether nociceptors regulated pro-inflammatory cytokine production. At early time point of infection (6 h), RTX-treated mice showed faster kinetics in the induction of total inflammatory protein levels in the broncho-alveolar lavage fluid (BALF) (FIG. 27C), as well as TNF-α, IL-6 and CXCL-1 levels (FIG. 27D). By 12 h post-infection, TNF-α, IL-6 and CXCL-1 levels were markedly reduced in RTX-treated mice (FIG. 27D), as were levels for IL-1β and MCP-1 (data not shown). These data indicate that TRPV1+ neuron ablation leads to faster induction and resolution of cytokine levels during infection.

TRPV1 neurons suppress recruitment of neutrophils. Kinetics of immune cell influx into inflamed lungs during *S. aureus* infection was next analyzed by FACS analysis. RTX-treated mice displayed a striking increase in CD11b+ Ly6G+ lung neutrophil recruitment compared to vehicle-treated mice at 6 h and 12 h post-infection (FIGS. 28A and 28B). Trpv1-Dtr neuron-ablated mice showed increased neutrophil recruitment compared to PBS-treated controls at 12 h post-infection (FIG. 28C). As neutrophils are critical for bacterial clearance 23, it was hypothesized that neuronal modulation of neutrophil recruitment could play a major role in MRSA pneumonia. Neutrophils in RTX-treated mice were depleted using low-dose GR1 antibody treatment, which eliminated CD11b+Ly6G+ neutrophils in infected lungs compared to mice treated with control IgG (FIG. 28D). GR1 also reduced CD11b+Ly6Chi monocytes, but did not affect CD11b+Ly6Clo monocytes (data not shown). Neutrophil depletion in RTX-treated mice significantly increased their susceptibility to MRSA pneumonia: whereas 100% of GR1 treated RTX mice succumbed to infection, 0% of the control IgG-treated RTX mice died from infection (FIG. 28E). These experimental results were confirmed with an independent cohort of mice (data not shown). Neutrophils were also required for baseline protection against MRSA pneumonia (FIG. 28E). These data indicate that RTX-mediated enhancement of lung immunity requires neutrophils.

TRPV1 neurons regulate pulmonary neutrophil surveillance. Within lungs, neutrophils perform endothelial and parenchymal surveillance for pathogens 24, 25. Using intravital microscopy, the subpleural vascular bed was analyzed to assess whether neutrophil kinetics and patrolling of tissues were regulated by nociceptors. Compared to control mice, RTX-treated animals recruited significantly more neutrophils to pulmonary capillaries during early *S. aureus* pneumonia (FIGS. 29A and 29B and data not shown). In keeping with previous CFU data, less GFP-*S. aureus* in lungs of nociceptor-depleted animals was observed. Dynamic neutrophil behavioral phenotypes were analyzed for tethering, crawling and firm adhesion within the vasculature. Tethering is a rapid, transient neutrophil interaction with the vessel wall, which requires limited cellular activation. Adhesion indicates a more advanced state of activation mediated by integrins prior to tissue emigration. Crawling is a complex intravascular behavior requiring β2-integrin upregulation, occurring rapidly during lung host defense 24, 25. Neutrophils behaved differently during host defense between control and RTX-treated mice. In RTX-treated mice, a significant proportion of neutrophils demonstrated vascular crawling (FIG. 29C). Tracking individual pulmonary vascular neutrophils revealed significantly increased crawling distances (FIGS. 29D and 20E), a phenotype consistent with cellular activation and host defense against bacterial pathogens. Therefore, live imaging supports the contention that enhanced neutrophil function in the absence of nociceptors aids the eradication of bacterial pneumonia.

Nociceptor neurons regulate lung-resident γδ-T cell. It was next asked whether TRPV1+ neurons altered lung-resident immune cell populations in naïve mice, thus setting the stage for subsequent inflammatory responses. immune transcriptome datasets were first examined at the Immunological Genome Project (found on the world wide web at http://Immgen.org), finding that Trpv1 expression is absent across immune cell-types (data not shown). Analysis of a second transcriptional dataset 26 showed that Trpv1 was absent in immune cells, but highly expressed in DRG (data not shown). CD4+ T cells, B cells, neutrophils, and γδ T cells were purified from mouse lungs, and performed quantitative PCR analysis for Trpv1 compared to sensory ganglia. While Trpv1 was highly expressed in VG and DRG, it was undetectable in all lung immune cells analyzed (data not shown). These data indicate that Trpv1-Dtr or RTX-mediated ablation should specifically target nociceptors, but not have direct effects on immune cells. Spleens of RTX-treated and vehicle-treated mice were examined, and did not observe differences in populations of B220+ B cells, NK1.1+ cells, CD4+ T cells, CD8+ T cells, or γδ T cells; Trpv1-Dtr neuron-ablated mice showed similar results (data not shown).

It was next determined whether lung-resident immune cell-types differed in nociceptor-ablated mice at steady state. CD11b+ dendritic cells (CD11b+SiglecF-CD24+CD103-F4/80-MHCII+), CD103+ dendritic cells (CD11b-SiglecF-CD103+MHCII+), alveolar macrophages (SiglecF+CD11c+CD64+F4/80+), and interstitial macrophages (CD11b+CD24-CD64+F4/80+) did not differ between RTX-treated and vehicle-treated mice (data not shown and FIG. 30A). B cells, NK cells, and CD8+ T cells also did not differ; CD4+ T cells showed a minor increase in RTX-treated mice compared to controls (data not shown and FIG. 30B).

By contrast with most other immune cell-types, an increase in absolute numbers of lung-resident γδ T cells was observed in RTX-treated mice compared to vehicle-treated mice (FIG. 30C). Further subset analysis found that this increase was specific to Vγ1+ cells and Vγ1-Vγ2- cells, but not Vγ2+ cells (FIG. 30C and data not shown). A similar increase in γδ T cells in Nav1.8-Cre+/-/Dta mice was observed compared to control littermates (data not shown). γδ T cells reside within epithelial layers of lungs, skin, and gut, acting as first responders to infection 27. γδ T cell-deficient Tcrd-/- mice were next utilized to investigate their role in neuro-immune suppression. Wild-type (WT) or Tcrd-/- mice were treated with RTX to ablate TRPV1+ neurons, followed by S. aureus pneumonia (FIGS. 30D and 30E). Absence of γδ T cells was confirmed in Tcrd-/- mice using flow cytometry (FIG. 30D). Tcrd deficiency led to a loss of protection against MRSA infection and abrogated the survival enhancement due to RTX-treatment (FIG. 30E). This reversal of protective immunity correlated with an imbalance in core body temperature (FIG. 30E), and increased bacterial burdens in BALF isolated from RTX-treated Tcrd-/- mice compared to RTX-treated WT mice (data not shown). Tcrd-/- also show defective baseline immunity against MRSA pneumonia (FIG. 30E). While IL-6 levels were unaffected by Tcrd☐deficiency, levels of IL17A, a cytokine mediating protection against MRSA 28, was significantly decreased in Tcrd-/- mice (data not shown). Neutrophil recruitment did not differ in lungs of RTX-treated Tcrd-/- mice compared to RTX-treated WT mice (data not shown), indicating that γδ T cells and neutrophils are separately regulated.

Figure 30G:
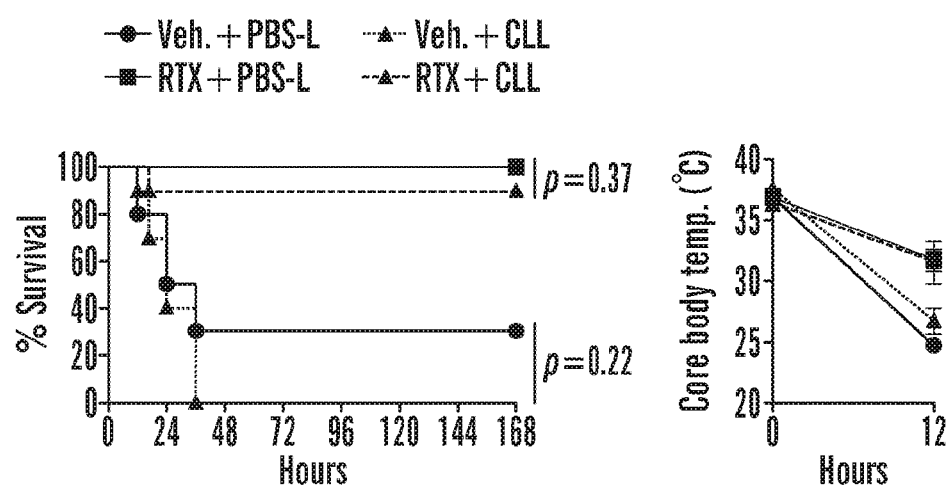

It was next determined whether alveolar macrophages mediated neuronal regulation of host defense (FIG. 30G). Mice were intra-tracheally instilled with clodronate-laden liposomes (CLL) to kill alveolar macrophages through phagocytosis-dependent apoptosis. PBS encapsulated liposomes (PBS-L) were used as control treatments. CLL treatment specifically eliminated alveolar macrophages (SiglecF+CD11c+CD64+F4/80+), but not interstitial macrophages or dendritic cells (FIG. 30F and data not shown). Alveolar macrophage depletion did not alter increased survival or core-body temperature maintenance of RTX-treated compared to vehicle-treated mice (FIG. 30G). Taken together, these results indicate that RTX-treatment mediated enhancement of MRSA immunity requires both γδ T cells and neutrophils but not alveolar macrophages.

Figure 31A:
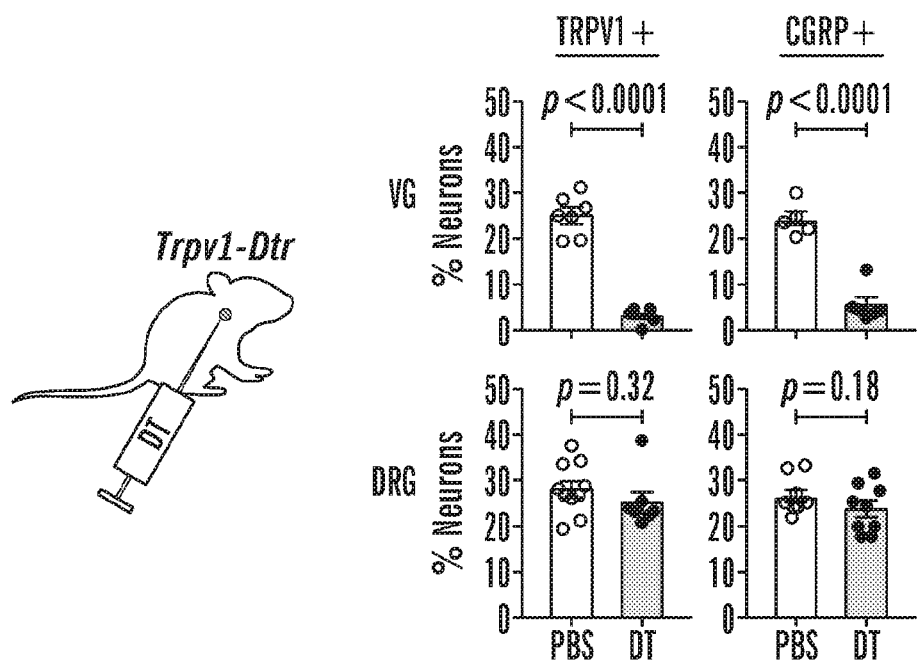
Figure 31B:
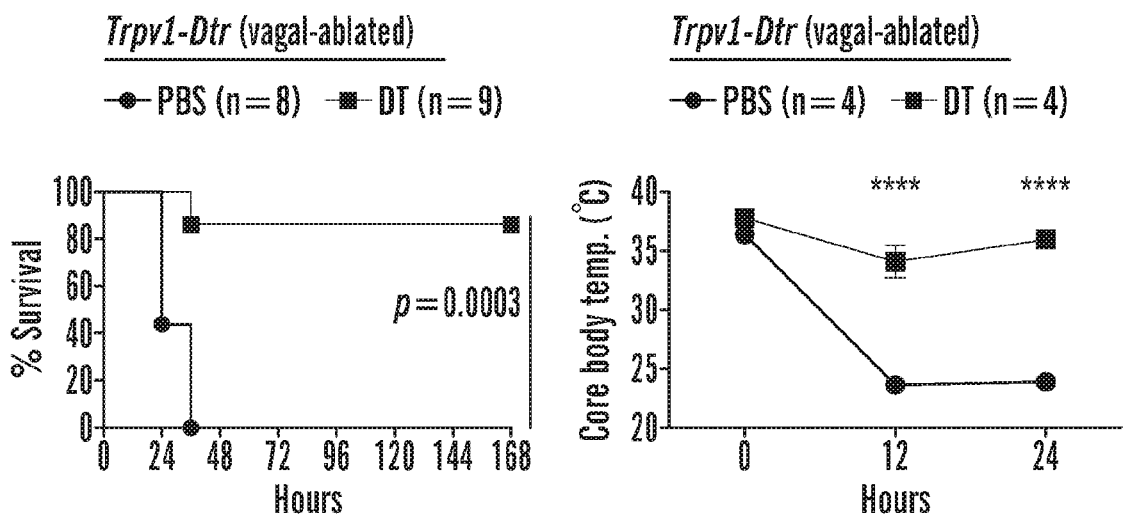
Figure 31C:
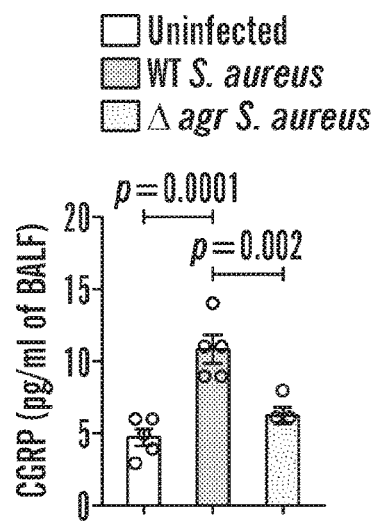
Figure 31D:
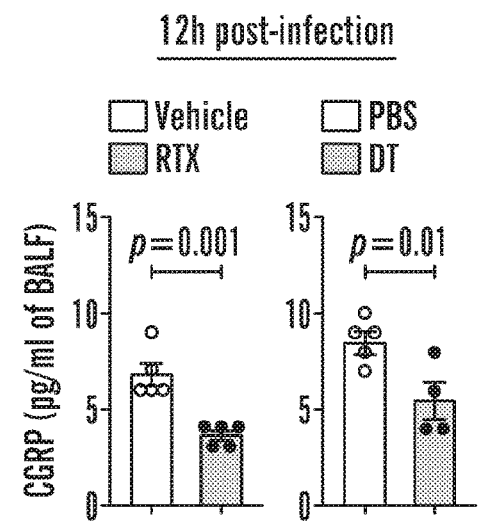
Figure 31E:
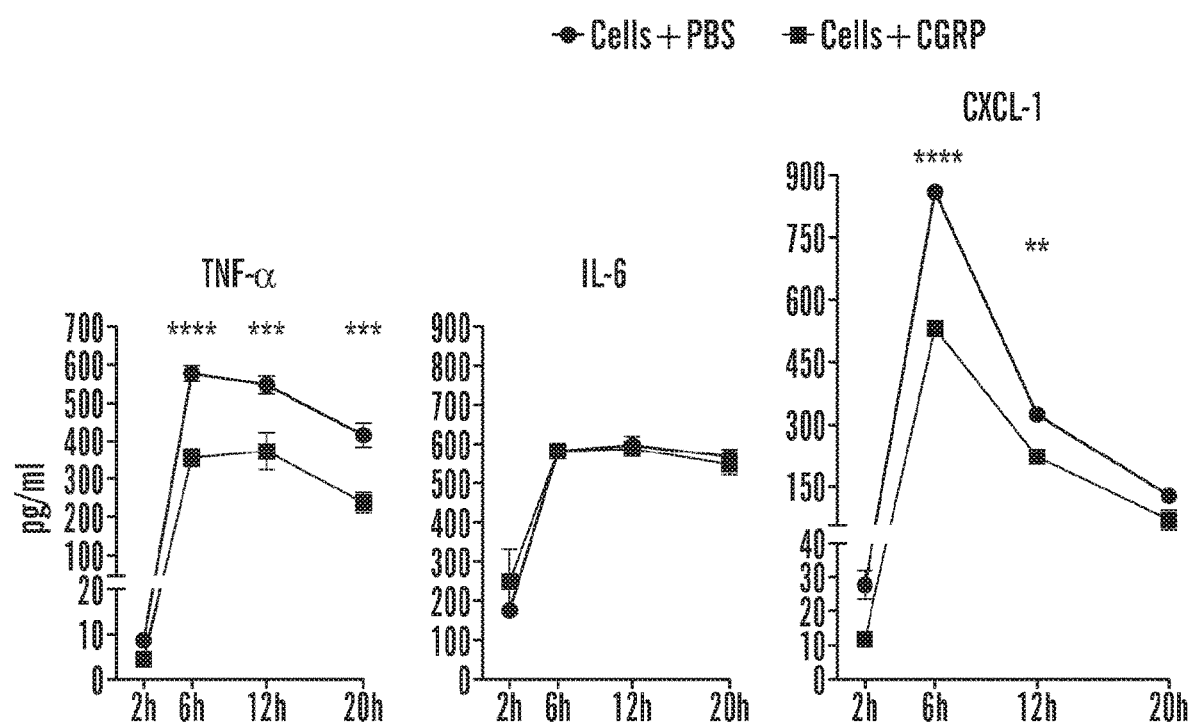
Figure 31F:
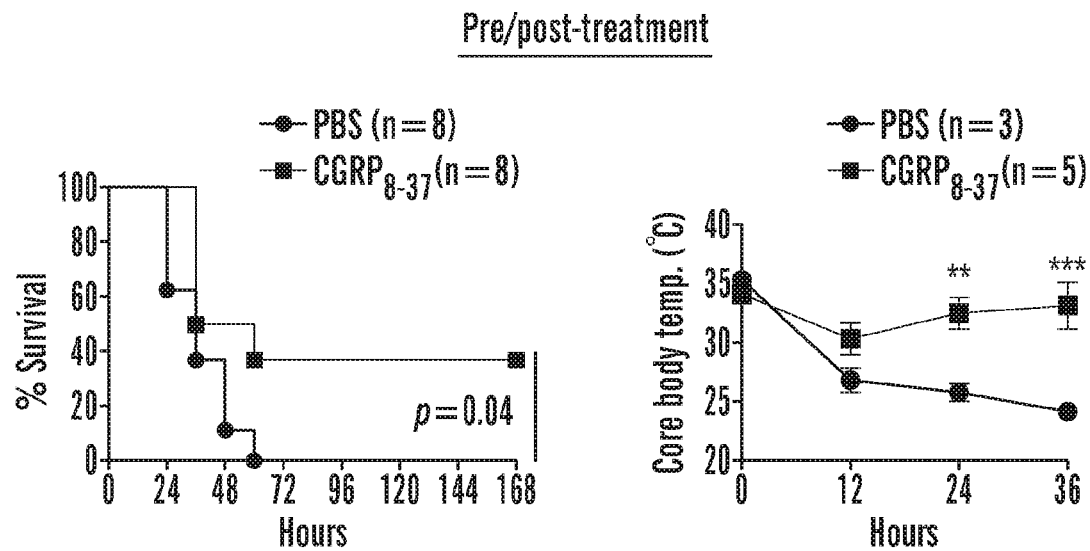
Figure 31G:
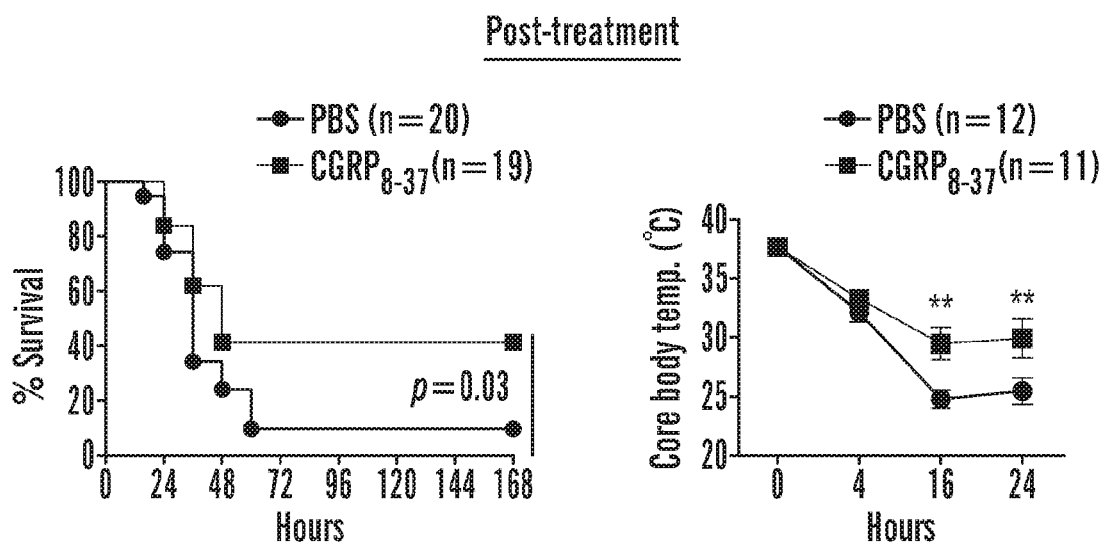

Ablation of vagal TRPV1 neurons improves host defense. The vagus nerve provides the major source of sensory innervation of the lung. The cell bodies of vagal afferents reside in fused ganglia at the base of the skull, controlling cough, breathing, and bronchoconstriction 5, 29. The experimental approaches thus far targeted all TRPV1+ cells, including both DRG and VG neurons. It was hypothesized that vagal TRPV1+ neurons may include the subset regulating neuro-immune suppression. To specifically target these neurons, bilateral intraganglionic DT injections were performed into vagal ganglia of 5-9 week old Trpv1-Dtr mice. Immunostaining showed that vagal but not DRG TRPV1+ neurons were specifically ablated (FIG. 31A and data not shown). Vagal TRPV1+ neuron ablation did not alter heart rate, oxygen saturation, perfusion, or respiratory rate (data not shown). Mice were rested two weeks following intraganglionic injections, and infected with a lethal dose of MRSA. A striking survival benefit was observed in vagal DT-injected Trpv1-Dtr mice compared to vagal PBS-injected mice, and better maintenance of core body temperature (FIG. 31B). All mice from the PBS-injected group died within 72 h after infection, whereas a 90% survival rate was observed among mice lacking vagal TRPV1 neurons (FIG. 31B). The increased survival in vagal DT-treated mice correlated with increased neutrophil recruitment and decreased lung bacterial burdens (data not shown).

Nociceptive neuropeptide CGRP modulates lung antimicrobial defenses. Nociceptor neurons actively communicate with the immune system through their release of neuropeptides stored within peripheral nerve terminals 30. The nociceptive neuropeptide CGRP inhibits TNF-α production in macrophages and suppresses lymph node hypertrophy in skin bacterial infection 30, 31. It was hypothesized that CGRP could mediate neuro-immune signaling during lethal bacterial pneumonia. It was found that CGRP levels were significantly increased in the BALF following S. aureus infection (FIG. 30C). Infection with a S. aureus strain mutant for agr, a key bicomponent quorum-sensing regulator of virulence factor expression 32, did not induce CGRP release into the BALF (FIG. 30C). S. aureus also directly induced cultured neuronal release of CGRP in vitro in a manner that was dependent on agr (data not shown).

TRPV1+ cells mediated CGRP release in the lungs, as CGRP levels were significantly reduced in the BALF of RTX-treated and vagal DT-treated TRPV1-Dtr mice compared to control infected mice at 12 h post-infection (FIG. 30D). CGRP levels were also significantly reduced in the BALF at steady state in nociceptor-depleted mice (data not shown).

It was next asked whether CGRP played a role in MRSA pneumonia. Quantitative PCR analysis showed that lung γδ T cells and neutrophils expressed Ramp1 and Calcrl, which encode the cognate CGRP receptor (FIGS. 34A and 34B). It was found that CGRP treatment inhibited lung cell production of TNF-α and CXCL1, but not IL-6 in response to MRSA infection (FIG. 30E). Increasing concentrations of CGRP also inhibited intracellular killing of S. aureus by mouse neutrophils (FIG. 35). To explore the involvement of CGRP in host defense, mice were treated with the competitive CGRP peptide antagonist, CGRP8-37 at time points before and after S. aureus lung infection (FIG. 30F). This treatment improved survival and core body temperature maintenance compared to vehicle treatment (FIG. 30F). It was next found that CGRP8-37 administered at time points after S. aureus infection also significantly improved survival and core body temperature (FIG. 30G). These data show that nociceptors mediate CGRP release during lung infections, and that post-infection blockade of CGRP signaling could benefit bacterial pneumonia.

Discussion

Nociceptor neurons and immune cells play key roles in protecting organisms from environmental dangers. It is potentially advantageous that interactions between these cell-types coordinate host responses to pathogen invasion. It was found that TRPV1+ afferents in the vagal ganglia played a critical role in modulating innate immune responses against MRSA lethal pneumonia. Targeting these neurons using Trpv1-Dtr mediated ablation (or RTX-treatment) improved survival, neutrophil and γδ T cell responses, and bacterial clearance. Nav1.8-cre/Dta mice, which target an overlapping though distinct nociceptor subset, showed a milder protective phenotype. Both strategies paradoxically resulted in increased bacterial dissemination. These data indicate that differences in phenotypes (lung clearance vs. barrier function) are mediated by distinct neuronal subsets. A recent study showed that Trpv1 expression in the adult DRG is mainly restricted to CGRP+ and substance P (SP)+ c-fibers 14. By contrast, Nav1.8 has been found to be expressed in myelinated A-fibers as well as C-fibers 33. Another study showed that Nav1.8-Cre/Dta mice still possessed CGRP+ neurons expressing TRPV121. Therefore, future experiments using more refined genetic tools will help distinguish the functional contributions of individual TRPV1+ and/or Nav1.8+ neuronal subsets in pulmonary immunity and barrier function.

Our work adds to recent studies showing major physiological roles for neuro-immune interactions at peripheral barrier tissues 34. In the respiratory tract, nociceptors actively crosstalk with immune cells to mediate allergic airway inflammation 5, 11, 12. Skin-innervating nociceptors drive inflammation and immune activation in mouse models of psoriasis 20, and contact dermatitis 35. In the gut, sympathetic neurons regulate macrophage tissue programming at homeostasis and during *Salmonella* infection 36.

It was found that nociceptors suppressed pulmonary γδ T cell and neutrophil mediated host defense during MRSA lung infections. A recent study found that nociceptors drive dendritic cell IL-23 production and γδ T cell activation during skin invasion by the fungal pathogen *C. albicans* 19. The observed phenotypic difference with this study herein is interesting, as differential interactions of vagal vs. somatosensory sensory neurons may occur with immune cell-types at different barrier sites. Diverse γδ-T cell populations seed mucosal and epithelial sites 27. In the skin, epidermal γδ T cells are mostly Vγ5+ that mediate barrier integrity, whereas dermal γδ T cells do not express Vγ5, but ~40% of them are Vγ4+ and are involved primarily in IL-17A production 37. IL-17 production by γδ-T cells has also been found to mediate host defense against *S. aureus* skin infections 28, 38. Heterogeneous subsets of γδ T cells are found in the respiratory tract, including Vγ1+, Vγ2+, and Vγ6+ populations 39.

It is striking that vagal sensory afferents, which comprise less than 5000 neurons, are able to potently regulate antimicrobial immunity. Distinct vagal afferents control physiological functions including breathing and nutrient sensation 29, 40. It would be interesting to ascertain how neuronal subsets differentially crosstalk with immune cells. Immune cells may utilize nerves as tracts for migration, as observed for dendritic cell interactions with Nav1.8+ nociceptors in skin 20. Lung-resident immune cells may be in proximity with vagal nerve afferents to set up local neuro-immune responses. Recently, the neuropeptide NMU was found to drive ILC2-mediated inflammation in the gut and lungs 41-43. It was found that nociceptors released the neuropeptide CGRP into the airways during infection and down-regulated immunity. CGRP has been previously linked to vasodilation and vascular permeability 44. CGRP suppressed CXCL1, an important chemokine for lung neutrophil chemoattraction 45. Furthermore, CGRP antagonism improved survival outcomes in MRSA infected mice, and is therefore a potential target for clinical application in pneumonia.

It is important to note that other mechanisms besides CGRP signaling could mediate nociceptor-immune signaling Nociceptors release glutamate, ATP, and other neuropeptides including SP, neurokinin A, VIP. They also up-regulate cytokines including CCL246 and CSF-1 following nerve injury 47. Vagal afferents may also induce sensori-autonomic neuro-immune reflexes including a "cholinergic anti-inflammatory reflex", which acts through vagal autonomic efferents to down-regulate peripheral macrophage TNF-α production 48.

The role of nociceptors in host defense could vary depending on the type of pathogenic invasion. While increased neutrophil influx benefits host protection against MRSA pneumonia, the same responses could lead to immunopathology in other infections. For example, influenza virus and severe acute respiratory syndrome (SARS) coronavirus cause pathology by over-activation of lung inflammation 49, 50. In pneumonia caused by *K. pneumoniae*, *E. coli*, and *S. pneumoniae*, bacterial dissemination is a primary cause of sepsis and mortality 51, 52. For MRSA-induced pneumonia, lethality is mainly mediated by damage to the lungs by secreted exotoxins (Hla, PVL) rather than bacterial dissemination 3, 53. These differences in bacterial pathogenesis may explain the observed differences in responses to distinct pathogens in nociceptor-ablated mice.

Our study demonstrates that nociceptors play a critical role in regulating pulmonary immunity and the outcome of bacterial lung infections. Targeting neuro-immune communication through CGRP or other molecular mechanisms could be an effective approach to enhance host protection against pneumonia.

Material and Methods

Mice. All animal experiments were approved by the Harvard Medical School Institutional Animal Care and Use Committee (IACUC) or by the University of Calgary Animal Care Committee. Mice were housed in a specific pathogen free animal facility at Harvard Medical School or University of Calgary. C57BL/6J, B6.Trpv1−/−, B6.Tcrd−/−, B6.Dta+/+, and B6129.Trpa1−/− mice were purchased from Jackson Laboratories. Trpv1-Dtr mice16 was provided by Mark Hoon (NIH). Nav1.8-cre mice21 were originally from John Wood (University College London). Nav1.8-cre+/− mice were bred with B6.Dta+/+ mice to generate Nav1.8-cre+/−/Dta mice and control littermates (Nav1.8-cre−/−/Dta). For Trpv1 and Trpa1 experiments, heterozygous mice were bred to produce WT, heterozygous, and knockout littermates. Age-matched 8-14 week old male and female mice were used for experiments.

Bacterial strains and cultures. The MRSA strain USA300/LAC54 was provided by Dr. Michael Otto (NIH). For infection, USA300/LAC was grown overnight (O/N) at 37° C. in Tryptic Soy Broth (TSB, Sigma) at 250 RPM, and sub-cultured at a 1:100 dilution for 3.5 h in TSB to mid-log phase. *Klebsiella pneumoniae* strain 43816 serotype 2 was purchased from American Type Culture Collection and was grown O/N at 37° C. in TSB at 250 RPM for infection. *Streptococcus pneumoniae* WU-2 strain from Richard Malley (Boston Children's Hospital) was grown at 37° C. with 5% $CO_2$ without shaking for 18 h in Todd's Hewitt broth (THB, Sigma) with 0.5% yeast extract, and sub-cultured at 1:10 dilution for 8 h in fresh THB/0.5% yeast extract to reach mid-log phase for infection. *Pseudomonas aeruginosa* strain PA01V from Gerald Pier (Brigham and Women's Hospital) was grown O/N at 37° C. in TSB at 250 RPM, and sub-cultured at 1:100 dilution for 4 h in TSB for infection. For all strains, cultures were centrifuged at 5000 rpm for 5 minutes, bacterial pellets washed and resuspended in phosphate-buffered saline (PBS). OD600 was measured to estimate bacterial density, followed by serial plating on Tryptic Soy Agar (TSA) plates to quantify colony forming units (CFU). For intravital imaging, a GFP-MRSA *S. aureus* transgenic bacteria was utilized and its construction previously reported 25.

Bacterial lung infections. For all bacterial infections, age-matched 8- to-14-week old male and female mice, weighing between 19-30 grams, were studied. For lethal infections, 50 µl containing 0.8-1.6×108 CFU *S. aureus* in PBS was intra-tracheally inoculated per mouse. Control animals were intra-tracheally infused with 50 µl PBS only. For sub-lethal infections, 2-4×107 CFU of *S. aureus* was used per mouse. For *S. pneumoniae* infections, 106 CFU in 50 µl PBS was intra-tracheally inoculated. For *K. pneumoniae* infections, 104 CFU in 50 µl PBS was intra-tracheally inoculated. For *P. aeruginosa* infections, 7×106 CFU in 50 µl PBS was intra-tracheally inoculated. Mice were monitored twice daily for morbidity and mortality. In some experiments, CGRP8-37 (Genscript) was administered intraperitoneally (i.p.) at 800 ng (256 pmoles) or 7.5 µg (2.4 nmoles) per dose in 200 µL PBS, at different time points relative to infection (0 h). Control mice received 200 µL PBS only.

Vital sign measurements. Heart rate, oxygen saturation and perfusion were measured under isoflurane anesthesia by Pulse Oximetry using the Kent Scientific PhysioSuite (Kent Scientific Corporation). For accuracy, measurements were performed three independent times on different days for the same mice, and values represent the average of three measurements. Pulse Oximetry could not be used on MRSA infected mice because they could not survive isoflurane anesthesia, and thus the measurements were only performed at steady state. Respiratory rates were determined by manually recording number of breaths per minute and averaged over three measurements. Core body temperature was measured using a rectal thermal probe (Bioseb).

Genetic and chemical ablation of TRPV1+ nociceptors. Trpv1-Dtr mice were treated with diphtheria toxin (DT) as previously described 5. Mice were injected i.p. with 200 ng of DT (Sigma Aldrich) dissolved in 100 µl PBS or with 100 µl PBS (vehicle) daily for a 21 day period. 5-7 week old male and female mice were used for these experiments. To chemically ablate TRPV1+ neurons, C57BL/6 mice 4 weeks of age were treated with RTX (Sigma) as described 19, 20. Mice were injected subcutaneously in the flank on consecutive days with three increasing doses of RTX (30, 70, 100 µg/kg) dissolved in 2% DMSO/0.15% Tween 80 in PBS. Control mice were treated with vehicle alone. For intravital imaging experiments, the same dosage for RTX treatment was used in 4-week old mice, except the vehicle for dissolution was DMSO (without Tween 80). RTX was diluted into DMSO (1 µg/up, and subsequently into saline prior to injections.

For vagal ganglia-targeted ablation, bilateral intraganglionic injections were performed of DT or PBS into Trpv1-Dtr mice as described 5. 20 ng DT in 120 nl PBS containing 1× fast green was injected into nodose/jugular/petrosal vagal ganglia using a nano-injector (Drummond scientific company). Mice were anesthetized using 1-3% isofluorane with oxygen. The vagal ganglion was exposed after a midline incision in the neck (~1.5 cm in length). DT was gently injected; this process was repeated for the vagal ganglion on the other side of the body.

Broncho-alveolar lavage fluid (BALF) analysis. Mice were euthanized by CO2 inhalation, the trachea exposed and cannulated with a 20-gauge catheter (BD insyte autoguard). BALF was collected 2 times by instilling 0.8 mL of cold PBS containing heparin and dextrose, centrifuged at 4000 rpm for 7 min at 4° C., and cell pellet separated from supernatant. Total BALF leukocytes were counted after red blood cell lysis (RBC lysis buffer, eBioscience) and subjected to flow cytometry. Cell-free BALF supernatant was filtered through a 0.22 µm filter and mixed with protease/phosphatase inhibitor cocktail, and kept at −80° C. for protein and cytokine analysis.

Bacterial load and cytokine measurements. Lungs and spleen tissues were homogenized in 1 ml sterile water using BB beads (Daisy Outdoor Products) in a Tissue Lyzer II (Qiagen). Lung, spleen homogenates, blood, or BALF was serially diluted in PBS and plated on TSA plates. Bacterial CFU were enumerated after overnight incubation of TSA plates at 37° C. Cytokine levels in lung homogenates and BALF were measured using enzyme-linked immunosorbent assay (ELISA) kits according to manufacturer's instructions (Biolegend).

Behavior tests. For behavioral assays, observers were blinded to treatment group and genotype. To measure heat sensitivity, mice were placed on a hot plate set at 52° C. (IITC Life Science). Latency to hindpaw lifting/licking/flinching was recorded, and stopped at a maximum of 60 seconds. For tail-flick assay, mice were kept vertically in a relaxed fashion with their tail immersed in a temperature-controlled water bath maintained at 52° C. The latency to a tail flick was recorded, with maximum of 60 seconds.

Immune cell depletion. For neutrophil depletion, an established protocol was followed 55. Mice were injected i.p. with 125 µg of GR1 (clone RB6-8C5, BioXCell, NH) (in 200 μl) per mouse 24 h before lung infection. Control mice received 125 μg of rat IgG (Jackson Immunoresearch). For depletion of alveolar macrophages, 100 μl Clodronate-laden liposomes (purchased from http://clodronateliposomes.org) were delivered intra-tracheally into mice 2 days before infection. Control mice received an equal volume of PBS-laden liposomes.

Lung barrier permeability assay. FITC-dextran (Mol Wt 4,000, Sigma) was intra-tracheally inoculated in 50 μl/mouse at 20 mg/kg of body weight. Control mice were inoculated with PBS. Four hours later, mice were euthanized, and blood collected by cardiac puncture. Blood was allowed to coagulate for 30 min at room temperature in the dark and centrifuged at 2500 g for 15 min. Fluorescence in serum was recorded using a plate reader (BioTek Synergy), and normalized to FITC-dextran standards (1.56-100 μg/ml).

Flow cytometry. Lung tissues were mechanically separated and minced, digested in DMEM (Life Technologies) containing 2% FBS and 1.5 mg/ml collagenase D (Roche) at 37° C. for 1 h at 250 rpm. The cell mixture was passed through a 18 gauge needle 3 times, filtered through a 70 μm cell strainer (BD), red blood cells lysed with RBC lysis buffer (eBioscience), treated with Fc Block (Biolegend), and resuspended in FACS buffer (PBS/2% FBS/1 mM EDTA). For splenocytes, spleens were mashed, filtered through a 70 μm strainer (BD), red blood cells lysed with RBC lysis buffer (eBioscience), treated with Fc Block, and resuspended in FACS buffer. Incubations with antibody cocktails were conducted on ice for 30 minutes, followed by two washes and resuspension in PBS/2% PFA with 1 mM EDTA prior to flow cytometry. Antibodies used for staining include: anti-CD11b-Brilliant Violet 605 (clone: M1/17, BioLegend), anti-CD45-APC/Cy7 (30-F11, BioLegend), anti-Ly-6G-alexa Fluor 488 (1A8, BioLegend), anti-Ly-6C-PerCP/Cy5.5 (HK1.4, BioLegend), anti-Gr1-FITC (RB6-8C5, BioLegend), anti-CD4 Pac Blue (GK1.5, BioLegend), anti-CD8α-PE/Cy7 (53-6.7, BioLegend), anti-CD11c-APC (N418, BioLegend), anti-CD64-Brilliant Violet 421 (X54-5/7.1, BioLegend), anti-SiglecF-Alexa Fluor 488 (E50-2440, BD Bioscience), anti-CD103 PE (2E7, BioLegend), anti-TCR γδ-PE (GL3, BioLegend), anti-F4/80-FITC (BM8, BioLegend), anti-NK1.1-PerCP/Cy5.5 (NK-1.1, BioLegend), anti-B220-APC (RA3-6B2, BioLegend), anti-CD3α-PE/Cy7 (17A2, BioLegend), anti-CD24 Brilliant Violet 510 (M1/69, BioLegend), anti-TCR-β Brilliant Violet 421 (H57-597, BioLegend), anti-TCR Vγ1.1-APC (2.11, BioLegend) and anti-TCR Vγ2-PE-Cy7 (UC3-10A6, eBioscience). Flow cytometry was conducted on a LSRII flow cytometer (BD). Data were collected with BD DIVA software, and files analyzed using FlowJo (Treestar, version 10.0.8r1). A live cell stain (eFluor 450, ebioscience) used to exclude dead cells. Positive staining and gates for each fluorescent marker was defined by comparing full stainsets with fluorescence minus one (FMO) control stainsets.

Fluorescence-activated cell sorting of lung immune cells. For FACS purification of lung-resident populations, antibodies against CD3ε (clone: 145-2C11), CD4 (clone: RM4-5), CD11b (clone: M1/70), Ly6G (clone: 1A8), CD19 (clone: 6D5), CD45 (clone: 30-F11), TCRβ (clone: H57-597) and TCRγ/δ (clone: GL3) from BioLegend. 7AAD from BD Pharmingen. Single cell suspensions were generated from lungs of 2-3 C57Bl/6J mice using lung dissociation kit (Miltenyi Biotec). Single-cell suspensions were incubated with CD90.2 MicroBeads (Miltenyi Biotec) and separated into CD90.2 positive and negative fractions. Both fractions were stained on ice with surface antibodies, live/dead marker 7AAD and sorted on a BD FACSAria (BD Biosciences). Different cell types were identified by the following gating strategies: B cells (7AAD−CD45+CD19+) and neutrophils (7AAD−CD45+CD11b+Ly6G+) were sorted from the pre-enriched CD90.2-cell fraction, while CD4+ T cells (7AAD−CD45+CD3+ TCRβ+CD4+) and TCRγδ T cells (7AAD−CD45+CD3+ TCRβ−TCRγδ+) were sorted from the pre-enriched CD90.2+ cell fraction.

Quantitative real-time PCR. The RNeasy Plus Mini Kit (Qiagen) was used to isolate RNA, which was reverse transcribed to cDNA using iScript cDNA Synthesis Kit (Bio-Rad). Relative gene expression was determined by quantitative real-time PCR on a ViiA7 System (Thermo Fisher Scientific) using TaqMan Fast Advanced Master Mix (Thermo Fisher Scientific) with the following primer/probe sets: Trpv1 (Mm01246300_m1), Ramp1 (Mm00489796_m1), Calcrl (Mm00516986_m1), and Actb (Applied Biosystems). Expression values relative to Actb (detected in the same sample by duplex qPCR) were calculated.

Neuronal cultures and CGRP analysis. DRG neuron cultures were grown as described 31. In brief, total DRGs were dissected from 8-12 week old mice, and digested in HEPES buffered saline (Sigma) containing 1 mg/mL Collagenase A and 3 mg/ml dispase II (Roche Applied Sciences) for 60 minutes at 37° C. The cell suspension was triturated with fire-polished Pasteur pipettes, followed by centrifugation over a 12% BSA (Sigma) gradient. The top layer of debris was discarded, and cell pellet resuspended in neurobasal (NB) media containing B27 (Life technologies). Neurons were plated on laminin-coated 96-well culture dishes in NB media containing B27, 50 ng/mL Nerve Growth Factor (Life Technologies) and penicillin/streptomycin (Life Technologies). Media was changed every other day. At day 7, DRG neurons were stimulated with S. aureus or 500 nM capsaicin (Sigma) for 30 min, and supernatant collected. CGRP levels in culture supernatant, BALF, or lung homogenates was determined using a CGRP EIA kit according to manufacturer's instructions (Cayman Chemical).

Gene Expression Analysis. Transcript levels were analyzed in mouse transcriptome datasets deposited at the Immunological Genome Project 56 (GEO Accession GSE15907). Datasets for CD4+, CD8+ T cells, B cells, γδ T cells, NK cells, macrophages, dendritic cells, neutrophils were analyzed. Trpv1 expression was also analyzed in the Mouse Gene Atlas MOE430 transcriptome dataset 26 (GEO Accession GSE1133). Microarray data was background corrected and normalized using Robust Multi-array Average (RMA) algorithm in GenePattern (Broad Institute). A heatmap for average transcript values was plotted using Morpheus (Broad Institute), Trpv1 levels were also plotted using Prism (Graphpad).

Lung histology. Whole lungs were dissected from mice following euthanasia, fixed and stored in 10% formalin (Sigma Aldrich). Samples were embedded, sectioned, and stained for haematoxylin and eosin (H&E) or for gram-positive bacteria using a Brown and Brenn stain by the Harvard Rodent Histopathology Core. Light microscopy of histological sections was conducted on a microscope (Nikon Ti-E Microscope).

Immunofluorescence and microscopy. For immunostaining, mice were perfused with PBS followed by 4% paraformaldehyde (PFA) in PBS. Vagal ganglia and thoracic DRG (T1-T13) were dissected and post-fixed for 2 h in 4% PFA/PBS at 4° C., incubated O/N at 4° C. with 30% sucrose/PBS, embedded in optimal cutting temperature (OCT, Tissue-tek, PA) and stored at −80° C. 12 μm cryosections were cut and immunostained with the following antibodies: Guinea pig anti-TRPV1 (Millipore, AB5566, dilution 1:1000), rabbit anti-CGRP (Sigma, C8198, dilution 1:5000), mouse anti-NF-200 (Millipore, MAB5266, dilution 1:1000), rabbit anti-βIII-tubulin (Tuj 1) (Abeam, ab18207, dilution 1:1000), mouse anti-βIII-tubulin (Abeam, ab7751, dilution 1:500). Secondary antibodies include DyLight-488 Donkey anti-rabbit IgG (Abeam, 1:500), CF-488A Goat anti-guinea pig IgG (Sigma, 1:500), Alexa 488 Donkey anti-mouse IgG (Abeam, 1:500), Alexa 594 Donkey anti-mouse IgG (Abeam, 1:500) and Alexa 594 Donkey anti-rabbit IgG (Abeam, 1:500). Sections were mounted in Vectashield, and imaged using a Nikon Ti-E Microscope with 10× magnification using NIS Elements software (Nikon, version AR3.22.08). For quantification of VG and DRG neuronal populations, images were analyzed by observers blinded to genotypes and treatment groups. β-tubulin-III was used as a general neuronal marker. Multiple fields were captured from 3 mice per group.

For immunostaining of lung sections, lungs were perfused with cold PBS and gravity inflated with 4% PFA/PBS. Following overnight fixation at 4° C., lungs were incubated 2 days in 30% sucrose/PBS, cryo-embedded in OCT, and stored at –80° C. until sectioned. 40 µm cryosections were blocked for 4 hours in PBS/10% donkey serum/2% bovine serum albumin (BSA)/0.8% Triton-X-100. Sections were incubated with rabbit anti-CGRP (C8198, Sigma) in a 1:5000 dilution in blocking solution (PBS/2% donkey serum/2% BSA/0.3% Triton-X-100) for 16-18 h at 4° C., followed by secondary antibody (Alexa 594 donkey anti-rabbit IgG H&L, Abeam, ab150076) in a 1:500 dilution in blocking solution at 4° C. Stained specimens were imaged on an inverted laser scanning confocal microscope (Olympus Fluoview FV1000).

Adobe Photoshop (Adobe) was used to quantify CGRP+ airway innervation in lung sections. The "Lasso Tool" was used to trace the circumference of each inner lung airway based on DAPI staining; Area enclosed (in pixels) was derived from the "Histogram Tool". The traced circumference was expanded by 162 pixels (100 µm) for each airway. The "Magic Wand Tool" was used to select the CGRP+ pixels within the circumscribed area and quantified out of the entire airway border, which is the percent area covered by CGRP+ nerve fibers.

Neutrophil isolation and bacterial killing. Mouse bone-marrow neutrophils were isolated using the EasySep™ Mouse Neutrophil Enrichment Kit following manufacturer's instructions (StemCell Technologies). Diff-Quick Stain kit (Thermo scientific) was used to confirm purity, with >95% found to be neutrophils. To perform bacterial killing assays, 2.5×10$^5$ neutrophils were co-cultured with 5×10$^5$ CFU of $S.$ $aureus$ (2 multiplicity of infection (MOI)) in DMEM (Gibco) containing 5% fetal bovine serum. CGRP (Genescript) was added at different concentrations, and cells incubated at 37° C. for indicated time points. Neutrophils were then centrifuged at 600 rpm for 2 min, the pellet washed twice with PBS, and incubated for 30 min with 200 µg/ml gentamicin. Neutrophils were lysed with 0.1% Triton X-100, and dilutions plated onto TSA plates to measure intracellular, viable bacteria. Lung cells were also isolated from C57BL/6J mice as described above in flow cytometry section and co-cultured with $S.$ $aureus$ (MOI 2) with or without CGRP (100 nM) at the indicated time points for measurement of IL-6, TNF-α and CXCL-1 levels in culture supernatant by specific ELISA kits (BioLegend).

Pulmonary intravital microscopy. After mice were anesthetized (100 mg/kg ketamine/10 mg/kg xylazine), they received a jugular vein catheter for administration of fluorescent antibodies or additional anesthetics. To visualize neutrophils and endothelium, 3.5 µg Alexa Fluor 594 conjugated anti-Ly6G antibody (clone 1A8, BioLegend) and 5 µg Alexa Fluor 647 conjugated anti-CD31 antibody (clone MEC13.3, BioLegend) were injected intravenously. Mice were placed on a heating pad maintained at 37° C. and connected to mechanical ventilation (Harvard Apparatus) after a tracheostomy is performed. Mice were kept in a right lateral decubitus position and their left lung was exposed after a thoracotomy and rib resection. A portion of the lung was immobilized via a gentle vacuum chamber with a glass slide fitted on top. A resonant-scanner confocal microscope (Leica SP8) equipped with a white light laser and three HyD spectral detectors and a 25×/0.9 water objective lens were used for intravital microscopy. Images were acquired every 10 s for a total of 10 min, three to five fields of view were observed. All videos and images were processed and analyzed using Leica software and Volocity software. For neutrophil behavior analysis, tethering was defined as rapid movement with blood flow and stop for less than 30 s. Adhesion was defined as neutrophils that remained stationary for 30 s or longer. Crawling was defined as polarized cells that maintained continuous contact with the endothelium while changing physical location for at least 30 s. Random neutrophils were tracked manually in 10-min videos by using Volocity software.

Sample Size and Statistical analysis. For survival studies, animal numbers between 5-20 mice per experimental group/genotype were used. For core body temperature measurements, animal numbers between 3-5 mice per group/genotype were used. For survival studies and core body temperature measurements, experiments were performed at least twice, and data from individual mice pooled from all experiments. For bacterial load recovery and FACS analyses, 4-18 mice per group/genotype were used. For measurement of cytokine and CGRP levels, 3-12 mice per group/genotype were used. Survival data were analyzed using the log-rank test; Bacterial load recovery, behavioral data, core body temperature, FACS and cytokine compared using Two-way ANOVA with Bonferroni post-tests, One-way ANOVA with Bonferroni post-tests, two-tailed unpaired t-tests for parametric analyses or Mann-Whitney test for non-parametric analyses. Data was plotted using Prism (Graphpad).

References for Example 9

1. Parker, D. & Prince, A. Immunopathogenesis of *Staphylococcus aureus* pulmonary infection. Semin Immunopathol 34, 281-297 (2012).
2. Tong, S. Y., Davis, J. S., Eichenberger, E., Holland, T. L. & Fowler, V. G., Jr. *Staphylococcus aureus* infections: epidemiology, pathophysiology, clinical manifestations, and management. Clin Microbiol Rev 28, 603-661 (2015).
3. Inoshima, I., et al. A *Staphylococcus aureus* pore-forming toxin subverts the activity of ADAM10 to cause lethal infection in mice. Nat Med 17, 1310-1314 (2011).
4. Mizgerd, J. P. Acute lower respiratory tract infection. N Engl J Med 358, 716-727 (2008).
5. Trankner, D., Hahne, N., Sugino, K., Hoon, M. A. & Zuker, C. Population of sensory neurons essential for asthmatic hyperreactivity of inflamed airways. Proc Natl Acad Sci USA 111, 11515-11520 (2014).

6. Chang, R. B., Strochlic, D. E., Williams, E. K., Umans, B. D. & Liberles, S. D. Vagal Sensory Neuron Subtypes that Differentially Control Breathing. Cell 161, 622-633 (2015).
7. Mazzone, S. B. & Undem, B. J. Vagal Afferent Innervation of the Airways in Health and Disease. Physiol Rev 96, 975-1024 (2016).
8. Basbaum, A. I., Bautista, D. M., Scherrer, G. & Julius, D. Cellular and molecular mechanisms of pain. Cell 139, 267-284 (2009).
9. Canning, B. J., Mori, N. & Mazzone, S. B. Vagal afferent nerves regulating the cough reflex. Respir Physiol Neurobiol 152, 223-242 (2006).
10. Dubin, A. E. & Patapoutian, A. Nociceptors: the sensors of the pain pathway. J Clin Invest 120, 3760-3772 (2010).
11. Caceres, A. I., et al. A sensory neuronal ion channel essential for airway inflammation and hyperreactivity in asthma. Proc Natl Acad Sci USA 106, 9099-9104 (2009).
12. Talbot, S., et al. Silencing Nociceptor Neurons Reduces Allergic Airway Inflammation. Neuron 87, 341-354 (2015).
13. Julius, D. TRP channels and pain. Annu Rev Cell Dev Biol 29, 355-384 (2013).
14. Cavanaugh, D. J., et al. Restriction of transient receptor potential vanilloid-1 to the peptidergic subset of primary afferent neurons follows its developmental downregulation in nonpeptidergic neurons. J Neurosci 31, 10119-10127 (2011).
15. Mishra, S. K. & Hoon, M. A. Ablation of TrpV1 neurons reveals their selective role in thermal pain sensation. Mol Cell Neurosci 43, 157-163 (2010).
16. Pogorzala, L. A., Mishra, S. K. & Hoon, M. A. The cellular code for mammalian thermosensation. J Neurosci 33, 5533-5541 (2013).
17. Mishra, S. K., Tisel, S. M., Orestes, P., Bhangoo, S. K. & Hoon, M. A. TRPV1-lineage neurons are required for thermal sensation. EMBO J 30, 582-593 (2011).
18. Kissin, I. & Szallasi, A. Therapeutic targeting of TRPV1 by resiniferatoxin, from preclinical studies to clinical trials. Current topics in medicinal chemistry 11, 2159-2170 (2011).
19. Kashem, S. W., et al. Nociceptive Sensory Fibers Drive Interleukin-23 Production from CD301b+ Dermal Dendritic Cells and Drive Protective Cutaneous Immunity. Immunity 43, 515-526 (2015).
20. Riol-Blanco, L., et al. Nociceptive sensory neurons drive interleukin-23-mediated psoriasiform skin inflammation. Nature 510, 157-161 (2014).
21. Abrahamsen, B., et al. The cell and molecular basis of mechanical, cold, and inflammatory pain. Science 321, 702-705 (2008).
22. Fernandes, E. S., et al. TRPV1 deletion enhances local inflammation and accelerates the onset of systemic inflammatory response syndrome. J Immunol 188, 5741-5751 (2012).
23. Rigby, K. M. & DeLeo, F. R. Neutrophils in innate host defense against *Staphylococcus aureus* infections. Semin Immunopathol 34, 237-259 (2012).
24. Yipp, B. G., et al. The Lung is a Host Defense Niche for Immediate Neutrophil-Mediated Vascular Protection. Sci Immunol 2(2017).
25. Yipp, B. G., et al. Infection-induced NETosis is a dynamic process involving neutrophil multitasking in vivo. Nat Med 18, 1386-1393 (2012).
26. Su, A. I., et al. A gene atlas of the mouse and human protein-encoding transcriptomes. Proc Natl Acad Sci USA 101, 6062-6067 (2004).
27. Zheng, J., Liu, Y., Lau, Y. L. & Tu, W. gammadelta-T cells: an unpolished sword in human anti-infection immunity. Cell Mol Immunol 10, 50-57 (2013).
28. Murphy, A. G., et al. *Staphylococcus aureus* infection of mice expands a population of memory gammadelta T cells that are protective against subsequent infection. J Immunol 192, 3697-3708 (2014).
29. Chang, R. B., Strochlic, D. E., Williams, E. K., Umans, B. D. & Liberles, S. D. Vagal Sensory Neuron Subtypes that Differentially Control Breathing. Cell 161, 622-633 (2015).
30. Pinho-Ribeiro, F. A., Verri, W. A., Jr. & Chiu, I. M. Nociceptor Sensory Neuron-Immune Interactions in Pain and Inflammation. Trends Immunol 38, 5-19 (2017).
31. Chiu, I. M., et al. Bacteria activate sensory neurons that modulate pain and inflammation. Nature 501, 52-57 (2013).
32. Cheung, G. Y., Wang, R., Khan, B. A., Sturdevant, D. E. & Otto, M. Role of the accessory gene regulator agr in community-associated methicillin-resistant *Staphylococcus aureus* pathogenesis. Infect Immun 79, 1927-1935 (2011).
33. Shields, S. D., et al. Nav1.8 expression is not restricted to nociceptors in mouse peripheral nervous system. Pain 153, 2017-2030 (2012).
34. Veiga-Femandes, H. & Mucida, D. Neuro-Immune Interactions at Barrier Surfaces. Cell 165, 801-811 (2016).
35. Liu, B., et al. IL-33/ST2 signaling excites sensory neurons and mediates itch response in a mouse model of poison ivy contact allergy. Proc Natl Acad Sci USA 113, E7572-E7579 (2016).
36. Gabanyi, I., et al. Neuro-immune Interactions Drive Tissue Programming in Intestinal Macrophages. Cell 164, 378-391 (2016).
37. Tay, S. S., Roediger, B., Tong, P. L., Tikoo, S. & Weninger, W. The Skin-Resident Immune Network. Curr Dermatol Rep 3, 13-22 (2014).
38. Cho, J. S., et al. IL-17 is essential for host defense against cutaneous *Staphylococcus aureus* infection in mice. J Clin Invest 120, 1762-1773 (2010).
39. Cheng, M. & Hu, S. Lung-resident gammadelta T cells and their roles in lung diseases. Immunology 151, 375-384 (2017).
40. Williams, E. K., et al. Sensory Neurons that Detect Stretch and Nutrients in the Digestive System. Cell 166, 209-221 (2016).
41. Cardoso, V., et al. Neuronal regulation of type 2 innate lymphoid cells via neuromedin U. Nature 549, 277-281 (2017).
42. Klose, C. S. N., et al. The neuropeptide neuromedin U stimulates innate lymphoid cells and type 2 inflammation. Nature 549, 282-286 (2017).
43. Wallrapp, A., et al. The neuropeptide NMU amplifies ILC2-driven allergic lung inflammation. Nature 549, 351-356 (2017).
44. Franco-Cereceda, A., et al. Cardiovascular effects of calcitonin gene-related peptides I and II in man. Circ Res 60, 393-397 (1987).
45. Sawant, K. V., et al. Chemokine CXCL1-Mediated Neutrophil Trafficking in the Lung: Role of CXCR2 Activation. J Innate Immun 7, 647-658 (2015).
46. Kwon, M. J., et al. CCL2 Mediates Neuron-Macrophage Interactions to Drive Proregenerative Macrophage Activation Following Preconditioning Injury. J Neurosci 35, 15934-15947 (2015).

47. Guan, Z., et al. Injured sensory neuron-derived CSF1 induces microglial proliferation and DAP12-dependent pain. Nat Neurosci 19, 94-101 (2016).
48. Pavlov, V. A., et al. Brain acetylcholinesterase activity controls systemic cytokine levels through the cholinergic anti-inflammatory pathway. Brain Behav Immun 23, 41-45 (2009).
49. de Jong, M. D., et al. Fatal outcome of human influenza A (H5N1) is associated with high viral load and hypercytokinemia. Nat Med 12, 1203-1207 (2006).
50. Tisoncik, J. R., et al. Into the eye of the cytokine storm. Microbiol Mol Biol Rev 76, 16-32 (2012).
51. Hommes, T. J., et al. DNAX-activating protein of 12 kDa impairs host defense in pneumococcal pneumonia. Crit Care Med 42, e783-790 (2014).
52. Xiong, H., et al. Innate Lymphocyte/Ly6C(hi) Monocyte Crosstalk Promotes *Klebsiella Pneumoniae* Clearance. Cell 165, 679-689 (2016).
53. Labandeira-Rey, M., et al. *Staphylococcus aureus* Panton-Valentine leukocidin causes necrotizing pneumonia. Science 315, 1130-1133 (2007).
54. Wang, R., et al. Identification of novel cytolytic peptides as key virulence determinants for community-associated MRSA. Nat Med 13, 1510-1514 (2007).
55. Ghasemlou, N., Chiu, I. M., Julien, J. P. & Woolf, C. J. CD11b+Ly6G-myeloid cells mediate mechanical inflammatory pain hypersensitivity. Proc Natl Acad Sci USA 112, E6808-6817 (2015).
56. Heng, T. S., Painter, M. W. & Immunological Genome Project, C. The Immunological Genome Project: networks of gene expression in immune cells. Nat Immunol 9, 1091-1094 (2008).

All publications cited herein expressly incorporated herein by reference in their entireties.

The invention claimed is:

1. A method for treating or preventing a microbial infection in a subject, the method comprising; administering to a subject in need thereof an agent that inhibits a peripheral neuron in an amount and for a duration sufficient to treat or prevent a microbial infection,
    wherein the microbial infection is a subcutaneous microbial infection, and
    wherein the agent is a botulinum neurotoxin selected from the group consisting of: botulinum neurotoxin serotype A, botulinum neurotoxin serotype B, botulinum neurotoxin serotype C, botulinum neurotoxin serotype D, botulinum neurotoxin serotype E, botulinum neurotoxin serotype F, and botulinum neurotoxin serotype G.

2. The method of claim 1, further comprising, prior to administering
    a) diagnosing a subject as having a microbial infection or being at risk for a microbial infection, or
    b) receiving the results of an assay that diagnoses a subject as having a microbial infection or being at risk for a microbial infection.

3. The method of claim 1, wherein the microbial infection is selected from the group consisting of: a *Streptococcus* infection, a *Staphylococcus* infection, a *Corynebacterium* infection, a *Listeria* infection, a *Clostridium* infection, a *Pseudomonas aeruginosa* infection, a *K. pneumoniae* infection, an *Escherichia coli* infection, a *Klebsiella* infection, an *Aeromonas* infection, a *Neisseria* infection, and a polymicrobial infection.

4. The method of claim 3, wherein the microbial infection comprises a bacterium which is resistant to at least one or more antibiotics.

5. The method of claim 1, further comprising administering to a subject an adjuvant and/or a second therapeutic agent.

6. The method of claim 5, wherein the second therapeutic agent is an antibiotic, antifungal, or antimicrobial agent.

7. A method for treating or preventing a chronic microbial infection in a subject, the method comprising administering to a subject in need thereof an agent that inhibits a peripheral neuron in an amount and for a duration sufficient to treat the microbial infection,
    wherein the chronic microbial infection is a subcutaneous microbial infection, and
    wherein the agent is a botulinum neurotoxin selected from the group consisting of: botulinum neurotoxin serotype A, botulinum neurotoxin serotype B, botulinum neurotoxin serotype C, botulinum neurotoxin serotype D, botulinum neurotoxin serotype E, botulinum neurotoxin serotype F, and botulinum neurotoxin serotype G.

8. The method of claim 7, wherein the chronic microbial infection is selected from the group consisting of: impetigo, bullous impetigo, furuncles, carbuncles, cellulitis, myositis, necrotizing fasciitis, and chronic recurrent erysipelas.

9. The method of claim 7, wherein the chronic microbial infection persists for at least two weeks.

10. The method of claim 7, further comprising, prior to administering
    a) diagnosing a subject as having or being at risk for a chronic microbial infection, or
    b) receiving the results of an assay that diagnoses a subject as having or being at risk for a chronic microbial infection.

11. The method of claim 7, wherein the chronic microbial infection comprises a bacterium which is resistant to at least one or more antibiotics.

12. The method of claim 11, wherein the microbial infection is methicillin-resistant *S. aureus* (MRSA), *Pseudomonas aeruginosa*, *K pneumoniae*, or *E. coli*.

\* \* \* \* \*

SEQUENCE LISTING

```
<160> NUMBER OF SEQ ID NOS: 16

<210> SEQ ID NO 1
<211> LENGTH: 37
<212> TYPE: PRT
<213> ORGANISM: Unknown
<220> FEATURE:
<223> OTHER INFORMATION: Description of Unknown:
      Alpha-CGRP sequence

<400> SEQUENCE: 1

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 2
<211> LENGTH: 37
<212> TYPE: PRT
<213> ORGANISM: Unknown
<220> FEATURE:
<223> OTHER INFORMATION: Description of Unknown:
      Beta-CGRP sequence

<400> SEQUENCE: 2

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
        35

<210> SEQ ID NO 3
<211> LENGTH: 681
<212> TYPE: DNA
<213> ORGANISM: Homo sapiens

<400> SEQUENCE: 3
gcctctctga tccaagccac ctcccgccag agaggtgtca tgggcttcca aaagttctcc        60
cccttcctgg ctctcagcat cttggtcctg ttgcaggcag gcagcctcca tgcagcacca       120
ttcaggtctg ccctggagag cagcccagca gacccggcca cgctcagtga ggacgaagcg       180
cgcctcctgc tggctgcact ggtgcaggac tatgtgcaga tgaaggccag tgagctggag       240
```

```
caggagcaag agagagaggg ctccagcctg gacagcccca gatctaagcg gtgcggtaat    300
ctgagtactt gcatgctggg cacatacacg caggacttca acaagtttca cacgttcccc    360
caaactgcaa ttggggttgg agcacctgga agaaaaggg atatgtccag cgacttggag     420
agagaccatc gccctcataa tcattgccca gaagagagcc tgtgacactg ccacctgtgt    480
gactcatcgg ctgcaggct tgctgagcag atcaggggt gtggtgaaga caactttgt      540 gcccaccaat gtgggttcca agcctttgg caggcgccgc agggaccttc aagcctgagc    600
agctgaatga ctcaagaagg tcacaataaa gctgaactcc ttttaatgtg taatgaaagc    660
aatttgtagg aaaggctcca t                                              681
```

```
<210> SEQ ID NO 4
<211> LENGTH: 1031
<212> TYPE: DNA
<213> ORGANISM: Homo sapiens

<400> SEQUENCE: 4
```

```
gcaggtgtgg tgttcatccc gggtcgaccg gccgctcgcg ctgccctgaa actctagtcg    60
ccagagaggc ggcatgggtt tccggaagtt ctccccttc ctggctctca gtatcttggt    120
cctgtaccag gcgggcagcc tccaggcggc gccattcagg tctgccctgg agagcagccc    180
agacccggcc acactcagta aagaggacg gcgcctcctg ctggctgcac tggtgcagga    240
ctatgtgcag atgaaggcca gtgagctgaa gcaggagcag gagacacagg gctccagctc    300
cgctgcccag aagagagcct gcaacactgc cacctgtgtg actcatcggc tggcaggctt    360
gctgagcaga tcagggggca tggtgaagag caacttcgtg cccaccaatg tgggttccaa    420
agcctttggc aggcgccgca gggaccttca agcctgagca gatgaatgac tccaggaaga    480
aggttatcat gaaactgaac tcaccatttc tattaatttc tgttggtaag aacttggtga    540
gaatgccccg tggaagatac acatgtttgc atcctaagat actgaaaaaa gggcacctt    600 gtcacttgaa aggaatgaaa ctgaatgcaa aataagctaa ttccatattt gctgtgcatc    660
atttttatat ttaattctat gtccagtaaa agtgatggca tctctcattg acttatctgg    720
tagcaaactg gttctttcgg agccatcctg ttgatcatgc agctccacca aaccttaggg    780
ggacgtgaaa tcactgcctg ttgtggtctc cgaggacaca tggtaatggt gatgctgtgc    840
cttgttatct aagaacatga ttgtataatt tgtttaagaa aatgtcaata ttgtgccatt    900
tgtgaacttc atcaagatta aaagcatatt ttgggtacat ttgtttcaaa accttggtga    960
tgcattacaa cttgttttct tatgtaataa taatgatgat gatgatgata ataataaata    1020
tttttgagtg c                                                         1031
```

```
<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccctctagag gtaaccttgt tactgctaat gc                                   32
```

```
<210> SEQ ID NO 6
<211> LENGTH: 30
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 6
cccggatccc agtgacagag tcaatgatgg                                                30

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cccgaattcg cgggtgtcaa taacagaact g                                              31

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cccggtaccc catatgggct cagggttgat c                                              31

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gggatgtgct gcaaggcg                                                             18

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acgacaggtt tcccgactg                                                            19

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgcggatccc acatagttat tgatagaat                                                 29

<210> SEQ ID NO 12
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 12
tccaggagca acttgagttg                                              20

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
caactcaagt tgctcctgga caaggtggta gcggaagtta                        40

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcgaagcttg taatccgata aggacaagt                                    29

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccggaattcg gcccaagaac ggagtgtat                                    29

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggagcatgct tatttacctg gcgtataact tccg                              34
```

UNITED STATES PATENT AND TRADEMARK OFFICE
CERTIFICATE OF CORRECTION

| | |
|---|---|
| PATENT NO. | : 11,400,136 B2 |
| APPLICATION NO. | : 16/624036 |
| DATED | : August 2, 2022 |
| INVENTOR(S) | : Felipe Almeida De Pinho Ribeiro et al. |

It is certified that error appears in the above-identified patent and that said Letters Patent is hereby corrected as shown below:

In the Specification

At Column 1, Lines 20-23:
"This invention was made with Government support under Grant numbers K22AI114810, DP2AT009499, and R01A1130019 awarded by the National Institutes of Health. The Government has certain rights in the invention." should be replaced with -- This invention was made with government support under AI114810, AT009499, AI070926, and AI130019 awarded by the National Institutes of Health. The government has certain rights in the invention. --

Signed and Sealed this
Twenty-third Day of April, 2024

Katherine Kelly Vidal
*Director of the United States Patent and Trademark Office*